United States Patent
Qi et al.

(10) Patent No.: US 11,773,411 B2
(45) Date of Patent: Oct. 3, 2023

(54) CHIMERIC PROTEINS AND METHODS OF REGULATING GENE EXPRESSION

(71) Applicant: The Board of Trustees of the Leland Stanford Junior University, Stanford, CA (US)

(72) Inventors: Lei S. Qi, Stanford, CA (US); P. C. Dave P. Dingal, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 250 days.

(21) Appl. No.: 17/097,946

(22) Filed: Nov. 13, 2020

(65) Prior Publication Data

US 2021/0062227 A1    Mar. 4, 2021

Related U.S. Application Data

(63) Continuation of application No. 16/570,827, filed on Sep. 13, 2019, now abandoned, which is a continuation of application No. 15/806,756, filed on Nov. 8, 2017, now Pat. No. 10,457,961, which is a continuation of application No. 15/403,058, filed on Jan. 10, 2017, now Pat. No. 9,856,497.

(60) Provisional application No. 62/399,902, filed on Sep. 26, 2016, provisional application No. 62/351,522, filed on Jun. 17, 2016, provisional application No. 62/277,322, filed on Jan. 11, 2016.

(51) Int. Cl.
*C12N 15/90* (2006.01)
*C12N 9/22* (2006.01)
*C07K 14/705* (2006.01)

(52) U.S. Cl.
CPC .......... *C12N 15/907* (2013.01); *C07K 14/705* (2013.01); *C12N 9/22* (2013.01); *C12Y 301/00* (2013.01); *H05K 999/99* (2013.01)

(58) Field of Classification Search
None
See application file for complete search history.

(56) References Cited

U.S. PATENT DOCUMENTS

| | | |
|---|---|---|
| 5,888,813 A | 3/1999 | Endl et al. |
| 7,049,076 B2 | 5/2006 | Lee et al. |
| 8,017,398 B2 | 9/2011 | Lee et al. |
| 8,349,619 B2 | 1/2013 | Rossner et al. |
| 8,546,553 B2 | 10/2013 | Terns et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,234,213 B2 | 1/2016 | Wu |
| 9,260,752 B1 | 2/2016 | May et al. |
| 9,580,480 B2 | 2/2017 | Lu et al. |
| 9,587,020 B2 | 3/2017 | Wu et al. |
| 9,593,338 B2 | 3/2017 | Liu et al. |
| 9,624,554 B2 | 4/2017 | Collins et al. |
| 9,772,328 B2 | 9/2017 | Stein et al. |
| 9,856,497 B2 | 1/2018 | Qi et al. |
| 10,336,807 B2 | 7/2019 | Qi et al. |
| 10,457,961 B2 | 10/2019 | Qi et al. |
| 11,111,287 B2 | 9/2021 | Qi et al. |
| 2004/0197346 A1 | 10/2004 | O'Hare et al. |
| 2006/0182741 A1 | 8/2006 | Bourel et al. |
| 2007/0224615 A1 | 9/2007 | Lee et al. |
| 2007/0231319 A1 | 10/2007 | Yednock |
| 2008/0274913 A1 | 11/2008 | Lee |
| 2010/0076057 A1 | 3/2010 | Sontheimer et al. |
| 2010/0093617 A1 | 4/2010 | Barrangou et al. |
| 2011/0217739 A1 | 9/2011 | Terns et al. |
| 2012/0077706 A1 | 3/2012 | Lee et al. |
| 2013/0011828 A1 | 1/2013 | Barrangou et al. |
| 2014/0068797 A1 | 3/2014 | Doudna et al. |
| 2014/0113376 A1 | 4/2014 | Sorek et al. |

(Continued)

FOREIGN PATENT DOCUMENTS

| | | |
|---|---|---|
| CA | 2619833 A1 | 3/2007 |
| CN | 102858985 A | 1/2013 |

(Continued)

OTHER PUBLICATIONS

An, R. et al., "Non-Enzymatic Depurination of Nucleic Acids: Factors and Mechanisms," PLoS ONE, 9(12):e115950, Dec. 2014, 17 pages.
Freeman, S. et al., "Wavelength dependence of pyrimidine dimer formation in DNA of human skin irradiated in situ with ultraviolet light," PNAS, 86:5605-5609, Jul. 1989.
Goodsell, D., "The Molecular Perspective: Ultraviolet Light and Pyrimidine Dimers," Stem Cells, 19:348-349, 2001.
Höbartner, C. et al., "Site-selective depurination by a periodate-dependent deoxyribozyme," Chem. Commun., 2007, 2255-2257.
U.S. Appl. No. 16/570,827, Non-Final Office Action, dated Aug. 10, 2022, 12 pages.
Wang, X. et al., "Specific recognition of DNA depurination by a luminescent terbium (III) complex," Chem. Sci., 4:3748-3752, 2013.

(Continued)

*Primary Examiner* — Laura B Goddard
(74) *Attorney, Agent, or Firm* — Kilpatrick Townsend & Stockton LLP

(57) ABSTRACT

The present disclosure provides systems, compositions and methods for regulating expression of a target polynucleotide in a cell. The systems, compositions and methods comprise a chimeric receptor polypeptide comprising a G-protein coupled receptor (GPCR) or a fragment thereof, a chimeric adaptor polypeptide, at least one actuator moiety and a cleavage moiety.

13 Claims, 49 Drawing Sheets

Specification includes a Sequence Listing.

(56) References Cited

U.S. PATENT DOCUMENTS

| | | |
|---|---|---|
| 2014/0179770 A1 | 6/2014 | Zhang et al. |
| 2014/0199767 A1 | 7/2014 | Barrangou et al. |
| 2014/0234851 A1 | 8/2014 | Leonard et al. |
| 2014/0271635 A1 | 9/2014 | Brogdon et al. |
| 2014/0273226 A1 | 9/2014 | Wu et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0315985 A1 | 10/2014 | May et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0377868 A1 | 12/2014 | Joung et al. |
| 2015/0024499 A1 | 1/2015 | Brouns et al. |
| 2015/0044772 A1 | 2/2015 | Zhao |
| 2015/0045546 A1 | 2/2015 | Siksnys et al. |
| 2015/0056705 A1 | 2/2015 | Conway et al. |
| 2015/0059010 A1 | 2/2015 | Cigan et al. |
| 2015/0211023 A1 | 7/2015 | Weinthal et al. |
| 2015/0232881 A1 | 8/2015 | Glucksmann et al. |
| 2015/0259684 A1 | 9/2015 | Mali et al. |
| 2015/0283265 A1 | 10/2015 | Peyman et al. |
| 2015/0284727 A1 | 10/2015 | Kim et al. |
| 2015/0291966 A1 | 10/2015 | Zhang et al. |
| 2015/0315576 A1 | 11/2015 | Caliando et al. |
| 2015/0322457 A1 | 11/2015 | Cho et al. |
| 2015/0344912 A1 | 12/2015 | Cho et al. |
| 2016/0010076 A1 | 1/2016 | Joung et al. |
| 2016/0017366 A1 | 1/2016 | Chen et al. |
| 2016/0024523 A1 | 1/2016 | Joung et al. |
| 2016/0024524 A1 | 1/2016 | Joung et al. |
| 2016/0046949 A1 | 2/2016 | May et al. |
| 2016/0046961 A1 | 2/2016 | Jinek et al. |
| 2016/0046962 A1 | 2/2016 | May et al. |
| 2016/0046963 A1 | 2/2016 | May et al. |
| 2016/0046978 A1 | 2/2016 | May et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0068887 A1 | 3/2016 | May et al. |
| 2016/0076020 A1 | 3/2016 | May et al. |
| 2016/0185862 A1 | 6/2016 | Wu et al. |
| 2016/0186152 A1 | 6/2016 | Brouns et al. |
| 2016/0186214 A1 | 6/2016 | Brouns et al. |
| 2016/0201089 A1 | 7/2016 | Gersbach et al. |
| 2017/0051310 A1 | 2/2017 | Doudna et al. |
| 2017/0051312 A1 | 2/2017 | Jinek et al. |
| 2017/0058282 A1 | 3/2017 | Lu et al. |
| 2017/0096680 A1 | 4/2017 | Lu et al. |
| 2017/0198308 A1 | 7/2017 | Qi et al. |
| 2018/0208636 A1 | 7/2018 | Lim et al. |
| 2018/0273980 A1 | 9/2018 | Qi et al. |
| 2018/0346543 A1 | 12/2018 | Qi et al. |
| 2019/0345220 A1 | 11/2019 | Qi et al. |
| 2020/0071729 A1 | 3/2020 | Qi et al. |

FOREIGN PATENT DOCUMENTS

| | | |
|---|---|---|
| EP | 1916903 B1 | 7/2010 |
| EP | 2336362 A1 | 6/2011 |
| EP | 2002021 B1 | 10/2011 |
| EP | 1644734 B1 | 11/2011 |
| EP | 2325332 B1 | 10/2012 |
| EP | 2771468 B1 | 2/2015 |
| EP | 2341149 B1 | 11/2016 |
| GB | 2518764 B | 3/2016 |
| GB | 2512246 B | 7/2016 |
| JP | 2015523856 A | 8/2015 |
| WO | 2005007822 A2 | 1/2005 |
| WO | 2007025097 A2 | 3/2007 |
| WO | 2007032793 A1 | 3/2007 |
| WO | 2007127538 A1 | 11/2007 |
| WO | 2007136815 A2 | 11/2007 |
| WO | 2007149807 A1 | 12/2007 |
| WO | 2012164565 A1 | 12/2012 |
| WO | 2013088446 A1 | 6/2013 |
| WO | 2013098244 A1 | 7/2013 |
| WO | 2013141680 A1 | 9/2013 |
| WO | 2013176772 A1 | 11/2013 |
| WO | 2014018423 A2 | 1/2014 |
| WO | 2014065596 A1 | 5/2014 |
| WO | 2014093479 A1 | 6/2014 |
| WO | 2014099744 A1 | 6/2014 |
| WO | 2014099750 A2 | 6/2014 |
| WO | 2014145252 A2 | 9/2014 |
| WO | 2014150624 A1 | 9/2014 |
| WO | 2014153118 A1 | 9/2014 |
| WO | 2014196932 A1 | 12/2014 |
| WO | 2014204728 A1 | 12/2014 |
| WO | 2014204729 A1 | 12/2014 |
| WO | 2015026887 A1 | 2/2015 |
| WO | 2015048577 A2 | 4/2015 |
| WO | 2015048690 A1 | 4/2015 |
| WO | 2015071474 A2 | 5/2015 |
| WO | 2015077789 A2 | 5/2015 |
| WO | 2015092024 A2 | 6/2015 |
| WO | WO 2015/092024 * | 6/2015 |
| WO | 2015139139 A1 | 9/2015 |
| WO | 2015142661 A1 | 9/2015 |
| WO | 2015148670 A1 | 10/2015 |
| WO | 2015148863 A2 | 10/2015 |
| WO | 2015150771 A1 | 10/2015 |
| WO | 2015155686 A2 | 10/2015 |
| WO | 2016011210 A2 | 1/2016 |
| WO | 2016070037 A2 | 5/2016 |
| WO | 2016115033 A1 | 7/2016 |
| WO | 2016138034 A1 | 9/2016 |
| WO | 2016149274 A1 | 9/2016 |
| WO | 2016193696 A1 | 12/2016 |
| WO | 2017040694 A2 | 3/2017 |
| WO | 2017044476 A1 | 3/2017 |
| WO | 2017059187 A1 | 4/2017 |
| WO | 2017123556 A1 | 7/2017 |
| WO | 2017123559 A2 | 7/2017 |

OTHER PUBLICATIONS

U.S. Appl. No. 15/403,058, Non-Final Office Action, dated Jul. 11, 2017, 19 pages.

U.S. Appl. No. 15/403,058, Notice of Allowance, dated Oct. 20, 2017, 5 pages.

U.S. Appl. No. 15/403,058, Restriction Requirement, dated May 15, 2017, 11 pages.

U.S. Appl. No. 15/806,756, Final Office Action, dated Jun. 19, 2019, 8 pages.

U.S. Appl. No. 15/806,756, Non-Final Office Action, dated Jan. 30, 2019, 11 pages.

U.S. Appl. No. 15/806,756, Notice of Allowance, dated Aug. 21, 2019, 6 pages.

U.S. Appl. No. 16/029,299, Non-Final Office Action, dated Dec. 10, 2018, 10 pages.

U.S. Appl. No. 16/029,299, Notice of Allowance, dated Apr. 4, 2019, 9 pages.

U.S. Appl. No. 16/029,299, Restriction Requirement, dated Oct. 9, 2018, 13 pages.

Barnea et al., "The Genetic Design of Signaling Cascades to Record Receptor Activation," PNAS, vol. 105, No. 1, Jan. 8, 2008, pp. 64-69.

Chavez et al., "Highly-Efficient Cas9-Mediated Transcriptional Programming," Nat. Methods, vol. 12, No. 4, Apr. 2015, pp. 326-328.

Cheng et al., "Multiplexed Activation of Endogenous Genes by CRISPR-on, An RNA-Guided Transcriptional Activator System," Cell Research, vol. 23, No. 10, Oct. 1, 2013, pp. 1163-1171.

Daringer et al., "Modular Extracellular Sensor Architecture for Engineering Mammalian Cell-based Devices," ACS Synthetic Biology, vol. 3, No. 12, Available Online at:—http://pubs.acs.org/doi/abs/10.1021/sb400128g, Dec. 19, 2014, pp. 892-902.

Dominguez et al., "Beyond Editing: Repurposing CRISPR-Cas9 for Precision Genome Regulation and Interrogation," Nature Review Molecular Cell Biology, vol. 17, No. 1, Jan. 2016, pp. 5-15.

(56) References Cited

OTHER PUBLICATIONS

Du et al., "CRISPR Technology for Genome Activation and Repression in Mammalian Cells," Cold Spring Harbor Protocols, vol. 2016, No. 1, Jan. 4, 2016, pp. 40-49.
Application No. EP17738809.7, Extended European Search Report, dated Jun. 14, 2019, 6 pages.
Application No. EP17738812.1, Extended European Search Report, dated Jun. 5, 2019, 6 pages.
Gilbert et al., "CRISPR-Mediated Modular RNA-Guided Regulation of Transcription in Eukaryotes," Cell, vol. 154, No. 2, Jul. 18, 2013, pp. 442-451.
Gilbert et al., "Genome-Scale CRISPR-Mediated Control of Gene Repression and Activation," Cell, vol. 159, No. 3, Oct. 23, 2014, pp. 647-661.
Hawkins et al., "Targeted Transcriptional Repression in Bacteria Using CRISPR Interference (CRISPRi)," Methods Mol. Biol., vol. 1311,, May 2015, pp. 349-362.
Invitrogen, "Tango™ GPR21-bla U2OS Cell-based Assay," Available Online at: https://www.thermofisher.com/order/catalog/product/K1840, Nov. 8, 2010, 12 pages.
Kobilka , "G Protein Coupled Receptor Structure and Activation," Biochimica et Biophysica Acta., vol. 1768, No. 4, Apr. 2007, pp. 794-807.
Kopan et al., "The Canonical Notch Signaling Pathway: Unfolding the Activation Mechanism," Cell, vol. 137, No. 2, Apr. 17, 2009, pp. 216-233.
Larson et al., "CRISPR Interference (CRISPRi) for Sequence-Specific Control of Gene Expression," Nature Protocols, vol. 8, No. 11, Nov. 2013, pp. 2180-2196.
Lim , "Designing Customized Cell Signaling Circuits," Nat. Rev. Mol. Cell Biol., vol. 11, No. 6, Jun. 2010, pp. 393-403.
Liu et al., "CRISPR-ERA: A Comprehensive Design Tool for CRISPR-mediated Gene Editing, Repression and Activation," Bioinformatics, vol. 31, No. 22, Nov. 15, 2015, pp. 3676-3678.
Lloyd et al., "Beyond The Antigen Receptor: Editing The Genome of T-cells for Cancer Adoptive Cellular Therapies," Frontiers in Immunology, vol. 4, No. 221, Aug. 5, 2013, pp. 1-7.
Lucks et al., "Versatile RNA-Sensing Transcriptional Regulators for Engineering Genetic Networks," PNAS, vol. 108, No. 21, May 24, 2011, pp. 8617-8622.
Mandegar et al., "Crispr Interference Efficiently Induces Specific and Reversible Gene Silencing in Human iPSCs," Cell Stem Cell, vol. 18, No. 4, Apr. 7, 2016, pp. 541-553.
Morsut et al., "Engineering Customized Cell Sensing and Response Behaviors Using Synthetic Notch Receptors," Cell, vol. 164, No. 4, Feb. 11, 2016, pp. 780-791.
Nunez et al., "Chemical and Biophysical Modulation of Cas9 for Tunable Genome Engineering," ACS Chem. Biol., 2016, vol. 11, No. 3, Available Online at: http://pubs.acs.org/doi/abs/10.1021/acschembio.5b01019, Mar. 18, 2016, pp. 681-688.
Application No. PCT/US2017/012881, International Preliminary Report on Patentability, dated Jul. 26, 2018, 38 pages.
Application No. PCT/US2017/012881, International Search Report and Written Opinion, dated May 15, 2017, 29 pages.
Application No. PCT/US2017/012885, International Preliminary Report on Patentability, dated Jul. 26, 2018, 12 pages.
Application No. PCT/US2017/012885, International Search Report and Written Opinion, dated Jun. 29, 2017, 18 pages.
Application No. PCT/US2017/012885, Invitation to Pay Additional Fees and, Where Applicable, Protest Fee dated May 8, 2017, 4 pages.
Qi et al., "Repurposing CRISPR as an RNA-guided Platform for Sequence-Specific Control of Gene Expression," Cell, vol. 152, No. 5, Feb. 28, 2013, pp. 1173-1183.
Roybal et al., "Precision Tumor Recognition by T Cells with Combinatorial Antigen-Sensing Circuits," Cell, vol. 164, No. 4, Feb. 11, 2016, pp. 770-779.
Tanaka et al., "Establishment of an Indicator Cell System For Hepatitis C Virus," Microbiol. Immunol., vol. 54, 2010, pp. 206-220.
Uniprot Knowledgebase (UNIPROTKB), Accession Q01705 (NOTC1_Mouse), Neurogenic locus notch homolog protein 1, Dec. 9, 2015, 21 pages.
Wang et al., "CRISPR/Cas9 in Genome Editing and Beyond," Annual Review of Biochemistry, vol. 85, Jun. 2, 2016, pp. 227-264.
Wehr et al., "Monitoring G Protein-Coupled Receptor Activation Using the Protein Fragment Complementation Technique Split-TEV," Methods in Molecular Biology, vol. 1272, Jan. 14, 2015, pp. 107-118.
Xiong et al., "CRISPR/Cas9 for Human Genome Engineering and Disease Research," Annual Review of Genomics and Human Genetics, vol. 17, Aug. 31, 2016, pp. 131-154.
Zalatan et al., "Engineering Complex Synthetic Transcriptional Programs with CRISPR RNA Scaffolds," Cell, vol. 160, No. 1-2, Jan. 15, 2015, pp. 339-350.
U.S. Appl. No. 16/414,721, Notice of Allowance, dated Jun. 18, 2021, 12 pages.

* cited by examiner

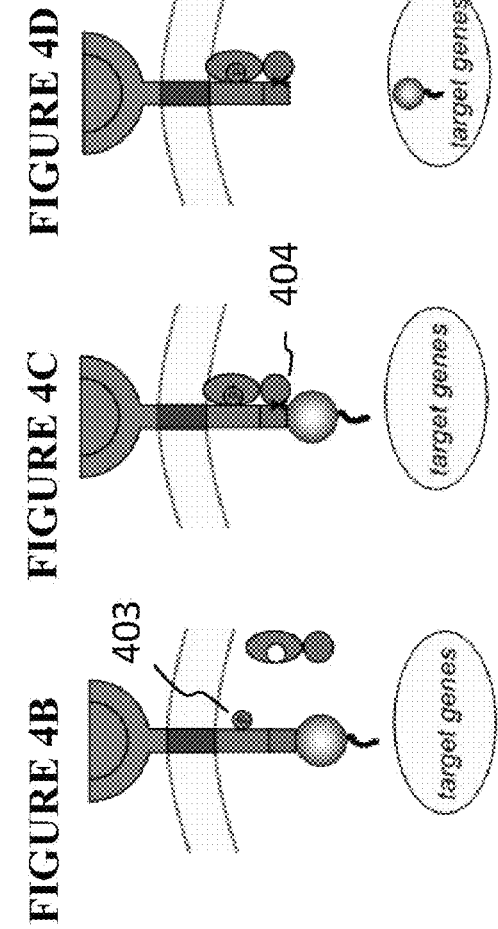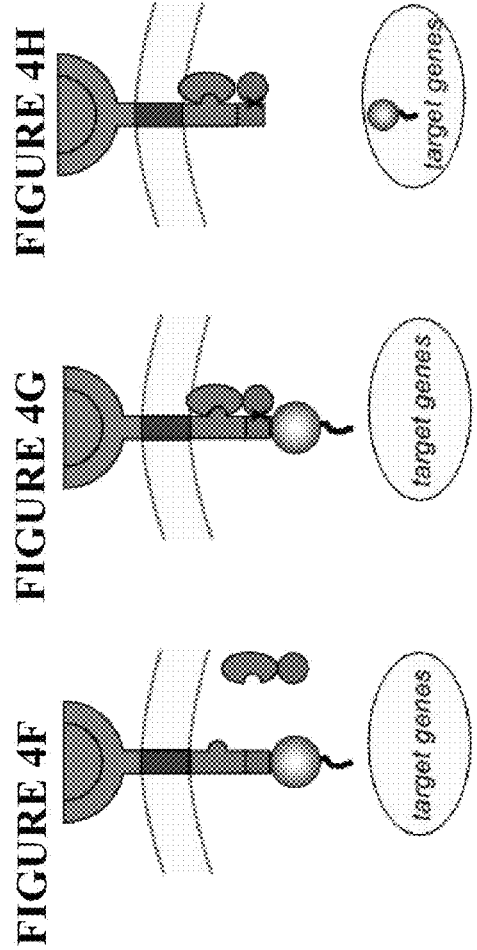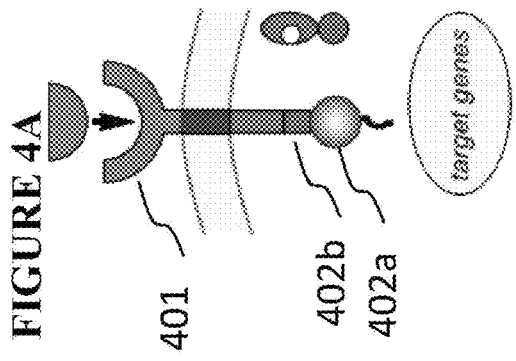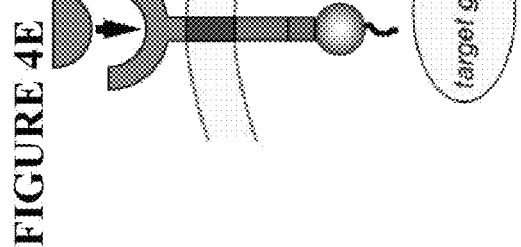

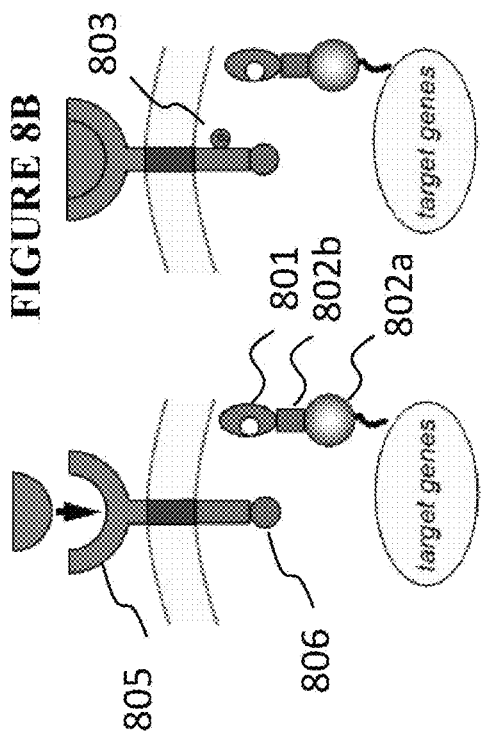
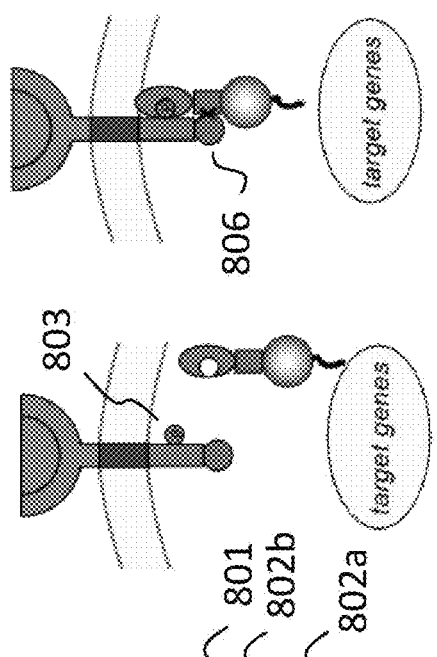
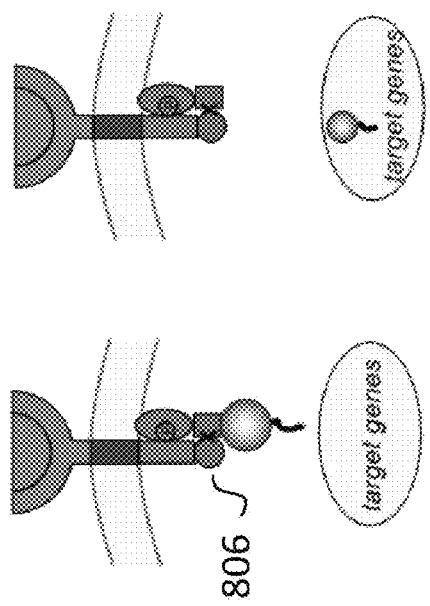
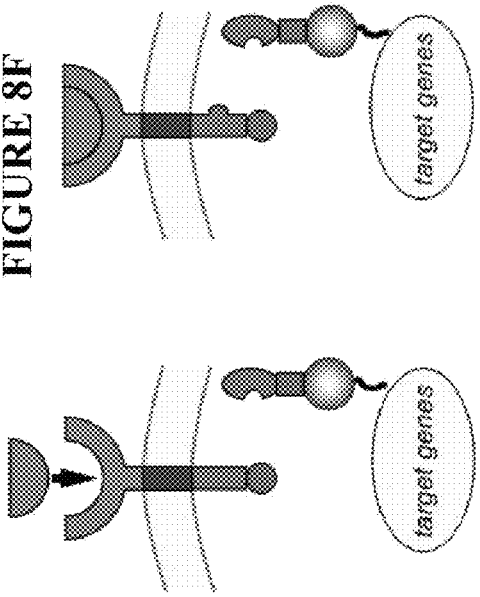
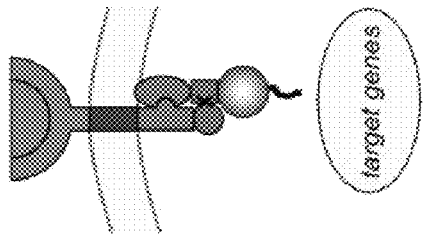
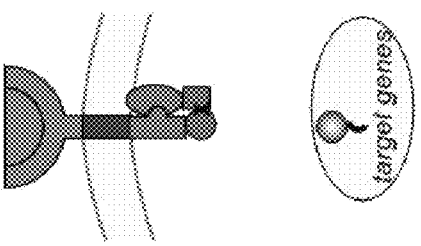

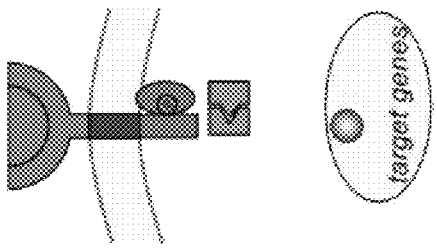
FIGURE 13A
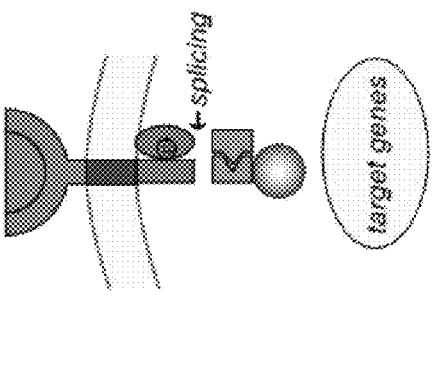
FIGURE 13B
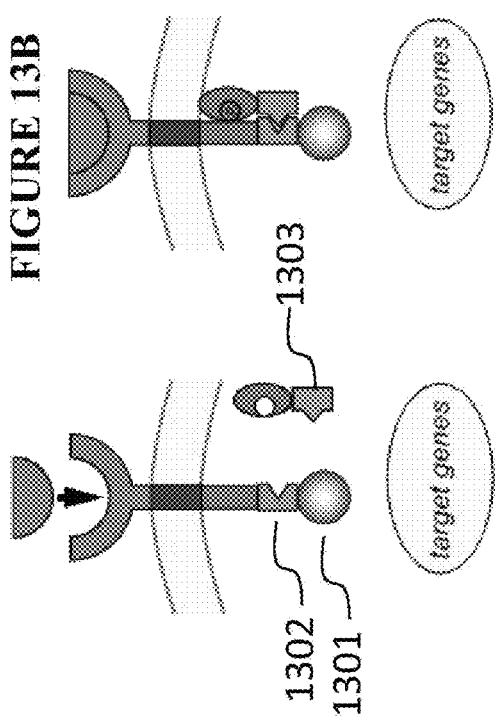
FIGURE 13C
FIGURE 13D
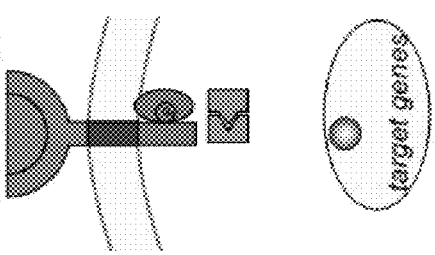
FIGURE 13E
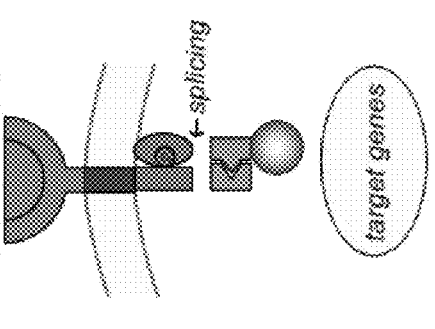
FIGURE 13F
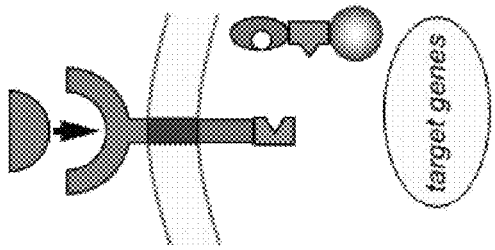
FIGURE 13G
FIGURE 13H

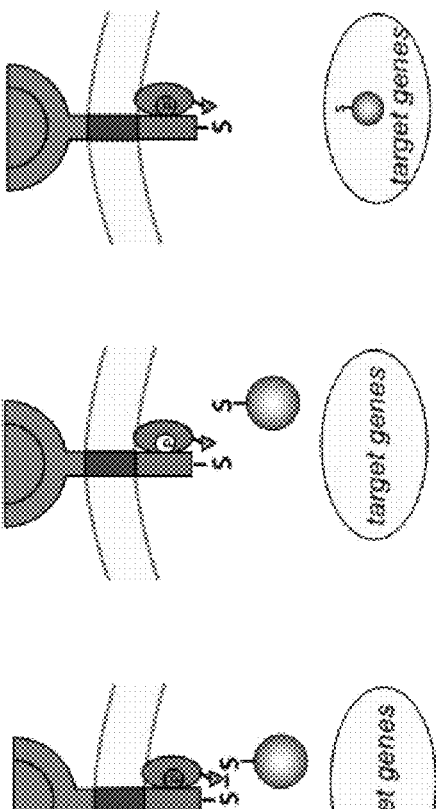
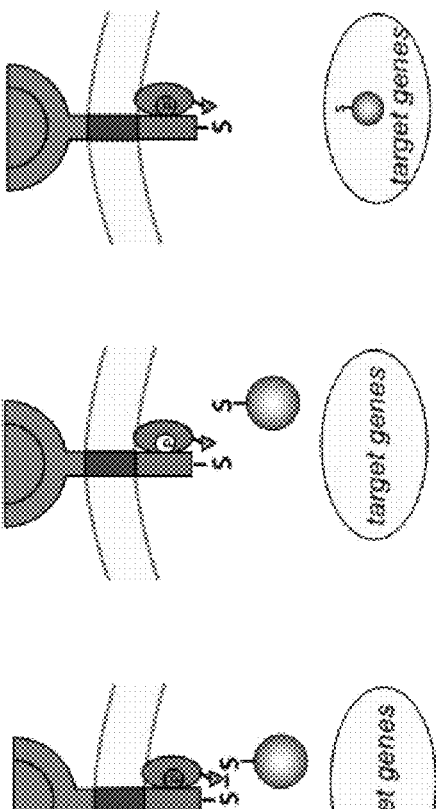
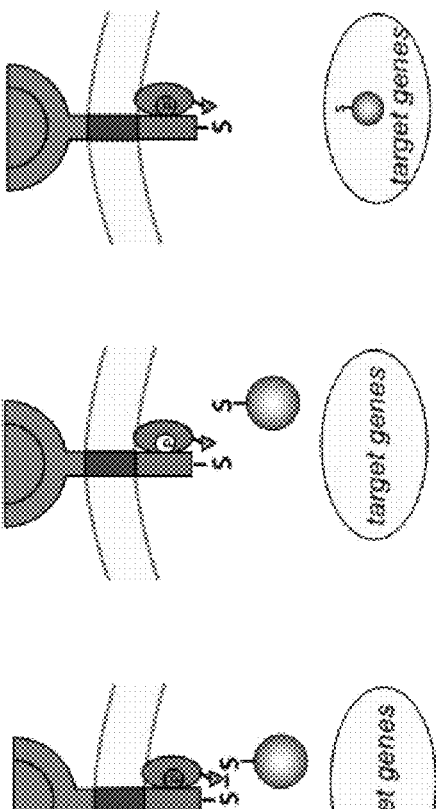
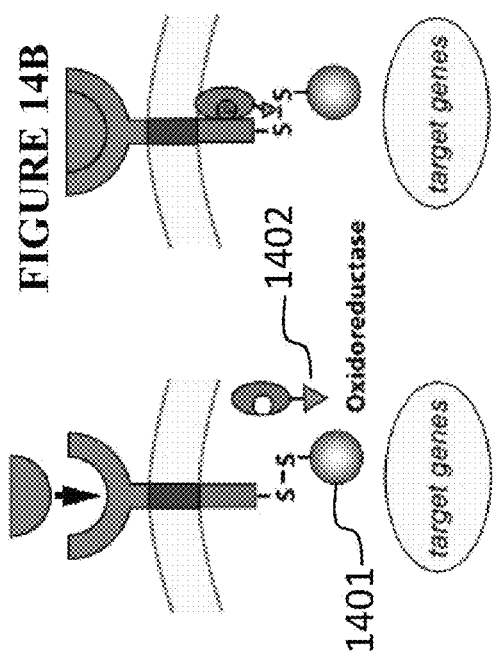
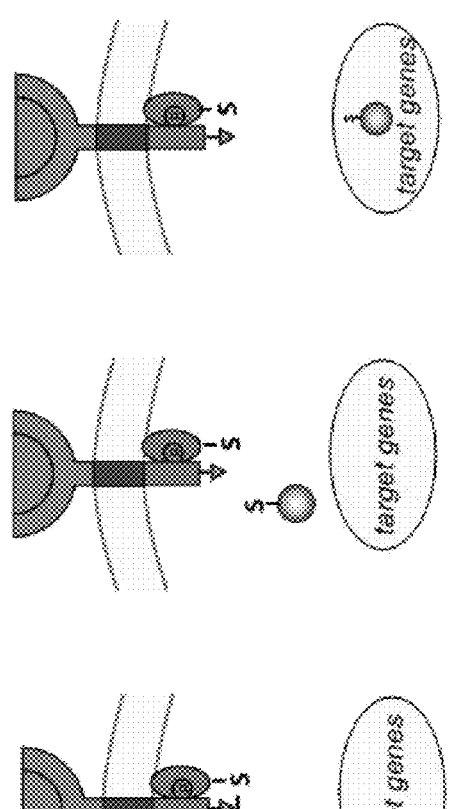
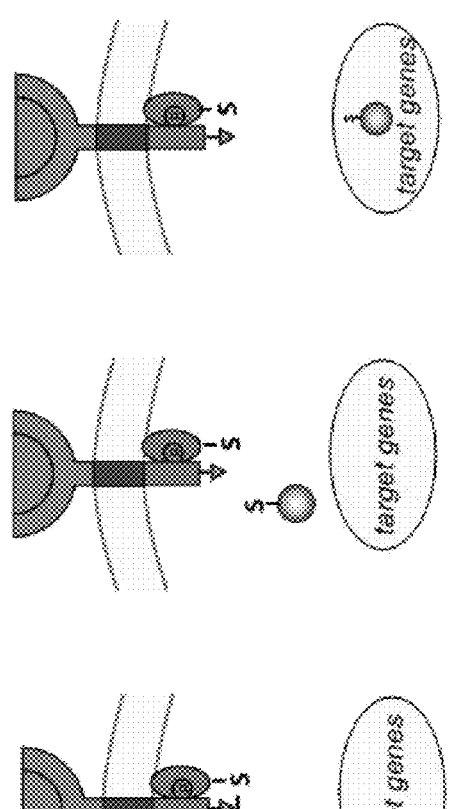
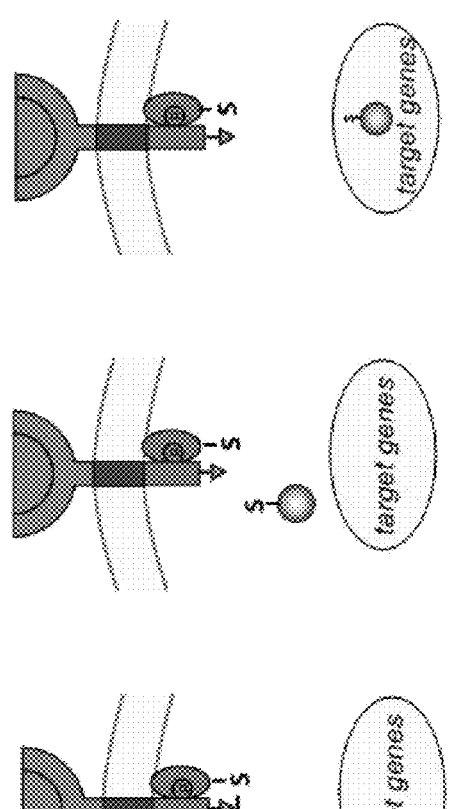
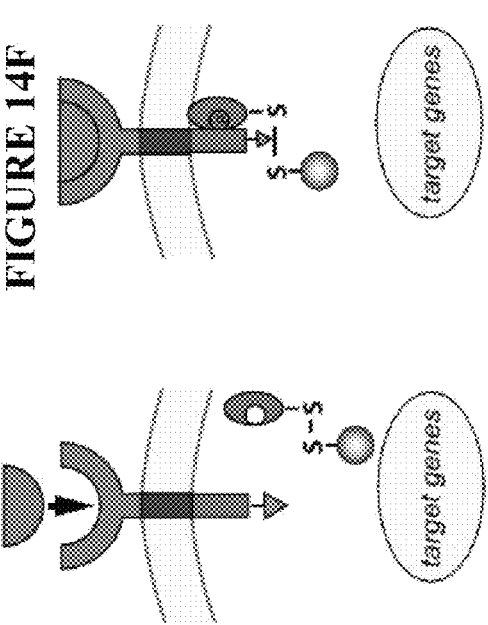

FIGURE 19A FIGURE 19B FIGURE 19C
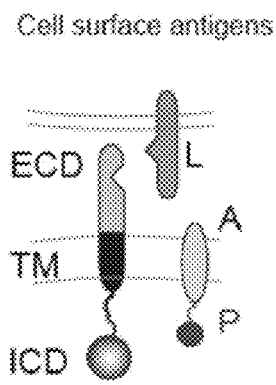
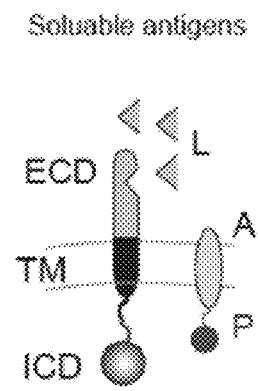
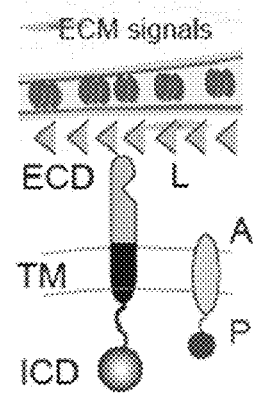
FIGURE 19D FIGURE 19E FIGURE 19F
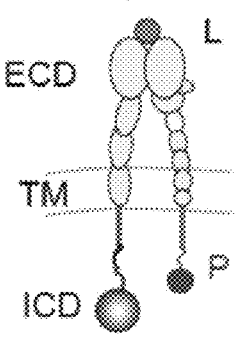
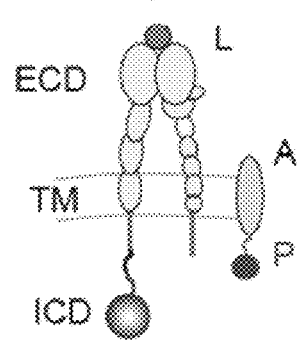
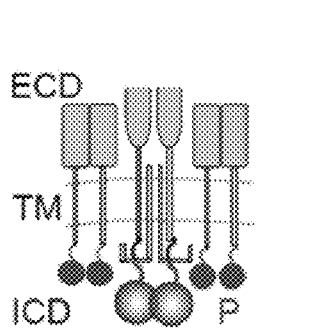

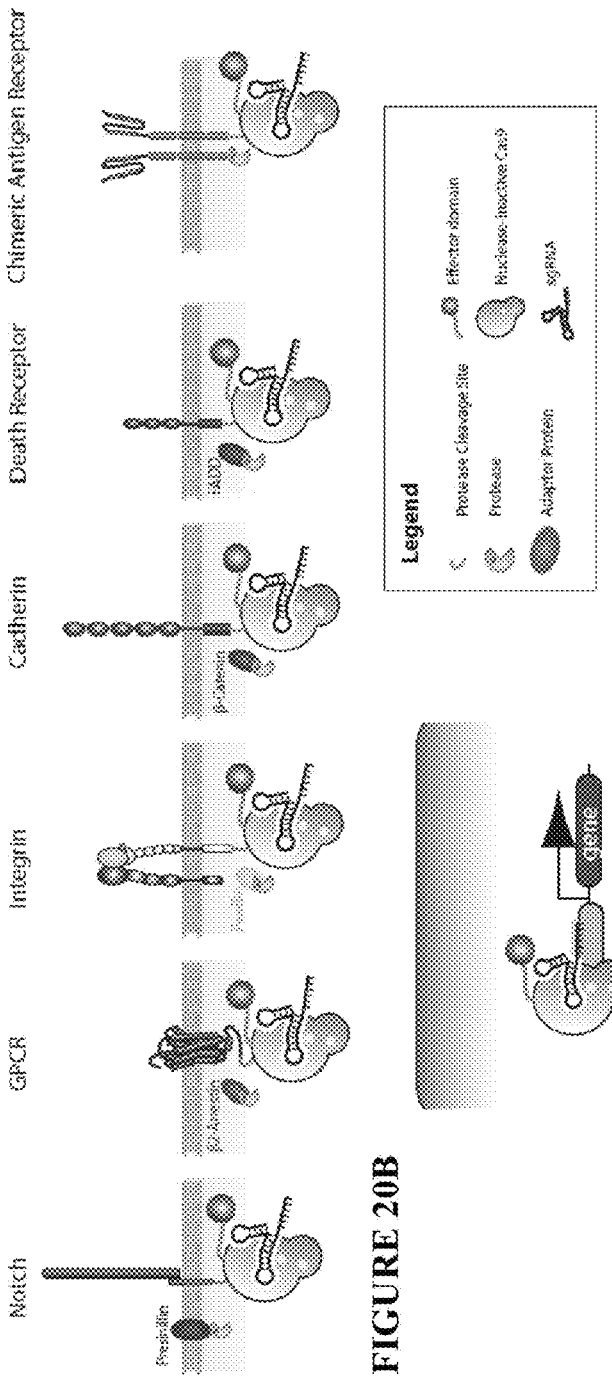

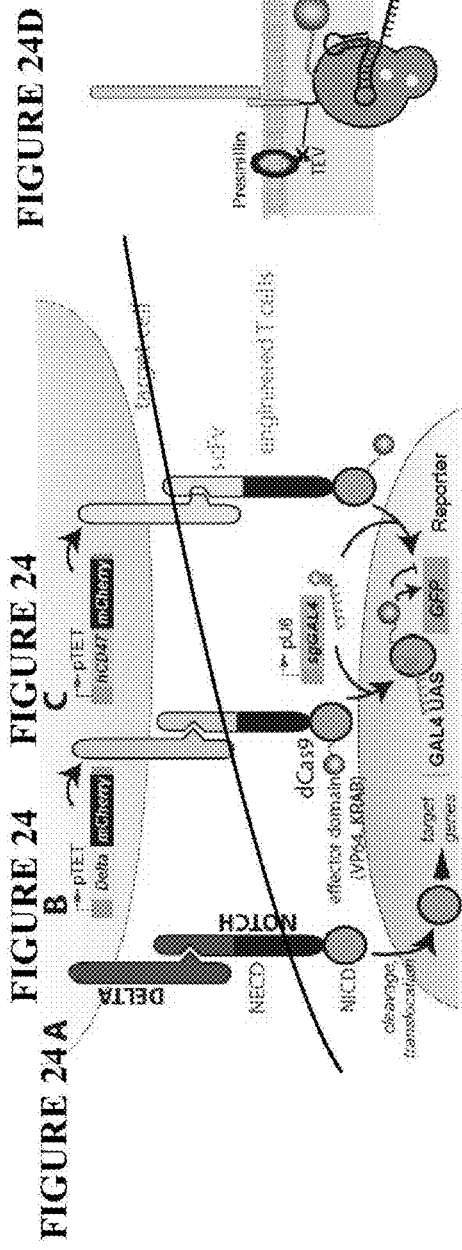
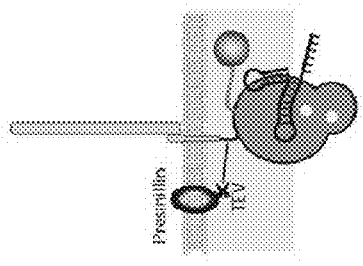
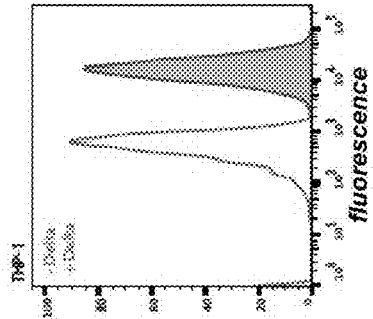
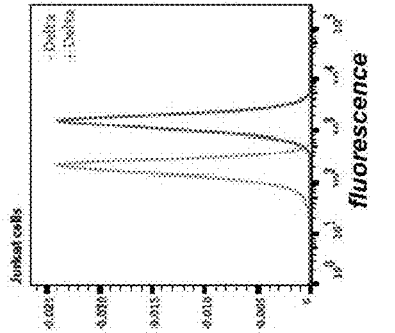
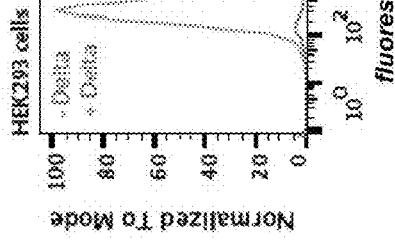
FIGURE 24A FIGURE 24B FIGURE 24C FIGURE 24D FIGURE 24E FIGURE 24F FIGURE 24G

FIGURE 25A

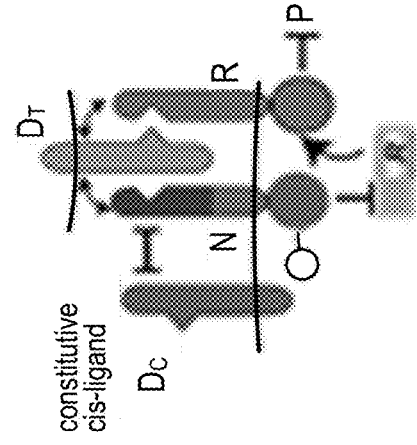

$$\frac{dR}{dt} = \beta_R - Y_R R - \frac{RD_T}{k_{RD_T}}$$

$$\frac{dP}{dt} = \frac{\alpha_p}{1+(RD_T)^{T_R}} - Y_R P$$

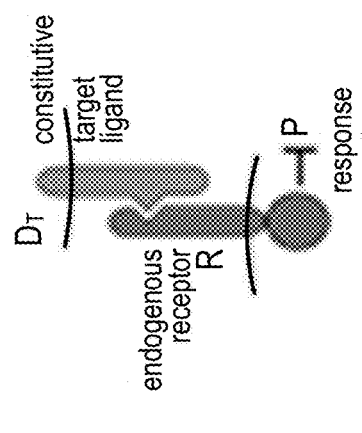

FIGURE 25B

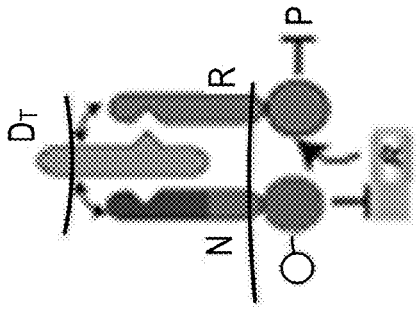

$$\frac{dR}{dt} = \frac{\beta_R}{1+(ND_T)^{T_R}} - Y_R R - \frac{RD_T}{k_{RD_T}}$$

$$\frac{dN}{dt} = \beta_N - Y_N N - \frac{ND_T}{k_{ND_T}}$$

$$\frac{dP}{dt} = \frac{\alpha_p}{1+(RD_T)^{Y_R}} - Y_R P$$

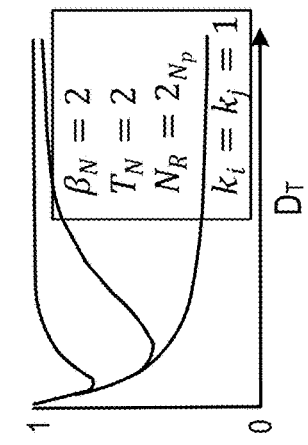

FIGURE 25C

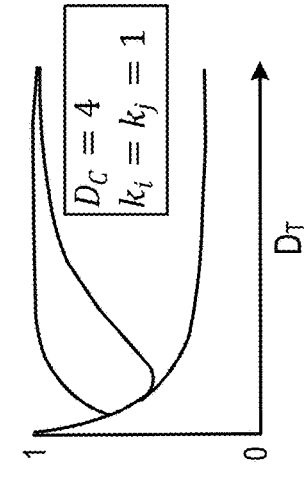

$$\frac{dR}{dt} = \frac{\beta_R}{1+(ND_T)^{T_R}} - Y_R R - \frac{RD_T}{k_{RD_T}}$$

$$\frac{dN}{dt} = \beta_N - Y_N N - \frac{ND_T}{k_{ND_T}} \cdot \frac{ND_C}{k_{ND_C}}$$

$$\frac{dP}{dt} = \frac{\alpha_p}{1+(RD_T)^{Y_R}} - Y_R P$$

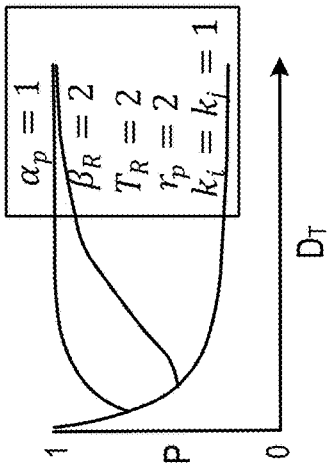

FIGURE 27A
FIGURE 27B
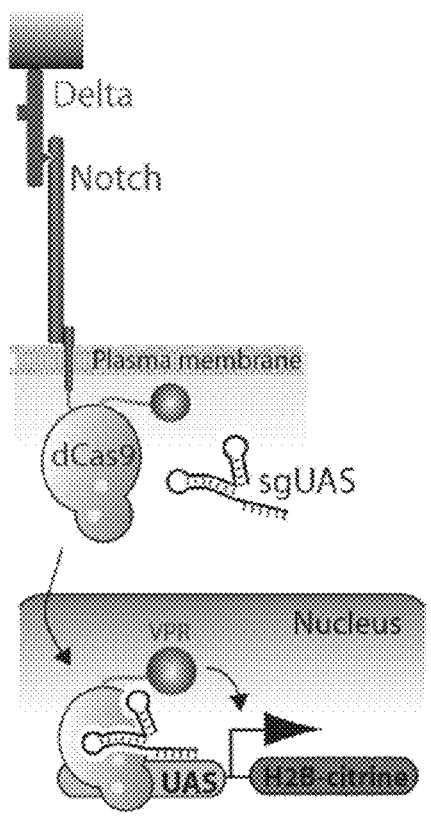
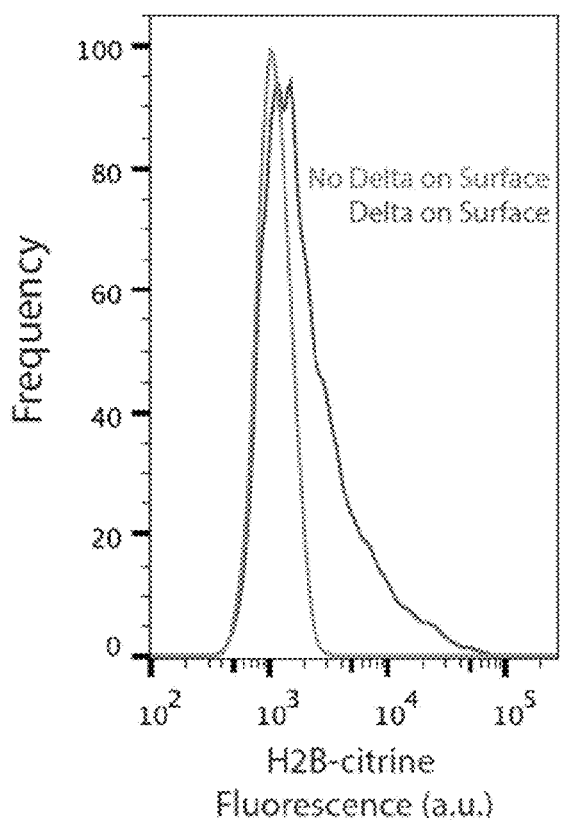

Development of chimeric Notch receptors

FIGURE 32A
FIGURE 32B
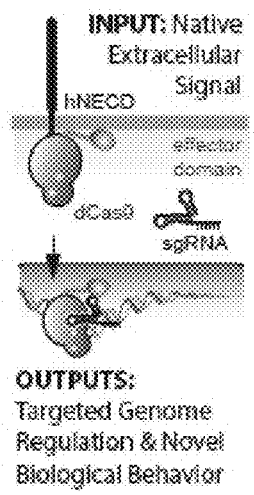
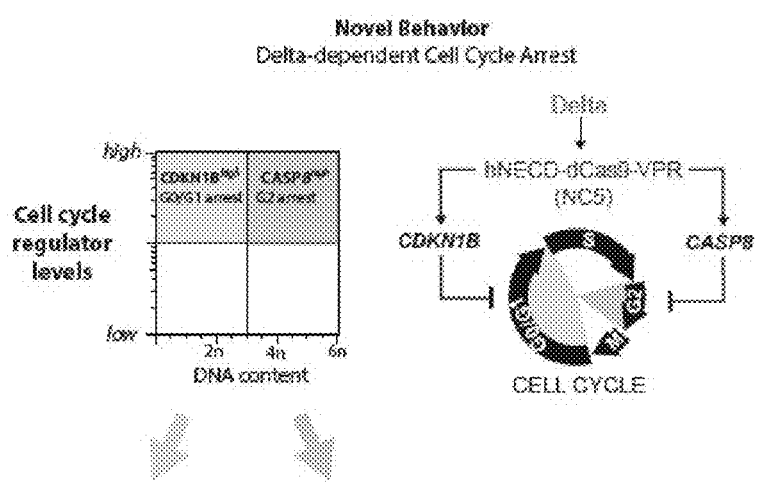
FIGURE 32C
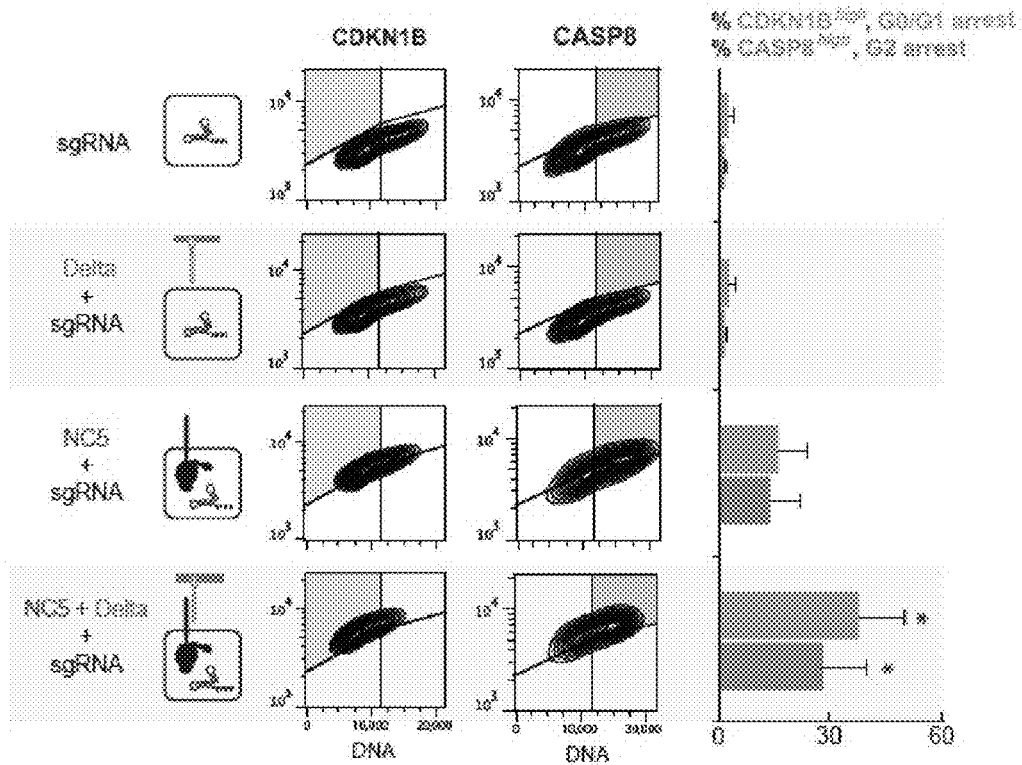

FIGURE 35C
FIGURE 35D
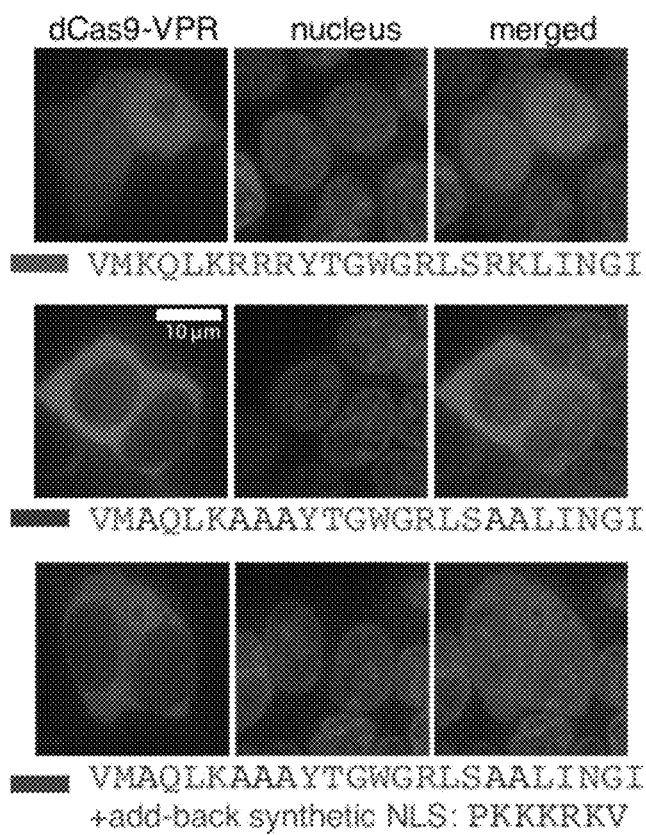
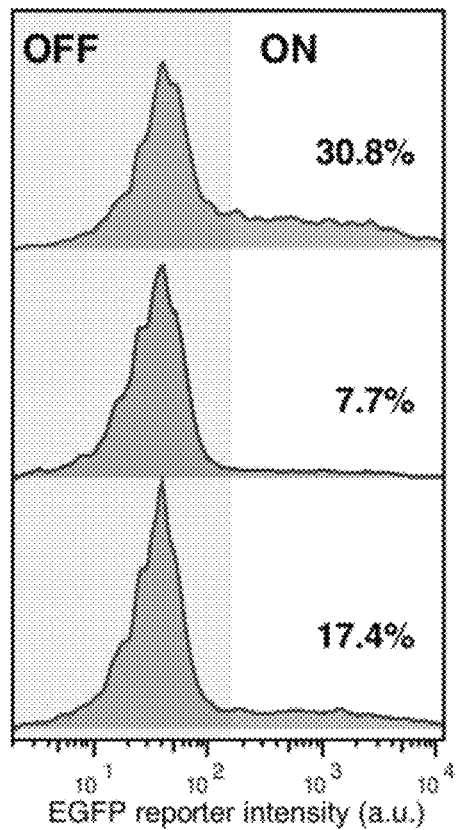

FIGURE 37A

Delta-binding unit of NECD: EGF repeats 11 & 12

```
Human     QDVDECSLGANPCEHAGKCINTLGSFECQCLQGYTGPRCEIDVTECVSNPCQNDATCLDQIGEFQCMCMPGYEGVHCE
Xenopus   NDVDECSLGANPCEHGGRCTNTLGSFQCNCPQGYAGPRCEIDVNECLSNPCQNDSTCLDQIGEFQCICMPGYEGLYCE
Zebrafish QDIDECSLGANPCEHGGRCLNTWGSFQCKCLQGYEGPRCEMDVNECKSNPCQNDATCLDQIGGFHCICMPGYEGVFCQ
Drosophila EDIDEDQG  SPCEHNGICVNTPGSYRCNCSQGFTGPRCBTNINECEGSHPCQNEGSCIDDPGTFRCVCNHEGFTGTQCE
                       *                  *        *     *      *     *      *          *
```

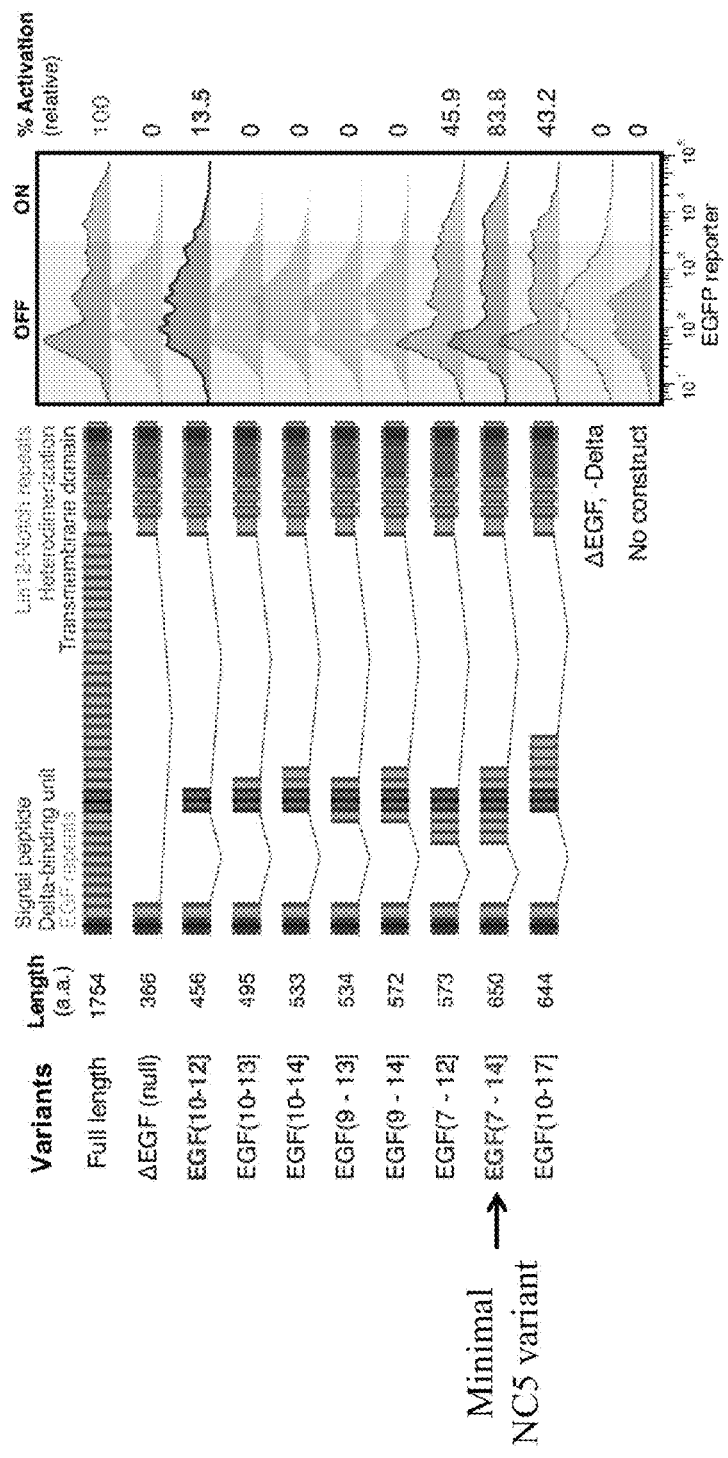

FIGURE 37B

SEQUENCE LISTING

```
<160> NUMBER OF SEQ ID NOS: 84

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct

<400> SEQUENCE: 1
gtacgttctc tatcactgat a                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
gtacgttctc tatcactgat a                                              21

<210> SEQ ID NO 3
<211> LENGTH: 2575
<212> TYPE: PRT
<213> ORGANISM: Artificial Sequence
<220> FEATURE:
<223> OTHER INFORMATION: Synthetic Construct

<400> SEQUENCE: 3

Met Lys Thr Ile Ile Ala Leu Ser Tyr Ile Phe Cys Leu Val Phe Ala
1               5                   10                  15

Asp Tyr Lys Asp Asp Asp Asp Ala Ser Ile Asp Met Glu Gly Ile Ser
            20                  25                  30

Ile Tyr Thr Ser Asp Asn Tyr Thr Glu Glu Met Gly Ser Gly Asp Tyr
        35                  40                  45

Asp Ser Met Lys Glu Pro Cys Phe Arg Glu Glu Asn Ala Asn Phe Asn
    50                  55                  60
```

-continued

```
Lys Ile Phe Leu Pro Thr Ile Tyr Ser Ile Ile Phe Leu Thr Gly Ile
 65                  70                  75                  80

Val Gly Asn Gly Leu Val Ile Leu Val Met Gly Tyr Gln Lys Lys Leu
                 85                  90                  95

Arg Ser Met Thr Asp Lys Tyr Arg Leu His Leu Ser Val Ala Asp Leu
            100                 105                 110

Leu Phe Val Ile Thr Leu Pro Phe Trp Ala Val Asp Ala Val Ala Asn
        115                 120                 125

Trp Tyr Phe Gly Asn Phe Leu Cys Lys Ala Val His Val Ile Tyr Thr
    130                 135                 140

Val Asn Leu Tyr Ser Ser Val Leu Ile Leu Ala Phe Ile Ser Leu Asp
145                 150                 155                 160

Arg Tyr Leu Ala Ile Val His Ala Thr Asn Ser Gln Arg Pro Arg Lys
                165                 170                 175

Leu Leu Ala Glu Lys Val Val Tyr Val Gly Val Trp Ile Pro Ala Leu
            180                 185                 190

Leu Leu Thr Ile Pro Asp Phe Ile Phe Ala Asn Val Ser Glu Ala Asp
        195                 200                 205

Asp Arg Tyr Ile Cys Asp Arg Phe Tyr Pro Asn Asp Leu Trp Val Val
    210                 215                 220

Val Phe Gln Phe Gln His Ile Met Val Gly Leu Ile Leu Pro Gly Ile
225                 230                 235                 240

Val Ile Leu Ser Cys Tyr Cys Ile Ile Ser Lys Leu Ser His Ser
                245                 250                 255

Lys Gly His Gln Lys Arg Lys Ala Leu Lys Thr Thr Val Ile Leu Ile
            260                 265                 270

Leu Ala Phe Phe Ala Cys Trp Leu Pro Tyr Tyr Ile Gly Ile Ser Ile
        275                 280                 285

Asp Ser Phe Ile Leu Leu Glu Ile Ile Lys Gln Gly Cys Glu Phe Glu
    290                 295                 300

Asn Thr Val His Lys Trp Ile Ser Ile Thr Glu Ala Leu Ala Phe Phe
305                 310                 315                 320

His Cys Cys Leu Asn Pro Ile Leu Tyr Ala Phe Leu Gly Ala Lys Phe
                325                 330                 335

Lys Thr Ser Ala Gln His Ala Leu Thr Ser Val Ser Arg Gly Ser Ser
            340                 345                 350

Leu Lys Ile Leu Ser Lys Gly Lys Arg Gly Gly His Ser Ser Val Ser
        355                 360                 365

Thr Glu Ser Glu Ser Ser Phe His Ser Ser Ile Asp Thr Gly Gly
    370                 375                 380

Arg Thr Pro Pro Ser Leu Gly Pro Gln Asp Glu Ser Cys Thr Thr Ala
385                 390                 395                 400

Ser Ser Ser Leu Ala Lys Asp Thr Ser Thr Gly Glu Asn Leu Tyr
                405                 410                 415

Phe Gln Leu Leu Glu Met Asp Lys Lys Tyr Ser Ile Gly Leu Ala Ile
            420                 425                 430

Gly Thr Asn Ser Val Gly Trp Ala Val Ile Thr Asp Glu Tyr Lys Val
        435                 440                 445

Pro Ser Lys Lys Phe Lys Val Leu Gly Asn Thr Asp Arg His Ser Ile
    450                 455                 460

Lys Lys Asn Leu Ile Gly Ala Leu Leu Phe Asp Ser Gly Glu Thr Ala
465                 470                 475                 480

Glu Ala Thr Arg Leu Lys Arg Thr Ala Arg Arg Arg Tyr Thr Arg Arg
```

```
                485                 490                 495
Lys Asn Arg Ile Cys Tyr Leu Gln Glu Ile Phe Ser Asn Glu Met Ala
                500                 505                 510

Lys Val Asp Asp Ser Phe Phe His Arg Leu Glu Glu Ser Phe Leu Val
                515                 520                 525

Glu Glu Asp Lys Lys His Glu Arg His Pro Ile Phe Gly Asn Ile Val
                530                 535                 540

Asp Glu Val Ala Tyr His Glu Lys Tyr Pro Thr Ile Tyr His Leu Arg
545                 550                 555                 560

Lys Lys Leu Val Asp Ser Thr Asp Lys Ala Asp Leu Arg Leu Ile Tyr
                565                 570                 575

Leu Ala Leu Ala His Met Ile Lys Phe Arg Gly His Phe Leu Ile Glu
                580                 585                 590

Gly Asp Leu Asn Pro Asp Asn Ser Asp Val Asp Lys Leu Phe Ile Gln
                595                 600                 605

Leu Val Gln Thr Tyr Asn Gln Leu Phe Glu Glu Asn Pro Ile Asn Ala
                610                 615                 620

Ser Gly Val Asp Ala Lys Ala Ile Leu Ser Ala Arg Leu Ser Lys Ser
625                 630                 635                 640

Arg Arg Leu Glu Asn Leu Ile Ala Gln Leu Pro Gly Glu Lys Lys Asn
                645                 650                 655

Gly Leu Phe Gly Asn Leu Ile Ala Leu Ser Leu Gly Leu Thr Pro Asn
                660                 665                 670

Phe Lys Ser Asn Phe Asp Leu Ala Glu Asp Ala Lys Leu Gln Leu Ser
                675                 680                 685

Lys Asp Thr Tyr Asp Asp Asp Leu Asp Asn Leu Leu Ala Gln Ile Gly
                690                 695                 700

Asp Gln Tyr Ala Asp Leu Phe Leu Ala Ala Lys Asn Leu Ser Asp Ala
705                 710                 715                 720

Ile Leu Leu Ser Asp Ile Leu Arg Val Asn Thr Glu Ile Thr Lys Ala
                725                 730                 735

Pro Leu Ser Ala Ser Met Ile Lys Arg Tyr Asp Glu His His Gln Asp
                740                 745                 750

Leu Thr Leu Leu Lys Ala Leu Val Arg Gln Gln Leu Pro Glu Lys Tyr
                755                 760                 765

Lys Glu Ile Phe Phe Asp Gln Ser Lys Asn Gly Tyr Ala Gly Tyr Ile
                770                 775                 780

Asp Gly Gly Ala Ser Gln Glu Glu Phe Tyr Lys Phe Ile Lys Pro Ile
785                 790                 795                 800

Leu Glu Lys Met Asp Gly Thr Glu Glu Leu Leu Val Lys Leu Asn Arg
                805                 810                 815

Glu Asp Leu Leu Arg Lys Gln Arg Thr Phe Asp Asn Gly Ser Ile Pro
                820                 825                 830

His Gln Ile His Leu Gly Glu Leu His Ala Ile Leu Arg Arg Gln Glu
                835                 840                 845

Asp Phe Tyr Pro Phe Leu Lys Asp Asn Arg Glu Lys Ile Glu Lys Ile
                850                 855                 860

Leu Thr Phe Arg Ile Pro Tyr Tyr Val Gly Pro Leu Ala Arg Gly Asn
865                 870                 875                 880

Ser Arg Phe Ala Trp Met Thr Arg Lys Ser Glu Glu Thr Ile Thr Pro
                885                 890                 895

Trp Asn Phe Glu Glu Val Val Asp Lys Gly Ala Ser Ala Gln Ser Phe
                900                 905                 910
```

```
Ile Glu Arg Met Thr Asn Phe Asp Lys Asn Leu Pro Asn Glu Lys Val
        915                 920                 925

Leu Pro Lys His Ser Leu Leu Tyr Glu Tyr Phe Thr Val Tyr Asn Glu
930                 935                 940

Leu Thr Lys Val Lys Tyr Val Thr Glu Gly Met Arg Lys Pro Ala Phe
945                 950                 955                 960

Leu Ser Gly Glu Gln Lys Lys Ala Ile Val Asp Leu Leu Phe Lys Thr
                965                 970                 975

Asn Arg Lys Val Thr Val Lys Gln Leu Lys Glu Asp Tyr Phe Lys Lys
            980                 985                 990

Ile Glu Cys Phe Asp Ser Val Glu Ile Ser Gly Val Glu Asp Arg Phe
            995                 1000                1005

Asn Ala Ser Leu Gly Thr Tyr His Asp Leu Leu Lys Ile Ile Lys
        1010                1015                1020

Asp Lys Asp Phe Leu Asp Asn Glu Glu Asn Glu Asp Ile Leu Glu
        1025                1030                1035

Asp Ile Val Leu Thr Leu Thr Leu Phe Glu Asp Arg Glu Met Ile
        1040                1045                1050

Glu Glu Arg Leu Lys Thr Tyr Ala His Leu Phe Asp Asp Lys Val
        1055                1060                1065

Met Lys Gln Leu Lys Arg Arg Arg Tyr Thr Gly Trp Gly Arg Leu
        1070                1075                1080

Ser Arg Lys Leu Ile Asn Gly Ile Arg Asp Lys Gln Ser Gly Lys
        1085                1090                1095

Thr Ile Leu Asp Phe Leu Lys Ser Asp Gly Phe Ala Asn Arg Asn
        1100                1105                1110

Phe Met Gln Leu Ile His Asp Asp Ser Leu Thr Phe Lys Glu Asp
        1115                1120                1125

Ile Gln Lys Ala Gln Val Ser Gly Gln Gly Asp Ser Leu His Glu
        1130                1135                1140

His Ile Ala Asn Leu Ala Gly Ser Pro Ala Ile Lys Lys Gly Ile
        1145                1150                1155

Leu Gln Thr Val Lys Val Val Asp Glu Leu Val Lys Val Met Gly
        1160                1165                1170

Arg His Lys Pro Glu Asn Ile Val Ile Glu Met Ala Arg Glu Asn
        1175                1180                1185

Gln Thr Thr Gln Lys Gly Gln Lys Asn Ser Arg Glu Arg Met Lys
        1190                1195                1200

Arg Ile Glu Glu Gly Ile Lys Glu Leu Gly Ser Gln Ile Leu Lys
        1205                1210                1215

Glu His Pro Val Glu Asn Thr Gln Leu Gln Asn Glu Lys Leu Tyr
        1220                1225                1230

Leu Tyr Tyr Leu Gln Asn Gly Arg Asp Met Tyr Val Asp Gln Glu
        1235                1240                1245

Leu Asp Ile Asn Arg Leu Ser Asp Tyr Asp Val Asp Ala Ile Val
        1250                1255                1260

Pro Gln Ser Phe Leu Lys Asp Asp Ser Ile Asp Asn Lys Val Leu
        1265                1270                1275

Thr Arg Ser Asp Lys Asn Arg Gly Lys Ser Asp Asn Val Pro Ser
        1280                1285                1290

Glu Glu Val Val Lys Lys Met Lys Asn Tyr Trp Arg Gln Leu Leu
        1295                1300                1305
```

```
Asn Ala Lys Leu Ile Thr Gln Arg Lys Phe Asp Asn Leu Thr Lys
    1310                1315                1320

Ala Glu Arg Gly Gly Leu Ser Glu Leu Asp Lys Ala Gly Phe Ile
    1325                1330                1335

Lys Arg Gln Leu Val Glu Thr Arg Gln Ile Thr Lys His Val Ala
    1340                1345                1350

Gln Ile Leu Asp Ser Arg Met Asn Thr Lys Tyr Asp Glu Asn Asp
    1355                1360                1365

Lys Leu Ile Arg Glu Val Lys Val Ile Thr Leu Lys Ser Lys Leu
    1370                1375                1380

Val Ser Asp Phe Arg Lys Asp Phe Gln Phe Tyr Lys Val Arg Glu
    1385                1390                1395

Ile Asn Asn Tyr His His Ala His Asp Ala Tyr Leu Asn Ala Val
    1400                1405                1410

Val Gly Thr Ala Leu Ile Lys Lys Tyr Pro Lys Leu Glu Ser Glu
    1415                1420                1425

Phe Val Tyr Gly Asp Tyr Lys Val Tyr Asp Val Arg Lys Met Ile
    1430                1435                1440

Ala Lys Ser Glu Gln Glu Ile Gly Lys Ala Thr Ala Lys Tyr Phe
    1445                1450                1455

Phe Tyr Ser Asn Ile Met Asn Phe Phe Lys Thr Glu Ile Thr Leu
    1460                1465                1470

Ala Asn Gly Glu Ile Arg Lys Arg Pro Leu Ile Glu Thr Asn Gly
    1475                1480                1485

Glu Thr Gly Glu Ile Val Trp Asp Lys Gly Arg Asp Phe Ala Thr
    1490                1495                1500

Val Arg Lys Val Leu Ser Met Pro Gln Val Asn Ile Val Lys Lys
    1505                1510                1515

Thr Glu Val Gln Thr Gly Gly Phe Ser Lys Glu Ser Ile Leu Pro
    1520                1525                1530

Lys Arg Asn Ser Asp Lys Leu Ile Ala Arg Lys Lys Asp Trp Asp
    1535                1540                1545

Pro Lys Lys Tyr Gly Gly Phe Asp Ser Pro Thr Val Ala Tyr Ser
    1550                1555                1560

Val Leu Val Val Ala Lys Val Glu Lys Gly Lys Ser Lys Lys Leu
    1565                1570                1575

Lys Ser Val Lys Glu Leu Leu Gly Ile Thr Ile Met Glu Arg Ser
    1580                1585                1590

Ser Phe Glu Lys Asn Pro Ile Asp Phe Leu Glu Ala Lys Gly Tyr
    1595                1600                1605

Lys Glu Val Lys Lys Asp Leu Ile Ile Lys Leu Pro Lys Tyr Ser
    1610                1615                1620

Leu Phe Glu Leu Glu Asn Gly Arg Lys Arg Met Leu Ala Ser Ala
    1625                1630                1635

Gly Glu Leu Gln Lys Gly Asn Glu Leu Ala Leu Pro Ser Lys Tyr
    1640                1645                1650

Val Asn Phe Leu Tyr Leu Ala Ser His Tyr Glu Lys Leu Lys Gly
    1655                1660                1665

Ser Pro Glu Asp Asn Glu Gln Lys Gln Leu Phe Val Glu Gln His
    1670                1675                1680

Lys His Tyr Leu Asp Glu Ile Ile Glu Gln Ile Ser Glu Phe Ser
    1685                1690                1695

Lys Arg Val Ile Leu Ala Asp Ala Asn Leu Asp Lys Val Leu Ser
```

```
                    1700               1705                  1710

Ala Tyr Asn Lys His Arg Asp Lys Pro Ile Arg Glu Gln Ala Glu
    1715                1720                1725

Asn Ile Ile His Leu Phe Thr Leu Thr Asn Leu Gly Ala Pro Ala
    1730                1735                1740

Ala Phe Lys Tyr Phe Asp Thr Thr Ile Asp Arg Lys Arg Tyr Thr
    1745                1750                1755

Ser Thr Lys Glu Val Leu Asp Ala Thr Leu Ile His Gln Ser Ile
    1760                1765                1770

Thr Gly Leu Tyr Glu Thr Arg Ile Asp Leu Ser Gln Leu Gly Gly
    1775                1780                1785

Asp Ala Tyr Pro Tyr Asp Val Pro Asp Tyr Ala Ser Leu Gly Ser
    1790                1795                1800

Gly Asp Gly Ile Gly Ser Gly Ser Asn Gly Ser Ser Leu Asp Ala
    1805                1810                1815

Leu Asp Asp Phe Asp Leu Asp Met Leu Gly Ser Asp Ala Leu Asp
    1820                1825                1830

Asp Phe Asp Leu Asp Met Leu Gly Ser Asp Ala Leu Asp Asp Phe
    1835                1840                1845

Asp Leu Asp Met Leu Gly Ser Asp Ala Leu Asp Asp Phe Asp Leu
    1850                1855                1860

Asp Met Leu Gly Ser Pro Lys Lys Arg Lys Val Gly Ser Gln
    1865                1870                1875

Tyr Leu Pro Asp Thr Asp Asp Arg His Arg Ile Glu Glu Lys Arg
    1880                1885                1890

Lys Arg Thr Tyr Glu Thr Phe Lys Ser Ile Met Lys Lys Ser Pro
    1895                1900                1905

Phe Ser Gly Pro Thr Asp Pro Arg Pro Pro Arg Arg Ile Ala
    1910                1915                1920

Val Pro Ser Arg Ser Ser Ala Ser Val Pro Lys Pro Ala Pro Gln
    1925                1930                1935

Pro Tyr Pro Phe Thr Ser Ser Leu Ser Thr Ile Asn Tyr Asp Glu
    1940                1945                1950

Phe Pro Thr Met Val Phe Pro Ser Gly Gln Ile Ser Gln Ala Ser
    1955                1960                1965

Ala Leu Ala Pro Ala Pro Pro Gln Val Leu Pro Gln Ala Pro Ala
    1970                1975                1980

Pro Ala Pro Ala Pro Ala Met Val Ser Ala Leu Ala Gln Ala Pro
    1985                1990                1995

Ala Pro Val Pro Val Leu Ala Pro Gly Pro Pro Gln Ala Val Ala
    2000                2005                2010

Pro Pro Ala Pro Lys Pro Thr Gln Ala Gly Glu Gly Thr Leu Ser
    2015                2020                2025

Glu Ala Leu Leu Gln Leu Gln Phe Asp Asp Glu Asp Leu Gly Ala
    2030                2035                2040

Leu Leu Gly Asn Ser Thr Asp Pro Ala Val Phe Thr Asp Leu Ala
    2045                2050                2055

Ser Val Asp Asn Ser Glu Phe Gln Gln Leu Leu Asn Gln Gly Ile
    2060                2065                2070

Pro Val Ala Pro His Thr Thr Glu Pro Met Leu Met Glu Tyr Pro
    2075                2080                2085

Glu Ala Ile Thr Arg Leu Val Thr Gly Ala Gln Arg Pro Pro Asp
    2090                2095                2100
```

Pro Ala Pro Ala Pro Leu Gly Ala Pro Gly Leu Pro Asn Gly Leu
    2105                2110                2115

Leu Ser Gly Asp Glu Asp Phe Ser Ser Ile Ala Asp Met Asp Phe
    2120                2125                2130

Ser Ala Leu Leu Ser Gln Ile Ser Ser Gly Ser Gly Ser Gly Ser
    2135                2140                2145

Arg Asp Ser Arg Glu Gly Met Phe Leu Pro Lys Pro Glu Ala Gly
    2150                2155                2160

Ser Ala Ile Ser Asp Val Phe Glu Gly Arg Glu Val Cys Gln Pro
    2165                2170                2175

Lys Arg Ile Arg Pro Phe His Pro Pro Gly Ser Pro Trp Ala Asn
    2180                2185                2190

Arg Pro Leu Pro Ala Ser Leu Ala Pro Thr Pro Thr Gly Pro Val
    2195                2200                2205

His Glu Pro Val Gly Ser Leu Thr Pro Ala Pro Val Pro Gln Pro
    2210                2215                2220

Leu Asp Pro Ala Pro Ala Val Thr Pro Glu Ala Ser His Leu Leu
    2225                2230                2235

Glu Asp Pro Asp Glu Glu Thr Ser Gln Ala Val Lys Ala Leu Arg
    2240                2245                2250

Glu Met Ala Asp Thr Val Ile Pro Gln Lys Glu Ala Ala Ile
    2255                2260                2265

Cys Gly Gln Met Asp Leu Ser His Pro Pro Arg Gly His Leu
    2270                2275                2280

Asp Glu Leu Thr Thr Thr Leu Glu Ser Met Thr Glu Asp Leu Asn
    2285                2290                2295

Leu Asp Ser Pro Leu Thr Pro Glu Leu Asn Glu Ile Leu Asp Thr
    2300                2305                2310

Phe Leu Asn Asp Glu Cys Leu Leu His Ala Met His Ile Ser Thr
    2315                2320                2325

Gly Leu Ser Ile Phe Asp Thr Ser Leu Phe Leu Met Val Ser Lys
    2330                2335                2340

Gly Glu Glu Asp Asn Met Ala Ile Ile Lys Glu Phe Met Arg Phe
    2345                2350                2355

Lys Val His Met Glu Gly Ser Val Asn Gly His Glu Phe Glu Ile
    2360                2365                2370

Glu Gly Glu Gly Glu Gly Arg Pro Tyr Glu Gly Thr Gln Thr Ala
    2375                2380                2385

Lys Leu Lys Val Thr Lys Gly Gly Pro Leu Pro Phe Ala Trp Asp
    2390                2395                2400

Ile Leu Ser Pro Gln Phe Met Tyr Gly Ser Lys Ala Tyr Val Lys
    2405                2410                2415

His Pro Ala Asp Ile Pro Asp Tyr Leu Lys Leu Ser Phe Pro Glu
    2420                2425                2430

Gly Phe Lys Trp Glu Arg Val Met Asn Phe Glu Asp Gly Gly Val
    2435                2440                2445

Val Thr Val Thr Gln Asp Ser Ser Leu Gln Asp Gly Glu Phe Ile
    2450                2455                2460

Tyr Lys Val Lys Leu Arg Gly Thr Asn Phe Pro Ser Asp Gly Pro
    2465                2470                2475

Val Met Gln Lys Lys Thr Met Gly Trp Glu Ala Ser Ser Glu Arg
    2480                2485                2490

Met Tyr Pro Glu Asp Gly Ala Leu Lys Gly Glu Ile Lys Gln Arg
2495                2500                2505

Leu Lys Leu Lys Asp Gly Gly His Tyr Asp Ala Glu Val Lys Thr
2510                2515                2520

Thr Tyr Lys Ala Lys Lys Pro Val Gln Leu Pro Gly Ala Tyr Asn
2525                2530                2535

Val Asn Ile Lys Leu Asp Ile Thr Ser His Asn Glu Asp Tyr Thr
2540                2545                2550

Ile Val Glu Gln Tyr Glu Arg Ala Glu Gly Arg His Ser Thr Gly
2555                2560                2565

Gly Met Asp Glu Leu Tyr Lys
2570                2575

<210> SEQ ID NO 4
<211> LENGTH: 379
<212> TYPE: PRT
<213> ORGANISM: Artificial Sequence
<220> FEATURE:
<223> OTHER INFORMATION: Synthetic Construct

<400> SEQUENCE: 4

Met Lys Thr Ile Ile Ala Leu Ser Tyr Ile Phe Cys Leu Val Phe Ala
1               5                   10                  15

Asp Tyr Lys Asp Asp Asp Asp Ala Ser Ile Asp Met Glu Gly Ile Ser
                20                  25                  30

Ile Tyr Thr Ser Asp Asn Tyr Thr Glu Glu Met Gly Ser Gly Asp Tyr
            35                  40                  45

Asp Ser Met Lys Glu Pro Cys Phe Arg Glu Glu Asn Ala Asn Phe Asn
        50                  55                  60

Lys Ile Phe Leu Pro Thr Ile Tyr Ser Ile Ile Phe Leu Thr Gly Ile
65                  70                  75                  80

Val Gly Asn Gly Leu Val Ile Leu Val Met Gly Tyr Gln Lys Lys Leu
                85                  90                  95

Arg Ser Met Thr Asp Lys Tyr Arg Leu His Leu Ser Val Ala Asp Leu
            100                 105                 110

Leu Phe Val Ile Thr Leu Pro Phe Trp Ala Val Asp Ala Val Ala Asn
        115                 120                 125

Trp Tyr Phe Gly Asn Phe Leu Cys Lys Ala Val His Val Ile Tyr Thr
130                 135                 140

Val Asn Leu Tyr Ser Ser Val Leu Ile Leu Ala Phe Ile Ser Leu Asp
145                 150                 155                 160

Arg Tyr Leu Ala Ile Val His Ala Thr Asn Ser Gln Arg Pro Arg Lys
                165                 170                 175

Leu Leu Ala Glu Lys Val Val Tyr Val Gly Val Trp Ile Pro Ala Leu
            180                 185                 190

Leu Leu Thr Ile Pro Asp Phe Ile Phe Ala Asn Val Ser Glu Ala Asp
        195                 200                 205

Asp Arg Tyr Ile Cys Asp Arg Phe Tyr Pro Asn Asp Leu Trp Val Val
    210                 215                 220

Val Phe Gln Phe Gln His Ile Met Val Gly Leu Ile Leu Pro Gly Ile
225                 230                 235                 240

Val Ile Leu Ser Cys Tyr Cys Ile Ile Ile Ser Lys Leu Ser His Ser
                245                 250                 255

Lys Gly His Gln Lys Arg Lys Ala Leu Lys Thr Thr Val Ile Leu Ile
            260                 265                 270

```
Leu Ala Phe Phe Ala Cys Trp Leu Pro Tyr Tyr Ile Gly Ile Ser Ile
            275                 280                 285

Asp Ser Phe Ile Leu Leu Glu Ile Ile Lys Gln Gly Cys Glu Phe Glu
    290                 295                 300

Asn Thr Val His Lys Trp Ile Ser Ile Thr Glu Ala Leu Ala Phe Phe
305                 310                 315                 320

His Cys Cys Leu Asn Pro Ile Leu Tyr Ala Phe Leu Gly Ala Lys Phe
                325                 330                 335

Lys Thr Ser Ala Gln His Ala Leu Thr Ser Val Ser Arg Gly Ser Ser
            340                 345                 350

Leu Lys Ile Leu Ser Lys Gly Lys Arg Gly Gly His Ser Ser Val Ser
            355                 360                 365

Thr Glu Ser Glu Ser Ser Ser Phe His Ser Ser
    370                 375

<210> SEQ ID NO 5
<211> LENGTH: 27
<212> TYPE: PRT
<213> ORGANISM: Artificial Sequence
<220> FEATURE:
<223> OTHER INFORMATION: Synthetic Construct

<400> SEQUENCE: 5

Gly Arg Thr Pro Pro Ser Leu Gly Pro Gln Asp Glu Ser Cys Thr Thr
1               5                   10                  15

Ala Ser Ser Ser Leu Ala Lys Asp Thr Ser Ser
            20                  25

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Glu Asn Leu Tyr Phe Gln Leu
1               5

<210> SEQ ID NO 7
<211> LENGTH: 1368
<212> TYPE: PRT
<213> ORGANISM: Artificial Sequence
<220> FEATURE:
<223> OTHER INFORMATION: Synthetic Construct

<400> SEQUENCE: 7

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
```

```
            100                 105                 110
His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135             140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
            210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525
```

```
Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940
```

-continued

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr

```
              1340                1345                1350
Gly Leu Tyr Glu Thr Arg Ile Asp Leu Ser Gln Leu Gly Gly Asp
         1355                1360                1365

<210> SEQ ID NO 8
<211> LENGTH: 522
<212> TYPE: PRT
<213> ORGANISM: Artificial Sequence
<220> FEATURE:
<223> OTHER INFORMATION: Synthetic Construct

<400> SEQUENCE: 8

Asp Ala Leu Asp Asp Phe Asp Leu Asp Met Leu Gly Ser Asp Ala Leu
 1               5                  10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu Gly Ser Pro Lys Lys Lys Arg Lys Val Gly Ser Gln Tyr Leu
 50                  55                  60

Pro Asp Thr Asp Asp Arg His Arg Ile Glu Glu Lys Arg Lys Arg Thr
 65                  70                  75                  80

Tyr Glu Thr Phe Lys Ser Ile Met Lys Lys Ser Pro Phe Ser Gly Pro
                 85                  90                  95

Thr Asp Pro Arg Pro Pro Arg Arg Ile Ala Val Pro Ser Arg Ser
            100                 105                 110

Ser Ala Ser Val Pro Lys Pro Ala Pro Gln Pro Tyr Pro Phe Thr Ser
        115                 120                 125

Ser Leu Ser Thr Ile Asn Tyr Asp Glu Phe Pro Thr Met Val Phe Pro
130                 135                 140

Ser Gly Gln Ile Ser Gln Ala Ser Ala Leu Ala Pro Ala Pro Pro Gln
145                 150                 155                 160

Val Leu Pro Gln Ala Pro Ala Pro Ala Pro Ala Met Val Ser
                165                 170                 175

Ala Leu Ala Gln Ala Pro Ala Pro Val Pro Val Leu Ala Pro Gly Pro
            180                 185                 190

Pro Gln Ala Val Ala Pro Pro Ala Pro Lys Pro Thr Gln Ala Gly Glu
        195                 200                 205

Gly Thr Leu Ser Glu Ala Leu Leu Gln Leu Gln Phe Asp Asp Glu Asp
    210                 215                 220

Leu Gly Ala Leu Leu Gly Asn Ser Thr Asp Pro Ala Val Phe Thr Asp
225                 230                 235                 240

Leu Ala Ser Val Asp Asn Ser Glu Phe Gln Gln Leu Leu Asn Gln Gly
                245                 250                 255

Ile Pro Val Ala Pro His Thr Thr Glu Pro Met Leu Met Glu Tyr Pro
            260                 265                 270

Glu Ala Ile Thr Arg Leu Val Thr Gly Ala Gln Arg Pro Pro Asp Pro
        275                 280                 285

Ala Pro Ala Pro Leu Gly Ala Pro Gly Leu Pro Asn Gly Leu Leu Ser
    290                 295                 300

Gly Asp Glu Asp Phe Ser Ser Ile Ala Asp Met Asp Phe Ser Ala Leu
305                 310                 315                 320

Leu Ser Gln Ile Ser Ser Gly Ser Gly Ser Arg Asp Ser Arg
                325                 330                 335

Glu Gly Met Phe Leu Pro Lys Pro Glu Ala Gly Ser Ala Ile Ser Asp
```

```
                    340                 345                 350
Val Phe Glu Gly Arg Glu Val Cys Gln Pro Lys Arg Ile Arg Pro Phe
            355                 360                 365

His Pro Pro Gly Ser Pro Trp Ala Asn Arg Pro Leu Pro Ala Ser Leu
        370                 375                 380

Ala Pro Thr Pro Thr Gly Pro Val His Glu Pro Val Gly Ser Leu Thr
385                 390                 395                 400

Pro Ala Pro Val Pro Gln Pro Leu Asp Pro Ala Pro Val Thr Pro
                405                 410                 415

Glu Ala Ser His Leu Leu Glu Asp Pro Asp Glu Glu Thr Ser Gln Ala
            420                 425                 430

Val Lys Ala Leu Arg Glu Met Ala Asp Thr Val Ile Pro Gln Lys Glu
        435                 440                 445

Glu Ala Ala Ile Cys Gly Gln Met Asp Leu Ser His Pro Pro Arg
                450                 455                 460

Gly His Leu Asp Glu Leu Thr Thr Thr Leu Glu Ser Met Thr Glu Asp
465                 470                 475                 480

Leu Asn Leu Asp Ser Pro Leu Thr Pro Glu Leu Asn Glu Ile Leu Asp
                485                 490                 495

Thr Phe Leu Asn Asp Glu Cys Leu Leu His Ala Met His Ile Ser Thr
                500                 505                 510

Gly Leu Ser Ile Phe Asp Thr Ser Leu Phe
            515                 520

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Pro Lys Lys Lys Arg Lys Val
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Tyr Pro Tyr Asp Val Pro Asp Tyr
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Gly Ile Gly Ser Gly Ser Asn Gly Ser Ser
1               5                   10

<210> SEQ ID NO 12
<211> LENGTH: 2951
<212> TYPE: PRT
<213> ORGANISM: Artificial Sequence
```

<220> FEATURE:
<223> OTHER INFORMATION: Synthetic Construct

<400> SEQUENCE: 12

```
Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
            35                  40                  45

Thr Asn Ser Thr Phe Leu Gln Glu Gly Met Pro Thr Ser Ala Arg Cys
50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
                100                 105                 110

Gln Ile Gln Pro Gln Gln Leu Val Leu Arg Leu Arg Ser Gly Glu Pro
            115                 120                 125

Gln Thr Phe Thr Leu Lys Phe Lys Arg Ala Glu Asp Tyr Pro Ile Asp
130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
            195                 200                 205

Ser Glu Gln Asn Cys Thr Ser Pro Phe Ser Tyr Lys Asn Val Leu Ser
210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
            275                 280                 285

Lys Leu Gly Gly Ile Val Leu Pro Asn Asp Gly Gln Cys His Leu Glu
            290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
                340                 345                 350

Pro Lys Ser Ala Val Gly Thr Leu Ser Ala Asn Ser Ser Asn Val Ile
            355                 360                 365

Gln Leu Ile Ile Asp Ala Tyr Asn Ser Leu Ser Ser Glu Val Ile Leu
            370                 375                 380

Glu Asn Gly Lys Leu Ser Glu Gly Val Thr Ile Ser Tyr Lys Ser Tyr
385                 390                 395                 400
```

```
Cys Lys Asn Gly Val Asn Gly Thr Gly Glu Asn Gly Arg Lys Cys Ser
            405                 410                 415
Asn Ile Ser Ile Gly Asp Glu Val Gln Phe Glu Ile Ser Ile Thr Ser
            420                 425                 430
Asn Lys Cys Pro Lys Lys Asp Ser Asp Ser Phe Lys Ile Arg Pro Leu
            435                 440                 445
Gly Phe Thr Glu Glu Val Glu Val Ile Leu Gln Tyr Ile Cys Val Cys
        450                 455                 460
Glu Cys Gln Ser Glu Gly Ile Pro Glu Ser Pro Lys Cys His Glu Gly
465                 470                 475                 480
Asn Gly Thr Phe Glu Cys Gly Ala Cys Arg Cys Asn Glu Gly Arg Val
            485                 490                 495
Gly Arg His Cys Glu Cys Ser Thr Asp Glu Val Asn Ser Glu Asp Met
            500                 505                 510
Asp Ala Tyr Cys Arg Lys Glu Asn Ser Ser Glu Ile Cys Ser Asn Asn
            515                 520                 525
Gly Glu Cys Val Cys Gly Gln Cys Val Cys Arg Lys Arg Asp Asn Thr
            530                 535                 540
Asn Glu Ile Tyr Ser Gly Lys Phe Cys Glu Cys Asp Asn Phe Asn Cys
545                 550                 555                 560
Asp Arg Ser Asn Gly Leu Ile Cys Gly Gly Asn Gly Val Cys Lys Cys
                    565                 570                 575
Arg Val Cys Glu Cys Asn Pro Asn Tyr Thr Gly Ser Ala Cys Asp Cys
            580                 585                 590
Ser Leu Asp Thr Ser Thr Cys Glu Ala Ser Asn Gly Gln Ile Cys Asn
            595                 600                 605
Gly Arg Gly Ile Cys Glu Cys Gly Val Cys Lys Cys Thr Asp Pro Lys
        610                 615                 620
Phe Gln Gly Gln Thr Cys Glu Met Cys Gln Thr Cys Leu Gly Val Cys
625                 630                 635                 640
Ala Glu His Lys Glu Cys Val Gln Cys Arg Ala Phe Asn Lys Gly Glu
            645                 650                 655
Lys Lys Asp Thr Cys Thr Gln Glu Cys Ser Tyr Phe Asn Ile Thr Lys
            660                 665                 670
Val Glu Ser Arg Asp Lys Leu Pro Gln Pro Val Gln Pro Asp Pro Val
            675                 680                 685
Ser His Cys Lys Glu Lys Asp Val Asp Asp Cys Trp Phe Tyr Phe Thr
        690                 695                 700
Tyr Ser Val Asn Gly Asn Asn Glu Val Met Val His Val Val Glu Asn
705                 710                 715                 720
Pro Glu Cys Pro Thr Gly Pro Asp Ile Ile Pro Ile Val Ala Gly Val
                    725                 730                 735
Val Ala Gly Ile Val Leu Ile Gly Leu Ala Leu Leu Leu Ile Trp Lys
            740                 745                 750
Leu Leu Met Ile Ile His Asp Arg Arg Glu Phe Ala Lys Phe Glu Lys
            755                 760                 765
Glu Lys Met Asn Ala Lys Trp Asp Thr Gly Glu Asn Pro Ile Tyr Lys
            770                 775                 780
Ser Ala Val Thr Thr Val Val Asn Pro Lys Tyr Glu Gly Lys Glu Asn
785                 790                 795                 800
Leu Tyr Phe Gln Leu Ala Ser Met Asp Lys Lys Tyr Ser Ile Gly Leu
                    805                 810                 815
```

```
Ala Ile Gly Thr Asn Ser Val Gly Trp Ala Val Ile Thr Asp Glu Tyr
820                     825                     830

Lys Val Pro Ser Lys Lys Phe Lys Val Leu Gly Asn Thr Asp Arg His
        835                     840                     845

Ser Ile Lys Lys Asn Leu Ile Gly Ala Leu Leu Phe Asp Ser Gly Glu
        850                     855                     860

Thr Ala Glu Ala Thr Arg Leu Lys Arg Thr Ala Arg Arg Tyr Thr
865                     870                     875                     880

Arg Arg Lys Asn Arg Ile Cys Tyr Leu Gln Glu Ile Phe Ser Asn Glu
                885                     890                     895

Met Ala Lys Val Asp Asp Ser Phe Phe His Arg Leu Glu Glu Ser Phe
        900                     905                     910

Leu Val Glu Glu Asp Lys Lys His Glu Arg His Pro Ile Phe Gly Asn
        915                     920                     925

Ile Val Asp Glu Val Ala Tyr His Glu Lys Tyr Pro Thr Ile Tyr His
        930                     935                     940

Leu Arg Lys Lys Leu Val Asp Ser Thr Asp Lys Ala Asp Leu Arg Leu
945                     950                     955                     960

Ile Tyr Leu Ala Leu Ala His Met Ile Lys Phe Arg Gly His Phe Leu
                965                     970                     975

Ile Glu Gly Asp Leu Asn Pro Asp Asn Ser Asp Val Asp Lys Leu Phe
        980                     985                     990

Ile Gln Leu Val Gln Thr Tyr Asn Gln Leu Phe Glu Glu Asn Pro Ile
        995                     1000                    1005

Asn Ala Ser Gly Val Asp Ala Lys Ala Ile Leu Ser Ala Arg Leu
        1010                    1015                    1020

Ser Lys Ser Arg Arg Leu Glu Asn Leu Ile Ala Gln Leu Pro Gly
        1025                    1030                    1035

Glu Lys Lys Asn Gly Leu Phe Gly Asn Leu Ile Ala Leu Ser Leu
        1040                    1045                    1050

Gly Leu Thr Pro Asn Phe Lys Ser Asn Phe Asp Leu Ala Glu Asp
        1055                    1060                    1065

Ala Lys Leu Gln Leu Ser Lys Asp Thr Tyr Asp Asp Asp Leu Asp
        1070                    1075                    1080

Asn Leu Leu Ala Gln Ile Gly Asp Gln Tyr Ala Asp Leu Phe Leu
        1085                    1090                    1095

Ala Ala Lys Asn Leu Ser Asp Ala Ile Leu Leu Ser Asp Ile Leu
        1100                    1105                    1110

Arg Val Asn Thr Glu Ile Thr Lys Ala Pro Leu Ser Ala Ser Met
        1115                    1120                    1125

Ile Lys Arg Tyr Asp Glu His His Gln Asp Leu Thr Leu Leu Lys
        1130                    1135                    1140

Ala Leu Val Arg Gln Gln Leu Pro Glu Lys Tyr Lys Glu Ile Phe
        1145                    1150                    1155

Phe Asp Gln Ser Lys Asn Gly Tyr Ala Gly Tyr Ile Asp Gly Gly
        1160                    1165                    1170

Ala Ser Gln Glu Glu Phe Tyr Lys Phe Ile Lys Pro Ile Leu Glu
        1175                    1180                    1185

Lys Met Asp Gly Thr Glu Glu Leu Leu Val Lys Leu Asn Arg Glu
        1190                    1195                    1200

Asp Leu Leu Arg Lys Gln Arg Thr Phe Asp Asn Gly Ser Ile Pro
        1205                    1210                    1215

His Gln Ile His Leu Gly Glu Leu His Ala Ile Leu Arg Arg Gln
```

```
                      1220                1225                1230

Glu  Asp  Phe  Tyr  Pro  Phe  Leu  Lys  Asp  Asn  Arg  Glu  Lys  Ile  Glu
     1235                1240                1245

Lys  Ile  Leu  Thr  Phe  Arg  Ile  Pro  Tyr  Val  Gly  Pro  Leu  Ala
     1250                1255                1260

Arg  Gly  Asn  Ser  Arg  Phe  Ala  Trp  Met  Thr  Arg  Lys  Ser  Glu  Glu
     1265                1270                1275

Thr  Ile  Thr  Pro  Trp  Asn  Phe  Glu  Glu  Val  Val  Asp  Lys  Gly  Ala
     1280                1285                1290

Ser  Ala  Gln  Ser  Phe  Ile  Glu  Arg  Met  Thr  Asn  Phe  Asp  Lys  Asn
     1295                1300                1305

Leu  Pro  Asn  Glu  Lys  Val  Leu  Pro  Lys  His  Ser  Leu  Leu  Tyr  Glu
     1310                1315                1320

Tyr  Phe  Thr  Val  Tyr  Asn  Glu  Leu  Thr  Lys  Val  Lys  Tyr  Val  Thr
     1325                1330                1335

Glu  Gly  Met  Arg  Lys  Pro  Ala  Phe  Leu  Ser  Gly  Glu  Gln  Lys  Lys
     1340                1345                1350

Ala  Ile  Val  Asp  Leu  Leu  Phe  Lys  Thr  Asn  Arg  Lys  Val  Thr  Val
     1355                1360                1365

Lys  Gln  Leu  Lys  Glu  Asp  Tyr  Phe  Lys  Lys  Ile  Glu  Cys  Phe  Asp
     1370                1375                1380

Ser  Val  Glu  Ile  Ser  Gly  Val  Glu  Asp  Arg  Phe  Asn  Ala  Ser  Leu
     1385                1390                1395

Gly  Thr  Tyr  His  Asp  Leu  Leu  Lys  Ile  Ile  Lys  Asp  Lys  Asp  Phe
     1400                1405                1410

Leu  Asp  Asn  Glu  Glu  Asn  Glu  Asp  Ile  Leu  Glu  Asp  Ile  Val  Leu
     1415                1420                1425

Thr  Leu  Thr  Leu  Phe  Glu  Asp  Arg  Glu  Met  Ile  Glu  Glu  Arg  Leu
     1430                1435                1440

Lys  Thr  Tyr  Ala  His  Leu  Phe  Asp  Asp  Lys  Val  Met  Lys  Gln  Leu
     1445                1450                1455

Lys  Arg  Arg  Arg  Tyr  Thr  Gly  Trp  Gly  Arg  Leu  Ser  Arg  Lys  Leu
     1460                1465                1470

Ile  Asn  Gly  Ile  Arg  Asp  Lys  Gln  Ser  Gly  Lys  Thr  Ile  Leu  Asp
     1475                1480                1485

Phe  Leu  Lys  Ser  Asp  Gly  Phe  Ala  Asn  Arg  Asn  Phe  Met  Gln  Leu
     1490                1495                1500

Ile  His  Asp  Asp  Ser  Leu  Thr  Phe  Lys  Glu  Asp  Ile  Gln  Lys  Ala
     1505                1510                1515

Gln  Val  Ser  Gly  Gln  Gly  Asp  Ser  Leu  His  Glu  His  Ile  Ala  Asn
     1520                1525                1530

Leu  Ala  Gly  Ser  Pro  Ala  Ile  Lys  Lys  Gly  Ile  Leu  Gln  Thr  Val
     1535                1540                1545

Lys  Val  Val  Asp  Glu  Leu  Val  Lys  Val  Met  Gly  Arg  His  Lys  Pro
     1550                1555                1560

Glu  Asn  Ile  Val  Ile  Glu  Met  Ala  Arg  Glu  Asn  Gln  Thr  Thr  Gln
     1565                1570                1575

Lys  Gly  Gln  Lys  Asn  Ser  Arg  Glu  Arg  Met  Lys  Arg  Ile  Glu  Glu
     1580                1585                1590

Gly  Ile  Lys  Glu  Leu  Gly  Ser  Gln  Ile  Leu  Lys  Glu  His  Pro  Val
     1595                1600                1605

Glu  Asn  Thr  Gln  Leu  Gln  Asn  Glu  Lys  Leu  Tyr  Leu  Tyr  Tyr  Leu
     1610                1615                1620
```

-continued

```
Gln Asn Gly Arg Asp Met Tyr Val Asp Gln Glu Leu Asp Ile Asn
    1625                1630                1635

Arg Leu Ser Asp Tyr Asp Val Asp Ala Ile Val Pro Gln Ser Phe
    1640                1645                1650

Leu Lys Asp Asp Ser Ile Asp Asn Lys Val Leu Thr Arg Ser Asp
    1655                1660                1665

Lys Asn Arg Gly Lys Ser Asp Asn Val Pro Ser Glu Glu Val Val
    1670                1675                1680

Lys Lys Met Lys Asn Tyr Trp Arg Gln Leu Leu Asn Ala Lys Leu
    1685                1690                1695

Ile Thr Gln Arg Lys Phe Asp Asn Leu Thr Lys Ala Glu Arg Gly
    1700                1705                1710

Gly Leu Ser Glu Leu Asp Lys Ala Gly Phe Ile Lys Arg Gln Leu
    1715                1720                1725

Val Glu Thr Arg Gln Ile Thr Lys His Val Ala Gln Ile Leu Asp
    1730                1735                1740

Ser Arg Met Asn Thr Lys Tyr Asp Glu Asn Asp Lys Leu Ile Arg
    1745                1750                1755

Glu Val Lys Val Ile Thr Leu Lys Ser Lys Leu Val Ser Asp Phe
    1760                1765                1770

Arg Lys Asp Phe Gln Phe Tyr Lys Val Arg Glu Ile Asn Asn Tyr
    1775                1780                1785

His His Ala His Asp Ala Tyr Leu Asn Ala Val Val Gly Thr Ala
    1790                1795                1800

Leu Ile Lys Lys Tyr Pro Lys Leu Glu Ser Glu Phe Val Tyr Gly
    1805                1810                1815

Asp Tyr Lys Val Tyr Asp Val Arg Lys Met Ile Ala Lys Ser Glu
    1820                1825                1830

Gln Glu Ile Gly Lys Ala Thr Ala Lys Tyr Phe Phe Tyr Ser Asn
    1835                1840                1845

Ile Met Asn Phe Phe Lys Thr Glu Ile Thr Leu Ala Asn Gly Glu
    1850                1855                1860

Ile Arg Lys Arg Pro Leu Ile Glu Thr Asn Gly Glu Thr Gly Glu
    1865                1870                1875

Ile Val Trp Asp Lys Gly Arg Asp Phe Ala Thr Val Arg Lys Val
    1880                1885                1890

Leu Ser Met Pro Gln Val Asn Ile Val Lys Lys Thr Glu Val Gln
    1895                1900                1905

Thr Gly Gly Phe Ser Lys Glu Ser Ile Leu Pro Lys Arg Asn Ser
    1910                1915                1920

Asp Lys Leu Ile Ala Arg Lys Lys Asp Trp Asp Pro Lys Lys Tyr
    1925                1930                1935

Gly Gly Phe Asp Ser Pro Thr Val Ala Tyr Ser Val Leu Val Val
    1940                1945                1950

Ala Lys Val Glu Lys Gly Lys Ser Lys Lys Leu Lys Ser Val Lys
    1955                1960                1965

Glu Leu Leu Gly Ile Thr Ile Met Glu Arg Ser Ser Phe Glu Lys
    1970                1975                1980

Asn Pro Ile Asp Phe Leu Glu Ala Lys Gly Tyr Lys Glu Val Lys
    1985                1990                1995

Lys Asp Leu Ile Ile Lys Leu Pro Lys Tyr Ser Leu Phe Glu Leu
    2000                2005                2010
```

```
Glu Asn Gly Arg Lys Arg Met Leu Ala Ser Ala Gly Glu Leu Gln
2015                     2020                2025

Lys Gly Asn Glu Leu Ala Leu Pro Ser Lys Tyr Val Asn Phe Leu
2030                     2035                2040

Tyr Leu Ala Ser His Tyr Glu Lys Leu Lys Gly Ser Pro Glu Asp
2045                     2050                2055

Asn Glu Gln Lys Gln Leu Phe Val Glu Gln His Lys His Tyr Leu
2060                     2065                2070

Asp Glu Ile Ile Glu Gln Ile Ser Glu Phe Ser Lys Arg Val Ile
2075                     2080                2085

Leu Ala Asp Ala Asn Leu Asp Lys Val Leu Ser Ala Tyr Asn Lys
2090                     2095                2100

His Arg Asp Lys Pro Ile Arg Glu Gln Ala Glu Asn Ile Ile His
2105                     2110                2115

Leu Phe Thr Leu Thr Asn Leu Gly Ala Pro Ala Ala Phe Lys Tyr
2120                     2125                2130

Phe Asp Thr Thr Ile Asp Arg Lys Arg Tyr Thr Ser Thr Lys Glu
2135                     2140                2145

Val Leu Asp Ala Thr Leu Ile His Gln Ser Ile Thr Gly Leu Tyr
2150                     2155                2160

Glu Thr Arg Ile Asp Leu Ser Gln Leu Gly Gly Asp Ala Tyr Pro
2165                     2170                2175

Tyr Asp Val Pro Asp Tyr Ala Ser Leu Gly Ser Gly Asp Ala Leu
2180                     2185                2190

Asp Asp Phe Asp Leu Asp Met Leu Gly Ser Asp Ala Leu Asp Asp
2195                     2200                2205

Phe Asp Leu Asp Met Leu Gly Ser Asp Ala Leu Asp Asp Phe Asp
2210                     2215                2220

Leu Asp Met Leu Gly Ser Asp Ala Leu Asp Asp Phe Asp Leu Asp
2225                     2230                2235

Met Leu Gly Ser Pro Lys Lys Arg Lys Val Gly Ser Gln Tyr
2240                     2245                2250

Leu Pro Asp Thr Asp Asp Arg His Arg Ile Glu Glu Lys Arg Lys
2255                     2260                2265

Arg Thr Tyr Glu Thr Phe Lys Ser Ile Met Lys Lys Ser Pro Phe
2270                     2275                2280

Ser Gly Pro Thr Asp Pro Arg Pro Pro Pro Arg Arg Ile Ala Val
2285                     2290                2295

Pro Ser Arg Ser Ser Ala Ser Val Pro Lys Pro Ala Pro Gln Pro
2300                     2305                2310

Tyr Pro Phe Thr Ser Ser Leu Ser Thr Ile Asn Tyr Asp Glu Phe
2315                     2320                2325

Pro Thr Met Val Phe Pro Ser Gly Gln Ile Ser Gln Ala Ser Ala
2330                     2335                2340

Leu Ala Pro Ala Pro Pro Gln Val Leu Pro Gln Ala Pro Ala Pro
2345                     2350                2355

Ala Pro Ala Pro Ala Met Val Ser Ala Leu Ala Gln Ala Pro Ala
2360                     2365                2370

Pro Val Pro Val Leu Ala Pro Gly Pro Pro Gln Ala Val Ala Pro
2375                     2380                2385

Pro Ala Pro Lys Pro Thr Gln Ala Gly Glu Gly Thr Leu Ser Glu
2390                     2395                2400

Ala Leu Leu Gln Leu Gln Phe Asp Asp Glu Asp Leu Gly Ala Leu
```

```
                        2405                      2410                      2415
Leu Gly Asn Ser Thr Asp Pro Ala Val Phe Thr Asp Leu Ala Ser
            2420                      2425                      2430

Val Asp Asn Ser Glu Phe Gln Gln Leu Leu Asn Gln Gly Ile Pro
            2435                      2440                      2445

Val Ala Pro His Thr Thr Glu Pro Met Leu Met Glu Tyr Pro Glu
            2450                      2455                      2460

Ala Ile Thr Arg Leu Val Thr Gly Ala Gln Arg Pro Pro Asp Pro
            2465                      2470                      2475

Ala Pro Ala Pro Leu Gly Ala Pro Gly Leu Pro Asn Gly Leu Leu
            2480                      2485                      2490

Ser Gly Asp Glu Asp Phe Ser Ser Ile Ala Asp Met Asp Phe Ser
            2495                      2500                      2505

Ala Leu Leu Ser Gln Ile Ser Ser Gly Ser Gly Ser Gly Ser Arg
            2510                      2515                      2520

Asp Ser Arg Glu Gly Met Phe Leu Pro Lys Pro Glu Ala Gly Ser
            2525                      2530                      2535

Ala Ile Ser Asp Val Phe Glu Gly Arg Glu Val Cys Gln Pro Lys
            2540                      2545                      2550

Arg Ile Arg Pro Phe His Pro Pro Gly Ser Pro Trp Ala Asn Arg
            2555                      2560                      2565

Pro Leu Pro Ala Ser Leu Ala Pro Thr Pro Thr Gly Pro Val His
            2570                      2575                      2580

Glu Pro Val Gly Ser Leu Thr Pro Ala Pro Val Pro Gln Pro Leu
            2585                      2590                      2595

Asp Pro Ala Pro Ala Val Thr Pro Glu Ala Ser His Leu Leu Glu
            2600                      2605                      2610

Asp Pro Asp Glu Glu Thr Ser Gln Ala Val Lys Ala Leu Arg Glu
            2615                      2620                      2625

Met Ala Asp Thr Val Ile Pro Gln Lys Glu Glu Ala Ala Ile Cys
            2630                      2635                      2640

Gly Gln Met Asp Leu Ser His Pro Pro Arg Gly His Leu Asp
            2645                      2650                      2655

Glu Leu Thr Thr Thr Leu Glu Ser Met Thr Glu Asp Leu Asn Leu
            2660                      2665                      2670

Asp Ser Pro Leu Thr Pro Glu Leu Asn Glu Ile Leu Asp Thr Phe
            2675                      2680                      2685

Leu Asn Asp Glu Cys Leu Leu His Ala Met His Ile Ser Thr Gly
            2690                      2695                      2700

Leu Ser Ile Phe Asp Thr Ser Leu Phe Leu Met Val Ser Lys Gly
            2705                      2710                      2715

Glu Glu Asp Asn Met Ala Ile Ile Lys Glu Phe Met Arg Phe Lys
            2720                      2725                      2730

Val His Met Glu Gly Ser Val Asn Gly His Glu Phe Glu Ile Glu
            2735                      2740                      2745

Gly Glu Gly Glu Gly Arg Pro Tyr Glu Gly Thr Gln Thr Ala Lys
            2750                      2755                      2760

Leu Lys Val Thr Lys Gly Gly Pro Leu Pro Phe Ala Trp Asp Ile
            2765                      2770                      2775

Leu Ser Pro Gln Phe Met Tyr Gly Ser Lys Ala Tyr Val Lys His
            2780                      2785                      2790

Pro Ala Asp Ile Pro Asp Tyr Leu Lys Leu Ser Phe Pro Glu Gly
            2795                      2800                      2805
```

```
Phe Lys Trp Glu Arg Val Met Asn Phe Glu Asp Gly Gly Val Val
    2810                2815                2820

Thr Val Thr Gln Asp Ser Ser Leu Gln Asp Gly Glu Phe Ile Tyr
2825                2830                2835

Lys Val Lys Leu Arg Gly Thr Asn Phe Pro Ser Asp Gly Pro Val
2840                2845                2850

Met Gln Lys Lys Thr Met Gly Trp Glu Ala Ser Ser Glu Arg Met
2855                2860                2865

Tyr Pro Glu Asp Gly Ala Leu Lys Gly Glu Ile Lys Gln Arg Leu
2870                2875                2880

Lys Leu Lys Asp Gly Gly His Tyr Asp Ala Glu Val Lys Thr Thr
2885                2890                2895

Tyr Lys Ala Lys Lys Pro Val Gln Leu Pro Gly Ala Tyr Asn Val
2900                2905                2910

Asn Ile Lys Leu Asp Ile Thr Ser His Asn Glu Asp Tyr Thr Ile
2915                2920                2925

Val Glu Gln Tyr Glu Arg Ala Glu Gly Arg His Ser Thr Gly Gly
2930                2935                2940

Met Asp Glu Leu Tyr Lys Leu Glu
2945                2950

<210> SEQ ID NO 13
<211> LENGTH: 798
<212> TYPE: PRT
<213> ORGANISM: Artificial Sequence
<220> FEATURE:
<223> OTHER INFORMATION: Synthetic Construct

<400> SEQUENCE: 13

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205
```

-continued

Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
                260                 265                 270

Leu Leu Val Phe Ser Thr Asp Ala Gly Phe His Phe Ala Gly Asp Gly
                275                 280                 285

Lys Leu Gly Gly Ile Val Leu Pro Asn Asp Gly Gln Cys His Leu Glu
290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Ile Gln Thr Ile Phe Ala
                325                 330                 335

Val Thr Glu Glu Phe Gln Pro Val Tyr Lys Glu Leu Lys Asn Leu Ile
                340                 345                 350

Pro Lys Ser Ala Val Gly Thr Leu Ser Ala Asn Ser Ser Asn Val Ile
                355                 360                 365

Gln Leu Ile Ile Asp Ala Tyr Asn Ser Leu Ser Ser Glu Val Ile Leu
370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
                420                 425                 430

Asn Lys Cys Pro Lys Lys Asp Ser Asp Ser Phe Lys Ile Arg Pro Leu
                435                 440                 445

Gly Phe Thr Glu Glu Val Glu Val Ile Leu Gln Tyr Ile Cys Val Cys
                450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
                500                 505                 510

Asp Ala Tyr Cys Arg Lys Glu Asn Ser Ser Glu Ile Cys Ser Asn Asn
                515                 520                 525

Gly Glu Cys Val Cys Gly Gln Cys Val Cys Arg Lys Arg Asp Asn Thr
530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
                580                 585                 590

Ser Leu Asp Thr Ser Thr Cys Glu Ala Ser Asn Gly Gln Ile Cys Asn
                595                 600                 605

Gly Arg Gly Ile Cys Glu Cys Gly Val Cys Lys Cys Thr Asp Pro Lys
610                 615                 620

```
Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
            645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
            675                 680                 685

Ser His Cys Lys Glu Lys Asp Val Asp Asp Cys Trp Phe Tyr Phe Thr
            690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
            725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
            755                 760                 765

Glu Lys Met Asn Ala Lys Trp Asp Thr Gly Glu Asn Pro Ile Tyr Lys
770                 775                 780

Ser Ala Val Thr Thr Val Val Asn Pro Lys Tyr Glu Gly Lys
785                 790                 795

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Glu Asn Leu Tyr Phe Gln Leu
1               5

<210> SEQ ID NO 15
<211> LENGTH: 1368
<212> TYPE: PRT
<213> ORGANISM: Artificial Sequence
<220> FEATURE:
<223> OTHER INFORMATION: Synthetic Construct

<400> SEQUENCE: 15

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125
```

```
His Glu Lys Tyr Pro Thr Ile Tyr His Leu Arg Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540
```

-continued

```
Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
```

```
                965                 970                 975
Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                1000                1005

Val Tyr Gly Asp Tyr Lys Val Tyr Asp Val Arg Lys Met Ile Ala
   1010                1015                1020

Lys Ser Glu Gln Glu Ile Gly Lys Ala Thr Ala Lys Tyr Phe Phe
   1025                1030                1035

Tyr Ser Asn Ile Met Asn Phe Phe Lys Thr Glu Ile Thr Leu Ala
   1040                1045                1050

Asn Gly Glu Ile Arg Lys Arg Pro Leu Ile Glu Thr Asn Gly Glu
   1055                1060                1065

Thr Gly Glu Ile Val Trp Asp Lys Gly Arg Asp Phe Ala Thr Val
   1070                1075                1080

Arg Lys Val Leu Ser Met Pro Gln Val Asn Ile Val Lys Lys Thr
   1085                1090                1095

Glu Val Gln Thr Gly Gly Phe Ser Lys Glu Ser Ile Leu Pro Lys
   1100                1105                1110

Arg Asn Ser Asp Lys Leu Ile Ala Arg Lys Lys Asp Trp Asp Pro
   1115                1120                1125

Lys Lys Tyr Gly Gly Phe Asp Ser Pro Thr Val Ala Tyr Ser Val
   1130                1135                1140

Leu Val Val Ala Lys Val Glu Lys Gly Lys Ser Lys Lys Leu Lys
   1145                1150                1155

Ser Val Lys Glu Leu Leu Gly Ile Thr Ile Met Glu Arg Ser Ser
   1160                1165                1170

Phe Glu Lys Asn Pro Ile Asp Phe Leu Glu Ala Lys Gly Tyr Lys
   1175                1180                1185

Glu Val Lys Lys Asp Leu Ile Ile Lys Leu Pro Lys Tyr Ser Leu
   1190                1195                1200

Phe Glu Leu Glu Asn Gly Arg Lys Arg Met Leu Ala Ser Ala Gly
   1205                1210                1215

Glu Leu Gln Lys Gly Asn Glu Leu Ala Leu Pro Ser Lys Tyr Val
   1220                1225                1230

Asn Phe Leu Tyr Leu Ala Ser His Tyr Glu Lys Leu Lys Gly Ser
   1235                1240                1245

Pro Glu Asp Asn Glu Gln Lys Gln Leu Phe Val Glu Gln His Lys
   1250                1255                1260

His Tyr Leu Asp Glu Ile Ile Glu Gln Ile Ser Glu Phe Ser Lys
   1265                1270                1275

Arg Val Ile Leu Ala Asp Ala Asn Leu Asp Lys Val Leu Ser Ala
   1280                1285                1290

Tyr Asn Lys His Arg Asp Lys Pro Ile Arg Glu Gln Ala Glu Asn
   1295                1300                1305

Ile Ile His Leu Phe Thr Leu Thr Asn Leu Gly Ala Pro Ala Ala
   1310                1315                1320

Phe Lys Tyr Phe Asp Thr Thr Ile Asp Arg Lys Arg Tyr Thr Ser
   1325                1330                1335

Thr Lys Glu Val Leu Asp Ala Thr Leu Ile His Gln Ser Ile Thr
   1340                1345                1350

Gly Leu Tyr Glu Thr Arg Ile Asp Leu Ser Gln Leu Gly Gly Asp
   1355                1360                1365
```

<210> SEQ ID NO 16
<211> LENGTH: 522
<212> TYPE: PRT
<213> ORGANISM: Artificial Sequence
<220> FEATURE:
<223> OTHER INFORMATION: Synthetic Construct

<400> SEQUENCE: 16

```
Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu Gly Ser Pro Lys Lys Arg Lys Val Gly Ser Gln Tyr Leu
50                  55                  60

Pro Asp Thr Asp Asp Arg His Arg Ile Glu Glu Lys Arg Lys Arg Thr
65                  70                  75                  80

Tyr Glu Thr Phe Lys Ser Ile Met Lys Lys Ser Pro Phe Ser Gly Pro
                85                  90                  95

Thr Asp Pro Arg Pro Pro Pro Arg Arg Ile Ala Val Pro Ser Arg Ser
            100                 105                 110

Ser Ala Ser Val Pro Lys Pro Ala Pro Gln Pro Tyr Pro Phe Thr Ser
            115                 120                 125

Ser Leu Ser Thr Ile Asn Tyr Asp Glu Phe Pro Thr Met Val Phe Pro
        130                 135                 140

Ser Gly Gln Ile Ser Gln Ala Ser Ala Leu Ala Pro Ala Pro Pro Gln
145                 150                 155                 160

Val Leu Pro Gln Ala Pro Ala Pro Ala Pro Ala Met Val Ser
                165                 170                 175

Ala Leu Ala Gln Ala Pro Ala Pro Val Pro Val Leu Ala Pro Gly Pro
            180                 185                 190

Pro Gln Ala Val Ala Pro Pro Ala Pro Lys Pro Thr Gln Ala Gly Glu
        195                 200                 205

Gly Thr Leu Ser Glu Ala Leu Leu Gln Leu Gln Phe Asp Asp Glu Asp
    210                 215                 220

Leu Gly Ala Leu Leu Gly Asn Ser Thr Asp Pro Ala Val Phe Thr Asp
225                 230                 235                 240

Leu Ala Ser Val Asp Asn Ser Glu Phe Gln Gln Leu Leu Asn Gln Gly
                245                 250                 255

Ile Pro Val Ala Pro His Thr Thr Glu Pro Met Leu Met Glu Tyr Pro
            260                 265                 270

Glu Ala Ile Thr Arg Leu Val Thr Gly Ala Gln Arg Pro Pro Asp Pro
        275                 280                 285

Ala Pro Ala Pro Leu Gly Ala Pro Gly Leu Pro Asn Gly Leu Leu Ser
    290                 295                 300

Gly Asp Glu Asp Phe Ser Ser Ile Ala Asp Met Asp Phe Ser Ala Leu
305                 310                 315                 320

Leu Ser Gln Ile Ser Ser Ser Gly Ser Gly Ser Arg Asp Ser Arg
                325                 330                 335

Glu Gly Met Phe Leu Pro Lys Pro Glu Ala Gly Ser Ala Ile Ser Asp
            340                 345                 350

Val Phe Glu Gly Arg Glu Val Cys Gln Pro Lys Arg Ile Arg Pro Phe
        355                 360                 365
```

```
His Pro Pro Gly Ser Pro Trp Ala Asn Arg Pro Leu Pro Ala Ser Leu
    370                 375                 380

Ala Pro Thr Pro Thr Gly Pro Val His Glu Pro Val Gly Ser Leu Thr
385                 390                 395                 400

Pro Ala Pro Val Pro Gln Pro Leu Asp Pro Ala Pro Ala Val Thr Pro
                405                 410                 415

Glu Ala Ser His Leu Leu Glu Asp Pro Asp Glu Glu Thr Ser Gln Ala
            420                 425                 430

Val Lys Ala Leu Arg Glu Met Ala Asp Thr Val Ile Pro Gln Lys Glu
        435                 440                 445

Glu Ala Ala Ile Cys Gly Gln Met Asp Leu Ser His Pro Pro Pro Arg
    450                 455                 460

Gly His Leu Asp Glu Leu Thr Thr Thr Leu Glu Ser Met Thr Glu Asp
465                 470                 475                 480

Leu Asn Leu Asp Ser Pro Leu Thr Pro Glu Leu Asn Glu Ile Leu Asp
                485                 490                 495

Thr Phe Leu Asn Asp Glu Cys Leu Leu His Ala Met His Ile Ser Thr
            500                 505                 510

Gly Leu Ser Ile Phe Asp Thr Ser Leu Phe
        515                 520

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Pro Lys Lys Lys Arg Lys Val
1               5

<210> SEQ ID NO 18
<211> LENGTH: 238
<212> TYPE: PRT
<213> ORGANISM: Artificial Sequence
<220> FEATURE:
<223> OTHER INFORMATION: Synthetic Construct

<400> SEQUENCE: 18

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
```

```
                130                 135                 140
Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
                180                 185                 190

Gln Leu Pro Gly Ala Tyr Asn Val Asn Ile Lys Leu Asp Ile Thr Ser
                195                 200                 205

His Asn Glu Asp Tyr Thr Ile Val Glu Gln Tyr Glu Arg Ala Glu Gly
                210                 215                 220

Arg His Ser Thr Gly Gly Met Asp Glu Leu Tyr Lys Leu Glu
225                 230                 235

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Tyr Pro Tyr Asp Val Pro Asp Tyr Ala
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

Gly Ser Gly Ser Gly Ser
1               5

<210> SEQ ID NO 21
<211> LENGTH: 3917
<212> TYPE: PRT
<213> ORGANISM: Artificial Sequence
<220> FEATURE:
<223> OTHER INFORMATION: Synthetic Construct

<400> SEQUENCE: 21

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
            35                  40                  45

Gly Gly Ala Phe Val Gly Pro Arg Cys Gln Asp Pro Asn Pro Cys Leu
        50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
                100                 105                 110

Asn Gly Gly Thr Cys Asp Leu Leu Thr Leu Thr Glu Tyr Lys Cys Arg
            115                 120                 125
```

```
Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540
```

```
Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Ala Gly
    850                 855                 860

Gln Thr Cys Glu Val Asp Ile Asn Glu Cys Val Leu Ser Pro Cys Arg
865                 870                 875                 880

His Gly Ala Ser Cys Gln Asn Thr His Gly Gly Tyr Arg Cys His Cys
                885                 890                 895

Gln Ala Gly Tyr Ser Gly Arg Asn Cys Glu Thr Asp Ile Asp Asp Cys
            900                 905                 910

Arg Pro Asn Pro Cys His Asn Gly Gly Ser Cys Thr Asp Gly Ile Asn
        915                 920                 925

Thr Ala Phe Cys Asp Cys Leu Pro Gly Phe Arg Gly Thr Phe Cys Glu
    930                 935                 940

Glu Asp Ile Asn Glu Cys Ala Ser Asp Pro Cys Arg Asn Gly Ala Asn
945                 950                 955                 960

Cys Thr Asp Cys Val Asp Ser Tyr Thr Cys Thr Cys Pro Ala Gly Phe
```

```
                965                 970                 975
Ser Gly Ile His Cys Glu Asn Asn Thr Pro Asp Cys Thr Glu Ser Ser
            980                 985                 990
Cys Phe Asn Gly Gly Thr Cys Val Asp Gly Ile Asn Ser Phe Thr Cys
            995                 1000                1005
Leu Cys Pro Pro Gly Phe Thr Gly Ser Tyr Cys Gln His Asp Val
    1010                1015                1020
Asn Glu Cys Asp Ser Gln Pro Cys Leu His Gly Gly Thr Cys Gln
    1025                1030                1035
Asp Gly Cys Gly Ser Tyr Arg Cys Thr Cys Pro Gln Gly Tyr Thr
    1040                1045                1050
Gly Pro Asn Cys Gln Asn Leu Val His Trp Cys Asp Ser Ser Pro
    1055                1060                1065
Cys Lys Asn Gly Gly Lys Cys Trp Gln Thr His Thr Gln Tyr Arg
    1070                1075                1080
Cys Glu Cys Pro Ser Gly Trp Thr Gly Leu Tyr Cys Asp Val Pro
    1085                1090                1095
Ser Val Ser Cys Glu Val Ala Ala Gln Arg Gln Gly Val Asp Val
    1100                1105                1110
Ala Arg Leu Cys Gln His Gly Gly Leu Cys Val Asp Ala Gly Asn
    1115                1120                1125
Thr His His Cys Arg Cys Gln Ala Gly Tyr Thr Gly Ser Tyr Cys
    1130                1135                1140
Glu Asp Leu Val Asp Glu Cys Ser Pro Ser Pro Cys Gln Asn Gly
    1145                1150                1155
Ala Thr Cys Thr Asp Tyr Leu Gly Gly Tyr Ser Cys Lys Cys Val
    1160                1165                1170
Ala Gly Tyr His Gly Val Asn Cys Ser Glu Glu Ile Asp Glu Cys
    1175                1180                1185
Leu Ser His Pro Cys Gln Asn Gly Gly Thr Cys Leu Asp Leu Pro
    1190                1195                1200
Asn Thr Tyr Lys Cys Ser Cys Pro Arg Gly Thr Gln Gly Val His
    1205                1210                1215
Cys Glu Ile Asn Val Asp Asp Cys Asn Pro Pro Val Asp Pro Val
    1220                1225                1230
Ser Arg Ser Pro Lys Cys Phe Asn Asn Gly Thr Cys Val Asp Gln
    1235                1240                1245
Val Gly Gly Tyr Ser Cys Thr Cys Pro Pro Gly Phe Val Gly Glu
    1250                1255                1260
Arg Cys Glu Gly Asp Val Asn Glu Cys Leu Ser Asn Pro Cys Asp
    1265                1270                1275
Ala Arg Gly Thr Gln Asn Cys Val Gln Arg Val Asn Asp Phe His
    1280                1285                1290
Cys Glu Cys Arg Ala Gly His Thr Gly Arg Arg Cys Glu Ser Val
    1295                1300                1305
Ile Asn Gly Cys Lys Gly Lys Pro Cys Lys Asn Gly Gly Thr Cys
    1310                1315                1320
Ala Val Ala Ser Asn Thr Ala Arg Gly Phe Ile Cys Lys Cys Pro
    1325                1330                1335
Ala Gly Phe Glu Gly Ala Thr Cys Glu Asn Asp Ala Arg Thr Cys
    1340                1345                1350
Gly Ser Leu Arg Cys Leu Asn Gly Gly Thr Cys Ile Ser Gly Pro
    1355                1360                1365
```

```
Arg Ser Pro Thr Cys Leu Cys Leu Gly Pro Phe Thr Gly Pro Glu
    1370            1375                1380

Cys Gln Phe Pro Ala Ser Ser Pro Cys Leu Gly Gly Asn Pro Cys
    1385            1390                1395

Tyr Asn Gln Gly Thr Cys Glu Pro Thr Ser Glu Ser Pro Phe Tyr
    1400            1405                1410

Arg Cys Leu Cys Pro Ala Lys Phe Asn Gly Leu Leu Cys His Ile
    1415            1420                1425

Leu Asp Tyr Ser Phe Gly Gly Gly Ala Gly Arg Asp Ile Pro Pro
    1430            1435                1440

Pro Leu Ile Glu Glu Ala Cys Glu Leu Pro Glu Cys Gln Glu Asp
    1445            1450                1455

Ala Gly Asn Lys Val Cys Ser Leu Gln Cys Asn Asn His Ala Cys
    1460            1465                1470

Gly Trp Asp Gly Gly Asp Cys Ser Leu Asn Phe Asn Asp Pro Trp
    1475            1480                1485

Lys Asn Cys Thr Gln Ser Leu Gln Cys Trp Lys Tyr Phe Ser Asp
    1490            1495                1500

Gly His Cys Asp Ser Gln Cys Asn Ser Ala Gly Cys Leu Phe Asp
    1505            1510                1515

Gly Phe Asp Cys Gln Arg Ala Glu Gly Gln Cys Asn Pro Leu Tyr
    1520            1525                1530

Asp Gln Tyr Cys Lys Asp His Phe Ser Asp Gly His Cys Asp Gln
    1535            1540                1545

Gly Cys Asn Ser Ala Glu Cys Glu Trp Asp Gly Leu Asp Cys Ala
    1550            1555                1560

Glu His Val Pro Glu Arg Leu Ala Ala Gly Thr Leu Val Val Val
    1565            1570                1575

Val Leu Met Pro Pro Glu Gln Leu Arg Asn Ser Ser Phe His Phe
    1580            1585                1590

Leu Arg Glu Leu Ser Arg Val Leu His Thr Asn Val Val Phe Lys
    1595            1600                1605

Arg Asp Ala His Gly Gln Gln Met Ile Phe Pro Tyr Tyr Gly Arg
    1610            1615                1620

Glu Glu Glu Leu Arg Lys His Pro Ile Lys Arg Ala Ala Glu Gly
    1625            1630                1635

Trp Ala Ala Pro Asp Ala Leu Leu Gly Gln Val Lys Ala Ser Leu
    1640            1645                1650

Leu Pro Gly Gly Ser Glu Gly Gly Arg Arg Arg Glu Leu Asp
    1655            1660                1665

Pro Met Asp Val Arg Gly Ser Ile Val Tyr Leu Glu Ile Asp Asn
    1670            1675                1680

Arg Gln Cys Val Gln Ala Ser Ser Gln Cys Phe Gln Ser Ala Thr
    1685            1690                1695

Asp Val Ala Ala Phe Leu Gly Ala Leu Ala Ser Leu Gly Ser Leu
    1700            1705                1710

Asn Ile Pro Tyr Lys Ile Glu Ala Val Gln Ser Glu Thr Val Glu
    1715            1720                1725

Pro Pro Pro Pro Ala Gln Leu His Phe Met Tyr Val Ala Ala Ala
    1730            1735                1740

Ala Phe Val Leu Leu Phe Phe Val Gly Cys Gly Val Leu Leu Ser
    1745            1750                1755
```

```
Arg Lys Arg Arg Arg Ala Ser Met Asp Lys Lys Tyr Ser Ile Gly
    1760            1765            1770

Leu Ala Ile Gly Thr Asn Ser Val Gly Trp Ala Val Ile Thr Asp
    1775            1780            1785

Glu Tyr Lys Val Pro Ser Lys Lys Phe Lys Val Leu Gly Asn Thr
    1790            1795            1800

Asp Arg His Ser Ile Lys Lys Asn Leu Ile Gly Ala Leu Leu Phe
    1805            1810            1815

Asp Ser Gly Glu Thr Ala Glu Ala Thr Arg Leu Lys Arg Thr Ala
    1820            1825            1830

Arg Arg Arg Tyr Thr Arg Arg Lys Asn Arg Ile Cys Tyr Leu Gln
    1835            1840            1845

Glu Ile Phe Ser Asn Glu Met Ala Lys Val Asp Asp Ser Phe Phe
    1850            1855            1860

His Arg Leu Glu Glu Ser Phe Leu Val Glu Glu Asp Lys Lys His
    1865            1870            1875

Glu Arg His Pro Ile Phe Gly Asn Ile Val Asp Glu Val Ala Tyr
    1880            1885            1890

His Glu Lys Tyr Pro Thr Ile Tyr His Leu Arg Lys Lys Leu Val
    1895            1900            1905

Asp Ser Thr Asp Lys Ala Asp Leu Arg Leu Ile Tyr Leu Ala Leu
    1910            1915            1920

Ala His Met Ile Lys Phe Arg Gly His Phe Leu Ile Glu Gly Asp
    1925            1930            1935

Leu Asn Pro Asp Asn Ser Asp Val Asp Lys Leu Phe Ile Gln Leu
    1940            1945            1950

Val Gln Thr Tyr Asn Gln Leu Phe Glu Glu Asn Pro Ile Asn Ala
    1955            1960            1965

Ser Gly Val Asp Ala Lys Ala Ile Leu Ser Ala Arg Leu Ser Lys
    1970            1975            1980

Ser Arg Arg Leu Glu Asn Leu Ile Ala Gln Leu Pro Gly Glu Lys
    1985            1990            1995

Lys Asn Gly Leu Phe Gly Asn Leu Ile Ala Leu Ser Leu Gly Leu
    2000            2005            2010

Thr Pro Asn Phe Lys Ser Asn Phe Asp Leu Ala Glu Asp Ala Lys
    2015            2020            2025

Leu Gln Leu Ser Lys Asp Thr Tyr Asp Asp Asp Leu Asp Asn Leu
    2030            2035            2040

Leu Ala Gln Ile Gly Asp Gln Tyr Ala Asp Leu Phe Leu Ala Ala
    2045            2050            2055

Lys Asn Leu Ser Asp Ala Ile Leu Leu Ser Asp Ile Leu Arg Val
    2060            2065            2070

Asn Thr Glu Ile Thr Lys Ala Pro Leu Ser Ala Ser Met Ile Lys
    2075            2080            2085

Arg Tyr Asp Glu His His Gln Asp Leu Thr Leu Leu Lys Ala Leu
    2090            2095            2100

Val Arg Gln Gln Leu Pro Glu Lys Tyr Lys Glu Ile Phe Phe Asp
    2105            2110            2115

Gln Ser Lys Asn Gly Tyr Ala Gly Tyr Ile Asp Gly Gly Ala Ser
    2120            2125            2130

Gln Glu Glu Phe Tyr Lys Phe Ile Lys Pro Ile Leu Glu Lys Met
    2135            2140            2145

Asp Gly Thr Glu Glu Leu Leu Val Lys Leu Asn Arg Glu Asp Leu
```

```
                    2150                2155                2160

Leu Arg Lys Gln Arg Thr Phe Asp Asn Gly Ser Ile Pro His Gln
    2165                2170                2175

Ile His Leu Gly Glu Leu His Ala Ile Leu Arg Arg Gln Glu Asp
    2180                2185                2190

Phe Tyr Pro Phe Leu Lys Asp Asn Arg Glu Lys Ile Glu Lys Ile
    2195                2200                2205

Leu Thr Phe Arg Ile Pro Tyr Tyr Val Gly Pro Leu Ala Arg Gly
    2210                2215                2220

Asn Ser Arg Phe Ala Trp Met Thr Arg Lys Ser Glu Glu Thr Ile
    2225                2230                2235

Thr Pro Trp Asn Phe Glu Glu Val Val Asp Lys Gly Ala Ser Ala
    2240                2245                2250

Gln Ser Phe Ile Glu Arg Met Thr Asn Phe Asp Lys Asn Leu Pro
    2255                2260                2265

Asn Glu Lys Val Leu Pro Lys His Ser Leu Leu Tyr Glu Tyr Phe
    2270                2275                2280

Thr Val Tyr Asn Glu Leu Thr Lys Val Lys Tyr Val Thr Glu Gly
    2285                2290                2295

Met Arg Lys Pro Ala Phe Leu Ser Gly Glu Gln Lys Lys Ala Ile
    2300                2305                2310

Val Asp Leu Leu Phe Lys Thr Asn Arg Lys Val Thr Val Lys Gln
    2315                2320                2325

Leu Lys Glu Asp Tyr Phe Lys Lys Ile Glu Cys Phe Asp Ser Val
    2330                2335                2340

Glu Ile Ser Gly Val Glu Asp Arg Phe Asn Ala Ser Leu Gly Thr
    2345                2350                2355

Tyr His Asp Leu Leu Lys Ile Ile Lys Asp Lys Asp Phe Leu Asp
    2360                2365                2370

Asn Glu Glu Asn Glu Asp Ile Leu Glu Asp Ile Val Leu Thr Leu
    2375                2380                2385

Thr Leu Phe Glu Asp Arg Glu Met Ile Glu Glu Arg Leu Lys Thr
    2390                2395                2400

Tyr Ala His Leu Phe Asp Asp Lys Val Met Lys Gln Leu Lys Arg
    2405                2410                2415

Arg Arg Tyr Thr Gly Trp Gly Arg Leu Ser Arg Lys Leu Ile Asn
    2420                2425                2430

Gly Ile Arg Asp Lys Gln Ser Gly Lys Thr Ile Leu Asp Phe Leu
    2435                2440                2445

Lys Ser Asp Gly Phe Ala Asn Arg Asn Phe Met Gln Leu Ile His
    2450                2455                2460

Asp Asp Ser Leu Thr Phe Lys Glu Asp Ile Gln Lys Ala Gln Val
    2465                2470                2475

Ser Gly Gln Gly Asp Ser Leu His Glu His Ile Ala Asn Leu Ala
    2480                2485                2490

Gly Ser Pro Ala Ile Lys Lys Gly Ile Leu Gln Thr Val Lys Val
    2495                2500                2505

Val Asp Glu Leu Val Lys Val Met Gly Arg His Lys Pro Glu Asn
    2510                2515                2520

Ile Val Ile Glu Met Ala Arg Glu Asn Gln Thr Thr Gln Lys Gly
    2525                2530                2535

Gln Lys Asn Ser Arg Glu Arg Met Lys Arg Ile Glu Glu Gly Ile
    2540                2545                2550
```

```
Lys Glu Leu Gly Ser Gln Ile Leu Lys Glu His Pro Val Glu Asn
2555                2560                2565

Thr Gln Leu Gln Asn Glu Lys Leu Tyr Leu Tyr Tyr Leu Gln Asn
2570                2575                2580

Gly Arg Asp Met Tyr Val Asp Gln Glu Leu Asp Ile Asn Arg Leu
2585                2590                2595

Ser Asp Tyr Asp Val Asp Ala Ile Val Pro Gln Ser Phe Leu Lys
2600                2605                2610

Asp Asp Ser Ile Asp Asn Lys Val Leu Thr Arg Ser Asp Lys Asn
2615                2620                2625

Arg Gly Lys Ser Asp Asn Val Pro Ser Glu Glu Val Val Lys Lys
2630                2635                2640

Met Lys Asn Tyr Trp Arg Gln Leu Leu Asn Ala Lys Leu Ile Thr
2645                2650                2655

Gln Arg Lys Phe Asp Asn Leu Thr Lys Ala Glu Arg Gly Gly Leu
2660                2665                2670

Ser Glu Leu Asp Lys Ala Gly Phe Ile Lys Arg Gln Leu Val Glu
2675                2680                2685

Thr Arg Gln Ile Thr Lys His Val Ala Gln Ile Leu Asp Ser Arg
2690                2695                2700

Met Asn Thr Lys Tyr Asp Glu Asn Asp Lys Leu Ile Arg Glu Val
2705                2710                2715

Lys Val Ile Thr Leu Lys Ser Lys Leu Val Ser Asp Phe Arg Lys
2720                2725                2730

Asp Phe Gln Phe Tyr Lys Val Arg Glu Ile Asn Asn Tyr His His
2735                2740                2745

Ala His Asp Ala Tyr Leu Asn Ala Val Val Gly Thr Ala Leu Ile
2750                2755                2760

Lys Lys Tyr Pro Lys Leu Glu Ser Glu Phe Val Tyr Gly Asp Tyr
2765                2770                2775

Lys Val Tyr Asp Val Arg Lys Met Ile Ala Lys Ser Glu Gln Glu
2780                2785                2790

Ile Gly Lys Ala Thr Ala Lys Tyr Phe Phe Tyr Ser Asn Ile Met
2795                2800                2805

Asn Phe Phe Lys Thr Glu Ile Thr Leu Ala Asn Gly Glu Ile Arg
2810                2815                2820

Lys Arg Pro Leu Ile Glu Thr Asn Gly Glu Thr Gly Glu Ile Val
2825                2830                2835

Trp Asp Lys Gly Arg Asp Phe Ala Thr Val Arg Lys Val Leu Ser
2840                2845                2850

Met Pro Gln Val Asn Ile Val Lys Lys Thr Glu Val Gln Thr Gly
2855                2860                2865

Gly Phe Ser Lys Glu Ser Ile Leu Pro Lys Arg Asn Ser Asp Lys
2870                2875                2880

Leu Ile Ala Arg Lys Lys Asp Trp Asp Pro Lys Lys Tyr Gly Gly
2885                2890                2895

Phe Asp Ser Pro Thr Val Ala Tyr Ser Val Leu Val Val Ala Lys
2900                2905                2910

Val Glu Lys Gly Lys Ser Lys Lys Leu Lys Ser Val Lys Glu Leu
2915                2920                2925

Leu Gly Ile Thr Ile Met Glu Arg Ser Ser Phe Glu Lys Asn Pro
2930                2935                2940
```

```
Ile Asp Phe Leu Glu Ala Lys Gly Tyr Lys Glu Val Lys Lys Asp
2945                2950                2955

Leu Ile Ile Lys Leu Pro Lys Tyr Ser Leu Phe Glu Leu Glu Asn
2960                2965                2970

Gly Arg Lys Arg Met Leu Ala Ser Ala Gly Glu Leu Gln Lys Gly
2975                2980                2985

Asn Glu Leu Ala Leu Pro Ser Lys Tyr Val Asn Phe Leu Tyr Leu
2990                2995                3000

Ala Ser His Tyr Glu Lys Leu Lys Gly Ser Pro Glu Asp Asn Glu
3005                3010                3015

Gln Lys Gln Leu Phe Val Glu Gln His Lys His Tyr Leu Asp Glu
3020                3025                3030

Ile Ile Glu Gln Ile Ser Glu Phe Ser Lys Arg Val Ile Leu Ala
3035                3040                3045

Asp Ala Asn Leu Asp Lys Val Leu Ser Ala Tyr Asn Lys His Arg
3050                3055                3060

Asp Lys Pro Ile Arg Glu Gln Ala Glu Asn Ile Ile His Leu Phe
3065                3070                3075

Thr Leu Thr Asn Leu Gly Ala Pro Ala Ala Phe Lys Tyr Phe Asp
3080                3085                3090

Thr Thr Ile Asp Arg Lys Arg Tyr Thr Ser Thr Lys Glu Val Leu
3095                3100                3105

Asp Ala Thr Leu Ile His Gln Ser Ile Thr Gly Leu Tyr Glu Thr
3110                3115                3120

Arg Ile Asp Leu Ser Gln Leu Gly Gly Asp Ala Tyr Pro Tyr Asp
3125                3130                3135

Val Pro Asp Tyr Ala Ser Leu Gly Ser Gly Asp Gly Ile Gly Ser
3140                3145                3150

Gly Ser Asn Gly Ser Ser Leu Asp Ala Leu Asp Asp Phe Asp Leu
3155                3160                3165

Asp Met Leu Gly Ser Asp Ala Leu Asp Asp Phe Asp Leu Asp Met
3170                3175                3180

Leu Gly Ser Asp Ala Leu Asp Phe Asp Leu Asp Met Leu Gly
3185                3190                3195

Ser Asp Ala Leu Asp Asp Phe Asp Leu Asp Met Leu Gly Ser Gly
3200                3205                3210

Gly Ser Gly Ser Gln Tyr Leu Pro Asp Thr Asp Asp Arg His Arg
3215                3220                3225

Ile Glu Glu Lys Arg Lys Arg Thr Tyr Glu Thr Phe Lys Ser Ile
3230                3235                3240

Met Lys Lys Ser Pro Phe Ser Gly Pro Thr Asp Pro Arg Pro Pro
3245                3250                3255

Pro Arg Arg Ile Ala Val Pro Ser Arg Ser Ser Ala Ser Val Pro
3260                3265                3270

Lys Pro Ala Pro Gln Pro Tyr Pro Phe Thr Ser Ser Leu Ser Thr
3275                3280                3285

Ile Asn Tyr Asp Glu Phe Pro Thr Met Val Phe Pro Ser Gly Gln
3290                3295                3300

Ile Ser Gln Ala Ser Ala Leu Ala Pro Ala Pro Pro Gln Val Leu
3305                3310                3315

Pro Gln Ala Pro Ala Pro Ala Pro Ala Pro Ala Met Val Ser Ala
3320                3325                3330

Leu Ala Gln Ala Pro Ala Pro Val Pro Val Leu Ala Pro Gly Pro
```

-continued

```
            3335                3340                3345

Pro Gln Ala Val Ala Pro Pro Ala Pro Lys Pro Thr Gln Ala Gly
        3350                3355                3360

Glu Gly Thr Leu Ser Glu Ala Leu Leu Gln Leu Gln Phe Asp Asp
        3365                3370                3375

Glu Asp Leu Gly Ala Leu Leu Gly Asn Ser Thr Asp Pro Ala Val
        3380                3385                3390

Phe Thr Asp Leu Ala Ser Val Asp Asn Ser Glu Phe Gln Gln Leu
        3395                3400                3405

Leu Asn Gln Gly Ile Pro Val Ala Pro His Thr Thr Glu Pro Met
        3410                3415                3420

Leu Met Glu Tyr Pro Glu Ala Ile Thr Arg Leu Val Thr Gly Ala
        3425                3430                3435

Gln Arg Pro Pro Asp Pro Ala Pro Ala Pro Leu Gly Ala Pro Gly
        3440                3445                3450

Leu Pro Asn Gly Leu Leu Ser Gly Asp Glu Asp Phe Ser Ser Ile
        3455                3460                3465

Ala Asp Met Asp Phe Ser Ala Leu Leu Ser Gln Ile Ser Ser Gly
        3470                3475                3480

Ser Gly Ser Gly Ser Arg Asp Ser Arg Glu Gly Met Phe Leu Pro
        3485                3490                3495

Lys Pro Glu Ala Gly Ser Ala Ile Ser Asp Val Phe Glu Gly Arg
        3500                3505                3510

Glu Val Cys Gln Pro Lys Arg Ile Arg Pro Phe His Pro Pro Gly
        3515                3520                3525

Ser Pro Trp Ala Asn Arg Pro Leu Pro Ala Ser Leu Ala Pro Thr
        3530                3535                3540

Pro Thr Gly Pro Val His Glu Pro Val Gly Ser Leu Thr Pro Ala
        3545                3550                3555

Pro Val Pro Gln Pro Leu Asp Pro Ala Pro Ala Val Thr Pro Glu
        3560                3565                3570

Ala Ser His Leu Leu Glu Asp Pro Asp Glu Glu Thr Ser Gln Ala
        3575                3580                3585

Val Lys Ala Leu Arg Glu Met Ala Asp Thr Val Ile Pro Gln Lys
        3590                3595                3600

Glu Glu Ala Ala Ile Cys Gly Gln Met Asp Leu Ser His Pro Pro
        3605                3610                3615

Pro Arg Gly His Leu Asp Glu Leu Thr Thr Thr Leu Glu Ser Met
        3620                3625                3630

Thr Glu Asp Leu Asn Leu Asp Ser Pro Leu Thr Pro Glu Leu Asn
        3635                3640                3645

Glu Ile Leu Asp Thr Phe Leu Asn Asp Glu Cys Leu Leu His Ala
        3650                3655                3660

Met His Ile Ser Thr Gly Leu Ser Ile Phe Asp Thr Ser Leu Phe
        3665                3670                3675

Leu Met Val Ser Lys Gly Glu Glu Asp Asn Met Ala Ile Ile Lys
        3680                3685                3690

Glu Phe Met Arg Phe Lys Val His Met Glu Gly Ser Val Asn Gly
        3695                3700                3705

His Glu Phe Glu Ile Glu Gly Glu Gly Glu Gly Arg Pro Tyr Glu
        3710                3715                3720

Gly Thr Gln Thr Ala Lys Leu Lys Val Thr Lys Gly Gly Pro Leu
        3725                3730                3735
```

```
Pro Phe Ala Trp Asp Ile Leu Ser Pro Gln Phe Met Tyr Gly Ser
    3740            3745                3750

Lys Ala Tyr Val Lys His Pro Ala Asp Ile Pro Asp Tyr Leu Lys
    3755            3760                3765

Leu Ser Phe Pro Glu Gly Phe Lys Trp Glu Arg Val Met Asn Phe
    3770            3775                3780

Glu Asp Gly Gly Val Val Thr Val Thr Gln Asp Ser Ser Leu Gln
    3785            3790                3795

Asp Gly Glu Phe Ile Tyr Lys Val Lys Leu Arg Gly Thr Asn Phe
    3800            3805                3810

Pro Ser Asp Gly Pro Val Met Gln Lys Lys Thr Met Gly Trp Glu
    3815            3820                3825

Ala Ser Ser Glu Arg Met Tyr Pro Glu Asp Gly Ala Leu Lys Gly
    3830            3835                3840

Glu Ile Lys Gln Arg Leu Lys Leu Lys Asp Gly Gly His Tyr Asp
    3845            3850                3855

Ala Glu Val Lys Thr Thr Tyr Lys Ala Lys Lys Pro Val Gln Leu
    3860            3865                3870

Pro Gly Ala Tyr Asn Val Asn Ile Lys Leu Asp Ile Thr Ser His
    3875            3880                3885

Asn Glu Asp Tyr Thr Ile Val Glu Gln Tyr Glu Arg Ala Glu Gly
    3890            3895                3900

Arg His Ser Thr Gly Gly Met Asp Glu Leu Tyr Lys Leu Glu
    3905            3910                3915

<210> SEQ ID NO 22
<211> LENGTH: 1734
<212> TYPE: PRT
<213> ORGANISM: Artificial Sequence
<220> FEATURE:
<223> OTHER INFORMATION: Synthetic Construct

<400> SEQUENCE: 22

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
            35                  40                  45

Gly Gly Ala Phe Val Gly Pro Arg Cys Gln Asp Pro Asn Pro Cys Leu
        50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175
```

```
Gln Asp Val Asn Glu Cys Gly Gln Lys Pro Gly Leu Cys Arg His Gly
                180                 185                 190
Gly Thr Cys His Asn Glu Val Gly Ser Tyr Arg Cys Val Cys Arg Ala
            195                 200                 205
Thr His Thr Gly Pro Asn Cys Glu Arg Pro Tyr Val Pro Cys Ser Pro
        210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
                245                 250                 255
Asn Ile Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
    290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
            340                 345                 350
Arg Val Ala Ser Phe Tyr Cys Glu Cys Pro His Gly Arg Thr Gly Leu
        355                 360                 365
Leu Cys His Leu Asn Asp Ala Cys Ile Ser Asn Pro Cys Asn Glu Gly
    370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ser Leu Gly Ala Asn Pro Cys Glu His Ala Gly Lys Cys Ile Asn Thr
            420                 425                 430
Leu Gly Ser Phe Glu Cys Gln Cys Leu Gln Gly Tyr Thr Gly Pro Arg
        435                 440                 445
Cys Glu Ile Asp Val Asn Glu Cys Val Ser Asn Pro Cys Gln Asn Asp
    450                 455                 460
Ala Thr Cys Leu Asp Gln Ile Gly Glu Phe Gln Cys Ile Cys Met Pro
465                 470                 475                 480
Gly Tyr Glu Gly Val His Cys Glu Val Asn Thr Asp Glu Cys Ala Ser
                485                 490                 495
Ser Pro Cys Leu His Asn Gly Arg Cys Leu Asp Lys Ile Asn Glu Phe
            500                 505                 510
Gln Cys Glu Cys Pro Thr Gly Phe Thr Gly His Leu Cys Gln Tyr Asp
        515                 520                 525
Val Asp Glu Cys Ala Ser Thr Pro Cys Lys Asn Gly Ala Lys Cys Leu
    530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
                565                 570                 575
Tyr Gly Ser Cys Lys Asp Gly Val Ala Thr Phe Thr Cys Leu Cys Arg
            580                 585                 590
```

-continued

```
Pro Gly Tyr Thr Gly His His Cys Glu Thr Asn Ile Asn Glu Cys Ser
            595                 600                 605
Ser Gln Pro Cys Arg His Gly Thr Cys Gln Asp Arg Asp Asn Ala
610                 615                 620
Tyr Leu Cys Phe Cys Leu Lys Gly Thr Gly Pro Asn Cys Glu Ile
625                 630                 635                 640
Asn Leu Asp Asp Cys Ala Ser Ser Pro Cys Asp Ser Gly Thr Cys Leu
                645                 650                 655
Asp Lys Ile Asp Gly Tyr Glu Cys Ala Cys Glu Pro Gly Tyr Thr Gly
            660                 665                 670
Ser Met Cys Asn Ile Asn Ile Asp Glu Cys Ala Gly Asn Pro Cys His
            675                 680                 685
Asn Gly Gly Thr Cys Glu Asp Gly Ile Asn Gly Phe Thr Cys Arg Cys
            690                 695                 700
Pro Glu Gly Tyr His Asp Pro Thr Cys Leu Ser Glu Val Asn Glu Cys
705                 710                 715                 720
Asn Ser Asn Pro Cys Val His Gly Ala Cys Arg Asp Ser Leu Asn Gly
                725                 730                 735
Tyr Lys Cys Asp Cys Asp Pro Gly Trp Ser Gly Thr Asn Cys Asp Ile
            740                 745                 750
Asn Asn Asn Glu Cys Glu Ser Asn Pro Cys Val Asn Gly Gly Thr Cys
            755                 760                 765
Lys Asp Met Thr Ser Gly Tyr Val Cys Thr Cys Arg Glu Gly Phe Ser
770                 775                 780
Gly Pro Asn Cys Gln Thr Asn Ile Asn Glu Cys Ala Ser Asn Pro Cys
785                 790                 795                 800
Leu Asn Gln Gly Thr Cys Ile Asp Asp Val Ala Gly Tyr Lys Cys Asn
                805                 810                 815
Cys Leu Leu Pro Tyr Thr Gly Ala Thr Cys Glu Val Val Leu Ala Pro
            820                 825                 830
Cys Ala Pro Ser Pro Cys Arg Asn Gly Gly Glu Cys Arg Gln Ser Glu
            835                 840                 845
Asp Tyr Glu Ser Phe Ser Cys Val Cys Pro Thr Gly Trp Gln Ala Gly
850                 855                 860
Gln Thr Cys Glu Val Asp Ile Asn Glu Cys Val Leu Ser Pro Cys Arg
865                 870                 875                 880
His Gly Ala Ser Cys Gln Asn Thr His Gly Gly Tyr Arg Cys His Cys
                885                 890                 895
Gln Ala Gly Tyr Ser Gly Arg Asn Cys Glu Thr Asp Ile Asp Asp Cys
            900                 905                 910
Arg Pro Asn Pro Cys His Asn Gly Gly Ser Cys Thr Asp Gly Ile Asn
            915                 920                 925
Thr Ala Phe Cys Asp Cys Leu Pro Gly Phe Arg Gly Thr Phe Cys Glu
930                 935                 940
Glu Asp Ile Asn Glu Cys Ala Ser Asp Pro Cys Arg Asn Gly Ala Asn
945                 950                 955                 960
Cys Thr Asp Cys Val Asp Ser Tyr Thr Cys Thr Cys Pro Ala Gly Phe
                965                 970                 975
Ser Gly Ile His Cys Glu Asn Asn Thr Pro Asp Cys Thr Glu Ser Ser
            980                 985                 990
Cys Phe Asn Gly Gly Thr Cys Val  Asp Gly Ile Asn Ser  Phe Thr Cys
            995                 1000                1005
Leu Cys  Pro Pro Gly Phe Thr  Gly Ser Tyr Cys Gln  His Asp Val
```

-continued

```
        1010                1015                1020
Asn Glu Cys Asp Ser Gln Pro Cys Leu His Gly Gly Thr Cys Gln
        1025                1030                1035
Asp Gly Cys Gly Ser Tyr Arg Cys Thr Cys Pro Gln Gly Tyr Thr
        1040                1045                1050
Gly Pro Asn Cys Gln Asn Leu Val His Trp Cys Asp Ser Ser Pro
        1055                1060                1065
Cys Lys Asn Gly Gly Lys Cys Trp Gln Thr His Thr Gln Tyr Arg
        1070                1075                1080
Cys Glu Cys Pro Ser Gly Trp Thr Gly Leu Tyr Cys Asp Val Pro
        1085                1090                1095
Ser Val Ser Cys Glu Val Ala Ala Gln Arg Gln Gly Val Asp Val
        1100                1105                1110
Ala Arg Leu Cys Gln His Gly Gly Leu Cys Val Asp Ala Gly Asn
        1115                1120                1125
Thr His His Cys Arg Cys Gln Ala Gly Tyr Thr Gly Ser Tyr Cys
        1130                1135                1140
Glu Asp Leu Val Asp Glu Cys Ser Pro Ser Pro Cys Gln Asn Gly
        1145                1150                1155
Ala Thr Cys Thr Asp Tyr Leu Gly Gly Tyr Ser Cys Lys Cys Val
        1160                1165                1170
Ala Gly Tyr His Gly Val Asn Cys Ser Glu Glu Ile Asp Glu Cys
        1175                1180                1185
Leu Ser His Pro Cys Gln Asn Gly Gly Thr Cys Leu Asp Leu Pro
        1190                1195                1200
Asn Thr Tyr Lys Cys Ser Cys Pro Arg Gly Thr Gln Gly Val His
        1205                1210                1215
Cys Glu Ile Asn Val Asp Asp Cys Asn Pro Pro Val Asp Pro Val
        1220                1225                1230
Ser Arg Ser Pro Lys Cys Phe Asn Asn Gly Thr Cys Val Asp Gln
        1235                1240                1245
Val Gly Gly Tyr Ser Cys Thr Cys Pro Pro Gly Phe Val Gly Glu
        1250                1255                1260
Arg Cys Glu Gly Asp Val Asn Glu Cys Leu Ser Asn Pro Cys Asp
        1265                1270                1275
Ala Arg Gly Thr Gln Asn Cys Val Gln Arg Val Asn Asp Phe His
        1280                1285                1290
Cys Glu Cys Arg Ala Gly His Thr Gly Arg Arg Cys Glu Ser Val
        1295                1300                1305
Ile Asn Gly Cys Lys Gly Lys Pro Cys Lys Asn Gly Gly Thr Cys
        1310                1315                1320
Ala Val Ala Ser Asn Thr Ala Arg Gly Phe Ile Cys Lys Cys Pro
        1325                1330                1335
Ala Gly Phe Glu Gly Ala Thr Cys Glu Asn Asp Ala Arg Thr Cys
        1340                1345                1350
Gly Ser Leu Arg Cys Leu Asn Gly Gly Thr Cys Ile Ser Gly Pro
        1355                1360                1365
Arg Ser Pro Thr Cys Leu Cys Leu Gly Pro Phe Thr Gly Pro Glu
        1370                1375                1380
Cys Gln Phe Pro Ala Ser Ser Pro Cys Leu Gly Gly Asn Pro Cys
        1385                1390                1395
Tyr Asn Gln Gly Thr Cys Glu Pro Thr Ser Glu Ser Pro Phe Tyr
        1400                1405                1410
```

```
Arg Cys Leu Cys Pro Ala Lys Phe Asn Gly Leu Leu Cys His Ile
    1415            1420                1425

Leu Asp Tyr Ser Phe Gly Gly Ala Gly Arg Asp Ile Pro Pro
    1430            1435                1440

Pro Leu Ile Glu Glu Ala Cys Glu Leu Pro Glu Cys Gln Glu Asp
    1445            1450                1455

Ala Gly Asn Lys Val Cys Ser Leu Gln Cys Asn His Ala Cys
    1460            1465                1470

Gly Trp Asp Gly Asp Cys Ser Leu Asn Phe Asn Asp Pro Trp
    1475            1480                1485

Lys Asn Cys Thr Gln Ser Leu Gln Cys Trp Lys Tyr Phe Ser Asp
    1490            1495                1500

Gly His Cys Asp Ser Gln Cys Asn Ser Ala Gly Cys Leu Phe Asp
    1505            1510                1515

Gly Phe Asp Cys Gln Arg Ala Glu Gly Gln Cys Asn Pro Leu Tyr
    1520            1525                1530

Asp Gln Tyr Cys Lys Asp His Phe Ser Asp Gly His Cys Asp Gln
    1535            1540                1545

Gly Cys Asn Ser Ala Glu Cys Glu Trp Asp Gly Leu Asp Cys Ala
    1550            1555                1560

Glu His Val Pro Glu Arg Leu Ala Ala Gly Thr Leu Val Val Val
    1565            1570                1575

Val Leu Met Pro Pro Glu Gln Leu Arg Asn Ser Ser Phe His Phe
    1580            1585                1590

Leu Arg Glu Leu Ser Arg Val Leu His Thr Asn Val Val Phe Lys
    1595            1600                1605

Arg Asp Ala His Gly Gln Gln Met Ile Phe Pro Tyr Tyr Gly Arg
    1610            1615                1620

Glu Glu Glu Leu Arg Lys His Pro Ile Lys Arg Ala Ala Glu Gly
    1625            1630                1635

Trp Ala Ala Pro Asp Ala Leu Leu Gly Gln Val Lys Ala Ser Leu
    1640            1645                1650

Leu Pro Gly Gly Ser Glu Gly Gly Arg Arg Arg Glu Leu Asp
    1655            1660                1665

Pro Met Asp Val Arg Gly Ser Ile Val Tyr Leu Glu Ile Asp Asn
    1670            1675                1680

Arg Gln Cys Val Gln Ala Ser Ser Gln Cys Phe Gln Ser Ala Thr
    1685            1690                1695

Asp Val Ala Ala Phe Leu Gly Ala Leu Ala Ser Leu Gly Ser Leu
    1700            1705                1710

Asn Ile Pro Tyr Lys Ile Glu Ala Val Gln Ser Glu Thr Val Glu
    1715            1720                1725

Pro Pro Pro Pro Ala Gln
    1730

<210> SEQ ID NO 23
<211> LENGTH: 20
<212> TYPE: PRT
<213> ORGANISM: Artificial Sequence
<220> FEATURE:
<223> OTHER INFORMATION: Synthetic Construct

<400> SEQUENCE: 23

Leu His Phe Met Tyr Val Ala Ala Ala Ala Phe Val Leu Leu Phe Phe
1               5                   10                  15
```

Val Gly Cys Gly
        20

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Val Leu Leu Ser Arg Lys Arg Arg Arg
1               5

<210> SEQ ID NO 25
<211> LENGTH: 1367
<212> TYPE: PRT
<213> ORGANISM: Artificial Sequence
<220> FEATURE:
<223> OTHER INFORMATION: Synthetic Construct

<400> SEQUENCE: 25

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu

```
            275                 280                 285
Phe Leu Ala Ala Lys Asn Leu Ser Asp Ala Ile Leu Leu Ser Asp Ile
290                 295                 300
Leu Arg Val Asn Thr Glu Ile Thr Lys Ala Pro Leu Ser Ala Ser Met
305                 310                 315                 320
Ile Lys Arg Tyr Asp Glu His His Gln Asp Leu Thr Leu Leu Lys Ala
            325                 330                 335
Leu Val Arg Gln Gln Leu Pro Glu Lys Tyr Lys Glu Ile Phe Phe Asp
            340                 345                 350
Gln Ser Lys Asn Gly Tyr Ala Gly Tyr Ile Asp Gly Gly Ala Ser Gln
            355                 360                 365
Glu Glu Phe Tyr Lys Phe Ile Lys Pro Ile Leu Glu Lys Met Asp Gly
            370                 375                 380
Thr Glu Glu Leu Leu Val Lys Leu Asn Arg Glu Asp Leu Leu Arg Lys
385                 390                 395                 400
Gln Arg Thr Phe Asp Asn Gly Ser Ile Pro His Gln Ile His Leu Gly
            405                 410                 415
Glu Leu His Ala Ile Leu Arg Arg Gln Glu Asp Phe Tyr Pro Phe Leu
            420                 425                 430
Lys Asp Asn Arg Glu Lys Ile Glu Lys Ile Leu Thr Phe Arg Ile Pro
            435                 440                 445
Tyr Tyr Val Gly Pro Leu Ala Arg Gly Asn Ser Arg Phe Ala Trp Met
450                 455                 460
Thr Arg Lys Ser Glu Glu Thr Ile Thr Pro Trp Asn Phe Glu Glu Val
465                 470                 475                 480
Val Asp Lys Gly Ala Ser Ala Gln Ser Phe Ile Glu Arg Met Thr Asn
            485                 490                 495
Phe Asp Lys Asn Leu Pro Asn Glu Lys Val Leu Pro Lys His Ser Leu
            500                 505                 510
Leu Tyr Glu Tyr Phe Thr Val Tyr Asn Glu Leu Thr Lys Val Lys Tyr
            515                 520                 525
Val Thr Glu Gly Met Arg Lys Pro Ala Phe Leu Ser Gly Glu Gln Lys
            530                 535                 540
Lys Ala Ile Val Asp Leu Leu Phe Lys Thr Asn Arg Lys Val Thr Val
545                 550                 555                 560
Lys Gln Leu Lys Glu Asp Tyr Phe Lys Lys Ile Glu Cys Phe Asp Ser
            565                 570                 575
Val Glu Ile Ser Gly Val Glu Asp Arg Phe Asn Ala Ser Leu Gly Thr
            580                 585                 590
Tyr His Asp Leu Leu Lys Ile Ile Lys Asp Lys Asp Phe Leu Asp Asn
            595                 600                 605
Glu Glu Asn Glu Asp Ile Leu Glu Asp Ile Val Leu Thr Leu Thr Leu
            610                 615                 620
Phe Glu Asp Arg Glu Met Ile Glu Glu Arg Leu Lys Thr Tyr Ala His
625                 630                 635                 640
Leu Phe Asp Asp Lys Val Met Lys Gln Leu Lys Arg Arg Arg Tyr Thr
            645                 650                 655
Gly Trp Gly Arg Leu Ser Arg Lys Leu Ile Asn Gly Ile Arg Asp Lys
            660                 665                 670
Gln Ser Gly Lys Thr Ile Leu Asp Phe Leu Lys Ser Asp Gly Phe Ala
            675                 680                 685
Asn Arg Asn Phe Met Gln Leu Ile His Asp Asp Ser Leu Thr Phe Lys
            690                 695                 700
```

```
Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
            725                 730                 735

Leu Gln Thr Val Lys Val Val Asp Glu Leu Val Lys Val Met Gly Arg
        740                 745                 750

His Lys Pro Glu Asn Ile Val Ile Glu Met Ala Arg Glu Asn Gln Thr
    755                 760                 765

Thr Gln Lys Gly Gln Lys Asn Ser Arg Glu Arg Met Lys Arg Ile Glu
770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp Ala Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
        995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110
```

```
Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 26
<211> LENGTH: 530
<212> TYPE: PRT
<213> ORGANISM: Artificial Sequence
<220> FEATURE:
<223> OTHER INFORMATION: Synthetic Construct

<400> SEQUENCE: 26

Asp Gly Ile Gly Ser Gly Ser Asn Gly Ser Ser Leu Asp Ala Leu Asp
1               5                   10                  15

Asp Phe Asp Leu Asp Met Leu Gly Ser Asp Ala Leu Asp Asp Phe Asp
                20                  25                  30

Leu Asp Met Leu Gly Ser Asp Ala Leu Asp Asp Phe Asp Leu Asp Met
            35                  40                  45

Leu Gly Ser Asp Ala Leu Asp Asp Phe Asp Leu Asp Met Leu Gly Ser
        50                  55                  60

Gly Gly Ser Gly Ser Gln Tyr Leu Pro Asp Thr Asp Asp Arg His Arg
65                  70                  75                  80

Ile Glu Glu Lys Arg Lys Arg Thr Tyr Glu Thr Phe Lys Ser Ile Met
                85                  90                  95
```

```
Lys Lys Ser Pro Phe Ser Gly Pro Thr Asp Pro Arg Pro Pro Arg
             100                 105                 110

Arg Ile Ala Val Pro Ser Arg Ser Ala Ser Val Pro Lys Pro Ala
        115                 120                 125

Pro Gln Pro Tyr Pro Phe Thr Ser Ser Leu Ser Thr Ile Asn Tyr Asp
    130                 135                 140

Glu Phe Pro Thr Met Val Phe Pro Ser Gly Gln Ile Ser Gln Ala Ser
145                 150                 155                 160

Ala Leu Ala Pro Ala Pro Pro Gln Val Leu Pro Gln Ala Pro Ala Pro
                165                 170                 175

Ala Pro Ala Pro Ala Met Val Ser Ala Leu Ala Gln Ala Pro Ala Pro
            180                 185                 190

Val Pro Val Leu Ala Pro Gly Pro Pro Gln Ala Val Ala Pro Pro Ala
        195                 200                 205

Pro Lys Pro Thr Gln Ala Gly Glu Gly Thr Leu Ser Glu Ala Leu Leu
    210                 215                 220

Gln Leu Gln Phe Asp Asp Glu Asp Leu Gly Ala Leu Leu Gly Asn Ser
225                 230                 235                 240

Thr Asp Pro Ala Val Phe Thr Asp Leu Ala Ser Val Asp Asn Ser Glu
                245                 250                 255

Phe Gln Gln Leu Leu Asn Gln Gly Ile Pro Val Ala Pro His Thr Thr
            260                 265                 270

Glu Pro Met Leu Met Glu Tyr Pro Glu Ala Ile Thr Arg Leu Val Thr
        275                 280                 285

Gly Ala Gln Arg Pro Pro Asp Pro Ala Pro Ala Pro Leu Gly Ala Pro
290                 295                 300

Gly Leu Pro Asn Gly Leu Leu Ser Gly Asp Glu Asp Phe Ser Ser Ile
305                 310                 315                 320

Ala Asp Met Asp Phe Ser Ala Leu Leu Ser Gln Ile Ser Ser Gly Ser
                325                 330                 335

Gly Ser Gly Ser Arg Asp Ser Arg Glu Gly Met Phe Leu Pro Lys Pro
            340                 345                 350

Glu Ala Gly Ser Ala Ile Ser Asp Val Phe Glu Gly Arg Glu Val Cys
        355                 360                 365

Gln Pro Lys Arg Ile Arg Pro Phe His Pro Pro Gly Ser Pro Trp Ala
    370                 375                 380

Asn Arg Pro Leu Pro Ala Ser Leu Ala Pro Thr Pro Thr Gly Pro Val
385                 390                 395                 400

His Glu Pro Val Gly Ser Leu Thr Pro Ala Pro Val Pro Gln Pro Leu
                405                 410                 415

Asp Pro Ala Pro Ala Val Thr Pro Glu Ala Ser His Leu Leu Glu Asp
            420                 425                 430

Pro Asp Glu Glu Thr Ser Gln Ala Val Lys Ala Leu Arg Glu Met Ala
        435                 440                 445

Asp Thr Val Ile Pro Gln Lys Glu Glu Ala Ala Ile Cys Gly Gln Met
    450                 455                 460

Asp Leu Ser His Pro Pro Pro Arg Gly His Leu Asp Glu Leu Thr Thr
465                 470                 475                 480

Thr Leu Glu Ser Met Thr Glu Asp Leu Asn Leu Asp Ser Pro Leu Thr
                485                 490                 495

Pro Glu Leu Asn Glu Ile Leu Asp Thr Phe Leu Asn Asp Glu Cys Leu
            500                 505                 510

Leu His Ala Met His Ile Ser Thr Gly Leu Ser Ile Phe Asp Thr Ser
```

```
                515                 520                 525

Leu Phe
    530

<210> SEQ ID NO 27
<211> LENGTH: 238
<212> TYPE: PRT
<213> ORGANISM: Artificial Sequence
<220> FEATURE:
<223> OTHER INFORMATION: Synthetic Construct

<400> SEQUENCE: 27

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Leu Glu
225                 230                 235

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Tyr Pro Tyr Asp Val Pro Asp Tyr Ala
1               5

<210> SEQ ID NO 29
<211> LENGTH: 11
<212> TYPE: PRT
<213> ORGANISM: Artificial Sequence
<220> FEATURE:
```

<223> OTHER INFORMATION: Synthetic Construct

<400> SEQUENCE: 29

Asp Gly Ile Gly Ser Gly Ser Asn Gly Ser Ser
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic Construct

<400> SEQUENCE: 30

Arg Ser Gln Gln Glu Ala Ala Lys Lys Phe Phe
1               5                   10

<210> SEQ ID NO 31
<211> LENGTH: 24
<212> TYPE: PRT
<213> ORGANISM: Artificial Sequence
<220> FEATURE:
<223> OTHER INFORMATION: Synthetic Construct

<400> SEQUENCE: 31

Val Met Lys Gln Leu Lys Arg Arg Arg Tyr Thr Gly Trp Gly Arg Leu
1               5                   10                  15

Ser Arg Lys Leu Ile Asn Gly Ile
            20

<210> SEQ ID NO 32
<211> LENGTH: 24
<212> TYPE: PRT
<213> ORGANISM: Artificial Sequence
<220> FEATURE:
<223> OTHER INFORMATION: Synthetic Construct

<400> SEQUENCE: 32

Val Met Ala Gln Leu Lys Ala Ala Ala Tyr Thr Gly Trp Gly Arg Leu
1               5                   10                  15

Ser Ala Ala Leu Ile Asn Gly Ile
            20

<210> SEQ ID NO 33
<211> LENGTH: 113
<212> TYPE: DNA
<213> ORGANISM: S. pyogenes
<220> FEATURE:
<221> NAME/KEY: misc_feature
<222> LOCATION: (1)..(20)
<223> OTHER INFORMATION: n = any nucleotide

<400> SEQUENCE: 33
nnnnnnnnnn nnnnnnnnnn gtttaagagc tatgctggaa acagcatagc aagtttaaat      60
aaggctagtc cgttatcaac ttgaaaaagt ggcaccgagt cggtgctttt ttt           113

<210> SEQ ID NO 34
<211> LENGTH: 104
<212> TYPE: DNA
<213> ORGANISM: S. aureus
<220> FEATURE:
<221> NAME/KEY: misc_feature
<222> LOCATION: (1)..(23)
<223> OTHER INFORMATION: n = any nucleotide

<400> SEQUENCE: 34
nnnnnnnnnn nnnnnnnnnn nnngttttag tactctggaa acagaatcta ctaaaacaag    60
gcaaaatgcc gtgtttatct cgtcaacttg ttggcgagat tttt    104

<210> SEQ ID NO 35
<211> LENGTH: 19
<212> TYPE: DNA
<213> ORGANISM: Artificial Sequence
<220> FEATURE:
<223> OTHER INFORMATION: Synthetic Construct

<400> SEQUENCE: 35
gtactccgac ctctagtgt    19

<210> SEQ ID NO 36
<211> LENGTH: 23
<212> TYPE: DNA
<213> ORGANISM: Artificial Sequence
<220> FEATURE:
<223> OTHER INFORMATION: Synthetic Construct

<400> SEQUENCE: 36 ggtgccttc cgcccatttt ccc    23

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct

<400> SEQUENCE: 37
gaccaggatg ggcaccaccc    20

<210> SEQ ID NO 38
<211> LENGTH: 20
<212> TYPE: DNA
<213> ORGANISM: Artificial Sequence
<220> FEATURE:
<223> OTHER INFORMATION: Synthetic Construct

<400> SEQUENCE: 38
ggctggcgag cgcggcctta    20

<210> SEQ ID NO 39
<211> LENGTH: 326
<212> TYPE: PRT
<213> ORGANISM: Artificial Sequence
<220> FEATURE:
<223> OTHER INFORMATION: Synthetic Construct

<400> SEQUENCE: 39

Ile Leu Asp Tyr Ser Phe Thr Gly Gly Ala Gly Arg Asp Ile Pro Pro
1               5                   10                  15

Pro Gln Ile Glu Glu Ala Cys Glu Leu Pro Cys Gln Val Asp Ala
            20                  25                  30

Gly Asn Lys Val Cys Asn Leu Gln Cys Asn Asn His Ala Cys Gly Trp
        35                  40                  45

Asp Gly Gly Asp Cys Ser Leu Asn Phe Asn Asp Pro Trp Lys Asn Cys
    50                  55                  60

Thr Gln Ser Leu Gln Cys Trp Lys Tyr Phe Ser Asp Gly His Cys Asp
65                  70                  75                  80

Ser Gln Cys Asn Ser Ala Gly Cys Leu Phe Asp Gly Phe Asp Cys Gln

```
                    85                  90                  95
Leu Thr Glu Gly Gln Cys Asn Pro Leu Tyr Asp Gln Tyr Cys Lys Asp
                100                 105                 110

His Phe Ser Asp Gly His Cys Asp Gln Gly Cys Asn Ser Ala Glu Cys
                115                 120                 125

Glu Trp Asp Gly Leu Asp Cys Ala Glu His Val Pro Glu Arg Leu Ala
        130                 135                 140

Ala Gly Thr Leu Val Leu Val Val Leu Pro Pro Asp Gln Leu Arg
145                 150                 155                 160

Asn Asn Ser Phe His Phe Leu Arg Glu Leu Ser His Val Leu His Thr
                165                 170                 175

Asn Val Val Phe Lys Arg Asp Ala Gln Gly Gln Gln Met Ile Phe Pro
                180                 185                 190

Tyr Tyr Gly His Glu Glu Glu Leu Arg Lys His Pro Ile Lys Arg Ser
                195                 200                 205

Thr Val Gly Trp Ala Thr Ser Ser Leu Leu Pro Gly Thr Ser Gly Gly
        210                 215                 220

Arg Gln Arg Arg Glu Leu Asp Pro Met Asp Ile Arg Gly Ser Ile Val
225                 230                 235                 240

Tyr Leu Glu Ile Asp Asn Arg Gln Cys Val Gln Ser Ser Ser Gln Cys
                245                 250                 255

Phe Gln Ser Ala Thr Asp Val Ala Ala Phe Leu Gly Ala Leu Ala Ser
                260                 265                 270

Leu Gly Ser Leu Asn Ile Pro Tyr Lys Ile Glu Ala Val Lys Ser Glu
        275                 280                 285

Pro Val Glu Pro Pro Leu Pro Ser Gln Leu His Leu Met Tyr Val Ala
        290                 295                 300

Ala Ala Ala Phe Val Leu Leu Phe Phe Val Gly Cys Gly Val Leu Leu
305                 310                 315                 320

Ser Arg Lys Arg Arg
                325

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

Pro Lys Lys Lys Arg Lys Val
1               5

<210> SEQ ID NO 41
<211> LENGTH: 16
<212> TYPE: PRT
<213> ORGANISM: Artificial Sequence
<220> FEATURE:
<223> OTHER INFORMATION: Synthetic Construct

<400> SEQUENCE: 41

Lys Arg Pro Ala Ala Thr Lys Lys Ala Gly Gln Ala Lys Lys Lys Lys
1               5                   10                  15

<210> SEQ ID NO 42
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 42

Pro Ala Ala Lys Arg Val Lys Leu Asp
1               5

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct

<400> SEQUENCE: 43

Arg Gln Arg Arg Asn Glu Leu Lys Arg Ser Pro
1               5                   10

<210> SEQ ID NO 44
<211> LENGTH: 38
<212> TYPE: PRT
<213> ORGANISM: Artificial Sequence
<220> FEATURE:
<223> OTHER INFORMATION: Synthetic Construct

<400> SEQUENCE: 44

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 45
<211> LENGTH: 42
<212> TYPE: PRT
<213> ORGANISM: Artificial Sequence
<220> FEATURE:
<223> OTHER INFORMATION: Synthetic Construct

<400> SEQUENCE: 45

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 46
<211> LENGTH: 8
<212> TYPE: PRT
<213> ORGANISM: Artificial Sequence
<220> FEATURE:
<223> OTHER INFORMATION: Synthetic Construct

<400> SEQUENCE: 46

Val Ser Arg Lys Arg Pro Arg Pro
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 47

Pro Pro Lys Lys Ala Arg Glu Asp
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Construct

<400> SEQUENCE: 48

Pro Gln Pro Lys Lys Lys Pro Leu
1               5

<210> SEQ ID NO 49
<211> LENGTH: 12
<212> TYPE: PRT
<213> ORGANISM: Artificial Sequence
<220> FEATURE:
<223> OTHER INFORMATION: Synthetic Construct

<400> SEQUENCE: 49

Ser Ala Leu Ile Lys Lys Lys Lys Lys Met Ala Pro
1               5                   10

<210> SEQ ID NO 50
<211> LENGTH: 5
<212> TYPE: PRT
<213> ORGANISM: Artificial Sequence
<220> FEATURE:
<223> OTHER INFORMATION: Synthetic Construct

<400> SEQUENCE: 50

Asp Arg Leu Arg Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic Construct

<400> SEQUENCE: 51

Pro Lys Gln Lys Lys Arg Lys
1               5

<210> SEQ ID NO 52
<211> LENGTH: 10
<212> TYPE: PRT
<213> ORGANISM: Artificial Sequence
<220> FEATURE:
<223> OTHER INFORMATION: Synthetic Construct

<400> SEQUENCE: 52

Arg Lys Leu Lys Lys Lys Ile Lys Lys Leu
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53
```

```
Arg Glu Lys Lys Lys Phe Leu Lys Arg Arg
1               5                   10
```

<210> SEQ ID NO 54
<211> LENGTH: 20
<212> TYPE: PRT
<213> ORGANISM: Artificial Sequence
<220> FEATURE:
<223> OTHER INFORMATION: Synthetic Construct

<400> SEQUENCE: 54

```
Lys Arg Lys Gly Asp Glu Val Asp Gly Val Asp Glu Val Ala Lys Lys
1               5                   10                  15

Lys Ser Lys Lys
            20
```

<210> SEQ ID NO 55
<211> LENGTH: 17
<212> TYPE: PRT
<213> ORGANISM: Artificial Sequence
<220> FEATURE:
<223> OTHER INFORMATION: Synthetic Construct

<400> SEQUENCE: 55

```
Arg Lys Cys Leu Gln Ala Gly Met Asn Leu Glu Ala Arg Lys Thr Lys
1               5                   10                  15

Lys
```

<210> SEQ ID NO 56
<211> LENGTH: 236
<212> TYPE: PRT
<213> ORGANISM: Artificial Sequence
<220> FEATURE:
<223> OTHER INFORMATION: Synthetic Construct

<400> SEQUENCE: 56

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
```

```
                180             185             190
Gln Leu Pro Gly Ala Tyr Asn Val Asn Ile Lys Leu Asp Ile Thr Ser
            195                 200                 205

His Asn Glu Asp Tyr Thr Ile Val Glu Gln Tyr Arg Ala Glu Gly
    210                 215                 220

Arg His Ser Thr Gly Gly Met Asp Glu Leu Tyr Lys
225                 230                 235

<210> SEQ ID NO 57
<211> LENGTH: 78
<212> TYPE: PRT
<213> ORGANISM: Homo Sapiens

<400> SEQUENCE: 57

Gln Asp Val Asp Glu Cys Ser Leu Gly Ala Asn Pro Cys Glu His Ala
1               5                   10                  15

Gly Lys Cys Ile Asn Ile Leu Gly Ser Phe Glu Cys Gln Cys Leu Gln
            20                  25                  30

Gly Tyr Thr Gly Pro Arg Cys Glu Ile Asp Val Asn Glu Cys Val Ser
        35                  40                  45

Asn Pro Cys Gln Asn Asp Ala Thr Cys Leu Asp Gln Ile Gly Glu Phe
    50                  55                  60

Gln Cys Met Cys Met Pro Gly Tyr Glu Gly Val His Cys Glu
65                  70                  75

<210> SEQ ID NO 58
<211> LENGTH: 78
<212> TYPE: PRT
<213> ORGANISM: Unknown
<220> FEATURE:
<223> OTHER INFORMATION: Unknown Xenopus species

<400> SEQUENCE: 58

Asn Asp Val Asp Glu Cys Ser Leu Gly Ala Asn Pro Cys Glu His Gly
1               5                   10                  15

Gly Arg Cys Thr Asn Thr Leu Gly Ser Phe Gln Cys Asn Cys Pro Gln
            20                  25                  30

Gly Tyr Ala Gly Pro Arg Cys Glu Ile Asp Val Asn Glu Cys Leu Ser
        35                  40                  45

Asn Pro Cys Gln Asn Asp Ser Thr Cys Leu Asp Gln Ile Gly Glu Phe
    50                  55                  60

Gln Cys Ile Cys Met Pro Gly Tyr Glu Gly Leu Tyr Cys Glu
65                  70                  75

<210> SEQ ID NO 59
<211> LENGTH: 78
<212> TYPE: PRT
<213> ORGANISM: Danio rerio

<400> SEQUENCE: 59

Gln Asp Ile Asp Glu Cys Ser Leu Gly Ala Asn Pro Cys Glu His Gly
1               5                   10                  15

Gly Arg Cys Leu Asn Thr Lys Gly Ser Phe Gln Cys Lys Cys Leu Gln
            20                  25                  30

Gly Tyr Glu Gly Pro Arg Cys Glu Met Asp Val Asn Glu Cys Asn Ser
        35                  40                  45

Asn Pro Cys Gln Asn Asp Ala Thr Cys Leu Asp Gln Ile Gly Gly Phe
    50                  55                  60
```

```
His Cys Ile Cys Met Pro Gly Tyr Glu Gly Val Phe Cys Gln
 65                  70                  75
```

<210> SEQ ID NO 60
<211> LENGTH: 77
<212> TYPE: PRT
<213> ORGANISM: Unknown
<220> FEATURE:
<223> OTHER INFORMATION: Unknown Drosophila species

<400> SEQUENCE: 60

```
Glu Asp Ile Asp Glu Cys Asp Gln Gly Ser Pro Cys Glu His Asn Gly
 1               5                  10                  15

Ile Cys Val Asn Thr Pro Gly Ser Tyr Arg Cys Asn Cys Ser Gln Gly
             20                  25                  30

Phe Thr Gly Pro Arg Cys Glu Thr Asn Ile Asn Glu Cys Glu Ser His
         35                  40                  45

Pro Cys Gln Asn Glu Gly Ser Cys Leu Asp Asp Pro Gly Thr Glu Arg
     50                  55                  60

Cys Val Cys Met Pro Gly Phe Thr Gly Thr Gln Cys Glu
 65                  70                  75
```

<210> SEQ ID NO 61
<211> LENGTH: 5
<212> TYPE: PRT
<213> ORGANISM: Artificial Sequence
<220> FEATURE:
<223> OTHER INFORMATION: Synthetic Caspase-1 recognition sequence
<220> FEATURE:
<221> NAME/KEY: VARIANT
<222> LOCATION: (1)..(1)
<223> OTHER INFORMATION: Xaa = Phe, Leu, Trp, or Tyr
<220> FEATURE:
<221> NAME/KEY: VARIANT
<222> LOCATION: (2)..(2)
<223> OTHER INFORMATION: Xaa = any amino acid
<220> FEATURE:
<221> NAME/KEY: VARIANT
<222> LOCATION: (3)..(3)
<223> OTHER INFORMATION: Xaa = Ala, His, or Thr
<220> FEATURE:
<221> NAME/KEY: VARIANT
<222> LOCATION: (5)..(5)
<223> OTHER INFORMATION: Xaa = any amino acid except for Asp, Glu, Lys,
      Pro, Gln, or Arg

<400> SEQUENCE: 61

```
Xaa Xaa Xaa Asp Xaa
 1               5
```

<210> SEQ ID NO 62
<211> LENGTH: 5
<212> TYPE: PRT
<213> ORGANISM: Artificial Sequence
<220> FEATURE:
<223> OTHER INFORMATION: Synthetic Caspase-10 recognition sequence
<220> FEATURE:
<221> NAME/KEY: VARIANT
<222> LOCATION: (5)..(5)
<223> OTHER INFORMATION: Xaa = any amino acid

<400> SEQUENCE: 62

```
Ile Glu Ala Asp Xaa
 1               5
```

<210> SEQ ID NO 63
<211> LENGTH: 5
<212> TYPE: PRT

```
<213> ORGANISM: Artificial Sequence
<220> FEATURE:
<223> OTHER INFORMATION: Synthetic Caspase-2 recognition sequence
<220> FEATURE:
<221> NAME/KEY: VARIANT
<222> LOCATION: (5)..(5)
<223> OTHER INFORMATION: Xaa = any amino acid execpt for Asp, Glu, Lys,
      Pro, Gln, or Arg

<400> SEQUENCE: 63

Asp Val Ala Asp Xaa
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Caspase-2 recognition sequence
<220> FEATURE:
<221> NAME/KEY: VARIANT
<222> LOCATION: (5)..(5)
<223> OTHER INFORMATION: Xaa = any amino acid execpt for Asp, Glu, Lys,
      Pro, Gln, or Arg

<400> SEQUENCE: 64

Asp Glu His Asp Xaa
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic Caspase-3 recognition sequence
<220> FEATURE:
<221> NAME/KEY: VARIANT
<222> LOCATION: (5)..(5)
<223> OTHER INFORMATION: Xaa = any amino acid execpt for Asp, Glu, Lys,
      Pro, Gln, or Arg

<400> SEQUENCE: 65

Asp Met Gln Asp Xaa
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic Caspase-3 recognition sequence
<220> FEATURE:
<221> NAME/KEY: VARIANT
<222> LOCATION: (5)..(5)
<223> OTHER INFORMATION: Xaa = any amino acid execpt for Asp, Glu, Lys,
      Pro, Gln, or Arg

<400> SEQUENCE: 66

Asp Glu Val Asp Xaa
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic Caspase-4 recognition sequence
<220> FEATURE:
<221> NAME/KEY: VARIANT
<222> LOCATION: (5)..(5)
<223> OTHER INFORMATION: Xaa = any amino acid execpt for Asp, Glu, Lys,
```

Pro, Gln, or Arg

<400> SEQUENCE: 67

Leu Glu Val Asp Xaa
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic Caspase-4 recognition sequence
<220> FEATURE:
<221> NAME/KEY: VARIANT
<222> LOCATION: (1)..(1)
<223> OTHER INFORMATION: Xaa = Leu or Trp
<220> FEATURE:
<221> NAME/KEY: VARIANT
<222> LOCATION: (5)..(5)
<223> OTHER INFORMATION: Xaa = any amino acid execpt for Asp, Glu, Lys,
      Pro, Gln, or Arg

<400> SEQUENCE: 68

Xaa Glu His Asp Xaa
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic Caspase-5 recognition sequence
<220> FEATURE:
<221> NAME/KEY: VARIANT
<222> LOCATION: (1)..(1)
<223> OTHER INFORMATION: Xaa =  Leu or Trp
<220> FEATURE:
<221> NAME/KEY: VARIANT
<222> LOCATION: (5)..(5)
<223> OTHER INFORMATION: Xaa =  any amino acid

<400> SEQUENCE: 69

Xaa Glu His Asp Xaa
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic Caspase-6 recognition sequence
<220> FEATURE:
<221> NAME/KEY: VARIANT
<222> LOCATION: (3)..(3)
<223> OTHER INFORMATION: Xaa = His or Ile
<220> FEATURE:
<221> NAME/KEY: VARIANT
<222> LOCATION: (5)..(5)
<223> OTHER INFORMATION: any amino acid execpt for Asp, Glu, Lys, Pro,
      Gln, or Arg

<400> SEQUENCE: 70

Val Glu Xaa Asp Xaa
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic Caspase-7 recognition sequence

```
<220> FEATURE:
<221> NAME/KEY: VARIANT
<222> LOCATION: (5)..(5)
<223> OTHER INFORMATION: Xaa = any amino acid execpt for Asp, Glu, Lys,
      Pro, Gln, or Arg

<400> SEQUENCE: 71

Asp Glu Val Asp Xaa
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic Caspase-8 recognition sequence
<220> FEATURE:
<221> NAME/KEY: VARIANT
<222> LOCATION: (1)..(1)
<223> OTHER INFORMATION: Xaa = Ile or Leu
<220> FEATURE:
<221> NAME/KEY: VARIANT
<222> LOCATION: (5)..(5)
<223> OTHER INFORMATION: Xaa = any amino acid execpt for Asp, Glu, Lys,
      Pro, Gln, or Arg

<400> SEQUENCE: 72

Xaa Glu Thr Asp Xaa
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic Caspase-9 recognition sequence
<220> FEATURE:
<221> NAME/KEY: VARIANT
<222> LOCATION: (5)..(5)
<223> OTHER INFORMATION: Xaa = any amino acid

<400> SEQUENCE: 73

Leu Glu His Asp Xaa
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic Enterokinase recognition sequence
<220> FEATURE:
<221> NAME/KEY: VARIANT
<222> LOCATION: (1)..(3)
<223> OTHER INFORMATION: Xaa = Asp or Glu
<220> FEATURE:
<221> NAME/KEY: VARIANT
<222> LOCATION: (5)..(5)
<223> OTHER INFORMATION: Xaa = any amino acid

<400> SEQUENCE: 74

Xaa Xaa Xaa Lys Xaa
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic Factor Xa recognition sequence
<220> FEATURE:
```

```
<221> NAME/KEY: VARIANT
<222> LOCATION: (1)..(1)
<223> OTHER INFORMATION: Xaa = Ala, Phe, Gly, Ile, Leu, Thr, Val, or Met
<220> FEATURE:
<221> NAME/KEY: VARIANT
<222> LOCATION: (2)..(2)
<223> OTHER INFORMATION: Xaa = Asp or Glu
<220> FEATURE:
<221> NAME/KEY: VARIANT
<222> LOCATION: (5)..(5)
<223> OTHER INFORMATION: Xaa = any amino acid

<400> SEQUENCE: 75

Xaa Xaa Gly Arg Xaa
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic Granzyme B recognition sequence
<220> FEATURE:
<221> NAME/KEY: VARIANT
<222> LOCATION: (5)..(5)
<223> OTHER INFORMATION: Xaa = any amino acid

<400> SEQUENCE: 76

Ile Glu Pro Asp Xaa
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic HRV3C protease recognition sequence

<400> SEQUENCE: 77

Leu Glu Val Leu Phe Gln Gly Pro
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic Pepsin A recognition sequence
<220> FEATURE:
<221> NAME/KEY: VARIANT
<222> LOCATION: (1)..(1)
<223> OTHER INFORMATION: Xaa = any amino acid except His, Lys, or Arg
<220> FEATURE:
<221> NAME/KEY: VARIANT
<222> LOCATION: (2)..(2)
<223> OTHER INFORMATION: Xaa = any amino acid except Pro
<220> FEATURE:
<221> NAME/KEY: VARIANT
<222> LOCATION: (3)..(3)
<223> OTHER INFORMATION: Xaa = any amino acid except Arg
<220> FEATURE:
<221> NAME/KEY: VARIANT
<222> LOCATION: (4)..(4)
<223> OTHER INFORMATION: Xaa = Phe, Leu, Trp, or Tyr
<220> FEATURE:
<221> NAME/KEY: VARIANT
<222> LOCATION: (5)..(5)
<223> OTHER INFORMATION: Xaa = any amino acid execpt Pro

<400> SEQUENCE: 78

Xaa Xaa Xaa Xaa Xaa
1               5
```

```
<210> SEQ ID NO 79
<211> LENGTH: 5
<212> TYPE: PRT
<213> ORGANISM: Artificial Sequence
<220> FEATURE:
<223> OTHER INFORMATION: Synthetic Pepsin A recognition sequence
<220> FEATURE:
<221> NAME/KEY: VARIANT
<222> LOCATION: (1)..(1)
<223> OTHER INFORMATION: Xaa = any amino acid except His, Lys, or Arg
<220> FEATURE:
<221> NAME/KEY: VARIANT
<222> LOCATION: (2)..(2)
<223> OTHER INFORMATION: Xaa = any amino acid except Pro
<220> FEATURE:
<221> NAME/KEY: VARIANT
<222> LOCATION: (3)..(3)
<223> OTHER INFORMATION: Xaa = Phe, Leu, Trp, or Tyr
<220> FEATURE:
<221> NAME/KEY: VARIANT
<222> LOCATION: (4)..(4)
<223> OTHER INFORMATION: Xaa = any amino acid
<220> FEATURE:
<221> NAME/KEY: VARIANT
<222> LOCATION: (5)..(5)
<223> OTHER INFORMATION: Xaa = any amino acid except Pro

<400> SEQUENCE: 79

Xaa Xaa Xaa Xaa Xaa
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Pepsin A (low specificity)
      recognition sequence
<220> FEATURE:
<221> NAME/KEY: VARIANT
<222> LOCATION: (1)..(1)
<223> OTHER INFORMATION: Xaa = any amino acid except His, Lys, or Arg
<220> FEATURE:
<221> NAME/KEY: VARIANT
<222> LOCATION: (2)..(2)
<223> OTHER INFORMATION: Xaa = any amino acid except Pro
<220> FEATURE:
<221> NAME/KEY: VARIANT
<222> LOCATION: (3)..(3)
<223> OTHER INFORMATION: Xaa = any amino acid except Arg
<220> FEATURE:
<221> NAME/KEY: VARIANT
<222> LOCATION: (4)..(4)
<223> OTHER INFORMATION: Xaa = Phe or Leu
<220> FEATURE:
<221> NAME/KEY: VARIANT
<222> LOCATION: (5)..(5)
<223> OTHER INFORMATION: Xaa = any amino acid except Pro

<400> SEQUENCE: 80

Xaa Xaa Xaa Xaa Xaa
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic Pepsin A (low specificity)
      recognition sequence
<220> FEATURE:
<221> NAME/KEY: VARIANT
<222> LOCATION: (1)..(1)
```

```
<223> OTHER INFORMATION: Xaa = any amino acid except His, Lys, or Arg
<220> FEATURE:
<221> NAME/KEY: VARIANT
<222> LOCATION: (2)..(2)
<223> OTHER INFORMATION: Xaa = any amino acid except Pro
<220> FEATURE:
<221> NAME/KEY: VARIANT
<222> LOCATION: (3)..(3)
<223> OTHER INFORMATION: Xaa = Phe or Leu
<220> FEATURE:
<221> NAME/KEY: VARIANT
<222> LOCATION: (4)..(4)
<223> OTHER INFORMATION: Xaa = any amino acid
<220> FEATURE:
<221> NAME/KEY: VARIANT
<222> LOCATION: (5)..(5)
<223> OTHER INFORMATION: Xaa = any amino acid except Pro

<400> SEQUENCE: 81

Xaa Xaa Xaa Xaa Xaa
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic TEV protease recognition sequence
<220> FEATURE:
<221> NAME/KEY: VARIANT
<222> LOCATION: (2)..(3)
<223> OTHER INFORMATION: Xaa = any amino acid
<220> FEATURE:
<221> NAME/KEY: VARIANT
<222> LOCATION: (5)..(5)
<223> OTHER INFORMATION: Xaa = any amino acid
<220> FEATURE:
<221> NAME/KEY: VARIANT
<222> LOCATION: (7)..(7)
<223> OTHER INFORMATION: Xaa = Gly or Ser

<400> SEQUENCE: 82

Glu Xaa Xaa Tyr Xaa Gln Xaa
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic Thrombin recognition sequence
<220> FEATURE:
<221> NAME/KEY: VARIANT
<222> LOCATION: (1)..(2)
<223> OTHER INFORMATION: Xaa = any amino acid
<220> FEATURE:
<221> NAME/KEY: VARIANT
<222> LOCATION: (6)..(6)
<223> OTHER INFORMATION: Xaa = any amino acid

<400> SEQUENCE: 83

Xaa Xaa Gly Arg Gly Xaa
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic Thrombin recognition sequence
<220> FEATURE:
<221> NAME/KEY: VARIANT
<222> LOCATION: (1)..(2)
```

```
<223> OTHER INFORMATION: Xaa = Ala, Phe, Gly, Ile, Leu, Thr, Val, or Trp
<220> FEATURE:
<221> NAME/KEY: VARIANT
<222> LOCATION: (5)..(6)
<223> OTHER INFORMATION: Xaa = any amino acid except Asp or Glu

<400> SEQUENCE: 84

Xaa Xaa Pro Arg Xaa Xaa
1               5
```

CHIMERIC PROTEINS AND METHODS OF REGULATING GENE EXPRESSION

CROSS-REFERENCE

The present application is a continuation of U.S. application Ser. No. 16/570,827 filed Sep. 13, 2019; which is a continuation of U.S. application Ser. No. 15/806,756 filed Nov. 8, 2017, which issued on Oct. 29, 2019 as U.S. Pat. No. 10,457,961; which is a continuation of U.S. application Ser. No. 15/403,058 filed Jan. 10, 2017, which issued on Jan. 2, 2018 as U.S. Pat. No. 9,856,497; which application claims the benefit of U.S. Provisional Application Nos. 62/277,322 filed Jan. 11, 2016, 62/351,522 filed Jun. 17, 2016, and 62/399,902 filed Sep. 26, 2016; the full disclosures of which are incorporated herein by reference in their entirety for all purposes.

REFERENCE TO A SEQUENCE LISTING

The Sequence Listing written in file 079445-1219444-000860US_SequenceListing.txt, created on Nov. 12, 2020, 189,218 bytes, machine format IBM-PC, MS-Windows operating system, is incorporated herein by reference in its entirety for all purposes.

BACKGROUND

Regulation of cell activities can involve the binding of a ligand to a membrane-bound receptor comprising an extracellular ligand binding domain and an intracellular (e.g., cytoplasmic) signaling domain. The formation of a complex between a ligand and the ligand binding domain can result in a conformational and/or chemical modification in the receptor which can result in a signal transduced within the cell. In some situations, the cytoplasmic portion of the receptor is phosphorylated (e.g., trans- and/or auto-phosphorylated), resulting in a change in its activity. These events can be coupled with secondary messengers and/or the recruitment of co-factor proteins. In some instances, the change in the cytoplasmic portion results in binding to other proteins (e.g., co-factor proteins and/or other receptors). These other proteins can be activated and then carry out various functions within a cell.

Conditional gene expression systems allow for conditional regulation of one or more target genes. Conditional gene expression systems such as drug-inducible gene expression systems allow for the activation and/or deactivation of gene expression in response to a stimulus, such as the presence of a drug. Currently available systems, however, can be limited due to imprecise control, insufficient levels of induction (e.g., activation and/or deactivation of gene expression), and lack of specificity.

SUMMARY

In view of the foregoing, there exists a considerable need for alternative compositions and methods to carry out conditional regulation of gene expression, for example by regulating expression of a target polynucleotide. In an aspect, the present disclosure provides a system for regulating expression of a target polynucleotide in a cell. The system comprises: (a) a chimeric receptor polypeptide comprising a G-protein coupled receptor (GPCR) or a fragment thereof, that undergoes a receptor modification including a conformational change or chemical modification upon binding to a ligand for the GPCR; (b) a chimeric adaptor polypeptide that binds the chimeric receptor polypeptide in response to the receptor modification; (c) a gene modulating polypeptide (GMP) comprising an actuator moiety linked to a cleavage recognition site, wherein upon cleavage of the cleavage recognition site, the actuator moiety is activated to complex with a target polynucleotide; and (d) a cleavage moiety that cleaves the cleavage recognition site when in proximity to the cleavage recognition site; wherein: (i) the GMP forms a portion of an intracellular region of the chimeric receptor polypeptide, and the cleavage moiety forms a portion of the chimeric adaptor polypeptide; (ii) the GMP forms a portion of the chimeric adaptor polypeptide, and the cleavage moiety forms a portion of an intracellular region of the chimeric receptor polypeptide; or (iii) the cleavage moiety is complexed with a second adaptor polypeptide that binds the chimeric receptor polypeptide in response to the receptor modification, and the GMP forms a portion of the chimeric adaptor polypeptide. In some embodiments, the receptor modification is phosphorylation.

In some embodiments, the actuator moiety is a Cas protein, and the system further comprises a guide RNA that complexes with the Cas protein. In some embodiments, the Cas protein substantially lacks DNA cleavage activity.

In some embodiments, the GMP forms a portion of an intracellular region of the chimeric receptor polypeptide, and the cleavage moiety forms a portion of the chimeric adaptor polypeptide. In some embodiments, the GMP forms a portion of the chimeric adaptor polypeptide, and the cleavage moiety forms a portion of an intracellular region of the chimeric receptor polypeptide. In some embodiments, the cleavage moiety is complexed with a second adaptor polypeptide that binds the chimeric receptor polypeptide in response to the receptor modification, and the GMP forms a portion of the chimeric adaptor polypeptide.

In some embodiments, (i) the GMP forms a portion of the chimeric adaptor polypeptide, (ii) cleavage of the cleavage recognition site is effective to release the chimeric adaptor polypeptide from the receptor, and (iii) the system comprises a further chimeric adaptor polypeptide comprising a GMP that binds to the chimeric receptor polypeptide that has undergone the receptor modification.

In some embodiments, the cleavage recognition site comprises a polypeptide sequence, and the cleavage moiety comprises protease activity.

In some embodiments, the actuator moiety comprises an activator effective to increase expression of the target polynucleotide.

In some embodiments, the chimeric receptor polypeptide is linked to at least one targeting sequence which directs transport of the chimeric receptor polypeptide to a specific region of a cell. In some embodiments, the chimeric adaptor polypeptide is linked to at least one targeting sequence which directs transport of the chimeric adaptor polypeptide to a specific region of a cell. In some embodiments, the chimeric receptor polypeptide is linked to a polypeptide folding domain. In some embodiments, the chimeric adaptor polypeptide is linked to a polypeptide folding domain.

In an aspect, the present disclosure provides a method of regulating expression of a target polynucleotide in a cell. The method comprises: (a) exposing a chimeric receptor polypeptide to an antigen, wherein (i) the chimeric receptor polypeptide is modified upon exposure to the antigen, and (ii) the receptor modification comprises a conformational change or a chemical modification; (b) binding a chimeric adaptor polypeptide to the chimeric receptor polypeptide in response to the receptor modification to form a complex between a gene modulating polypeptide (GMP) and a cleavage moiety, wherein the GMP comprises an actuator moiety linked to a cleavage recognition site; and (c) cleaving the cleavage recognition site with the cleavage moiety, wherein upon cleavage of the cleavage recognition site, the actuator moiety complexes with a target polynucleotide thereby regulating expression of the target polynucleotide in the cell; wherein: (i) the GMP forms a portion of an intracellular region of the chimeric receptor polypeptide, and the cleavage moiety forms a portion of the chimeric adaptor polypeptide; (ii) the cleavage moiety forms a portion of the chimeric adaptor polypeptide, and the GMP forms a portion of an intracellular region of the chimeric receptor; or (iii) the cleavage moiety is complexed with a second adaptor polypeptide that binds the receptor in response to the receptor modification, and the GMP forms a portion of the chimeric adaptor polypeptide. In some embodiments, the receptor modification is phosphorylation.

In some embodiments, the actuator moiety is a Cas protein that forms a complex with a guide RNA. In some embodiments, the Cas protein substantially lacks DNA cleavage activity.

In some embodiments, (i) the GMP forms a portion of the chimeric adaptor polypeptide, (ii) the chimeric adaptor polypeptide is released from the receptor polypeptide following cleavage of the cleavage recognition site, and (iii) a further chimeric adaptor polypeptide comprising a GMP binds the receptor polypeptide that has undergone the receptor modification.

In some embodiments, the receptor modification comprises modification at multiple modification sites, and each modification site is effective to bind a chimeric adaptor polypeptide.

In some embodiments, the cleavage recognition site comprises a polypeptide sequence, and the cleavage moiety comprises protease activity.

In some embodiments, the actuator moiety comprises an activator effective to increase expression of the target polynucleotide.

In an aspect, the present disclosure provides a chimeric adaptor polypeptide. The chimeric adaptor polypeptide comprises: (a) a receptor binding moiety that binds a receptor that has undergone a modification upon binding to an antigen; and (b) a gene modulating polypeptide (GMP) linked to the receptor binding moiety, wherein the GMP comprises an actuator moiety linked to a cleavage recognition site; wherein: (i) the cleavage recognition site is cleavable by a cleavage moiety in response to receptor binding; and (ii) the actuator moiety is operable to complex with a target polynucleotide in response to cleavage of the cleavage recognition site.

In some embodiments, the receptor binding moiety binds a receptor comprising a G-protein coupled receptor (GPCR) or a fragment thereof.

In some embodiments, the actuator moiety is operable to translocate to a cell nucleus after cleavage of the cleavage recognition sequence. In some embodiments, the actuator moiety is a Cas protein that forms a complex with a guide RNA. In some embodiments, the Cas protein substantially lacks DNA cleavage activity.

In some embodiments, the cleavage recognition site comprises a polypeptide sequence that is a recognition sequence for the cleavage moiety. In some embodiments, the cleavage moiety comprises protease activity.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 4A-D illustrate schematically the release of an actuator moiety from a GMP in a system comprising a receptor which undergoes phosphorylation; FIGS. 4E-4H illustrate schematically the release of an actuator moiety from a GMP in a system comprising a receptor which undergoes a conformational change.

FIGS. 8A-8D illustrate schematically the release of an actuator moiety from a GMP in a system comprising a receptor which undergoes phosphorylation; FIGS. 8E-8H illustrate schematically the release of an actuator moiety from a GMP in a system comprising a receptor which undergoes a conformational change.

FIGS. 13A-13D illustrate schematically a system in which the cleavage recognition site comprises an intein sequence; FIGS. 13E-13H illustrate an alternative arrangement of a system in which the cleavage recognition site comprises an intein sequence.

FIGS. 14A-D illustrate schematically a system in which the cleavage recognition site comprises a disulfide bond; FIGS. 14E-14H illustrate an alternative arrangement of a system in which the cleavage recognition site comprises a disulfide bond.

FIGS. 19A-19F show engineered chimeric antigen receptors with gene modulation domains and in some cases, their associated adaptor-proteases. FIG. 19A depicts such recombinant receptors that bind to cell surface antigens. FIG. 19B depicts recombinant receptors for gene modulation that can bind soluble antigens. FIG. 19C illustrates gene modulating, engineered receptors that can bind to extracellular matrix (ECM) signals. FIG. 19D illustrates dimerizing receptors. One of the receptors includes an extracellular domain (ECD), a transmembrane domain (TM), an intracellular domain (ICD), a peptide-cleavage sequence, and a gene modulating effector domain. The other receptor of the dimer includes an ECD, TM, ICD, and a protease. FIG. 19E shows another example of dimerizing receptors that can modulate gene expression or edit genes. One of the dimerizing receptors can include an ECD, TM, ICD, peptide-cleavage sequence, and a gene modulating effector domain. The other receptor of the dimer can include an ECD, TM and ICD, and not a protease. The protease that cleaves this dimerizing receptor can be fused to an adaptor protein that associates to the activated dimerizing receptor. FIG. 19F shows an example of an oligomerizing receptor that includes engineered chimeric antigen receptors fused to gene modulation domains.

FIGS. 20A and 20B provides different chimeric antigen receptors and illustrates the binding of a dCas9-activator domain guided to a target gene by an sgRNA. FIG. 20A shows recombinant chimeric antigen receptor polypeptides and in some cases, their associated adaptor-protease polypeptides such as Notch and presenillin-proteases, GPCRs and β2-arrestin-proteases, integrins and paxillin-proteases, cadherins and β-catenin-proteases, death receptors and FADD-proteases, and chimeric antigen receptors.

FIG. 22A depicts a schematic diagram of a chimeric antigen integrin-dCas9 activator. FIG. 22B shows an integrin-dCas9 complex that is responsive to fibronectin. Upon binding to an sgRNA specific to the reporter gene, the recombinant complex activated transcription of the reporter (H2B-GFP).

FIG. 23A shows a scheme of target gene regulation by GPCR based chimeric antigen receptor-dCas9 activators. FIG. 23B shows that the CXCR4-dCas9 polypeptide was responsive to CXCL12 and activated the luminescent reporter.

FIGS. 24A-24G show exemplary embodiments of modular chimeric artificial Notch receptors of the present invention. FIG. 24A shows a wild-type Notch bound to its ligand Delta. After the receptor is activated by binding Delta, the ICD is cleaved by a protease and translocates to the nucleus to regulate target genes. FIG. 24B shows a chimeric artificial Notch receptor where the Notch ICD has been replaced with a dCas9 fusion protein. The dCas9 fusion protein can include an effector domain such as an activator domain, e.g., VP64 domain or a repressor domain, e.g., KRAB domain. FIG. 24C shows another chimeric artificial Notch receptor containing a dCas9 fusion protein where the Notch ECD has been replaced with a CD47-binding scFv. FIG. 24D shows an exemplary modular chimeric artificial Notch receptor and an adapter-protease fusion protein (presinillin-TEV protease) expressed on the surface of a cell such as an immune cell. The modular chimeric artificial Notch receptor can contain a dCas9 fusion polypeptide, a linker, and an effector domain. Upon Delta-Notch binding, the presinillin can associate with the chimeric artificial Notch receptor. Then, the TEV protease can cleave the peptide cleavage domain of the chimeric artificial Notch receptor. Activation of a fluorescent reporter in cells expressing the Notch-dCas9-activator is shown in FIG. 24E for HEK293 cells, in FIG. 24F for Jurkat cells, and in FIG. 24G in THP-1 macrophages.

FIGS. 25A-25C show theoretical models for reshaping the endogenous response of the Notch receptor using the chimeric antigen Notch receptors described herein. FIG. 25A shows the repression of the endogenous phagocytic response of a receiving cell expressing endogenous Notch upon binding Delta expressed on a signaling cell. FIG. 25B shows that the engineered caN receptor can be created to rewire the endogenous phagocytic response to an external Delta signal. FIG. 25C shows that the engineered caN receptor can be produced to shift the repression of the cell's endogenous phagocytic response to activation upon Delta binding.

FIGS. 27A and 27B show that the Notch-dCas9 activator is guided by a sgUAS (SEQ ID NO:1; gtactccgacctctagtgt) to a UAS promoter and activates transcription of a reporter gene (H2B-citrine). FIG. 27A provides a schematic diagram of the process. FIG. 27B shows that the Notch-dCas9 activator is responsive to Delta.

FIG. 28A provides a schematic diagram of ligand binding of the CXCR4-dCas9-VPR polypeptide that is complexed with a sgRNA (sgTET; SEQ ID NO:2; gtacgttctctatcactgata). FIG. 28A also shows a β2-arrestin-protease fusion protein that can associated with the engineered chimeric antigen receptor. The diagram also shows (1) translocation of free dCas9-VPR into the nucleus, (2) binding of the sgTET-dCas9-VPR complex to a TetO promoter that regulates transcription of the luciferase gene, and (3) transcription of the reporter. FIG. 28B shows that transcription of luciferase gene is regulated by CXCL2 binding to the CXCR4-dCas9-VPR polypeptide.

FIG. 29A shows a schematic diagram of transcriptional activation of the reporter upon ligand binding to the integrin-dCas9-VPR polypeptide. FIG. 29B shows that the integrin-based engineered chimeric antigen receptor-dCas9 complex induced reporter expression in response to signals from the ECM.

FIG. 30A shows a schematic diagram of a split dCas9 effector tethered to separate engineered receptors. FIG. 30B provides a schematic diagram of a chimeric receptor-tTa polypeptide that, upon binding to its ligand, induces expression of a TetO-driven chimeric receptor-dCas9 polypeptide.

FIG. 31A illustrates activation of Notch1 receptors involving cleavage and nuclear translocation of the Notch intracellular domain, which can be replaced by or engineered to promote expression of Cas9 derivatives. The fusion of effector domains to Cas9 and a user-defined single-guide RNA (sgRNA) sequence allow for targeted gene regulation. FIG. 31B shows schematic designs of mCherry-tagged chimeric receptor constructs that were initially tested for cellular localization and Delta-dependent reporter activation. The human codon-optimized nuclease-dead Cas9 (dCas9) and tripartite activator domains (VP64, p65, and Rta; VPR) are fused immediately after the Notch1 extracellular domain (hNECD) and transmembrane domain. Construct NC5 comprises maturation signals derived from a known ER export signal. FIG. 31C shows a schematic of a Chinese hamster ovary (CHO) cell line integrated with an Upstream Activating Sequence (UAS) or CSL-binding (not shown) promoters that drive a Histone 2B (H2B)-citrine reporter gene and a stably integrated promoter-targeting sgRNA (e.g., sgUAS or sasgCSL, respectively) used to validate gene-activation efficiency of chimeric receptors when cultured with or without surface-immobilized Delta. Activation of NC5 receptors by immobilized Delta ligands leads to cleavage and nuclear translocation of dCas9-VPR. dCas9-VPR complexed with a sequence-specific sgRNA (e.g., sgUAS or sasgCSL) allows for binding of the complex to the promoter and activation of H2B-citrine gene. FIG. 31D shows example microscopy images of CHO cells transfected with the NC5 chimera resulting in H2B expression when exposed to immobilized Delta for 4 days. Scale bar, 20 m. FIG. 31E shows relative H2B levels (normalized expression) in CHO UAS-H2B clones stably selected for NC5 (S. pyogenes dCas9, and sgUAS) or in CHO CSL-H2B clones with wild-type human Notch1 or NC5 (S. aureus dCas9, and sasgCSL) and cultured on bare or immobilized-Delta surfaces for 4 days (n=3). Mean SEM. FIG. 31F shows percentage of cells that activate H2B-citrine in CHO UAS-H2B clones stably selected for NC5 (S. pyogenes dCas9, and sgUAS) or in CHO 12×CSL-H2B clones with wild-type human Notch1 or NC5 (S. aureus dCas9, and sasgCSL) and cultured on bare or immobilized-Delta surfaces for 4 days (n=3). Mean SEM, **p<0.01, compared to (−Delta) controls. FIG. 31G illustrates activation of NC5 receptors by immobilized Delta ligand resulting in cleavage and nuclear translocation of dCas9-VPR. FIG. 31H shows EGFP reporter intensity historgrams from HEK293T reporter cells stably expressing a tet-inducible EGFP gene and a targeting sgRNA (sgTET) in the presence of dCas9-VPR, NC5+Delta+DAPT, NC5+Delta, NC5−Delta, and no construct. FIG. 31I shows contour plots (where the same number of cells fall between each pair of contour lines) of EGFP activation of HEK293T reporter cells transfected with NC5 receptor and cultured on various concentrations of immobilized Delta for 3 days.

FIG. 32A illustrates a schematic of a synthetic Cas9-receptor system in accordance with an embodiment described herein. Modulation of target endogenous genes is responsive to extracellular signals, such as Delta. A variety of downstream cellular behaviors can be triggered from native extracellular inputs, depending on design of the system. FIG. 32B left shows CDKN1B activation via hNECD-dCas9-VPR (construct NC5) induces a Delta-dependent cell-cycle arrest at G0/G1 phase. Right shows a schematic representation of Delta-dependent cleavage of dCas9-VPR from NC5 leading to CDKN1B-high and G0/G1-arrested cells (with 2n DNA), in accordance with an embodiment. FIG. 32C shows example flow-cytometry plots and percentage quantification (shaded regions) of CDKN1B-high and G0/G1-arrested cells under different culture conditions: HEK293 cells with sgRNA only, sgRNA+Delta, sgRNA+NC5, or sgRNA+NC5+Delta. NC5 was transiently transfected in sgCDKN1B-integrated cells, which were then cultured on Delta-coated or bare surfaces for 4 days. n=3, Mean SEM. G0/G1 arrested cells correspond to the top left shaded corner of the plots, and the top bar of each pair in the bar graph. G2 arrested cells correspond to the top right shaded corner of the plots, and bottom bar of each pair in the bar graph.

FIG. 35C shows by microscopy impaired nuclear localization and EGFP reporter activation in HEK293T cells when the iNLS motif is disrupted (SEQ ID NO: 31, 32, 9). FIGS. 35C and 35D show visually by microscopy and quantitatively that adding a synthetic NLS to the N-terminus of iNLS-mutated dCas9-VPR partially restores EGFP activation.

FIG. 36A shows schematically Delta-dependent DNA-cutting with an NC5 variant: hNECD fused to wild-type *S. pyogenes* nuclease-active Cas9 (hNECD-Cas9). FIG. 36B shows the efficacy of gene editing/cutting with hNECD-Cas9 in CHO cells with stably integrated EGFP and a targeting sgRNA (sgEGFP). FIG. 36C shows an example schematic for two sgRNAs (short bars to left and right of "sgCXCR4") that were stably expressed in HEK293T cells and were designed to target the 5' untranslated region (UTR) and intron 1 of CXCR4. Scale bar, 1000 bp. FIG. 36D, top panel, shows example results from a T7E1 endonuclease to assay the extent of Delta-induced hNECD-Cas9-mediated modification of CXCR4 gene in HEK293T cells, as detected by amount of products cleaved by T7E1 in SDS-PAGE gels. The bottom panel shows example results for frequency of CXCR4 indel mutations. FIG. 36E shows example results for the quantification of flow cytometry-based immunofluorescence staining of CXCR4 protein expression in HEK293T cells.

FIG. 37A shows alignment of EGF-11 and -12 repeats of human, *Xenopus*, zebrafish, and *Drosophila* homologs (SEQ ID NO: 57-60). Identical residues are indicated in gray boxes. Asterisk (*) marks conserved cysteine and $Ca^{2+}$-binding consensus residues. FIG. 37B shows variable activation levels of various EGF deletion variants (as evaluated by reporter assay).

FIG. 39A illustrates schematically the use of minimal NC5 receptor variant to elicit Delta-dependent arrest of the cell cycle. FIG. 39B depicts cellular arrest at the G0/G1 phase resulting from CDKN1B overexpression. FIGS. 39C and 39D shows that in cells with dCas9-VPR and sgCDKN1B, CDKN1B upregulation was concomitant with G0/G1 enrichment, and in cells with dCas9-VPR and non-targeting gsRNA, a minimal increase in CDKN1B was observed.

FIGS. 39E and 39F show abrogation of Delta-induced CDKN1B upregulation and G0/G1 arrest in cells with DAPT.

DETAILED DESCRIPTION

Figure 1:
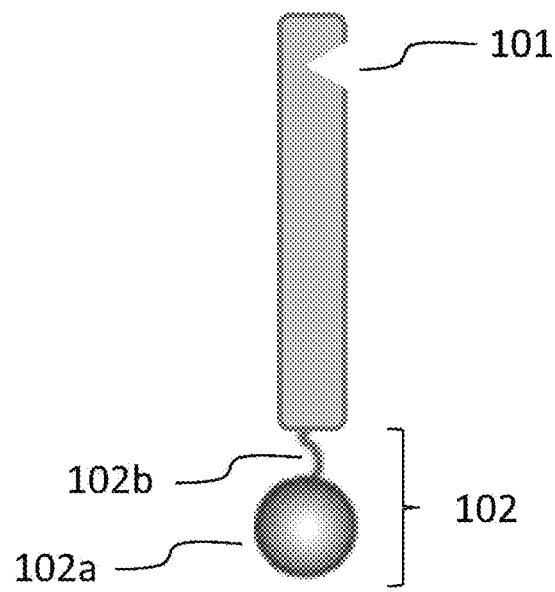
FIG. 1 shows an exemplary chimeric receptor polypeptide comprising an antigen interacting domain and a gene modulating polypeptide (GMP).

The practice of some methods disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R.I. Freshney, ed. (2010)).

As used in the specification and claims, the singular forms "a", "an" and "the" include plural references unless the context clearly dictates otherwise. For example, the term "a chimeric transmembrane receptor" includes a plurality of chimeric transmembrane receptors.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

As used herein, a "cell" can generally refer to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. Agardh*, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g. a cell can be a synthetically made, sometimes termed an artificial cell).

The term "nucleotide," as used herein, generally refers to a base-sugar-phosphate combination. A nucleotide can comprise a synthetic nucleotide. A nucleotide can comprise a synthetic nucleotide analog. Nucleotides can be monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [aS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide may be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA] ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g. biotin-11-dUTP, biotin-16-dUTP, biotin-20-dUTP).

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide can be exogenous or endogenous to a cell. A polynucleotide can exist in a cell-free environment. A polynucleotide can be a gene or fragment thereof. A polynucleotide can be DNA. A polynucleotide can be RNA. A polynucleotide can have any three dimensional structure, and can perform any function, known or unknown. A polynucleotide can comprise one or more analogs (e.g. altered backbone, sugar, or nucleobase). If present, modifications to the nucleotide structure can be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or flurescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides can be interrupted by non-nucleotide components.

The terms "target polynucleotide" and "target nucleic acid," as used herein, refer to a nucleic acid or polynucleotide which is targeted by an actuator moiety of the present disclosure. A target nucleic acid can be DNA. A target nucleic acid can be RNA. A target nucleic acid can refer to a chromosomal sequence or an extrachromosomal sequence, (e.g., an episomal sequence, a minicircle sequence, a mitochondrial sequence, a chloroplast sequence, etc.). A target nucleic acid can be a nucleic acid sequence that may not be related to any other sequence in a nucleic acid sample by a single nucleotide substitution. A target nucleic acid can be a nucleic acid sequence that may not be related to any other sequence in a nucleic acid sample by a 2, 3, 4, 5, 6, 7, 8, 9, or 10 nucleotide substitutions. In some embodiments, the substitution may not occur within 5, 10, 15, 20, 25, 30, or 35 nucleotides of the 5' end of a target nucleic acid. In some embodiments, the substitution may not occur within 5, 10, 15, 20, 25, 30, 35 nucleotides of the 3' end of a target nucleic acid. In general, the term "target sequence" refers to a nucleic acid sequence on a single strand of a target nucleic acid. The target sequence can be a portion of a gene, a regulatory sequence, genomic DNA, cell free nucleic acid including cfDNA and/or cfRNA, cDNA, a fusion gene, and RNA including mRNA, miRNA, rRNA, and others.

The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and can include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene can refer to an "endogenous gene" or a native gene in its natural location in the genome of an organism. A gene can refer to an "exogenous gene" or a non-native gene. A non-native gene can refer to a gene not normally found in the host organism but which is introduced into the host organism by gene transfer. A non-native gene can also refer to a gene not in its natural location in the genome of an organism. A non-native gene can also refer to a naturally occurring nucleic acid or polypeptide sequence that comprises mutations, insertions and/or deletions (e.g., non-native sequence).

The terms "transfection" or "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The term "expression" refers to one or more processes by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides can be collectively referred to as "gene product." If the polynucleotide is derived from genomic DNA, expression can include splicing of the mRNA in a eukaryotic cell. "Up-regulated," with reference to expression, generally refers to an increased expression level of a polynucleotide (e.g., RNA such as mRNA) and/or polypeptide sequence relative to its expression level in a wild-type state while "down-regulated" generally refers to a decreased expression level of a polynucleotide (e.g., RNA such as mRNA) and/or polypeptide sequence relative to its expression in a wild-type state. Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "expression cassette," "expression construct," or "expression vector" refers to a nucleic acid that includes a nucleotide sequence such as a coding sequence and a template sequence, and sequences necessary for expression of the coding sequence. The expression cassette can be viral or non-viral. For instance, an expression cassette includes a nucleic acid construct, which when introduced into a host cell, results in transcription and/or translation of a RNA or polypeptide, respectively. Antisense constructs or sense constructs that are not or cannot be translated are expressly included by this definition. One of skill will recognize that the inserted polynucleotide sequence need not be identical, but may be only substantially similar to a sequence of the gene from which it was derived.

A "plasmid," as used herein, generally refers to a non-viral expression vector, e.g., a nucleic acid molecule that encodes for genes and/or regulatory elements necessary for the expression of genes. A "viral vector," as used herein, generally refers to a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

The term "promoter," as used herein, refers to a polynucleotide sequence capable of driving transcription of a coding sequence in a cell. Thus, promoters used in the polynucleotide constructs of the disclosure include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions, developmental conditions, or drug or chemical conditions.

The terms "complement," "complements," "complementary," and "complementarity," as used herein, generally refer to a sequence that is fully complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, can be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment can be assessed using any suitable parameters of a chosen algorithm, including default parameters.

Complementarity can be perfect or substantial/sufficient. Perfect complementarity between two nucleic acids can mean that the two nucleic acids can form a duplex in which every base in the duplex is bonded to a complementary base by Watson-Crick pairing. Substantial or sufficient complementary can mean that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods.

The terms "peptide," "polypeptide," and "protein" are used interchangeably herein to refer to a polymer of at least two amino acid residues joined by peptide bond(s). This term does not connote a specific length of polymer, nor is it intended to imply or distinguish whether the peptide is produced using recombinant techniques, chemical or enzymatic synthesis, or is naturally occurring. The terms apply to naturally occurring amino acid polymers as well as amino acid polymers comprising at least one modified amino acid. In some cases, the polymer can be interrupted by non-amino acids. The terms include amino acid chains of any length, including full length proteins, and proteins with or without secondary and/or tertiary structure (e.g., domains). The terms also encompass an amino acid polymer that has been modified, for example, by disulfide bond formation, glycosylation, lipidation, acetylation, phosphorylation, oxidation, and any other manipulation such as conjugation with a labeling component. The terms "amino acid" and "amino acids," as used herein, generally refer to natural and non-natural amino acids, including, but not limited to, modified amino acids and amino acid analogues. Modified amino acids can include natural amino acids and non-natural amino acids, which have been chemically modified to include a group or a chemical moiety not naturally present on the amino acid. Amino acid analogues can refer to amino acid derivatives. The term "amino acid" includes both D-amino acids and L-amino acids.

The terms "derivative," "variant," and "fragment," when used herein with reference to a polypeptide, refers to a polypeptide related to a wild type polypeptide, for example either by amino acid sequence, structure (e.g., secondary and/or tertiary), activity (e.g., enzymatic activity) and/or function. Derivatives, variants and fragments of a polypeptide can comprise one or more amino acid variations (e.g., mutations, insertions, and deletions), truncations, modifications, or combinations thereof compared to a wild type polypeptide.

The term "percent (%) identity," as used herein, refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment, for purposes of determining percent identity, can be achieved in various ways that are within the skill in the art, for instance, using publicly available computer software such as BLAST, ALIGN, or Megalign (DNASTAR) software. Percent identity of two sequences can be calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence.

The term "gene modulating polypeptide" or "GMP," as used herein, refers to a polypeptide comprising at least an actuator moiety capable of regulating expression or activity of a gene and/or editing a nucleic acid sequence. A GMP can comprise additional peptide sequences which are not involved in modulating gene expression, for example cleavage recognition sites, linker sequences, targeting sequences, etc.

The terms "actuator moiety," "actuator domain," and "gene modulating domain," as used herein, refers to a moiety which can regulate expression or activity of a gene and/or edit a nucleic acid sequence, whether exogenous or endogenous. An actuator moiety can regulate expression of a gene at the transcription level and/or the translation level. An actuator moiety can regulate gene expression at the transcription level, for example, by regulating the production of mRNA from DNA, such as chromosomal DNA or cDNA. In some embodiments, an actuator moiety recruits at least one transcription factor that binds to a specific DNA sequence, thereby controlling the rate of transcription of genetic information from DNA to mRNA. An actuator moiety can itself bind to DNA and regulate transcription by physical obstruction, for example preventing proteins such as RNA polymerase and other associated proteins from assembling on a DNA template. An actuator moiety can regulate expression of a gene at the translation level, for example, by regulating the production of protein from mRNA template. In some embodiments, an actuator moiety regulates gene expression by affecting the stability of an mRNA transcript. In some embodiments, an actuator moiety regulates expression of a gene by editing a nucleic acid sequence (e.g., a region of a genome). In some embodiments, an actuator moiety regulates expression of a gene by editing an mRNA template. Editing a nucleic acid sequence can, in some cases, alter the underlying template for gene expression.

A Cas protein referred to herein can be a type of protein or polypeptide. A Cas protein can refer to a nuclease. A Cas protein can refer to an endoribonuclease. A Cas protein can refer to any modified (e.g., shortened, mutated, lengthened) polypeptide sequence or homologue of the Cas protein. A Cas protein can be codon optimized. A Cas protein can be a codon-optimized homologue of a Cas protein. A Cas protein can be enzymatically inactive, partially active, constitutively active, fully active, inducible active and/or more active, (e.g. more than the wild type homologue of the protein or polypeptide.). A Cas protein can be Cas9. A Cas protein can be Cpf1. A Cas protein can be C2c2. A Cas protein (e.g., variant, mutated, enzymatically inactive and/or conditionally enzymatically inactive site-directed polypeptide) can bind to a target nucleic acid. The Cas protein (e.g., variant, mutated, enzymatically inactive and/or conditionally enzymatically inactive endoribonuclease) can bind to a target RNA or DNA.

The term "crRNA," as used herein, can generally refer to a nucleic acid with at least about 5%, 10%, 20%, 30%, 40%, 50%, 60%, 70%, 80%, 90%, 100% sequence identity and/or sequence similarity to a wild type exemplary crRNA (e.g., a crRNA from *S. pyogenes*). crRNA can generally refer to a nucleic acid with at most about 5%, 10%, 20%, 30%, 40%, 50%, 60%, 70%, 80%, 90%, 100% sequence identity and/or sequence similarity to a wild type exemplary crRNA (e.g., a crRNA from *S. pyogenes*). crRNA can refer to a modified form of a crRNA that can comprise a nucleotide change such as a deletion, insertion, or substitution, variant, mutation, or chimera. A crRNA can be a nucleic acid having at least about 60% identical to a wild type exemplary crRNA (e.g., a crRNA from *S. pyogenes*) sequence over a stretch of at least 6 contiguous nucleotides. For example, a crRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical, to a wild type exemplary crRNA sequence (e.g., a crRNA from *S. pyogenes*) over a stretch of at least 6 contiguous nucleotides The term "tracrRNA," as used herein, can generally refer to a nucleic acid with at least about 5%, 10%, 20%, 30%, 40%, 50%, 60%, 70%, 80%, 90%, 100% sequence identity and/or sequence similarity to a wild type exemplary tracrRNA sequence (e.g., a tracrRNA from *S. pyogenes*).

tracrRNA can refer to a nucleic acid with at most about 5%, 10%, 20%, 30%, 40%, 50%, 60%, 70%, 80%, 90%, 100% sequence identity and/or sequence similarity to a wild type exemplary tracrRNA sequence (e.g., a tracrRNA from *S. pyogenes*). tracrRNA can refer to a modified form of a tracrRNA that can comprise a nucleotide change such as a deletion, insertion, or substitution, variant, mutation, or chimera. A tracrRNA can refer to a nucleic acid that can be at least about 60% identical to a wild type exemplary tracrRNA (e.g., a tracrRNA from *S. pyogenes*) sequence over a stretch of at least 6 contiguous nucleotides. For example, a tracrRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical, to a wild type exemplary tracrRNA (e.g., a tracrRNA from *S. pyogenes*) sequence over a stretch of at least 6 contiguous nucleotides.

As used herein, a guide nucleic acid can refer to a nucleic acid that can hybridize to another nucleic acid. A guide nucleic acid can be RNA. A guide nucleic acid can be DNA. The guide nucleic acid can be programmed to bind to a sequence of nucleic acid site-specifically. The nucleic acid to be targeted, or the target nucleic acid, can comprise nucleotides. The guide nucleic acid can comprise nucleotides. A portion of the target nucleic acid can be complementary to a portion of the guide nucleic acid. The strand of a double-stranded target polynucleotide that is complementary to and hybridizes with the guide nucleic acid can be called the complementary strand. The strand of the double-stranded target polynucleotide that is complementary to the complementary strand, and therefore may not be complementary to the guide nucleic acid can be called noncomplementary strand. A guide nucleic acid can comprise a polynucleotide chain and can be called a "single guide nucleic acid". A guide nucleic acid can comprise two polynucleotide chains and can be called a "double guide nucleic acid". If not otherwise specified, the term "guide nucleic acid" can be inclusive, referring to both single guide nucleic acids and double guide nucleic acids.

A guide nucleic acid can comprise a segment that can be referred to as a "nucleic acid-targeting segment" or a "nucleic acid-targeting sequence." A nucleic acid-targeting nucleic acid can comprise a segment that can be referred to as a "protein binding segment" or "protein binding sequence" or "Cas protein binding segment".

The term "cleavage recognition site," as used herein, with reference to peptides, refers to a site of a peptide at which a chemical bond, such as a peptide bond or disulfide bond, can be cleaved. Cleavage can be achieved by various methods. Cleavage of peptide bonds can be facilitated, for example, by an enzyme such as a protease or by protein splicing (e.g., inteins). Cleavage of a disulfide bond can be facilitated, for example, by an enzyme such as an oxidoreductase.

The term "targeting sequence," as used herein, refers to a nucleotide sequence and the corresponding amino acid sequence which encodes a targeting polypeptide which mediates the localization (or retention) of a protein to a sub-cellular location, e.g., plasma membrane or membrane of a given organelle, nucleus, cytosol, mitochondria, endoplasmic reticulum (ER), Golgi, chloroplast, apoplast, peroxisome or other organelle. For example, a targeting sequence can direct a protein (e.g., a receptor polypeptide or an adaptor polypeptide) to a nucleus utilizing a nuclear localization signal (NLS); outside of a nucleus of a cell, for example to the cytoplasm, utilizing a nuclear export signal (NES); mitochondria utilizing a mitochondrial targeting signal; the endoplasmic reticulum (ER) utilizing an ER-retention signal; a peroxisome utilizing a peroxisomal targeting signal; plasma membrane utilizing a membrane localization signal; or combinations thereof.

As used herein, "fusion" can refer to a protein and/or nucleic acid comprising one or more non-native sequences (e.g., moieties). A fusion can comprise one or more of the same non-native sequences. A fusion can comprise one or more of different non-native sequences. A fusion can be a chimera. A fusion can comprise a nucleic acid affinity tag. A fusion can comprise a barcode. A fusion can comprise a peptide affinity tag. A fusion can provide for subcellular localization of the site-directed polypeptide (e.g., a nuclear localization signal (NLS) for targeting to the nucleus, a mitochondrial localization signal for targeting to the mitochondria, a chloroplast localization signal for targeting to a chloroplast, an endoplasmic reticulum (ER) retention signal, and the like). A fusion can provide a non-native sequence (e.g., affinity tag) that can be used to track or purify. A fusion can be a small molecule such as biotin or a dye such as alexa fluor dyes, Cyanine3 dye, Cyanine5 dye.

A fusion can refer to any protein with a functional effect. For example, a fusion protein can comprise methyltransferase activity, demethylase activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, or demyristoylation activity. An effector protein can modify a genomic locus. A fusion protein can be a fusion in a Cas protein. An fusion protein can be a non-native sequence in a Cas protein.

As used herein, "non-native" can refer to a nucleic acid or polypeptide sequence that is not found in a native nucleic acid or protein. Non-native can refer to affinity tags. Non-native can refer to fusions. Non-native can refer to a naturally occurring nucleic acid or polypeptide sequence that comprises mutations, insertions and/or deletions. A non-native sequence may exhibit and/or encode for an activity (e.g., enzymatic activity, methyltransferase activity, acetyltransferase activity, kinase activity, ubiquitinating activity, etc.) that can also be exhibited by the nucleic acid and/or polypeptide sequence to which the non-native sequence is fused. A non-native nucleic acid or polypeptide sequence may be linked to a naturally-occurring nucleic acid or polypeptide sequence (or a variant thereof) by genetic engineering to generate a chimeric nucleic acid and/or polypeptide sequence encoding a chimeric nucleic acid and/or polypeptide.

As used herein, "treating" or "treatment" refers to any one of the following: ameliorating one or more symptoms of disease, e.g., cancer; preventing the manifestation of such symptoms before they occur; slowing down or completely preventing the progression of the disease (as may be evident by longer periods between reoccurrence episodes, slowing down or prevention of the deterioration of symptoms, etc.);

enhancing the onset of a remission period; slowing down the irreversible damage caused in the progressive-chronic stage of the disease (both in the primary and secondary stages); delaying the onset of said progressive stage, or any combination thereof.

As used herein, "administer," "administering," "administration," and derivatives thereof refer to the methods that may be used to enable delivery of agents or compositions to the desired site of biological action. These methods include, but are not limited to parenteral administration (e.g., intravenous, subcutaneous, intraperitoneal, intramuscular, intravascular, intrathecal, intranasal, intravitreal, infusion and local injection), transmucosal injection, oral administration, administration as a suppository, and topical administration. Administration is by any route, including parenteral. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transplantation, etc. One skilled in the art will know of additional methods for administering a therapeutically effective amount of a composition of the present disclosure for preventing or relieving one or more symptoms associated with a disease.

Disclosed herein are systems, methods, and compositions for regulating expression of a target polynucleotide in a cell. In an aspect, the present disclosure provides a system for regulating expression of a target polynucleotide in a cell. An exemplary system comprises (a) a chimeric receptor polypeptide that is modified upon binding an antigen, wherein receptor modification comprises a conformational change or chemical modification, (b) a chimeric adaptor polypeptide that binds the receptor in response to the receptor modification, (c) a gene modulating polypeptide (GMP) comprising an actuator moiety linked to a cleavage recognition site, wherein upon cleavage of the cleavage recognition site, the actuator moiety is activated to complex with a target polynucleotide, and (d) a cleavage moiety that cleaves the cleavage recognition site when in proximity to the cleavage recognition site. The chimeric receptor polypeptide, chimeric adaptor polypeptide, gene modulating polypeptide (GMP), and cleavage moiety of a subject system can be arranged in a variety of configurations. Exemplary, non-limiting configurations are described herein. In some embodiments, the GMP forms a portion of an intracellular region of the chimeric receptor polypeptide, and the cleavage moiety forms a portion of the chimeric adaptor polypeptide. In some embodiments, the GMP forms a portion of the chimeric adaptor polypeptide, and the cleavage moiety forms a portion of an intracellular region of the chimeric receptor polypeptide. In some embodiments, the cleavage moiety is complexed with a second adaptor polypeptide that binds the chimeric receptor polypeptide in response to the receptor modification, and the GMP forms a portion of the chimeric adaptor polypeptide.

In an exemplary configuration, the GMP forms a portion of an intracellular region of the chimeric receptor polypeptide, and the cleavage moiety forms a portion of the chimeric adaptor polypeptide. A chimeric receptor polypeptide of an exemplary configuration can comprise (a) an antigen interacting domain, and (b) a gene modulating polypeptide (GMP) comprising an actuator moiety linked to a cleavage recognition site. FIG. 1 shows an exemplary chimeric receptor polypeptide. The receptor comprises an antigen interacting domain 101 and a gene modulating polypeptide (GMP) 102. The GMP 102 can comprise an actuator moiety 102a linked to a cleavage recognition site 102b.

In some embodiments, (i) the chimeric receptor polypeptide is modified in response to antigen binding, (ii) the cleavage recognition site is cleaved by a cleavage moiety in response to modification of the chimeric receptor polypeptide, (iii) the actuator moiety complexes with a target polynucleotide after being cleaved from the chimeric receptor polypeptide at the cleavage recognition site, and (iv) the chimeric receptor polypeptide does not comprise SEQ ID NO: 39.

SEQ ID NO: 39
ILDYSFTGGAGRDIPPPQIEEACELPECQVDAGNKVCNLQCNNHACGWDG

GDCSLNFNDPWKNCTQSLQCWKYFSDGHCDSQCNSAGCLFDGFDCQLTEG

QCNPLYDQYCKDHFSDGHCDQGCNSAECEWDGLDCAEHVPERLAAGTLVL

VVLLPPDQLRNNSFHFLRELSHVLHTNVVFKRDAQGQQMIFPYYGHEEEL

RKHPIKRSTVGWATSSLLPGTSGGRQRRELDPMDIRGSIVYLEIDNRQCV

QSSSQCFQSATDVAAFLGALASLGSLNIPYKIEAVKSEPVEPPLPSQLHL

MYVAAAAFVLLFFVGCGVLLSRKRRR

A chimeric receptor polypeptide of a subject system can comprise an endogenous receptor, or any derivative, variant or fragment thereof. A chimeric receptor polypeptide can bind specifically to at least one antigen (e.g., at least one ligand), for example via an antigen interacting domain (also referred to herein as an "extracellular sensor domain"). A chimeric receptor polypeptide can, in response to ligand binding, undergo a modification such as a conformational change and/or chemical modification. Such modification(s) can recruit to the receptor binding partners (e.g., partners such as proteins) including, but not limited to, signaling proteins involved in signaling events and various cellular processes. Signaling proteins, for example, can be involved in regulating (e.g., activating and/or de-activating) a cellular response such as programmed changes in gene expression via translational regulation; transcriptional regulation; and epigenetic modification including the regulation of methylation, acetylation, phosphorylation, ubiquitylation, sumoylation, ribosylation, and citrullination. Conformational changes of a chimeric receptor polypeptide can expose one or more regions of the receptor which was previously not exposed, and the exposed region can recruit and/or bind signaling protein(s). Chemical modifications on a receptor, for example phosphorylation and/or dephosphorylation (e.g., at tyrosine, serine, threonine, and/or any other suitable amino acid residue), can also recruit signaling proteins involved in regulating intracellular processes. Signaling proteins can bind directly to a receptor or indirectly to a receptor, for example as part of a larger complex.

Figure 2:
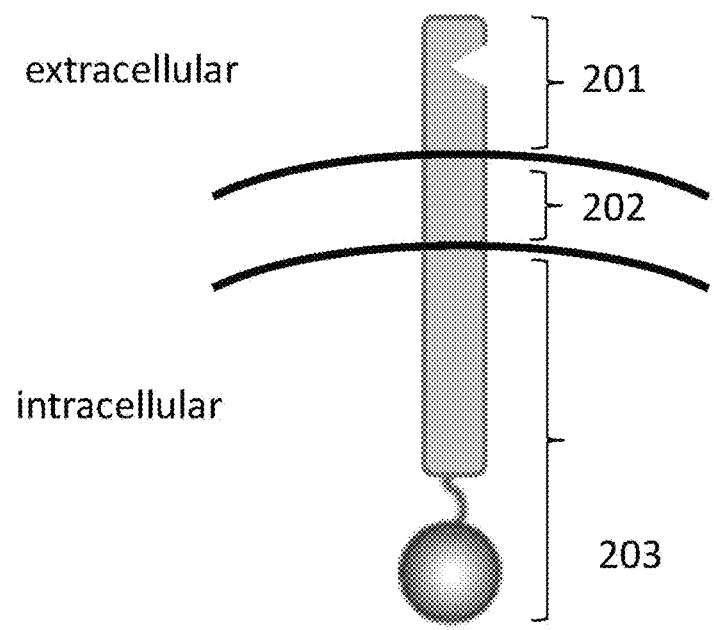
FIG. 2 shows an exemplary chimeric transmembrane receptor polypeptide.

In some embodiments, the chimeric receptor polypeptide is a transmembrane receptor. An exemplary transmembrane receptor is shown in FIG. 2. A transmembrane receptor can be embedded in a cell membrane and have at least an extracellular region 201, a region spanning a membrane 202 such as a plasma membrane, and an intracellular region 203. The antigen interacting domain can form a portion of the extracellular region, and the GMP can form a portion of the intracellular region. Membrane receptors can detect at least one signal, such as a small molecule, ion, or protein, from the surrounding environment (e.g., extracellular and/or intracellular environment) and can initiate a cellular response via at least one signaling cascade involving additional proteins and signaling molecules. Some receptors can translocate from one region of a cell to another, for example from the plasma membrane or cytoplasm to the nucleus and vice versa. Such translocation can be conditional upon ligand binding to the receptor. Examples of membrane receptors include, but are not limited to, Notch receptors; G-protein coupled receptors (GPCRs); integrin receptors; cadherin receptors; catalytic receptors including receptors possessing enzymatic activity and receptors which, rather than possessing intrinsic enzymatic activity, act by stimulating non-covalently associated enzymes (e.g., kinases); death receptors such as members of the tumor necrosis factor receptor (TNFR) superfamily; and immune receptors.

In some embodiments, a chimeric receptor polypeptide comprises a Notch receptor, or any derivative, variant or fragment thereof. Notch receptors are transmembrane proteins that mediate cell-cell contact signaling and play a central role in development and other aspects of cell-to-cell communication, e.g. communication between two contacting cells (receiver cell and sending cell). Notch receptors expressed in a receiver cell recognize their ligands (the delta family of proteins), expressed on a sending cell. The engagement of notch and delta on these contacting cells leads to two-step proteolysis of the notch receptor that ultimately causes the release of the intracellular portion of the receptor from the membrane into the cytoplasm.

In some embodiments, a chimeric receptor polypeptide comprises at least an extracellular region (e.g., ligand binding domain) of a Notch receptor, or any derivative, variant or fragment thereof. In some embodiments, a chimeric receptor polypeptide comprises at least a membrane spanning region of a Notch, or any derivative, variant or fragment thereof. In some embodiments, a chimeric receptor polypeptide comprises at least an intracellular region (e.g., cytoplasmic domain) of a Notch, or any derivative, variant or fragment thereof. A chimeric receptor polypeptide comprising a Notch, or any derivative, variant or fragment thereof, can recruit a binding partner. In some embodiments, ligand binding to a chimeric receptor comprising a Notch, or any derivative, variant or fragment thereof, results in a conformational change, chemical modification, or combination thereof, which recruits a binding partner to the receptor.

In some embodiments, a chimeric receptor polypeptide comprises a Notch, or any derivative, variant or fragment thereof, selected from Notch1, Notch2, Notch3, and Notch4 or any homolog thereof.

In some embodiments, a chimeric receptor polypeptide comprises a G-protein coupled receptor (GPCR), or any derivative, variant or fragment thereof. GPCRs are generally characterized by seven membrane-spanning a helices and can be arranged in a tertiary structure resembling a barrel, with the seven transmembrane helices forming a cavity within the plasma membrane that serves as a ligand-binding domain. Ligands can also bind elsewhere to a GPCR, for example to the extracellular loops and/or the N-terminal tail. Ligand binding can activate an associated G protein, which then functions in various signaling pathways. To de-activate this signaling, a GPCR can first be chemically modified by phosphorylation. Phosphorylation can then recruit co-adaptor proteins (e.g., arrestin proteins) for additional signaling.

In some embodiments, a chimeric receptor polypeptide comprises at least an extracellular region (e.g., ligand binding domain) of a GPCR, or any derivative, variant or fragment thereof. In some embodiments, a chimeric receptor polypeptide comprises at least a membrane spanning region of a GPCR, or any derivative, variant or fragment thereof. In some embodiments, a chimeric receptor polypeptide comprises at least an intracellular region (e.g., cytoplasmic domain) of a GPCR, or any derivative, variant or fragment thereof. A chimeric receptor polypeptide comprising a GPCR, or any derivative, variant or fragment thereof, can recruit a binding partner. In some embodiments, ligand binding to a chimeric receptor comprising a GPCR, or any derivative, variant or fragment thereof, results in a conformational change, chemical modification, or combination thereof, which recruits a binding partner to the receptor.

In some embodiments, a chimeric receptor polypeptide comprises a GPCR, or any derivative, variant or fragment thereof, selected from Class A Orphans; Class B Orphans; Class C Orphans; taste receptors, type 1; taste receptors, type 2; 5-hydroxytryptamine receptors; acetylcholine receptors (muscarinic); adenosine receptors; adhesion class GPCRs; adrenoceptors; angiotensin receptors; apelin receptor; bile acid receptor; bombesin receptors; bradykinin receptors; calcitonin receptors; calcium-sensing receptors; cannabinoid receptors; chemerin receptor; chemokine receptors; cholecystokinin receptors; class Frizzled GPCRs (e.g., Wnt receptors); complement peptide receptors; corticotropin-releasing factor receptors; dopamine receptors; endothelin receptors; G protein-coupled estrogen receptor; formylpeptide receptors; free fatty acid receptors; GABAB receptors; galanin receptors; ghrelin receptor; glucagon receptor family; glycoprotein hormone receptors; gonadotrophin-releasing hormone receptors; GPR18, GPR55 and GPR119; histamine receptors; hydroxycarboxylic acid receptors; kisspeptin receptor; leukotriene receptors; lysophospholipid (LPA) receptors; lysophospholipid (SiP) receptors; melanin-concentrating hormone receptors; melanocortin receptors; melatonin receptors; metabotropic glutamate receptors; motilin receptor; neuromedin U receptors; neuropeptide FF/neuropeptide AF receptors; neuropeptide S receptor; neuropeptide W/neuropeptide B receptors; neuropeptide Y receptors; neurotensin receptors; opioid receptors; orexin receptors; oxoglutarate receptor; P2Y receptors; parathyroid hormone receptors; platelet-activating factor receptor; prokineticin receptors; prolactin-releasing peptide receptor; prostanoid receptors; proteinase-activated receptors; QRFP receptor; relaxin family peptide receptors; somatostatin receptors; succinate receptor; tachykinin receptors; thyrotropin-releasing hormone receptors; trace amine receptor; urotensin receptor; vasopressin and oxytocin receptors; VIP and PACAP receptors.

In some embodiments, a chimeric receptor polypeptide comprises a GPCR selected from the group consisting of: 5-hydroxytryptamine (serotonin) receptor 1A (HTR1A), 5-hydroxytryptamine (serotonin) receptor 1B (HTR1B), 5-hydroxytryptamine (serotonin) receptor 1D (HTR1D), 5-hydroxytryptamine (serotonin) receptor 1E (HTR1E), 5-hydroxytryptamine (serotonin) receptor 1F (HTR1F), 5-hydroxytryptamine (serotonin) receptor 2A (HTR2A), 5-hydroxytryptamine (serotonin) receptor 2B (HTR2B), 5-hydroxytryptamine (serotonin) receptor 2C (HTR2C), 5-hydroxytryptamine (serotonin) receptor 4 (HTR4), 5-hydroxytryptamine (serotonin) receptor 5A (HTR5A), 5-hydroxytryptamine (serotonin) receptor 5B (HTR5BP), 5-hydroxytryptamine (serotonin) receptor 6 (HTR6), 5-hydroxytryptamine (serotonin) receptor 7, adenylate cyclase-coupled (HTR7), cholinergic receptor, muscarinic 1 (CHRM1), cholinergic receptor, muscarinic 2 (CHRM2), cholinergic receptor, muscarinic 3 (CHRM3), cholinergic receptor, muscarinic 4 (CHRM4), cholinergic receptor, muscarinic 5 (CHRM5), adenosine A1 receptor (ADORA1), adenosine A2a receptor (ADORA2A), adenosine A2b receptor (ADORA2B), adenosine A3 receptor (ADORA3), adhesion G protein-coupled receptor A1 (ADGRA1), adhesion G protein-coupled receptor A2 (ADGRA2), adhesion G protein-coupled receptor A3 (ADGRA3), adhesion G protein-coupled receptor B1 (ADGRB1), adhesion G protein-coupled receptor B2 (ADGRB2), adhesion G protein-coupled receptor B3 (ADGRB3), cadherin EGF LAG seven-pass G-type receptor 1 (CELSR1), cadherin EGF LAG seven-pass G-type receptor 2 (CELSR2), cadherin EGF LAG seven-pass G-type receptor 3 (CELSR3), adhesion G protein-coupled receptor D1 (ADGRD1), adhesion G protein-coupled receptor D2 (ADGRD2), adhesion G protein-coupled receptor E1 (ADGRE1), adhesion G protein-coupled receptor E2 (ADGRE2), adhesion G protein-coupled receptor E3 (ADGRE3), adhesion G protein-coupled receptor E4 (ADGRE4P), adhesion G protein-coupled receptor E5 (ADGRE5), adhesion G protein-coupled receptor F1 (ADGRF1), adhesion G protein-coupled receptor F2 (ADGRF2), adhesion G protein-coupled receptor F3 (ADGRF3), adhesion G protein-coupled receptor F4 (ADGRF4), adhesion G protein-coupled receptor F5 (ADGRF5), adhesion G protein-coupled receptor G1 (ADGRG1), adhesion G protein-coupled receptor G2 (ADGRG2), adhesion G protein-coupled receptor G3 (ADGRG3), adhesion G protein-coupled receptor G4 (ADGRG4), adhesion G protein-coupled receptor G5 (ADGRG5), adhesion G protein-coupled receptor G6 (ADGRG6), adhesion G protein-coupled receptor G7 (ADGRG7), adhesion G protein-coupled receptor L1 (ADGRL1), adhesion G protein-coupled receptor L2 (ADGRL2), adhesion G protein-coupled receptor L3 (ADGRL3), adhesion G protein-coupled receptor L4 (ADGRL4), adhesion G protein-coupled receptor V1 (ADGRV1), adrenoceptor alpha 1A (ADRA1A), adrenoceptor alpha 1B (ADRA1B), adrenoceptor alpha 1D (ADRA1D), adrenoceptor alpha 2A (ADRA2A), adrenoceptor alpha 2B (ADRA2B), adrenoceptor alpha 2C (ADRA2C), adrenoceptor beta 1 (ADRB1), adrenoceptor beta 2 (ADRB2), adrenoceptor beta 3 (ADRB3), angiotensin II receptor type 1 (AGTR1), angiotensin II receptor type 2 (AGTR2), apelin receptor (APLNR), G protein-coupled bile acid receptor 1 (GPBAR1), neuromedin B receptor (NMBR), gastrin releasing peptide receptor (GRPR), bombesin like receptor 3 (BRS3), bradykinin receptor B1 (BDKRB1), bradykinin receptor B2 (BDKRB2), calcitonin receptor (CALCR), calcitonin receptor like receptor (CALCRL), calcium sensing receptor (CASR), G protein-coupled receptor, class C (GPRC6A), cannabinoid receptor 1 (brain) (CNR1), cannabinoid receptor 2 (CNR2), chemerin chemokine-like receptor 1 (CMKLR1), chemokine (C-C motif) receptor 1 (CCR1), chemokine (C-C motif) receptor 2 (CCR2), chemokine (C-C motif) receptor 3 (CCR3), chemokine (C-C motif) receptor 4 (CCR4), chemokine (C-C motif) receptor 5 (gene/pseudogene) (CCR5), chemokine (C-C motif) receptor 6 (CCR6), chemokine (C-C motif) receptor 7 (CCR7), chemokine (C-C motif) receptor 8 (CCR8), chemokine (C-C motif) receptor 9 (CCR9), chemokine (C-C motif) receptor 10 (CCR10), chemokine (C-X-C motif) receptor 1 (CXCR1), chemokine (C-X-C motif) receptor 2 (CXCR2), chemokine (C-X-C motif) receptor 3 (CXCR3), chemokine (C-X-C motif) receptor 4 (CXCR4), chemokine (C-X-C motif) receptor 5 (CXCR5), chemokine (C-X-C motif) receptor 6 (CXCR6), chemokine (C-X3-C motif) receptor 1 (CX3CR1), chemokine (C motif) receptor 1 (XCR1), atypical chemokine receptor 1 (Duffy blood group) (ACKR1), atypical chemokine receptor 2 (ACKR2), atypical chemokine receptor 3 (ACKR3), atypical chemokine receptor 4 (ACKR4), chemokine (C-C motif) receptor-like 2 (CCRL2), cholecystokinin A receptor (CCKAR), cholecystokinin B receptor (CCKBR), G protein-coupled receptor 1 (GPR1), bombesin like receptor 3 (BRS3), G protein-coupled receptor 3 (GPR3), G protein-coupled receptor 4 (GPR4), G protein-coupled receptor 6 (GPR6), G protein-coupled receptor 12 (GPR12), G protein-coupled receptor 15 (GPR15), G protein-coupled receptor 17 (GPR17), G protein-coupled receptor 18 (GPR18), G protein-coupled receptor 19 (GPR19), G protein-coupled receptor 20 (GPR20), G protein-coupled receptor 21 (GPR21), G protein-coupled receptor 22 (GPR22), G protein-coupled receptor 25 (GPR25), G protein-coupled receptor 26 (GPR26), G protein-coupled receptor 27 (GPR27), G protein-coupled receptor 31 (GPR31), G protein-coupled receptor 32 (GPR32), G protein-coupled receptor 33 (gene/pseudogene) (GPR33), G protein-coupled receptor 34 (GPR34), G protein-coupled receptor 35 (GPR35), G protein-coupled receptor 37 (endothelin receptor type B-like) (GPR37), G protein-coupled receptor 37 like 1 (GPR37L1), G protein-coupled receptor 39 (GPR39), G protein-coupled receptor 42 (gene/pseudogene) (GPR42), G protein-coupled receptor 45 (GPR45), G protein-coupled receptor 50 (GPR50), G protein-coupled receptor 52 (GPR52), G protein-coupled receptor 55 (GPR55), G protein-coupled receptor 61 (GPR61), G protein-coupled receptor 62 (GPR62), G protein-coupled receptor 63 (GPR63), G protein-coupled receptor 65 (GPR65), G protein-coupled receptor 68 (GPR68), G protein-coupled receptor 75 (GPR75), G protein-coupled receptor 78 (GPR78), G protein-coupled receptor 79 (GPR79), G protein-coupled receptor 82 (GPR82), G protein-coupled receptor 83 (GPR83), G protein-coupled receptor 84 (GPR84), G protein-coupled receptor 85 (GPR85), G protein-coupled receptor 87 (GPR87), G protein-coupled receptor 88 (GPR88), G protein-coupled receptor 101 (GPR101), G protein-coupled receptor 119 (GPR119), G protein-coupled receptor 132 (GPR132), G protein-coupled receptor 135 (GPR135), G protein-coupled receptor 139 (GPR139), G protein-coupled receptor 141 (GPR141), G protein-coupled receptor 142 (GPR142), G protein-coupled receptor 146 (GPR146), G protein-coupled receptor 148 (GPR148), G protein-coupled receptor 149 (GPR149), G protein-coupled receptor 150 (GPR150), G protein-coupled receptor 151 (GPR151), G protein-coupled receptor 152 (GPR152), G protein-coupled receptor 153 (GPR153), G protein-coupled receptor 160 (GPR160), G protein-coupled receptor 161 (GPR161), G protein-coupled receptor 162 (GPR162), G protein-coupled receptor 171 (GPR171), G protein-coupled receptor 173 (GPR173), G protein-coupled receptor 174 (GPR174), G protein-coupled receptor 176 (GPR176), G protein-coupled receptor 182 (GPR182), G protein-coupled receptor 183 (GPR183), leucine-rich repeat containing G protein-coupled receptor 4 (LGR4), leucine-rich repeat containing G protein-coupled receptor 5 (LGR5), leucine-rich repeat containing G protein-coupled receptor 6 (LGR6), MAS1 proto-oncogene (MAS1), MAS1 proto-oncogene like (MAS1L), MAS related GPR family member D (MRGPRD), MAS related GPR family member E (MRGPRE), MAS related GPR family member F (MRGPRF), MAS related GPR family member G (MRGPRG), MAS related GPR family member X1 (MRGPRX1), MAS related GPR family member X2 (MRGPRX2), MAS related GPR family member X3 (MRGPRX3), MAS related GPR family member X4 (MRGPRX4), opsin 3 (OPN3), opsin 4 (OPN4), opsin 5 (OPN5), purinergic receptor P2Y (P2RY8), purinergic receptor P2Y (P2RY10), trace amine associated receptor 2 (TAAR2), trace amine associated receptor 3 (gene/pseudogene) (TAAR3), trace amine associated receptor 4 (TAAR4P), trace amine associated receptor 5 (TAAR5), trace amine associated receptor 6 (TAAR6), trace amine associated receptor 8 (TAAR8), trace amine associated receptor 9 (gene/pseudogene) (TAAR9), G protein-coupled receptor 156 (GPR156), G protein-coupled receptor 158 (GPR158), G protein-coupled receptor 179 (GPR179), G protein-coupled receptor, class C (GPRC5A), G protein-coupled receptor, class C (GPRC5B), G protein-coupled receptor, class C (GPRC5C), G protein-coupled receptor, class C (GPRC5D), frizzled class receptor 1 (FZD1), frizzled class receptor 2 (FZD2), frizzled class receptor 3 (FZD3), frizzled class receptor 4 (FZD4), frizzled class receptor 5 (FZD5), frizzled class receptor 6 (FZD6), frizzled class receptor 7 (FZD7), frizzled class receptor 8 (FZD8), frizzled class receptor 9 (FZD9), frizzled class receptor 10 (FZD10), smoothened, frizzled class receptor (SMO), complement component 3a receptor 1 (C3AR1), complement component 5a receptor 1 (C5AR1), complement component 5a receptor 2 (C5AR2), corticotropin releasing hormone receptor 1 (CRHR1), corticotropin releasing hormone receptor 2 (CRHR2), dopamine receptor D1 (DRD1), dopamine receptor D2 (DRD2), dopamine receptor D3 (DRD3), dopamine receptor D4 (DRD4), dopamine receptor D5 (DRD5), endothelin receptor type A (EDNRA), endothelin receptor type B (EDNRB), formyl peptide receptor 1 (FPR1), formyl peptide receptor 2 (FPR2), formyl peptide receptor 3 (FPR3), free fatty acid receptor 1 (FFAR1), free fatty acid receptor 2 (FFAR2), free fatty acid receptor 3 (FFAR3), free fatty acid receptor 4 (FFAR4), G protein-coupled receptor 42 (gene/pseudogene) (GPR42), gamma-aminobutyric acid (GABA) B receptor, 1 (GABBR1), gamma-aminobutyric acid (GABA) B receptor, 2 (GABBR2), galanin receptor 1 (GALR1), galanin receptor 2 (GALR2), galanin receptor 3 (GALR3), growth hormone secretagogue receptor (GHSR), growth hormone releasing hormone receptor (GHRHR), gastric inhibitory polypeptide receptor (GIPR), glucagon like peptide 1 receptor (GLP1R), glucagon-like peptide 2 receptor (GLP2R), glucagon receptor (GCGR), secretin receptor (SCTR), follicle stimulating hormone receptor (FSHR), luteinizing hormone/choriogonadotropin receptor (LHCGR), thyroid stimulating hormone receptor (TSHR), gonadotropin releasing hormone receptor (GNRHR), gonadotropin releasing hormone receptor 2 (pseudogene) (GNRHR2), G protein-coupled receptor 18 (GPR18), G protein-coupled receptor 55 (GPR55), G protein-coupled receptor 119 (GPR119), G protein-coupled estrogen receptor 1 (GPER1), histamine receptor H1 (HR1), histamine receptor H2 (HRH2), histamine receptor H3 (HRH3), histamine receptor H4 (HRH4), hydroxycarboxylic acid receptor 1 (HCAR1), hydroxycarboxylic acid receptor 2 (HCAR2), hydroxycarboxylic acid receptor 3 (HCAR3), KISS1 receptor (KISS1R), leukotriene B4 receptor (LTB4R), leukotriene B4 receptor 2 (LTB4R2), cysteinyl leukotriene receptor 1 (CYSLTR1), cysteinyl leukotriene receptor 2 (CYSLTR2), oxoeicosanoid (OXE) receptor 1 (OXER1), formyl peptide receptor 2 (FPR2), lysophosphatidic acid receptor 1 (LPAR1), lysophosphatidic acid receptor 2 (LPAR2), lysophosphatidic acid receptor 3 (LPAR3), lysophosphatidic acid receptor 4 (LPAR4), lysophosphatidic acid receptor 5 (LPAR5), lysophosphatidic acid receptor 6 (LPAR6), sphingosine-1-phosphate receptor 1 (S1PR1), sphingosine-1-phosphate receptor 2 (S1PR2), sphingosine-1-phosphate receptor 3 (SIPR3), sphingosine-1-phosphate receptor 4 (SIPR4), sphingosine-1-phosphate receptor 5 (S1PR5), melanin concentrating hormone receptor 1 (MCHR1), melanin concentrating hormone receptor 2 (MCHR2), melanocortin 1 receptor (alpha melanocyte stimulating hormone receptor) (MC1R), melanocortin 2 receptor (adrenocorticotropic hormone) (MC2R), melanocortin 3 receptor (MC3R), melanocortin 4 receptor (MC4R), melanocortin 5 receptor (MC5R), melatonin receptor 1A (MTNR1A), melatonin receptor 1B (MTNR1B), glutamate receptor, metabotropic 1 (GRM1), glutamate receptor, metabotropic 2 (GRM2), glutamate receptor, metabotropic 3 (GRM3), glutamate receptor, metabotropic 4 (GRM4), glutamate receptor, metabotropic 5 (GRM5), glutamate receptor, metabotropic 6 (GRM6), glutamate receptor, metabotropic 7 (GRM7), glutamate receptor, metabotropic 8 (GRM8), motilin receptor (MLNR), neuromedin U receptor 1 (NMUR1), neuromedin U receptor 2 (NMUR2), neuropeptide FF receptor 1 (NPFFR1), neuropeptide FF receptor 2 (NPFFR2), neuropeptide S receptor 1 (NPSR1), neuropeptides B/W receptor 1 (NPBWR1), neuropeptides B/W receptor 2 (NPBWR2), neuropeptide Y receptor Y1 (NPY1R), neuropeptide Y receptor Y2 (NPY2R), neuropeptide Y receptor Y4 (NPY4R), neuropeptide Y receptor Y5 (NPY5R), neuropeptide Y receptor Y6 (pseudogene) (NPY6R), neurotensin receptor 1 (high affinity) (NTSR1), neurotensin receptor 2 (NTSR2), opioid receptor, delta 1 (OPRD1), opioid receptor, kappa 1 (OPRK1), opioid receptor, mu 1 (OPRM1), opiate receptor-like 1 (OPRL1), hypocretin (orexin) receptor 1 (HCRTR1), hypocretin (orexin) receptor 2 (HCRTR2), G protein-coupled receptor 107 (GPR107), G protein-coupled receptor 137 (GPR137), olfactory receptor family 51 subfamily E member 1 (OR51E1), transmembrane protein, adipocyte associated 1 (TPRA1), G protein-coupled receptor 143 (GPR143), G protein-coupled receptor 157 (GPR157), oxoglutarate (alpha-ketoglutarate) receptor 1 (OXGR1), purinergic receptor P2Y (P2RY1), purinergic receptor P2Y (P2RY2), pyrimidinergic receptor P2Y (P2RY4), pyrimidinergic receptor P2Y (P2RY6), purinergic receptor P2Y (P2RY11), purinergic receptor P2Y (P2RY12), purinergic receptor P2Y (P2RY13), purinergic receptor P2Y (P2RY14), parathyroid hormone 1 receptor (PTH1R), parathyroid hormone 2 receptor (PTH2R), platelet-activating factor receptor (PTAFR), prokineticin receptor 1 (PROKR1), prokineticin receptor 2 (PROKR2), prolactin releasing hormone receptor (PRLHR), prostaglandin D2 receptor (DP) (PTGDR), prostaglandin D2 receptor 2 (PTGDR2), prostaglandin E receptor 1 (PTGER1), prostaglandin E receptor 2 (PTGER2), prostaglandin E receptor 3 (PTGER3), prostaglandin E receptor 4 (PTGER4), prostaglandin F receptor (PTGFR), prostaglandin 12 (prostacyclin) receptor (IP) (PTGIR), thromboxane A2 receptor (TBXA2R), coagulation factor II thrombin receptor (F2R), F2R like trypsin receptor 1 (F2RL1), coagulation factor II thrombin receptor like 2 (F2RL2), F2R like thrombin/trypsin receptor 3 (F2RL3), pyroglutamylated RFamide peptide receptor (QRFPR), relaxin/insulin-like family peptide receptor 1 (RXFP1), relaxin/insulin-like family peptide receptor 2 (RXFP2), relaxin/insulin-like family peptide receptor 3 (RXFP3), relaxin/insulin-like family peptide receptor 4 (RXFP4), somatostatin receptor 1 (SSTR1), somatostatin receptor 2 (SSTR2), somatostatin receptor 3 (SSTR3), somatostatin receptor 4 (SSTR4), somatostatin receptor 5 (SSTR5), succinate receptor 1 (SUCNR1), tachykinin receptor 1 (TACR1), tachykinin receptor 2 (TACR2), tachykinin receptor 3 (TACR3), taste 1 receptor member 1 (TAS1R1), taste 1 receptor member 2 (TAS1R2), taste 1 receptor member 3 (TAS1R3), taste 2 receptor member 1 (TAS2R1), taste 2 receptor member 3 (TAS2R3), taste 2 receptor member 4 (TAS2R4), taste 2 receptor member 5 (TAS2R5), taste 2 receptor member 7 (TAS2R7), taste 2 receptor member 8 (TAS2R8), taste 2 receptor member 9 (TAS2R9), taste 2 receptor member 10 (TAS2R10), taste 2 receptor member 13 (TAS2R13), taste 2 receptor member 14 (TAS2R14), taste 2 receptor member 16 (TAS2R16), taste 2 receptor member 19 (TAS2R19), taste 2 receptor member 20 (TAS2R20), taste 2 receptor member 30 (TAS2R30), taste 2 receptor member 31 (TAS2R31), taste 2 receptor member 38 (TAS2R38), taste 2 receptor member 39 (TAS2R39), taste 2 receptor member 40 (TAS2R40), taste 2 receptor member 41 (TAS2R41), taste 2 receptor member 42 (TAS2R42), taste 2 receptor member 43 (TAS2R43), taste 2 receptor member 45 (TAS2R45), taste 2 receptor member 46 (TAS2R46), taste 2 receptor member 50 (TAS2R50), taste 2 receptor member 60 (TAS2R60), thyrotropin-releasing hormone receptor (TRHR), trace amine associated receptor 1 (TAAR1), urotensin 2 receptor (UTS2R), arginine vasopressin receptor 1A (AVPR1A), arginine vasopressin receptor 1B (AVPR1B), arginine vasopressin receptor 2 (AVPR2), oxytocin receptor (OXTR), adenylate cyclase activating polypeptide 1 (pituitary) receptor type I (ADCYAP1R1), vasoactive intestinal peptide receptor 1 (VIPR1), vasoactive intestinal peptide receptor 2 (VIPR2), any derivative thereof, any variant thereof, and any fragment thereof.

A chimeric receptor polypeptide comprising a GPCR, or any derivative, variant or fragment thereof, can bind an antigen comprising any suitable GPCR ligand, or any derivative, variant or fragment thereof. Non-limiting examples of ligands which can be bound by a GPCR include (−)-adrenaline, (−)-noradrenaline, (lyso)phospholipid mediators, [des-Arg10]kallidin, [des-Arg9]bradykinin, [des-Gln14]ghrelin, [Hyp3]bradykinin, [Leu]enkephalin, [Met]enkephalin, 12-hydroxyheptadecatrienoic acid, 12R-HETE, 12S-HETE, 12S-HPETE, 15S-HETE, 17β-estradiol, 20-hydroxy-LTB4, 2-arachidonoylglycerol, 2-oleoyl-LPA, 3-hydroxyoctanoic acid, 5-hydroxytryptamine, 5-oxo-15-HETE, 5-oxo-ETE, 5-oxo-ETrE, 5-oxo-ODE, 5S-HETE, 5S-HPETE, 7α,25-dihydroxycholesterol, acetylcholine, ACTH, adenosine diphosphate, adenosine, adrenomedullin 2/intermedin, adrenomedullin, amylin, anandamide, angiotensin II, angiotensin III, annexin I, apelin receptor early endogenous ligand, apelin-13, apelin-17, apelin-36, aspirin triggered lipoxin A4, aspirin-triggered resolvin D1, ATP, beta-defensin 4A, big dynorphin, bovine adrenal medulla peptide 8-22, bradykinin, C3a, C5a, Ca2+, calcitonin gene related peptide, calcitonin, cathepsin G, CCK-33, CCK-4, CCK-8, CCL1, CCL11, CCL13, CCL14, CCL15, CCL16, CCL17, CCL19, CCL2, CCL20, CCL21, CCL22, CCL23, CCL24, CCL25, CCL26, CCL27, CCL28, CCL3, CCL4, CCL5, CCL7, CCL8, chemerin, chenodeoxycholic acid, cholic acid, corticotrophin-releasing hormone, CST-17, CX3CL1, CXCL1, CXCL10, CXCL11, CXCL12a, CXCL120, CXCL13, CXCL16, CXCL2, CXCL3, CXCL5, CXCL6, CXCL7, CXCL8, CXCL9, cysteinyl-leukotrienes (CysLTs), uracil nucleotides, deoxycholic acid, dihydrosphingosine-1-phosphate, dioleoylphosphatidic acid, dopamine, dynorphin A, dynorphin A-(1-13), dynorphin A-(1-8), dynorphin B, endomorphin-1, endothelin-1, endothelin-2, endothelin-3, F2L, Free fatty acids, FSH, GABA, galanin, galanin-like peptide, gastric inhibitory polypeptide, gastrin-17, gastrin-releasing peptide, ghrelin, GHRH, glucagon, glucagon-like peptide 1-(7-36) amide, glucagon-like peptide 1-(7-37), glucagon-like peptide 2, glucagon-like peptide 2-(3-33), GnRH I, GnRH II, GRP-(18-27), hCG, histamine, humanin, INSL3, INSL5, kallidin, kisspeptin-10, kisspeptin-13, kisspeptin-14, kisspeptin-54, kynurenic acid, large neuromedin N, large neurotensin, L-glutamic acid, LH, lithocholic acid, L-lactic acid, long chain carboxylic acids, LPA, LTB4, LTC4, LTD4, LTE4, LXA4, Lys-[Hyp3]-bradykinin, lysophosphatidylinositol, lysophosphatidylserine, Medium-chain-length fatty acids, melanin-concentrating hormone, melatonin, methylcarbamyl PAF, Mg2+, motilin, N-arachidonoylglycine, neurokinin A, neurokinin B, neuromedin B, neuromedin N, neuromedin S-33, neuromedin U-25, neuronostatin, neuropeptide AF, neuropeptide B-23, neuropeptide B-29, neuropeptide FF, neuropeptide S, neuropeptide SF, neuropeptide W-23, neuropeptide W-30, neuropeptide Y, neuropeptide Y-(3-36), neurotensin, nociceptin/orphanin FQ, N-oleoylethanolamide, obestatin, octopamine, orexin-A, orexin-B, Oxysterols, oxytocin, PACAP-27, PACAP-38, PAF, pancreatic polypeptide, peptide YY, PGD2, PGE2, PGF2α, PGI2, PGJ2, PHM, phosphatidylserine, PHV, prokineticin-1, prokineticin-2, prokineticin-2β, prosaposin, PrRP-20, PrRP-31, PTH, PTHrP, PTHrP-(1-36), QRFP43, relaxin, relaxin-1, relaxin-3, resolvin D1, resolvin E1, RFRP-1, RFRP-3, R-spondins, secretin, serine proteases, sphingosine 1-phosphate, sphingosylphosphorylcholine, SRIF-14, SRIF-28, substance P, succinic acid, thrombin, thromboxane A2, TIP39, T-kinin, TRH, TSH, tyramine, UDP-glucose, uridine diphosphate, urocortin 1, urocortin 2, urocortin 3, urotensin II-related peptide, urotensin-II, vasopressin, VIP, Wnt, Wnt-1, Wnt-10a, Wnt-10b, Wnt-11, Wnt-16, Wnt-2, Wnt-2b, Wnt-3, Wnt-3a, Wnt-4, Wnt-5a, Wnt-5b, Wnt-6, Wnt-7a, Wnt-7b, Wnt-8a, Wnt-8b, Wnt-9a, Wnt-9b, XCL1, XCL2, Zn2+, α-CGRP, α-ketoglutaric acid, α-MSH, α-neoendorphin, β-alanine, β-CGRP, β-D-hydroxybutyric acid, β-endorphin, β-MSH, β-neoendorphin, β-phenylethylamine, and γ-MSH.

In some embodiments, a chimeric receptor polypeptide comprises an integrin receptor, an integrin receptor subunit, or any derivative, variant or fragment thereof. Integrin receptors are transmembrane receptors that can function as bridges for cell-cell and cell-extracellular matrix (ECM) interactions. Integrin receptors are generally formed as heterodimers consisting of an α subunit and a β subunit which associate non-covalently. There exist at least 18 α subunits and at least 8 β subunits. Each subunit generally comprises an extracellular region (e.g., ligand binding domain), a region spanning a membrane, and an intracellular region (e.g., cytoplasmic domain). In some embodiments, a chimeric receptor polypeptide comprises at least an extracellular region (e.g., ligand binding domain) of an integrin subunit (e.g., α subunit or β subunit), or any derivative, variant or fragment thereof. In some embodiments, a chimeric receptor polypeptide comprises at least a region spanning a membrane of an integrin subunit (e.g., a subunit or R subunit), or any derivative, variant or fragment thereof. In some embodiments, a chimeric receptor polypeptide comprises at least an intracellular region (e.g., cytoplasmic domain) of an integrin subunit (e.g., a subunit or β subunit), or any derivative, variant or fragment thereof. A chimeric receptor polypeptide comprising an integrin subunit, or any derivative, variant or fragment thereof, can recruit a binding partner. In some embodiments, ligand binding to a chimeric receptor comprising an integrin subunit, or any derivative, variant or fragment thereof, results in a conformational change, chemical modification, or combination thereof, which recruits a binding partner to the receptor.

In some embodiments, a chimeric receptor polypeptide comprises an integrin receptor a subunit, or any derivative, variant or fragment thereof, selected from the group consisting of: α1, α2, α3, α4, α5, α6, α7, α8, α9, α10, α11, αV, αL, αM, αX, αD, αE, and αIIb. In some embodiments, a chimeric receptor polypeptide comprises an integrin receptor β subunit, or any derivative, variant or fragment thereof, selected from the group consisting of: β1, β2, β3, β4, β5, β6, β7, and β8. Chimeric receptor polypeptides comprising an α subunit, a β subunit, or any derivative, variant or fragment thereof, can heterodimerize (e.g., a subunit dimerizing with a subunit) to form an integrin receptor, or any derivative, variant or fragment thereof. Non-limiting examples of integrin receptors include an α1β1, α2β1, α3β1, α4β1, α5β1, α6β1, α7β1, α8β1, α9β1, α10β1, αVβ1, αLβ1, αMβ1, αX1β1, αD1β1, αIIbβ1, αEβ1, α1β2, α2β2, α3β2, α4β2, α5β2, α6β2, α7β2, α8β2, α9β2, α10α2, αVβ2, αLβ2, αMβ2, αXβ2, αDβ2, αIIbβ2, αEβ2, α1β3, α2β3, α3β3, α4β3, α5β3, α6β3, α7β3, α8β3, α9β3, α10β3, αVβ3, αLβ, αMβ, αXβ, αDβ3, αIIbβ3, αEβ, α1β4, α2β4, α3β4, α4β4, α5β4, α6β4, α7β4, α8β4, α9β4, α10β4, αVβ4, αLβ4, αMβ4, αXβ4, αDβ4, αIIbβ4, αEβ4, α1β5, α2β5, α3β5, α4β5, α5β5, α6β5, α7β5, α8β5, α9β5, α10β5, αVβ5, αLβ5, αMβ5, αXβ5, αDβ5, αIIbβ5, αEβ5, α1β6, α2β6, α3β6, α4β6, α5β6, α6β6, α7β6, α8β6, α9β6, α10β6, αVβ6, αLβ6, αMβ6, αXβ6, αDβ6, αIIbβ6, αEβ6, α1β7, α2β7, α3β7, α4β7, α5β7, α6β7, α7β7, α8β7, α9β7, α10β7, αVβ7, αLβ7, αMβ7, αXβ7, αDβ7, αIIbβ7, αEβ7, α1β8, α2β8, α3β8, α4β8, α5β8, α6β8, α7β8, α8β8, α9β8, α10β8, αVβ8, αLβ8, αMβ8, αXβ8, αDβ8, αIIbβ8, and αEβ8 receptor. A chimeric receptor polypeptide comprising an integrin subunit, or any derivative, variant or fragment thereof, can dimerize with an endogenous integrin subunit (e.g., wild-type integrin subunit).

A chimeric receptor polypeptide comprising an integrin subunit, or any derivative, variant or fragment thereof, can bind an antigen comprising any suitable integrin ligand, or any derivative, variant or fragment thereof. Non-limiting examples of ligands which can be bound by an integrin receptor include adenovirus penton base protein, beta-glucan, bone sialoprotein (BSP), *Borrelia burgdorferi, Candida albicans*, collagens (CN, e.g., CNI-IV), cytotactin/tenascin-C, decorsin, denatured collagen, disintegrins, E-cadherin, echovirus 1 receptor, epiligrin, Factor X, Fc epsilon RII (CD23), fibrin (Fb), fibrinogen (Fg), fibronectin (Fn), heparin, HIV Tat protein, iC3b, intercellular adhesion molecule (e.g., ICAM-1,2,3,4,5), invasin, L1 cell adhesion molecule (L1-CAM), laminin, lipopolysaccharide (LPS), MAdCAM-1, matrix metalloproteinase-2 (MMPe), neutrophil inhibitory factor (NIF), osteopontin (OP or OPN), plasminogen, prothrombin, sperm fertilin, thrombospondin (TSP), vascular cell adhesion molecule 1 (VCAM-1), vitronectin (VN or VTN), and von Willebrand factor (vWF).

In some embodiments, a chimeric receptor polypeptide comprises a cadherin molecule, or any derivative, variant or fragment thereof. Cadherin molecules, which can function as both ligands and receptors, refer to certain proteins involved in mediating cell adhesion. Cadherin molecules generally consist of five tandem repeated extracellular domains, a single membrane-spanning segment and a cytoplasmic region. E-cadherin, or CDH1, for example, consists of 5 repeats in the extracellular domain, one transmembrane domain, and an intracellular domain.

When E-cadherin is phosphorylated at a region of the intracellular domain, adaptor proteins such as beta-catenin and β120-catenin can bind to the receptor. In some embodiments, a chimeric receptor polypeptide comprises at least an extracellular region of a cadherin, or any derivative, variant or fragment thereof. In some embodiments, a chimeric receptor polypeptide comprises at least a region spanning a membrane of a cadherin, or any derivative, variant or fragment thereof. In some embodiments, a chimeric receptor polypeptide comprises at least an intracellular region (e.g., cytoplasmic domain) of a cadherin, or any derivative, variant or fragment thereof. A chimeric receptor polypeptide comprising a cadherin, or any derivative, variant or fragment thereof, can recruit a binding partner. In some embodiments, ligand binding to a chimeric receptor comprising a cadherin, or any derivative, variant or fragment thereof, results in a conformational change, chemical modification, combination thereof, which recruits a binding partner to the receptor.

A chimeric receptor polypeptide can comprise a cadherin, or any derivative, variant or fragment thereof, selected from a classical cadherin, a desmosoma cadherin, a protocadherin, and an unconventional cadherin. In some embodiments, a chimeric receptor polypeptide comprises a classical cadherin, or any derivative, variant or fragment thereof, selected from CDH1 (E-cadherin, epithelial), CDH2 (N-cadherin, neural), CDH12 (cadherin 12, type 2, N-cadherin 2), and CDH3 (P-cadherin, placental). In some embodiments, a chimeric receptor polypeptide comprises a desmosoma cadherin, or any derivative, variant or fragment thereof, selected from desmoglein (DSG1, DSG2, DSG3, DSG4) and desmocollin (DSC1, DSC2, DSC3). In some embodiments, a chimeric receptor polypeptide comprises a protocadherin, or any derivative, variant or fragment thereof, selected from PCDH1, PCDH10, PCDH11X, PCDH11Y, PCDH12, PCDH15, PCDH17, PCDH18, PCDH19, PCDH20, PCDH7, PCDH8, PCDH9, PCDHA1, PCDHA10, PCDHA11, PCDHA12, PCDHA13, PCDHA2, PCDHA3, PCDHA4, PCDHA5, PCDHA6, PCDHA7, PCDHA8, PCDHA9, PCDHAC1, PCDHAC2, PCDHB1, PCDHB10, PCDHB11, PCDHB12, PCDHB13, PCDHB14, PCDHB15, PCDHB16, PCDHB17, PCDHB18, PCDHB2, PCDHB3, PCDHB4, PCDHB5, PCDHB6, PCDHB7, PCDHB8, PCDHB9, PCDHGA1, PCDHGA10, PCDHGA11, PCDHGA12, PCDHGA2, PCDHGA3, PCDHGA4, PCDHGA5, PCDHGA6, PCDHGA7, PCDHGA8, PCDHGA9, PCDHGB1, PCDHGB2, PCDHGB3, PCDHGB4, PCDHGB5, PCDHGB6, PCDHGB7, PCDHGC3, PCDHGC4, PCDHGC5, FAT, FAT2, and FAT). In some embodiments, a chimeric receptor polypeptide comprises an unconventional cadherin selected from CDH4 (R-cadherin, retinal), CDH5 (VE-cadherin, vascular endothelial), CDH6 (K-cadherin, kidney), CDH7 (cadherin 7, type 2), CDH8 (cadherin 8, type 2), CDH9 (cadherin 9, type 2, T1-cadherin), CDH10 (cadherin 10, type 2, T2-cadherin), CDH11 (OB-cadherin, osteoblast), CDH13 (T-cadherin, H-cadherin, heart), CDH15 (M-cadherin, myotubule), CDH16 (KSP-cadherin), CDH17 (LI cadherin, liver-intestine), CDH18 (cadherin 18, type 2), CDH19 (cadherin 19, type 2), CDH20 (cadherin 20, type 2), CDH23 (cadherin 23, neurosensory epithelium), CDH24, CDH26, CDH28, CELSR1, CELSR2, CELSR3, CLSTN1, CLSTN2, CLSTN3, DCHS1, DCHS2, LOC389118, PCLKC, RESDA1, and RET.

A chimeric receptor polypeptide comprising a cadherin, or any derivative, variant or fragment thereof, can bind an antigen comprising any suitable cadherin ligand, or any derivative, variant or fragment thereof. A cadherin ligand can comprise, for example, another cadherin receptor (e.g., a cadherin receptor of a cell).

In some embodiments, a chimeric receptor polypeptide comprises a catalytic receptor, or any derivative, variant or fragment thereof. Examples of catalytic receptors include, but are not limited to, receptor tyrosine kinases (RTKs) and receptor threonine/serine kinases (RTSKs). Catalytic receptors such as RTKs and RTSKs possess certain enzymatic activities. RTKs, for example, can phosphorylate substrate proteins on tyrosine residues which can then act as binding sites for adaptor proteins. RTKs generally comprise an N-terminal extracellular ligand-binding domain, a single transmembrane α helix, and a cytosolic C-terminal domain with protein-tyrosine kinase activity. Some RTKs consist of single polypeptides while some are dimers consisting of two pairs of polypeptide chains, for example the insulin receptor and some related receptors. The binding of ligands to the extracellular domains of these receptors can activate the cytosolic kinase domains, resulting in phosphorylation of both the receptors themselves and intracellular target proteins that propagate the signal initiated by ligand binding. In some RTKs, ligand binding induces receptor dimerization. Some ligands (e.g., growth factors such as PDGF and NGF) are themselves dimers consisting of two identical polypeptide chains. These growth factors can directly induce dimerization by simultaneously binding to two different receptor molecules. Other growth factors (e.g., such as EGF) are monomers but have two distinct receptor binding sites that can crosslink receptors. Ligand-induced dimerization can result in autophosphorylation of the receptor, wherein the dimerized polypeptide chains cross-phosphorylate one another. Some receptors can multimerize.

In some embodiments, a chimeric receptor polypeptide comprises at least an extracellular region (e.g., ligand binding domain) of a catalytic receptor such as a RTK, or any derivative, variant or fragment thereof. In some embodiments, a chimeric receptor polypeptide comprises at least a membrane spanning region of a catalytic receptor such as a RTK, or any derivative, variant or fragment thereof. In some embodiments, a chimeric receptor polypeptide comprises at least an intracellular region (e.g., cytosolic domain) of a catalytic receptor such as a RTK, or any derivative, variant or fragment thereof. A chimeric receptor polypeptide comprising an RTK, or any derivative, variant or fragment thereof, can recruit a binding partner. In some embodiments, ligand binding to a chimeric receptor comprising an RTK, or any derivative, variant or fragment thereof, results in a conformational change, chemical modification, or combination thereof, which recruits a binding partner to the receptor.

In some embodiments, the chimeric receptor polypeptide comprises a class I RTK (e.g., the epidermal growth factor (EGF) receptor family including EGFR; the ErbB family including ErbB-2, ErbB-3, and ErbB-4), a class II RTK (e.g., the insulin receptor family including INSR, IGF-1R, and IRR), a class III RTK (e.g., the platelet-derived growth factor (PDGF) receptor family including PDGFR-α, PDGFR-β, CSF-1R, KIT/SCFR, and FLK2/FLT3), a class IV RTK (e.g., the fibroblast growth factor (FGF) receptor family including FGFR-1, FGFR-2, FGFR-3, and FGFR-4), a class V RTK (e.g., the vascular endothelial growth factor (VEGF) receptor family including VEGFR1, VEGFR2, and VEGFR3), a class VI RTK (e.g., the hepatocyte growth factor (HGF) receptor family including hepatocyte growth factor receptor (HGFR/MET) and RON), a class VII RTK (e.g., the tropomyosin receptor kinase (Trk) receptor family including TRKA, TRKB, and TRKC), a class VIII RTK (e.g., the ephrin (Eph) receptor family including EPHA1, EPHA2, EPHA3, EPHA4, EPHA5, EPHA6, EPHA7, EPHA8, EPHB1, EPHB2, EPHB3, EPHB4, EPHB5, and EPHB6), a class IX RTK (e.g., AXL receptor family such as AXL, MER, and TRYO3), a class X RTK (e.g., LTK receptor family such as LTK and ALK), a class XI RTK (e.g., TIE receptor family such as TIE and TEK), a class XII RTK (e.g., ROR receptor family ROR1 and ROR2), a class XIII RTK (e.g., the discoidin domain receptor (DDR) family such as DDR1 and DDR2), a class XIV RTK (e.g., RET receptor family such as RET), a class XV RTK (e.g., KLG receptor family including PTK7), a class XVI RTK (e.g., RYK receptor family including Ryk), a class XVII RTK (e.g., MuSK receptor family such as MuSK), or any derivative, variant or fragment thereof.

A chimeric receptor polypeptide comprising a RTK, or any derivative, variant or fragment thereof, can bind an antigen comprising any suitable RTK ligand, or any derivative, variant or fragment thereof. Non limiting examples of RTK ligands include growth factors, cytokines, and hormones. Growth factors include, for example, members of the epidermal growth factor family (e.g., epidermal growth factor or EGF, heparin-binding EGF-like growth factor or HB-EGF, transforming growth factor-α or TGF-α, amphiregulin or AR, epiregulin or EPR, epigen, betacellulin or BTC, neuregulin-1 or NRG1, neuregulin-2 or NRG2, neuregulin-3 or NRG3, and neuregulin-4 or NRG4), the fibroblast growth factor family (e.g., FGF1, FGF2, FGF3, FGF4, FGF5, FGF6, FGF7, FGF8, FGF9, FGF10, FGF11, FGF12, FGF13, FGF14, FGF15/19, FGF16, FGF17, FGF18, FGF20, FGF21, and FGF23), the vascular endothelial growth factor family (e.g., VEGF-A, VEGF-B, VEGF-C, VEGF-D, and PlGF), and the platelet-derived growth factor family (e.g., PDGFA, PDGFB, PDGFC, and PDGFD). Hormones include, for example, members of the insulin/IGF/relaxin family (e.g., insulin, insulin-like growth factors, relaxin family peptides including relaxin1, relaxin2, relaxin3, Leydig cell-specific insulin-like peptide (gene INSL3), early placenta insulin-like peptide (ELIP) (gene INSL4), insulin-like peptide 5 (gene INSL5), and insulin-like peptide 6).

In some embodiments, a chimeric receptor polypeptide comprises at least an extracellular region (e.g., ligand binding domain) of a catalytic receptor such as an RTSK, or any derivative, variant or fragment thereof. In some embodiments, a chimeric receptor polypeptide comprises at least a membrane spanning region of a catalytic receptor such as an RTSK, or any derivative, variant or fragment thereof. In some embodiments, a chimeric receptor polypeptide comprises at least an intracellular region (e.g., cytosolic domain) of a catalytic receptor such as an RTSK, or any derivative, variant or fragment thereof. A chimeric receptor polypeptide comprising an RTSK, or any derivative, variant or fragment thereof, can recruit a binding partner. In some embodiments, ligand binding to a chimeric receptor comprising an RTSK, or any derivative, variant or fragment thereof, results in a conformational change, chemical modification, or combination thereof, which recruits a binding partner to the receptor.

A chimeric receptor polypeptide comprising an RTSK, or any derivative, variant or fragment thereof, can phosphorylate a substrate at serine and/or threonine residues, and may select specific residues based on a consensus sequence. A chimeric receptor polypeptide can comprise a type I RTSK, type II RTSK, or any derivative, variant or fragment thereof. In some embodiments, a chimeric receptor polypeptide comprising a type I receptor serine/threonine kinase is inactive unless complexed with a type II receptor. In some embodiments, a chimeric receptor polypeptide comprising a type II receptor serine/threonine comprises a constitutively active kinase domain that can phosphorylate and activate a type I receptor when complexed with the type I receptor. A type II receptor serine/threonine kinase can phosphorylate the kinase domain of the type I partner, causing displacement of protein partners. Displacement of protein partners can allow binding and phosphorylation of other proteins, for example certain members of the SMAD family. A chimeric receptor polypeptide can comprise a type I receptor, or any derivative, variant or fragment thereof, selected from the group consisting of: ALK1 (ACVRL1), ALK2 (ACVR1A), ALK3 (BMPR1A), ALK4 (ACVR1B), ALK5 (TGFβR1), ALK6 (BMPR1B), and ALK7 (ACVR1C). A chimeric receptor polypeptide can comprise a type II receptor, or any derivative, variant or fragment thereof, selected from the group consisting of: TGFβR2, BMPR2, ACVR2A, ACVR2B, and AMHR2 (AMHR). In some embodiments, a chimeric receptor polypeptide comprises a TGF-β receptor, or any derivative, variant or fragment thereof.

In some embodiments, a chimeric receptor polypeptide comprises a receptor which stimulates non-covalently associated intracellular kinases, such as a Src kinase (e.g., c-Src, Yes, Fyn, Fgr, Lck, Hck, Blk, Lyn, and Frk) or a JAK kinase (e.g., JAK1, JAK2, JAK3, and TYK2) rather than possessing intrinsic enzymatic activity, or any derivative, variant or fragment thereof. These include the cytokine receptor superfamily such as receptors for cytokines and polypeptide hormones. Cytokine receptors generally contain an N-terminal extracellular ligand-binding domain, transmembrane a helices, and a C-terminal cytosolic domain. The cytosolic domains of cytokine receptors are generally devoid of any known catalytic activity. Cytokine receptors instead can function in association with non-receptor kinases (e.g., tyrosine kinases or threonine/serine kinases), which can be activated as a result of ligand binding to the receptor. In some embodiments, a chimeric receptor polypeptide comprises at least an extracellular region (e.g., ligand binding domain) of a catalytic receptor that non-covalently associates with an intracellular kinase (e.g., a cytokine receptor), or any derivative, variant or fragment thereof. In some embodiments, a chimeric receptor polypeptide comprises at least a membrane spanning region of a catalytic receptor that non-covalently associates with an intracellular kinase (e.g., a cytokine receptor), or any derivative, variant or fragment thereof. In some embodiments, a chimeric receptor polypeptide comprises at least an intracellular region (e.g., cytosolic domain) of a catalytic receptor that non-covalently associates with an intracellular kinase (e.g., a cytokine receptor), or any derivative, variant or fragment thereof. A chimeric receptor polypeptide comprising a catalytic receptor that non-covalently associates with an intracellular kinase, or any derivative, variant or fragment thereof, can recruit a binding partner. In some embodiments, ligand binding to a chimeric receptor comprising a catalytic receptor that non-covalently associates with an intracellular kinase, or any derivative, variant or fragment thereof, results in a conformational change, chemical modification, or combination thereof, which recruits a binding partner to the receptor.

In some embodiments, a chimeric receptor polypeptide comprises a cytokine receptor, for example a type I cytokine receptor or a type II cytokine receptor, or any derivative, variant or fragment thereof. In some embodiments, the chimeric receptor polypeptide comprises an interleukin receptor (e.g., IL-2R, IL-3R, IL-4R, IL-5R, IL-6R, IL-7R, IL-9R, IL-11R, IL-12R, IL-13R, IL-15R, IL-21R, IL-23R, IL-27R, and IL-31R), a colony stimulating factor receptor (e.g., erythropoietin receptor, CSF-1R, CSF-2R, GM-CSFR, and G-CSFR), a hormone receptor/neuropeptide receptor (e.g., growth hormone receptor, prolactin receptor, and leptin receptor), or any derivative, variant or fragment thereof. In some embodiments, the chimeric receptor polypeptide comprises a type II cytokine receptor, or any derivative, variant or fragment thereof. In some embodiments, the chimeric receptor polypeptide comprises an interferon receptor (e.g., IFNAR1, IFNAR2, and IFNGR), an interleukin receptor (e.g., IL-10R, IL-20R, IL-22R, and IL-28R), a tissue factor receptor (also called platelet tissue factor), or any derivative, variant or fragment thereof.

A chimeric receptor polypeptide comprising a cytokine receptor can bind an antigen comprising any suitable cytokine receptor ligand, or any derivative, variant or fragment thereof. Non-limiting examples of cytokine receptor ligands include interleukins (e.g., IL-2, IL-3, IL-4, IL-5, IL-6, IL-7, IL-9, IL-10, IL-11, IL-12, IL-13, IL-15, IL-20, IL-21, IL-22, IL-23, IL-27, IL-28, and IL-31), interferons (e.g., IFN-α, IFN-β, IFN-γ), colony stimulating factors (e.g., erythropoietin, macrophage colony-stimulating factor, granulocyte macrophage colony-stimulating factors or GM-CSFs, and granulocyte colony-stimulating factors or G-CSFs), and hormones (e.g., prolactin and leptin).

In some embodiments, a chimeric receptor polypeptide comprises a death receptor, a receptor containing a death domain, or any derivative, variant or fragment thereof. Death receptors are often involved in regulating apoptosis and inflammation. Death receptors include members of the TNF receptor family such as TNFR1, Fas receptor, DR4 (also known as TRAIL receptor 1 or TRAILR1) and DR5 (also known as TRAIL receptor 2 or TRAILR2). In some embodiments, a chimeric receptor polypeptide comprises at least an extracellular region (e.g., ligand binding domain) of a death receptor, or any derivative, variant or fragment thereof. In some embodiments, a chimeric receptor polypeptide comprises at least a membrane spanning region of a death receptor, or any derivative, variant or fragment thereof. In some embodiments, a chimeric receptor polypeptide comprises at least an intracellular region (e.g., cytosolic) domain of a death receptor, or any derivative, variant or fragment thereof. A chimeric receptor polypeptide comprising a death receptor, or any derivative, variant or fragment thereof, can undergo receptor oligomerization in response to ligand binding, which in turn can result in the recruitment of specialized adaptor proteins and activation of signaling cascades, such as caspase cascades. In some embodiments, a chimeric receptor polypeptide comprises a death receptor, or any derivative, variant or fragment thereof, results in a conformational change, chemical modification, or combination thereof, which recruits a binding partner to the receptor.

A chimeric receptor polypeptide comprising a death receptor can bind an antigen comprising any suitable ligand of a death receptor, or any derivative, variant or fragment thereof. Non-limiting examples of ligands bound by death receptors include TNFα, Fas ligand, and TNF-related apoptosis-inducing ligand (TRAIL).

In some embodiments, a chimeric receptor polypeptide comprises an immune receptor, or any derivative, variant or fragment thereof. Immune receptors include members of the immunoglobulin superfamily (IgSF) which share structural features with immunoglobulins, e.g., a domain known as an immunoglobulin domain or fold. IgSF members include, but are not limited to, cell surface antigen receptors, co-receptors and costimulatory molecules of the immune system, and molecules involved in antigen presentation to lymphocytes. In some embodiments, a chimeric receptor polypeptide comprises at least an extracellular region (e.g., ligand binding domain) of an immune receptor, or any derivative, variant or fragment thereof. In some embodiments, a chimeric receptor polypeptide comprises at least a region spanning a membrane of an immune receptor, or any derivative, variant or fragment thereof. In some embodiments, a chimeric receptor polypeptide comprises at least an intracellular region (e.g., cytoplasmic domain) of an immune receptor, or any derivative, variant or fragment thereof. A chimeric receptor polypeptide comprising an immune receptor, or any derivative, variant or fragment thereof, can recruit a binding partner. In some embodiments, ligand binding to a chimeric receptor comprising an immune receptor, or any derivative, variant or fragment thereof, results in a conformational change, chemical modification, or combination thereof, which recruits a binding partner to the receptor.

In some embodiments, a chimeric receptor polypeptide comprises a cell surface antigen receptor such as a T cell receptor (TCR), a B cell receptor (BCR), or any derivative, variant or fragment thereof. T cell receptors generally comprise two chains, either the TCR-alpha and -beta chains or the TCR-delta and -gamma chains. A chimeric receptor polypeptide comprising a TCR, or any derivative, variant or fragment thereof, can bind a major histocompatibility complex (MHC) protein. B cell receptors generally comprises a membrane bound immunoglobulin and a signal transduction moiety. A chimeric receptor comprising a BCR, or any derivative, variant or fragment thereof, can bind a cognate BCR antigen. In some embodiments, a chimeric receptor polypeptide comprises at least an immunoreceptor tyrosine-based activation motif (ITAM) found in the cytoplasmic domain of certain immune receptors. In some embodiments, a chimeric receptor polypeptide comprises at least an immunoreceptor tyrosine-based inhibition motif (ITIM) found in the cytoplasmic domain of certain immune receptors. Chimeric receptor polypeptides comprising ITAM and/or ITIM domains can be phosphorylated following ligand binding to an antigen interacting domain. The phosphorylated regions can serve as docking sites for other proteins involved in immune cell signaling.

The antigen interacting domain of a chimeric receptor polypeptide can bind a membrane bound antigen, for example an antigen bound to the extracellular surface of a cell (e.g., a target cell). In some embodiments, the antigen interacting domain binds a non-membrane bound antigen, for example an extracellular antigen that is secreted by a cell (e.g., a target cell) or an antigen located in the cytoplasm of a cell. Antigens (e.g., membrane bound and non-membrane bound) can be associated with a disease such as a viral, bacterial, and/or parasitic infection; inflammatory and/or autoimmune disease; or neoplasm such as a cancer and/or tumor. Cancer antigens, for example, are proteins produced by tumor cells that can elicit an immune response, particularly a T-cell mediated immune response. The selection of the antigen binding portions of a chimeric receptor polypeptide can depend on the particular type of cancer antigen to be targeted. In some embodiments, the tumor antigen comprises one or more antigenic cancer epitopes associated with a malignant tumor. Malignant tumors can express a number of proteins that can serve as target antigens for an immune attack. The antigen interaction domains can bind to cell surface signals, extracellular matrix (ECM), paracrine signals, juxtacrine signals, endocrine signals, autocrine signals, signals that can trigger or control genetic programs in cells, or any combination thereof. In some embodiments, interactions between the cell signals that bind to the recombinant chimeric receptor polypeptides involve a cell-cell interaction, cell-soluble chemical interaction, and cell-matrix or microenvironment interaction.

A gene modulating polypeptide (GMP) of a chimeric receptor polypeptide can comprise an actuator moiety linked to a cleavage recognition site. The actuator moiety can comprise a nuclease (e.g., DNA nuclease and/or RNA nuclease), modified nuclease (e.g., DNA nuclease and/or RNA nuclease) that is nuclease-deficient or has reduced nuclease activity compared to a wild-type nuclease, a derivative thereof, a variant thereof, or a fragment thereof. The actuator moiety can regulate expression or activity of a gene and/or edit the sequence of a nucleic acid (e.g., a gene and/or gene product). In some embodiments, the actuator moiety comprises a DNA nuclease such as an engineered (e.g., programmable or targetable) DNA nuclease to induce genome editing of a target DNA sequence. In some embodiments, the actuator moiety comprises a RNA nuclease such as an engineered (e.g., programmable or targetable) RNA nuclease to induce editing of a target RNA sequence. In some embodiments, the actuator moiety has reduced or minimal nuclease activity. An actuator moiety having reduced or minimal nuclease activity can regulate expression and/or activity of a gene by physical obstruction of a target polynucleotide or recruitment of additional factors effective to suppress or enhance expression of the target polynucleotide. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. In some embodiments, the actuator moiety is a nucleic acid-guided actuator moiety. In some embodiments, the actuator moiety is a DNA-guided actuator moiety. In some embodiments, the actuator moiety is an RNA-guided actuator moiety. An actuator moiety can regulate expression or activity of a gene and/or edit a nucleic acid sequence, whether exogenous or endogenous.

Any suitable nuclease can be used in an actuator moiety. Suitable nucleases include, but are not limited to, CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute (Ago) proteins (e.g., prokaryotic Argonaute (pAgo), archaeal Argonaute (aAgo), and eukaryotic Argonaute (eAgo)); any derivative thereof; any variant thereof; and any fragment thereof.

The regulation of genes can be of any gene of interest. It is contemplated that genetic homologues of a gene described herein are covered. For example, a gene can exhibit a certain identity and/or homology to genes disclosed herein. Therefore, it is contemplated that a gene that exhibits or exhibits about 50%, 55%, 60%, 65%, 70%, 075%, 80%, 81%, 82%, 83%, 84%, 85%, 86%, 87%, 88%, 89%, 90%, 91%, 92%, 93%, 94%, 95%, 96%, 97%, 98%, 99%, or 100% homology (at the nucleic acid or protein level) can be modified. It is also contemplated that a gene that exhibits or exhibits about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity (at the nucleic acid or protein level) can be modified.

In some embodiments, the actuator moiety comprises a CRISPR-associated (Cas) protein or a Cas nuclease which functions in a non-naturally occurring CRISPR (Clustered Regularly Interspaced Short Palindromic Repeats)/Cas (CRISPR-associated) system. In bacteria, this system can provide adaptive immunity against foreign DNA (Barrangou, R., et al, "CRISPR provides acquired resistance against viruses in prokaryotes," Science (2007) 315: 1709-1712; Makarova, K. S., et al, "Evolution and classification of the CRISPR-Cas systems," Nat Rev Microbiol (2011) 9:467-

477; Garneau, J. E., et al, "The CRISPR/Cas bacterial immune system cleaves bacteriophage and plasmid DNA," Nature (2010) 468:67-71; Sapranauskas, R., et al, "The *Streptococcus thermophilus* CRISPR/Cas system provides immunity in *Escherichia coli*," Nucleic Acids Res (2011) 39: 9275-9282).

In a wide variety of organisms including diverse mammals, animals, plants, and yeast, a CRISPR/Cas system (e.g., modified and/or unmodified) can be utilized as a genome engineering tool. A CRISPR/Cas system can comprise a guide nucleic acid such as a guide RNA (gRNA) complexed with a Cas protein for targeted regulation of gene expression and/or activity or nucleic acid editing. An RNA-guided Cas protein (e.g., a Cas nuclease such as a Cas9 nuclease) can specifically bind a target polynucleotide (e.g., DNA) in a sequence-dependent manner. The Cas protein, if possessing nuclease activity, can cleave the DNA (Gasiunas, G., et al, "Cas9-crRNA ribonucleoprotein complex mediates specific DNA cleavage for adaptive immunity in bacteria," Proc Natl Acad Sci USA (2012) 109: E2579-E2 86; Jinek, M., et al, "A programmable dual-RNA-guided DNA endonuclease in adaptive bacterial immunity," Science (2012) 337:816-821; Sternberg, S. H., et al, "DNA interrogation by the CRISPR RNA-guided endonuclease Cas9," Nature (2014) 507:62; Deltcheva, E., et al, "CRISPR RNA maturation by trans-encoded small RNA and host factor RNase III," Nature (2011) 471:602-607), and has been widely used for programmable genome editing in a variety of organisms and model systems (Cong, L., et al, "Multiplex genome engineering using CRISPR Cas systems," Science (2013) 339: 819-823; Jiang, W., et al, "RNA-guided editing of bacterial genomes using CRISPR-Cas systems," Nat. Biotechnol. (2013) 31: 233-239; Sander, J. D. & Joung, J. K, "CRISPR-Cas systems for editing, regulating and targeting genomes," Nature Biotechnol. (2014) 32:347-355).

In some cases, the Cas protein is mutated and/or modified to yield a nuclease deficient protein or a protein with decreased nuclease activity relative to a wild-type Cas protein. A nuclease deficient protein can retain the ability to bind DNA, but may lack or have reduced nucleic acid cleavage activity. An actuator moiety comprising a Cas nuclease (e.g., retaining wild-type nuclease activity, having reduced nuclease activity, and/or lacking nuclease acitivity) can function in a CRISPR/Cas system to regulate the level and/or activity of a target gene or protein (e.g., decrease, increase, or elimination). The Cas protein can bind to a target polynucleotide and prevent transcription by physical obstruction or edit a nucleic acid sequence to yield non-functional gene products.

Figure 3A:
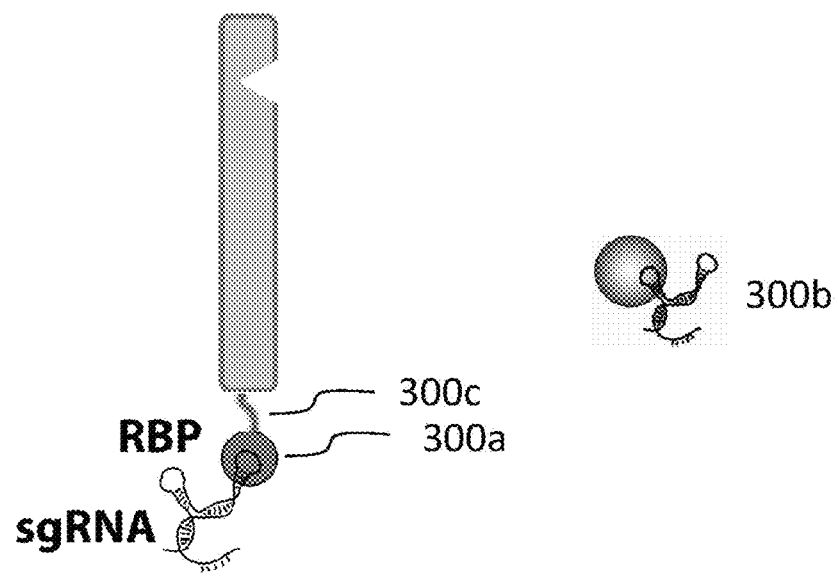
FIG. 3A shows an exemplary chimeric receptor polypeptide including an actuator moiety comprising an RNA-binding protein optionally complexed to a guide nucleic acid (e.g., sgRNA).

In some embodiments, the actuator moiety comprises a Cas protein that forms a complex with a guide nucleic acid, such as a guide RNA. In some embodiments, the actuator moiety comprises a Cas protein that forms a complex with a single guide nucleic acid, such as a single guide RNA (sgRNA). In some embodiments, the actuator moiety comprises a RNA-binding protein (RBP) optionally complexed with a guide nucleic acid, such as a guide RNA (e.g., sgRNA), which is able to form a complex with a Cas protein. FIG. 3A illustrates schematically a system comprising a chimeric receptor polypeptide in which the actuator moiety comprises an RNA-binding protein 300a optionally complexed with a guide nucleic acid (e.g., sgRNA). Upon release from the RNA-binding protein (RBP), for example by dissociation of the guide nucleic acid from the RBP or cleavage of the cleavage recognition site 300c, the guide nucleic acid can form a complex with a Cas protein 300b which is operable to regulate gene expression and/or activity or to edit a nucleic acid sequence. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. For example, an actuator moiety can comprise a Cas protein which lacks cleavage activity.

Figure 15:
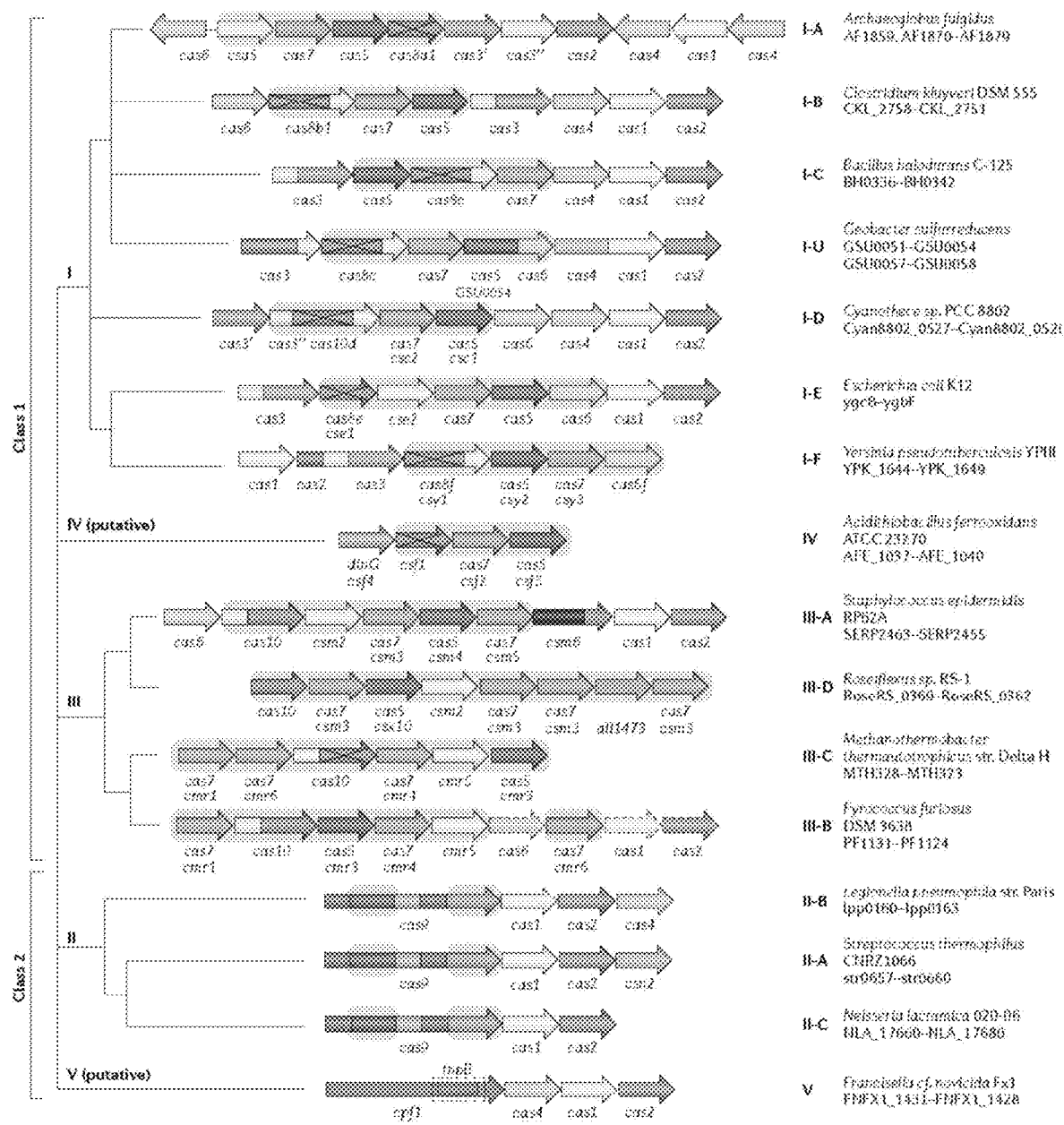
FIG. 15 shows an illustration adapted from FIG. 2 of Makarova, K. S. et al, "An updated evolutionary classification of CRISPR-Cas systems," Nat Rev Microbiol (2015) 13:722-736 providing architectures of the genomic loci for subtypes of CRISPR-Cas systems.

Any suitable CRISPR/Cas system can be used. A CRISPR/Cas system can be referred to using a variety of naming systems. Exemplary naming systems are provided in Makarova, K. S. et al, "An updated evolutionary classification of CRISPR-Cas systems," Nat Rev Microbiol (2015) 13:722-736 and Shmakov, S. et al, "Discovery and Functional Characterization of Diverse Class 2 CRISPR-Cas Systems," Mol Cell (2015) 60:1-13. A CRISPR/Cas system can be a type I, a type II, a type III, a type IV, a type V, a type VI system, or any other suitable CRISPR/Cas system. A CRISPR/Cas system as used herein can be a Class 1, Class 2, or any other suitably classified CRISPR/Cas system. Class 1 or Class 2 determination can be based upon the genes encoding the effector module. Class 1 systems generally have a multi-subunit crRNA-effector complex, whereas Class 2 systems generally have a single protein, such as Cas9, Cpf1, C2c1, C2c2, C2c3 or a crRNA-effector complex. A Class 1 CRISPR/Cas system can use a complex of multiple Cas proteins to effect regulation. A Class 1 CRISPR/Cas system can comprise, for example, type I (e.g., I, IA, IB, IC, ID, IE, IF, IU), type III (e.g., III, IIIA, IIIB, IIIC, IIID), and type IV (e.g., IV, IVA, IVB) CRISPR/Cas type. A Class 2 CRISPR/Cas system can use a single large Cas protein to effect regulation. A Class 2 CRISPR/Cas systems can comprise, for example, type II (e.g., II, IIA, IIB) and type V CRISPR/Cas type. CRISPR systems can be complementary to each other, and/or can lend functional units in trans to facilitate CRISPR locus targeting. FIG. 15 shows an illustration adapted from FIG. 2 of Makarova, K. S. et al, "An updated evolutionary classification of CRISPR-Cas systems," Nat Rev Microbiol (2015) 13:722-736 providing architectures of the genomic loci for subtypes of CRISPR-Cas systems.

An actuator moiety comprising a Cas protein can be a Class 1 or a Class 2 Cas protein. A Cas protein can be a type I, type II, type III, type IV, type V Cas protein, or type VI Cas protein. A Cas protein can comprise one or more domains. Non-limiting examples of domains include, guide nucleic acid recognition and/or binding domain, nuclease domains (e.g., DNase or RNase domains, RuvC, HNH), DNA binding domain, RNA binding domain, helicase domains, protein-protein interaction domains, and dimerization domains. A guide nucleic acid recognition and/or binding domain can interact with a guide nucleic acid. A nuclease domain can comprise catalytic activity for nucleic acid cleavage. A nuclease domain can lack catalytic activity to prevent nucleic acid cleavage. A Cas protein can be a chimeric Cas protein that is fused to other proteins or polypeptides. A Cas protein can be a chimera of various Cas proteins, for example, comprising domains from different Cas proteins.

Non-limiting examples of Cas proteins include c2c1, C2c2, c2c3, Cas1, Cas1B, Cas2, Cas3, Cas4, Cas5, Cas5e (CasD), Cas6, Cas6e, Cas6f, Cas7, Cas8a, Cas8a1, Cas8a2, Cas8b, Cas8c, Cas9 (Csn1 or Csxl2), Cas10, Cas10d, CaslO, CaslOd, CasF, CasG, CasH, Cpf1, Csy1, Csy2, Csy3, Csel (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu966, and homologs or modified versions thereof.

A Cas protein can be from any suitable organism. Non-limiting examples include *Streptococcus pyogenes, Streptococcus thermophilus, Streptococcus sp., Staphylococcus aureus, Nocardiopsis dassonvillei, Streptomyces pristinae spiralis, Streptomyces viridochromo* genes, *Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas sp., Crocosphaera watsonii, Cyanothece sp., Microcystis aeruginosa, Pseudomonas aeruginosa, Synechococcus sp., Acetohalobium arabaticum, Ammonfex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter sp., Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillatoria sp., Petrotoga mobilis, Thermosipho africanus, Acaryochloris marina, Leptotrichia shahii,* and *Francisella novicida.* In some aspects, the organism is *Streptococcus pyogenes* (*S. pyogenes*). In some aspects, the organism is *Staphylococcus aureus* (*S. aureus*). In some aspects, the organism is *Streptococcus thermophilus* (*S. thermophilus*).

A Cas protein can be derived from a variety of bacterial species including, but not limited to, *Veillonella atypical, Fusobacterium nucleatum, Filifactor alocis, Solobacterium moorei, Coprococcus catus, Treponema denticola, Peptoniphilus duerdenii, Catenibacterium mitsuokai, Streptococcus mutans, Listeria innocua, Staphylococcus pseudintermedius, Acidaminococcus intestine, Olsenella uli, Oenococcus kitaharae, Bifdobacterium bifdum, Lactobacillus rhamnosus, Lactobacillus gasseri, Finegoldia magna, Mycoplasma mobile, Mycoplasma gallisepticum, Mycoplasma ovipneumoniae, Mycoplasma canis, Mycoplasma synoviae, Eubacterium rectale, Streptococcus thermophilus, Eubacterium dolichum, Lactobacillus coryniformis* subsp. *Torquens, Ilyobacter polytropus, Ruminococcus albus, Akkermansia muciniphila, Acidothermus cellulolyticus, Bifidobacterium longum, Bifidobacterium dentium, Corynebacterium diphtheria, Elusimicrobium minutum, Nitratifractor salsuginis, Sphaerochaeta globus, Fibrobacter succinogenes* subsp. *Succinogenes, Bacteroides fragilis, Capnocytophaga ochracea, Rhodopseudomonas palustris, Prevotella micans, Prevotella ruminicola, Flavobacterium columnare, Aminomonas paucivorans, Rhodospirillum rubrum, Candidatus Puniceispirillum marinum, Verminephrobacter eiseniae, Ralstonia syzygii, Dinoroseobacter shibae, Azospirillum, Nitrobacter hamburgensis, Bradyrhizobium, Wolinella succinogenes, Campylobacter jejuni* subsp. *Jejuni, Helicobacter mustelae, Bacillus cereus, Acidovorax ebreus, Clostridium perfringens, Parvibaculum lavamentivorans, Roseburia intestinalis, Neisseria meningitidis, Pasteurella multocida* subsp. *Multocida, Sutterella wadsworthensis, proteobacterium, Legionella pneumophila, Parasutterella excrementihominis, Wolinella succinogenes,* and *Francisella novicida.*

A Cas protein as used herein can be a wildtype or a modified form of a Cas protein. A Cas protein can be an active variant, inactive variant, or fragment of a wild type or modified Cas protein. A Cas protein can comprise an amino acid change such as a deletion, insertion, substitution, variant, mutation, fusion, chimera, or any combination thereof relative to a wild-type version of the Cas protein. A Cas protein can be a polypeptide with at least about 5%, 10%, 20%, 30%, 40%, 50%, 60%, 70%, 80%, 90%, 91%, 92%, 93%, 94%, 95%, 96%, 97%, 98%, 99%, or 100% sequence identity or sequence similarity to a wild type exemplary Cas protein. A Cas protein can be a polypeptide with at most about 5%, 10%, 20%, 30%, 40%, 50%, 60%, 70%, 80%, 90%, 100% sequence identity and/or sequence similarity to a wild type exemplary Cas protein. Variants or fragments can comprise at least about 5%, 10%, 20%, 30%, 40%, 50%, 60%, 70%, 80%, 90%, 91%, 92%, 93%, 94%, 95%, 96%, 97%, 98%, 99%, or 100% sequence identity or sequence similarity to a wild type or modified Cas protein or a portion thereof. Variants or fragments can be targeted to a nucleic acid locus in complex with a guide nucleic acid while lacking nucleic acid cleavage activity.

A Cas protein can comprise one or more nuclease domains, such as DNase domains. For example, a Cas9 protein can comprise a RuvC-like nuclease domain and/or an HNH-like nuclease domain. The RuvC and HNH domains can each cut a different strand of double-stranded DNA to make a double-stranded break in the DNA. A Cas protein can comprise only one nuclease domain (e.g., Cpf1 comprises RuvC domain but lacks HNH domain).

A Cas protein can comprise an amino acid sequence having at least about 5%, 10%, 20%, 30%, 40%, 50%, 60%, 70%, 80%, 90%, 91%, 92%, 93%, 94%, 95%, 96%, 97%, 98%, 99%, or 100% sequence identity or sequence similarity to a nuclease domain (e.g., RuvC domain, HNH domain) of a wild-type Cas protein.

A Cas protein can be modified to optimize regulation of gene expression. A Cas protein can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein for regulating gene expression.

A Cas protein can be a fusion protein. For example, a Cas protein can be fused to a cleavage domain, an epigenetic modification domain, a transcriptional activation domain, or a transcriptional repressor domain. A Cas protein can also be fused to a heterologous polypeptide providing increased or decreased stability. The fused domain or heterologous polypeptide can be located at the N-terminus, the C-terminus, or internally within the Cas protein.

A Cas protein can be provided in any form. For example, a Cas protein can be provided in the form of a protein, such as a Cas protein alone or complexed with a guide nucleic acid. A Cas protein can be provided in the form of a nucleic acid encoding the Cas protein, such as an RNA (e.g., messenger RNA (mRNA)) or DNA. The nucleic acid encoding the Cas protein can be codon optimized for efficient translation into protein in a particular cell or organism.

Nucleic acids encoding Cas proteins can be stably integrated in the genome of the cell. Nucleic acids encoding Cas proteins can be operably linked to a promoter active in the cell. Nucleic acids encoding Cas proteins can be operably linked to a promoter in an expression construct. Expression constructs can include any nucleic acid constructs capable of directing expression of a gene or other nucleic acid sequence of interest (e.g., a Cas gene) and which can transfer such a nucleic acid sequence of interest to a target cell.

In some embodiments, a Cas protein is a dead Cas protein. A dead Cas protein can be a protein that lacks nucleic acid cleavage activity.

A Cas protein can comprise a modified form of a wild type Cas protein. The modified form of the wild type Cas protein can comprise an amino acid change (e.g., deletion, insertion, or substitution) that reduces the nucleic acid-cleaving activity of the Cas protein. For example, the modified form of the Cas protein can have less than 90%, less than 80%, less than 70%, less than 60%, less than 50%, less than 40%, less than 30%, less than 20%, less than 10%, less than 5%, or less than 1% of the nucleic acid-cleaving activity of the wild-type Cas protein (e.g., Cas9 from *S. pyogenes*). The modified form of Cas protein can have no substantial nucleic acid-cleaving activity. When a Cas protein is a modified form that has no substantial nucleic acid-cleaving activity, it can be referred to as enzymatically inactive and/or "dead" (abbreviated by "d"). A dead Cas protein (e.g., dCas, dCas9) can bind to a target polynucleotide but may not cleave the target polynucleotide. In some aspects, a dead Cas protein is a dead Cas9 protein.

A dCas9 polypeptide can associate with a single guide RNA (sgRNA) to activate or repress transcription of target DNA. sgRNAs can be introduced into cells expressing the engineered chimeric receptor polypeptide. In some cases, such cells contain one or more different sgRNAs that target the same nucleic acid. In other cases, the sgRNAs target different nucleic acids in the cell. The nucleic acids targeted by the guide RNA can be any that are expressed in a cell such as an immune cell. The nucleic acids targeted may be a gene involved in immune cell regulation. In some embodiments, the nucleic acid is associated with cancer. The nucleic acid associated with cancer can be a cell cycle gene, cell response gene, apoptosis gene, or phagocytosis gene. The recombinant guide RNA can be recognized by a CRISPR protein, a nuclease-null CRISPR protein, variants thereof, or derivatives thereof.

Enzymatically inactive can refer to a polypeptide that can bind to a nucleic acid sequence in a polynucleotide in a sequence-specific manner, but may not cleave a target polynucleotide. An enzymatically inactive site-directed polypeptide can comprise an enzymatically inactive domain (e.g. nuclease domain). Enzymatically inactive can refer to no activity. Enzymatically inactive can refer to substantially no activity. Enzymatically inactive can refer to essentially no activity. Enzymatically inactive can refer to an activity less than 1%, less than 2%, less than 3%, less than 4%, less than 5%, less than 6%, less than 7%, less than 8%, less than 9%, or less than 10% activity compared to a wild-type exemplary activity (e.g., nucleic acid cleaving activity, wild-type Cas9 activity).

One or a plurality of the nuclease domains (e.g., RuvC, HNH) of a Cas protein can be deleted or mutated so that they are no longer functional or comprise reduced nuclease activity. For example, in a Cas protein comprising at least two nuclease domains (e.g., Cas9), if one of the nuclease domains is deleted or mutated, the resulting Cas protein, known as a nickase, can generate a single-strand break at a CRISPR RNA (crRNA) recognition sequence within a double-stranded DNA but not a double-strand break. Such a nickase can cleave the complementary strand or the non-complementary strand, but may not cleave both. If all of the nuclease domains of a Cas protein (e.g., both RuvC and HNH nuclease domains in a Cas9 protein; RuvC nuclease domain in a Cpf1 protein) are deleted or mutated, the resulting Cas protein can have a reduced or no ability to cleave both strands of a double-stranded DNA. An example of a mutation that can convert a Cas9 protein into a nickase is a D10A (aspartate to alanine at position 10 of Cas9) mutation in the RuvC domain of Cas9 from *S. pyogenes*. H939A (histidine to alanine at amino acid position 839) or H840A (histidine to alanine at amino acid position 840) in the HNH domain of Cas9 from *S. pyogenes* can convert the Cas9 into a nickase. An example of a mutation that can convert a Cas9 protein into a dead Cas9 is a D10A (aspartate to alanine at position 10 of Cas9) mutation in the RuvC domain and H939A (histidine to alanine at amino acid position 839) or H840A (histidine to alanine at amino acid position 840) in the HNH domain of Cas9 from *S. pyogenes*.

A dead Cas protein can comprise one or more mutations relative to a wild-type version of the protein. The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type Cas protein. The mutation can result in one or more of the plurality of nucleic acid-cleaving domains retaining the ability to cleave the complementary strand of the target nucleic acid but reducing its ability to cleave the non-complementary strand of the target nucleic acid. The mutation can result in one or more of the plurality of nucleic acid-cleaving domains retaining the ability to cleave the non-complementary strand of the target nucleic acid but reducing its ability to cleave the complementary strand of the target nucleic acid. The mutation can result in one or more of the plurality of nucleic acid-cleaving domains lacking the ability to cleave the complementary strand and the non-complementary strand of the target nucleic acid. The residues to be mutated in a nuclease domain can correspond to one or more catalytic residues of the nuclease. For example, residues in the wild type exemplary *S. pyogenes* Cas9 polypeptide such as Asp10, His840, Asn854 and Asn856 can be mutated to inactivate one or more of the plurality of nucleic acid-cleaving domains (e.g., nuclease domains). The residues to be mutated in a nuclease domain of a Cas protein can correspond to residues Asp10, His840, Asn854 and Asn856 in the wild type *S. pyogenes* Cas9 polypeptide, for example, as determined by sequence and/or structural alignment.

As non-limiting examples, residues D10, G12, G17, E762, H840, N854, N863, H982, H983, A984, D986, and/or A987 (or the corresponding mutations of any of the Cas proteins) can be mutated. For example, e.g., D10A, G12A, G17A, E762A, H840A, N854A, N863A, H982A, H983A, A984A, and/or D986A. Mutations other than alanine substitutions can be suitable.

A D10A mutation can be combined with one or more of H840A, N854A, or N856A mutations to produce a Cas9 protein substantially lacking DNA cleavage activity (e.g., a dead Cas9 protein). A H840A mutation can be combined with one or more of D10A, N854A, or N856A mutations to produce a site-directed polypeptide substantially lacking DNA cleavage activity. A N854A mutation can be combined with one or more of H840A, D10A, or N856A mutations to produce a site-directed polypeptide substantially lacking DNA cleavage activity. A N856A mutation can be combined with one or more of H840A, N854A, or D10A mutations to produce a site-directed polypeptide substantially lacking DNA cleavage activity.

In some embodiments, a Cas protein is a Class 2 Cas protein. In some embodiments, a Cas protein is a type II Cas protein. In some embodiments, the Cas protein is a Cas9 protein, a modified version of a Cas9 protein, or derived from a Cas9 protein. For example, a Cas9 protein lacking cleavage activity. In some embodiments, the Cas9 protein is a Cas9 protein from S. pyogenes (e.g., SwissProt accession number Q99ZW2). In some embodiments, the Cas9 protein is a Cas9 from S. aureus (e.g., SwissProt accession number J7RUA5). In some embodiments, the Cas9 protein is a modified version of a Cas9 protein from S. pyogenes or S. Aureus. In some embodiments, the Cas9 protein is derived from a Cas9 protein from S. pyogenes or S. Aureus. For example, a S. pyogenes or S. Aureus Cas9 protein lacking cleavage activity.

Cas9 can generally refer to a polypeptide with at least about 5%, 10%, 20%, 30%, 40%, 50%, 60%, 70%, 80%, 90%, 100% sequence identity and/or sequence similarity to a wild type exemplary Cas9 polypeptide (e.g., Cas9 from S. pyogenes). Cas9 can refer to a polypeptide with at most about 5%, 10%, 20%, 30%, 40%, 50%, 60%, 70%, 80%, 90%, 100% sequence identity and/or sequence similarity to a wild type exemplary Cas9 polypeptide (e.g., from S. pyogenes). Cas9 can refer to the wildtype or a modified form of the Cas9 protein that can comprise an amino acid change such as a deletion, insertion, substitution, variant, mutation, fusion, chimera, or any combination thereof.

In some embodiments, an actuator moiety comprises a "zinc finger nuclease" or "ZFN." ZFNs refer to a fusion between a cleavage domain, such as a cleavage domain of FokI, and at least one zinc finger motif (e.g., at least 2, 3, 4, or 5 zinc finger motifs) which can bind polynucleotides such as DNA and RNA. The heterodimerization at certain positions in a polynucleotide of two individual ZFNs in certain orientation and spacing can lead to cleavage of the polynucleotide. For example, a ZFN binding to DNA can induce a double-strand break in the DNA. In order to allow two cleavage domains to dimerize and cleave DNA, two individual ZFNs can bind opposite strands of DNA with their C-termini at a certain distance apart. In some cases, linker sequences between the zinc finger domain and the cleavage domain can require the 5' edge of each binding site to be separated by about 5-7 base pairs. In some cases, a cleavage domain is fused to the C-terminus of each zinc finger domain. Exemplary ZFNs include, but are not limited to, those described in Urnov et al., Nature Reviews Genetics, 2010, 11:636-646; Gaj et al., Nat Methods, 2012, 9(8):805-7; U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; and U.S. Application Publication Nos. 2003/0232410 and 2009/0203140.

In some embodiments, an actuator moiety comprising a ZFN can generate a double-strand break in a target polynucleotide, such as DNA. A double-strand break in DNA can result in DNA break repair which allows for the introduction of gene modification(s) (e.g., nucleic acid editing). DNA break repair can occur via non-homologous end joining (NHEJ) or homology-directed repair (HDR). In HDR, a donor DNA repair template that contains homology arms flanking sites of the target DNA can be provided. In some embodiments, a ZFN is a zinc finger nickase which induces site-specific single-strand DNA breaks or nicks, thus resulting in HDR. Descriptions of zinc finger nickases are found, e.g., in Ramirez et al., Nucl Acids Res, 2012, 40(12):5560-8; Kim et al., Genome Res, 2012, 22(7):1327-33. In some embodiments, a ZFN binds a polynucleotide (e.g., DNA and/or RNA) but is unable to cleave the polynucleotide.

In some embodiments, the cleavage domain of an actuator moiety comprising a ZFN comprises a modified form of a wild type cleavage domain. The modified form of the cleavage domain can comprise an amino acid change (e.g., deletion, insertion, or substitution) that reduces the nucleic acid-cleaving activity of the cleavage domain. For example, the modified form of the cleavage domain can have less than 90%, less than 80%, less than 70%, less than 60%, less than 50%, less than 40%, less than 30%, less than 20%, less than 10%, less than 5%, or less than 1% of the nucleic acid-cleaving activity of the wild-type cleavage domain. The modified form of the cleavage domain can have no substantial nucleic acid-cleaving activity. In some embodiments, the cleavage domain is enzymatically inactive.

In some embodiments, an actuator moiety comprises a "TALEN" or "TAL-effector nuclease." TALENs refer to engineered transcription activator-like effector nucleases that generally contain a central domain of DNA-binding tandem repeats and a cleavage domain. TALENs can be produced by fusing a TAL effector DNA binding domain to a DNA cleavage domain. In some cases, a DNA-binding tandem repeat comprises 33-35 amino acids in length and contains two hypervariable amino acid residues at positions 12 and 13 that can recognize at least one specific DNA base pair. A transcription activator-like effector (TALE) protein can be fused to a nuclease such as a wild-type or mutated FokI endonuclease or the catalytic domain of FokI. Several mutations to FokI have been made for its use in TALENs, which, for example, improve cleavage specificity or activity. Such TALENs can be engineered to bind any desired DNA sequence. TALENs can be used to generate gene modifications (e.g., nucleic acid sequence editing) by creating a double-strand break in a target DNA sequence, which in turn, undergoes NHEJ or HDR. In some cases, a single-stranded donor DNA repair template is provided to promote HDR. Detailed descriptions of TALENs and their uses for gene editing are found, e.g., in U.S. Pat. Nos. 8,440,431; 8,440,432; 8,450,471; 8,586,363; and U.S. Pat. No. 8,697,853; Scharenberg et al., Curr Gene Ther, 2013, 13(4):291-303; Gaj et al., Nat Methods, 2012, 9(8):805-7; Beurdeley et al., Nat Commun, 2013, 4:1762; and Joung and Sander, Nat Rev Mol Cell Biol, 2013, 14(1):49-55.

In some embodiments, a TALEN is engineered for reduced nuclease activity. In some embodiments, the nuclease domain of a TALEN comprises a modified form of a wild type nuclease domain. The modified form of the nuclease domain can comprise an amino acid change (e.g., deletion, insertion, or substitution) that reduces the nucleic acid-cleaving activity of the nuclease domain. For example, the modified form of the nuclease domain can have less than 90%, less than 80%, less than 70%, less than 60%, less than 50%, less than 40%, less than 30%, less than 20%, less than 10%, less than 5%, or less than 1% of the nucleic acid-cleaving activity of the wild-type nuclease domain. The modified form of the nuclease domain can have no substantial nucleic acid-cleaving activity. In some embodiments, the nuclease domain is enzymatically inactive.

In some embodiments, the transcription activator-like effector (TALE) protein is fused to a domain that can modulate transcription and does not comprise a nuclease. In some embodiments, the transcription activator-like effector (TALE) protein is designed to function as a transcriptional activator. In some embodiments, the transcription activator-like effector (TALE) protein is designed to function as a transcriptional repressor. For example, the DNA-binding domain of the transcription activator-like effector (TALE) protein can be fused (e.g., linked) to one or more transcriptional activation domains, or to one or more transcriptional repression domains. Non-limiting examples of a transcriptional activation domain include a herpes simplex VP16 activation domain and a tetrameric repeat of the VP16 activation domain, e.g., a VP64 activation domain. A non-limiting example of a transcriptional repression domain includes a Kruppel-associated box domain.

In some embodiments, an actuator moiety comprises a meganuclease. Meganucleases generally refer to rare-cutting endonucleases or homing endonucleases that can be highly specific. Meganucleases can recognize DNA target sites ranging from at least 12 base pairs in length, e.g., from 12 to 40 base pairs, 12 to 50 base pairs, or 12 to 60 base pairs in length.

Meganucleases can be modular DNA-binding nucleases such as any fusion protein comprising at least one catalytic domain of an endonuclease and at least one DNA binding domain or protein specifying a nucleic acid target sequence. The DNA-binding domain can contain at least one motif that recognizes single- or double-stranded DNA. The meganuclease can be monomeric or dimeric. In some embodiments, the meganuclease is naturally-occurring (found in nature) or wild-type, and in other instances, the meganuclease is non-natural, artificial, engineered, synthetic, rationally designed, or man-made. In some embodiments, the meganuclease of the present disclosure includes an I-CreI meganuclease, I-CeuI meganuclease, I-MsoI meganuclease, I-SceI meganuclease, variants thereof, derivatives thereof, and fragments thereof. Detailed descriptions of useful meganucleases and their application in gene editing are found, e.g., in Silva et al., Curr Gene Ther, 2011, 11(1):11-27; Zaslavoskiy et al., BMC Bioinformatics, 2014, 15:191; Takeuchi et al., Proc Natl Acad Sci USA, 2014, 111(11): 4061-4066, and U.S. Pat. Nos. 7,842,489; 7,897,372; 8,021, 867; 8,163,514; 8,133,697; 8,021,867; 8,119,361; 8,119, 381; 8,124,36; and 8,129,134.

In some embodiments, the nuclease domain of a meganuclease comprises a modified form of a wild type nuclease domain. The modified form of the nuclease domain can comprise an amino acid change (e.g., deletion, insertion, or substitution) that reduces the nucleic acid-cleaving activity of the nuclease domain. For example, the modified form of the nuclease domain can have less than 90%, less than 80%, less than 70%, less than 60%, less than 50%, less than 40%, less than 30%, less than 20%, less than 10%, less than 5%, or less than 1% of the nucleic acid-cleaving activity of the wild-type nuclease domain. The modified form of the nuclease domain can have no substantial nucleic acid-cleaving activity. In some embodiments, the nuclease domain is enzymatically inactive. In some embodiments, a meganuclease can bind DNA but cannot cleave the DNA.

In some embodiments, the actuator moiety is fused to one or more transcription repressor domains, activator domains, epigenetic domains, recombinase domains, transposase domains, flippase domains, nickase domains, or any combination thereof. The activator domain can include one or more tandem activation domains located at the carboxyl terminus of the enzyme. In other cases, the actuator moiety includes one or more tandem repressor domains located at the carboxyl terminus of the protein. Non-limiting exemplary activation domains include GAL4, herpes simplex activation domain VP16, VP64 (a tetramer of the herpes simplex activation domain VP16), NF-κB p65 subunit, Epstein-Barr virus R transactivator (Rta) and are described in Chavez et al., Nat Methods, 2015, 12(4):326-328 and U.S. Patent App. Publ. No. 20140068797. Non-limiting exemplary repression domains include the KRAB (Krüppel-associated box) domain of Kox1, the Mad mSIN3 interaction domain (SID), ERF repressor domain (ERD), and are described in Chavez et al., Nat Methods, 2015, 12(4):326-328 and U.S.

Patent App. Publ. No. 20140068797. An actuator moiety can also be fused to a heterologous polypeptide providing increased or decreased stability. The fused domain or heterologous polypeptide can be located at the N-terminus, the C-terminus, or internally within the actuator moiety.

An actuator moiety can comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g. eBFP, eBFP2, Azurite, mKalamal, GFPuv, Sapphire, T-sapphire), cyan fluorescent proteins (e.g. eCFP, Cerulean, CyPet, AmCyanl, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly (NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, SI, T7, V5, VSV-G, histidine (His), biotin carboxyl carrier protein (BCCP), and calmodulin.

Figure 3B:
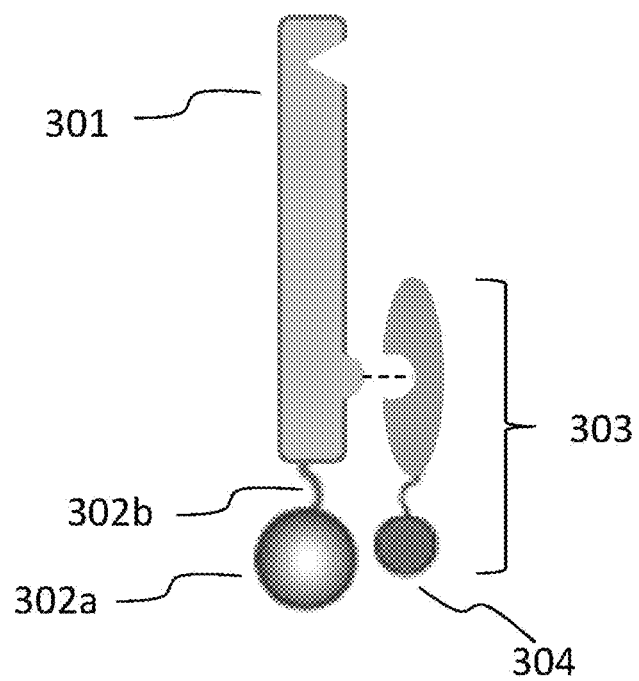
FIG. 3B shows an exemplary system comprising a chimeric receptor polypeptide and a chimeric adaptor polypeptide comprising a cleavage moiety.

The cleavage recognition site of a GMP can be flanked by the antigen interacting domain and the actuator moiety in some configurations of a chimeric receptor polypeptide. The actuator moiety can be released from the GMP by cleavage of the recognition site by a cleavage moiety. A cleavage moiety can recognize and/or cleave a cleavage recognition site, for example, when in proximity to the cleavage recognition site. A cleavage moiety can comprise a polypeptide sequence. The cleavage moiety can form a portion of the chimeric adaptor polypeptide. The cleavage moiety can form the N-terminus, C-terminus, or an internal portion of the chimeric adaptor polypeptide. In some embodiments, the cleavage moiety is complexed to the chimeric adaptor polypeptide. The cleavage moiety can be complexed to the N-terminus, C-terminus, or an internal portion of the chimeric adaptor polypeptide. FIG. 3B shows an exemplary arrangement of the various components of a subject system. The cleavage recognition site 302b of a GMP is flanked by the antigen interacting domain 301 and the actuator moiety 302a, and the cleavage moiety 304 forms a portion of a chimeric adaptor polypeptide 303.

FIGS. 4A-D illustrate schematically the release of an actuator moiety from a GMP. FIG. 4A shows the binding of an antigen to a transmembrane chimeric receptor polypeptide. The transmembrane chimeric receptor polypeptide comprises an extracellular region having an antigen interacting domain 401 and an intracellular region comprising a GMP. The GMP includes an actuator moiety 402a linked to a cleavage recognition site 402b. In response to antigen binding, the receptor is modified by phosphorylation 403 in the intracellular region of the receptor (FIG. 4B). Following receptor modification (e.g., phosphorylation), an adaptor protein comprising a receptor binding moiety is recruited to the receptor as shown in FIG. 4C. The receptor comprises a cleavage moiety 404; the cleavage moiety may be complexed with the adaptor or linked, for example by a peptide bond and/or peptide linker, to the receptor binding moiety. When in proximity to the cleavage recognition site, the cleavage moiety can cleave the recognition site to release the actuator moiety from the GMP as shown in FIG. 4D. Upon release, the actuator moiety can enter the nucleus to regulate the expression and/or activity of a target gene or edit a nucleic acid sequence. FIGS. 4E-H show an analogous system wherein receptor modification comprises a conformational change. In some embodiments, the adaptor protein is tethered to the membrane (e.g., as a membrane bound protein).

In some embodiments, the cleavage moiety only cleaves the recognition site when in proximity to the cleavage recognition site. The cleavage recognition site can comprise a polypeptide sequence that is a recognition sequence of a protease. The cleavage moiety can comprise protease activity which recognizes the polypeptide sequence. A cleavage moiety comprising protease activity can be a protease, or any derivative, variant or fragment thereof. A protease refers to any enzyme that performs proteolysis, in which polypeptides are cleaved into smaller polypeptides or amino acids. Various proteases are suitable for use as a cleavage moiety. Some proteases can be highly promiscuous such that a wide range of protein substrates are hydrolysed. Some proteases can be highly specific and only cleave substrates with a certain sequence, e.g., a cleavage recognition sequence or peptide cleavage domain. In some embodiments, the cleavage recognitions site comprises multiple cleavage recognition sequences, and each cleavage recognition sequence can be recognized by the same or different cleavage moiety comprising protease activity (e.g., protease). Sequence-specific proteases that can be used as cleavage moieties include, but are not limited to, superfamily CA proteases, e.g., families C1, C2, C6, C10, C12, C16, C19, C28, C31, C32, C33, C39, C47, C51, C54, C58, C64, C65, C66, C67, C70, C71, C76, C78, C83, C85, C86, C87, C93, C96, C98, and C101, including papain (*Carica papaya*), bromelain (*Ananas comosus*), cathepsin K (liverwort) and calpain (*Homo sapiens*); superfamily CD proteases, e.g., family C11, C13, C14, C25, C50, C80, and C84: such as caspase-1 (*Rattus norvegicus*) and separase (*Saccharomyces cerevisiae*); superfamily CE protease, e.g., family C5, C48, C55, C57, C63, and C79 including adenain (human adenovirus type 2); superfamily CF proteases, e.g., family C15 including pyroglutamyl-peptidase I (*Bacillus amyloliquefaciens*); superfamily CL proteases, e.g., family C60 and C82 including sortase A (*Staphylococcus aureus*); superfamily CM proteases, e.g. family C18 including hepatitis C virus peptidase 2 (hepatitis C virus); superfamily CN proteases, e.g., family C9 including sindbis virus-type nsP2 peptidase (sindbis virus); superfamily CO proteases, e.g., family C40 including dipeptidyl-peptidase VI (*Lysinibacillus sphaericus*); superfamily CP proteases, e.g., family C97 including DeSI-1 peptidase (*Mus musculus*); superfamily PA proteases, e.g., family C3, C4, C24, C30, C37, C62, C74, and C99 including TEV protease (Tobacco etch virus); superfamily PB proteases, e.g., family C44, C45, C59, C69, C89, and C95 including amidophosphoribosyltransferase precursor (*Homo sapiens*); superfamily PC proteases, families C26, and C56 including y-glutamyl hydrolase (*Rattus norvegicus*); superfamily PD proteases, e.g., family C46 including Hedgehog protein (*Drosophila melanogaster*); superfamily PE proteases, e.g., family P1 including DmpA aminopeptidase (*Ochrobactrum anthropi*); others proteases, e.g., family C7, C8, C21, C23, C27, C36, C42, C53 and C75. Additional proteases include serine proteases, e.g., those of superfamily SB, e.g., families S8 and S53 including subtilisin (*Bacillus licheniformis*); those of superfamily SC, e.g., families S9, S10, S15, S28, S33, and S37 including prolyl oligopeptidase (*Sus scrofa*); those of superfamily SE, e.g., families S11, S12, and S13 including D-Ala-D-Ala peptidase C (*Escherichia coli*); those of superfamily SF, e.g., families S24 and S26 including signal peptidase I (*Escherichia coli*); those of Superfamily SJ, e.g., families S16, S50, and S69 including lon-A peptidase (*Escherichia coli*); those of Superfamily SK, e.g., families S14, S41, and S49 including Clp protease (*Escherichia coli*); those of Superfamily SO, e.g., families S74 including Phage K1F endosialidase CIMCD self-cleaving protein (Enterobacteria phage K1F); those of superfamily SP, e.g., family S59 including nucleoporin 145 (*Homo sapiens*); those of superfamily SR, e.g., family S60 including Lactoferrin (*Homo sapiens*); those of superfamily SS, families S66 including murein tetrapeptidase LD-carboxypeptidase (*Pseudomonas aeruginosa*); those of superfamily ST, e.g., families S54 including rhomboid-1 (*Drosophila melanogaster*); those of superfamily PA, e.g., families S, S3, S6, S7, S29, S30, 531, S32, S39, S46, S55, S64, S65, and S75 including Chymotrypsin A (*Bos taurus*); those of superfamily PB, e.g., families S45 and S63 including penicillin G acylase precursor (*Escherichia coli*); those of superfamily PC, e.g., families S51 including dipeptidase E (*Escherichia coli*); those of superfamily PE, e.g., families P1 including DmpA aminopeptidase (*Ochrobactrum anthropi*); those unassigned, e.g., families S48, S62, S68, 571, S72, S79, and S81 threonine proteases, e.g., those of superfamily PB clan, e.g., families T1, T2, T3, and T6 including archaean proteasome, Rcomponent (*Thermoplasma acidophilum*); and those of superfamily PE clan, e.g., family T5 including ornithine acetyltransferase (*Saccharomyces cerevisiae*); aspartic proteases, e.g., BACE1, BACE2; cathepsin D; cathepsin E; chymosin; napsin-A; nepenthesin; pepsin; plasmepsin; presenilin; renin; and HIV-1 protease, and metalloproteinases, e.g., exopeptidases, metalloexopeptidases; endopeptidases, and metalloendopeptidases. A cleavage recognition sequence (e.g., polypeptide sequence) can be recognized by any of the proteases disclosed herein.

In some embodiments, the cleavage recognition site comprises a cleavage recognition sequence (e.g., polypeptide sequence or peptide cleavage domain) that is recognized by a protease selected from the group consisting of: achromopeptidase, aminopeptidase, ancrod, angiotensin converting enzyme, bromelain, calpain, calpain I, calpain II, carboxypeptidase A, carboxypeptidase B, carboxypeptidase G, carboxypeptidase P, carboxypeptidase W, carboxypeptidase Y, caspase 1, caspase 2, caspase 3, caspase 4, caspase 5, caspase 6, caspase 7, caspase 8, caspase 9, caspase 10, caspase 11, caspase 12, caspase 13, cathepsin B, cathepsin C, cathepsin D, cathepsin E, cathepsin G, cathepsin H, cathepsin L, chymopapain, chymase, chymotrypsin, clostripain, collagenase, complement C1r, complement C1s, complement Factor D, complement factor I, cucumisin, dipeptidyl peptidase IV, elastase (leukocyte), elastase (pancreatic), endoproteinase Arg-C, endoproteinase Asp-N, endoproteinase Glu-C, endoproteinase Lys-C, enterokinase, factor Xa, ficin, furin, granzyme A, granzyme B, HIV Protease, IGase, kallikrein tissue, leucine aminopeptidase (general), leucine aminopeptidase (cytosol), leucine aminopeptidase (microsomal), matrix metalloprotease, methionine aminopeptidase, neutrase, papain, pepsin, plasmin, prolidase, pronase E, prostate specific antigen, protease alkalophilic from *Streptomyces griseus*, protease from *Aspergillus*, protease from *Aspergillus saitoi*, protease from *Aspergillus sojae*, protease (*B. licheniformis*) (alkaline or alcalase), protease from *Bacillus polymyxa*, protease from *Bacillus* sp, protease from *Rhizopus* sp., protease, proteasomes, proteinase from *Aspergillus oryzae*, proteinase 3, proteinase A, proteinase K, protein C, pyroglutamate aminopeptidase, rennin, rennin, streptokinase, subtilisin, thermolysin, thrombin, tissue plasminogen activator, trypsin, tryptaseandurokinase.

Table 1 lists exemplary proteases and associated recognition sequences that can be used in systems of the disclosure.

TABLE 1

Exemplary proteases and associated recognition sequences

| Protease name | Synonyms | Recognition sequence |
|---|---|---|
| Arg-C | Arginyl peptidase, Endoproteinase Arg-C, Tissue kallikrein | R-x |
| Asp-N | Endoproteinase Asp-N, Peptidyl-Asp metalloendopeptidase | x-D |
| Asp-N (N-terminal Glu) | Endoproteinase Asp-N, Peptidyl-Asp metalloendopeptidase | x-[DE] |
| BNPS or NCS/urea | 3-Bromo-3-methyl-2-(2-nitrophenylthio)-3H-indole, BNPS-skatol, N-chlorosuccinimide/urea | W-x |
| Caspase-1 | ICE, Interleukin-1β-Converting Enzyme | [FLWY]-x-[AHT]-D-{DEKPQR} (SEQ ID NO: 61) |
| Caspase-10 | Flice2, Mch4 | I-E-A-D-x (SEQ ID NO: 62) |
| Caspase-2 | Ich-1, Nedd2 | D-V-A-D-{DEKPQR} (SEQ ID NO: 63 or D-E-H-D-{DEKPQR} (SEQ ID NO: 64) |
| Caspase-3 | Apopain, CPP32, Yama | D-M-Q-D-{DEKPQR} (SEQ ID NO: 65) or D-E-V-D-{DEKPQR} (SEQ ID NO: 66) |
| Caspase-4 | ICE(rel)II, Ich-2, TX | L-E-V-D-{DEKPQR} (SEQ ID NO: 67) or [LW]-E-H-D-{DEKPQR} (SEQ ID NO: 68) |
| Caspase-5 | ICE(rel)III, TY | [LW]-E-H-D-x (SEQ ID NO: 69) |
| Caspase-6 | Mch2 | V-E-[HI]-D-{DEKPQR} (SEQ ID NO: 70) |
| Caspase-7 | CMH-1, ICE-LAP3, Mch-3 | D-E-V-D-{DEKPQR} (SEQ ID NO: 71) |
| Caspase-8 | FLICE, MASH, Mch5 | [IL]-E-T-D-{DEKPQR} (SEQ ID NO: 72) |
| Caspase-9 | ICE-Lap6, Mch6 | L-E-H-D-x (SEQ ID NO: 73) |
| Chymotrypsin | | [FY]-{P} or W-{MP} |
| Chymotrypsin (low specificity) | | [FLY]-{P} or W-{MP} or M-{PY} or H-{DMPW} |
| Clostripain | Clostridiopeptidase B | R-x |
| CNBr | Cyanogen bromide | M-x |
| CNBr (methyl-Cys) | Cyanogen bromide | M-x or x-C |

TABLE 1-continued

Exemplary proteases and associated recognition sequences

| Protease name | Synonyms | Recognition sequence |
|---|---|---|
| CNBr (with acids) | Cyanogen bromide | [MW]-x |
| Enterokinase | Enteropeptidase | [DE](4)-K-x (SEQ ID NO: 74) |
| Factor Xa | Coagulation factor Xa | [AFGILTVM]-[DE]-G-R-x (SEQ ID NO: 75) |
| Formic acid | | D-x |
| Glu-C (AmAc buffer) | Endoproteinase Glu-C, V8 protease, Glutamyl endopeptidase | E-x |
| Glu-C (Phos buffer) | Endoproteinase Glu-C, V8 protease, Glutamyl endopeptidase | [DE]-x |
| Granzyme B | Cytotoxic T-lymphocyte proteinase 2, Granzyme-2, GranzymeB, Lymphocyte protease, SECT, T-cell serine protease 1-3E | I-E-P-D-x (SEQ ID NO: 76) |
| HRV3C protease | Human rhinovirus 3C protease, Picornain 3C, Protease 3C | L-E-V-L-F-Q-G-P (SEQ ID NO: 77) |
| Hydroxylamine | Hydroxylammonium | N-G |
| Iodosobenzoic acid | 2-Iodosobenzoic acid | W-x |
| Lys-C | Endoproteinase Lys-C, Lysyl endopeptidase | K-x |
| Lys-N | Endoproteinase Lys-N, Peptidyl-Lys metalloendopeptidase, *Armillaria mellea* neutral proteinase | x-K |
| Lys-N (Cys modified) | Endoproteinase Lys-N, Peptidyl-Lys metalloendopeptidase, *Armillaria mellea* neutral proteinase | x-[CK] |
| Mild acid hydrolysis | | D-P |
| NBS (long exposure) | N-Bromosuccinimide | [HWY]-x |
| NBS (short exposure) | N-Bromosuccinimide | [WY]-x |
| NTCB | 2-Nitro-5-thiocyanatobenzoic acid, 2-Nitro-5-thiocyanobenzoic acid | x-C |
| Pancreatic elastase | Pancreatopeptidase E, Elastase-1 | [AGSV]-x |
| Pepsin A | Pepsin | {HKR}-{P}-{R}-[FLWY]-{P} (SEQ ID NO: 78) or {HKR}-{P}-[FLWY]-x-{P} (SEQ ID NO: 79) |
| Pepsin A (low specificity) | Pepsin | {HKR}-{P}-{R}-[FL]-{P} (SEQ ID NO: 80) or {HKR}-{P}-[FL]-x-{P} (SEQ ID NO: 81) |
| Prolyl endopeptidase | Prolyl oligopeptidase, Post-proline cleaving enzyme | [HKR]-P-{P} |
| Proteinase K | Endopeptidase K, Peptidase K | [AEFILTVWY]-x |
| TEV protease endopeptidase | Tobacco etch virus protease, Nuclear-inclusion-a | E-x-x-Y-x-Q-[GS] (SEQ ID NO: 82) |
| Thermolysin | Thermophilic-bacterial protease | {DE}-[AFILMV]-{P} |

TABLE 1-continued

Exemplary proteases and associated recognition sequences

| Protease name | Synonyms | Recognition sequence |
|---|---|---|
| Thrombin | Factor IIa | x-x-G-R-G-x (SEQ ID NO: 83) or [AFGILTVW]-[AFGILTVW]-P-R-{DE}-{DE} (SEQ ID NO: 84) |
| Trypsin | Trypsin-1 | x-[KR]-{13} or W-K-P or M-R-P<br>But not:<br>[CD]-K-D or C-K-[HY] or C-R-K or R-R-[HR] |
| Trypsin (Arg blocked) | | K-{P} |
| Trypsin (Cys modified) | | [RKC]-{P} |
| Trypsin (Lys blocked) | | R-{P} |

Proteases selected for use as cleavage moieties can be selected based on desired characteristics such as peptide bond selectivity, activity at certain pHs, molecular mass, etc. The properties of exemplary proteases are provided in Table 2.

TABLE 2

Exemplary proteases and protease characteristics

| Protease | EC no. | Class | Peptide bond selectivity | pH optimum | Molecular mass (kDa) | Accession no. |
|---|---|---|---|---|---|---|
| Endoproteinase | | | | | | |
| Trypsin (bovine) | 3.4.21.4 | serine | $P_1$-$P_1^1$- ($P_1$ = Lys, Arg) | 8.0-9.0 | 23.5 | P00760$^S$ |
| Chymotrypsin (bovine) | 3.4.21.1 | serine | $P_1$-$P_1^1$- ($P_1$ = aromatic, $P_1^1$ = nonspecific) | 7.5-8.5 | 25 | P00766$^S$ |
| Endoproteinase Asp-N (Pseudomonas fragi) | 3.4.24.33 | metallo | $P_1$-Asp- (and -$P_1$, -cysteic acid) | 6.0-8.0 | 27 | φ |
| Endoproteinase Arg-C (mouse submaxillary gland) | φ | serine | -Arg-$P_1$- | 8.0-8.5 | 30 | n.a. |
| Endoproteinase Glu-C (V8 protease) (Staphylococcus aureus) | 3.4.21.19 | serine | -Glu-$P_1^1$- (and -Asp-$P_1^1$-) (2) | 8.0 | 27 | P04188$^S$ |
| Endoproteinase Lys-C (Lysobacter enzymogenes) | 3.4.21.50 | serine | -Lys-$P_1^1$- | 8.0 | $30^{NR}$ $33^R$ | S77957$^P$ |
| Pepsin (porcine) | 3.4.23.1 | aspartic | $P_1$,-$P_1^1$- ($P_1$ = hydrophobic preferred) | 2.0-4.0 | 34.5 | P00791$^S$ |
| Thermolysin (Bacillus thermoproteolyticus) | 3.4.24.27 | metallo | $P_1$-$P_1^1$- ($P_1$ = Leu, Phe, Ile, Val, Met, Ala) | 7.0-9.0 | 37.5 | P00800$^S$ |
| Elastase (porcine) | 3.4.21.36 | serine | ($P_1$-$P_1^1$- ($P_1$ = uncharged, nonaromatic) | 7.8-8.5 | 25.9 | P00772$^S$ |

TABLE 2-continued

Exemplary proteases and protease characteristics

| Protease | EC no. | Class | Peptide bond selectivity | pH optimum | Molecular mass (kDa) | Accession no. |
|---|---|---|---|---|---|---|
| Papain (Carica papaya) | 3.4.22.2 | cysteine | $P_1$-$P_1^1$- ($P_1$ = Arg, Lys preferred) | 6.0-7.0 | 23 | P00784$^S$ |
| Proteinase K (Tritirachium album) | 3.4.21.64 | serine | $P_1$-$P_1^1$- ($P_1$ = aromatic, hydrophobic preferred) | 7.5-12.0 | 18.5 | P06873$^S$ |
| Subtilisin (Bacillus subtilis) | 3.4.21.62 | serine | $P_1$-$P_1^1$- ($P_1$ = neutral/acidic preferred) | 7.0-11.0 | 30$^S$ 27.3$^L$ | P04189$^S$ |
| Clostripain (endoproteinase-Arg-C) (Clostridium histolyticum) | 3.4.22.8 | cysteine | -Arg-$P_1$- ($P_1$ = Pro preferred) | 7.1-7.6 | 59 | P09870$^S$ |
| Exopeptidase | | | | | | |
| Carboxypeptidase A (bovine) | 3.4.17.1 | metallo | $P_1$-$P_1^1$- ($P_1$ cannot Arg, Lys, Pro) | 7.0-8.0 | 34.5 | P00730$^S$ |
| Carboxypeptidase B (porcine) | 3.4.17.2 | metallo | $P_1$-$P_1^1$- ($P_1$ = Lys, Arg) | 7.0-9.0 | 34.6 | P00732$^S$ |
| Carboxypeptidase P (Penicillium janthinellum) | ϕ | serine | $P_1$-$P_1^1$- (nonspecific) | 4.0-5.0 | 51 | n.a. |
| Carboxypeptidase Y (yeast) | 3.4.16.5 | serine | $P_1$-$P_1^1$- (nonspecific) | 5.5-6.5 | 61 | P00729$^S$ |
| Cathepsin C | 3.4.14.1 | cysteine | X-$P_1$-$P_1^1$- (removes amino-terminal dipeptide) | 5.5 | 210 | n.a. |
| Acylamino-acid-releasing enzyme (porcine) | 3.4.19.1 | serine | Ac-$P_1$-$P_1^1$- ($P_1$ = Ser, Ala, Met preferred) | 7.5 | 80$^B$ 360$^P$ | P19205$^S$+ |
| Pyroglutamate aminopeptidase (bovine) | 3.4.19.3 | cysteine | $P_1$-$P_1^1$- ($P_1$ = 5-oxoproline or pyroglutamate) | 7.0-9.0 | 70-80$^B$ | n.a. |

In some embodiments, the cleavage recognition site comprises a first portion of an intein sequence that reacts with the second portion of the intein sequence to release the actuator moiety. A heterologous split intein system can be used to facilitate release of the actuator moiety from the chimeric receptor polypeptide. The actuator moiety can be covalently linked to the first portion of the intein sequence. The actuator moiety can be linked via its N-terminus or C-terminus to the first portion of the intein sequence. The second portion of the intein sequence can be a part of the chimeric adaptor polypeptide. The second portion of the intein sequence can serve as a cleavage moiety. The first portion or second portion of the intein sequence can be the N-terminal intein, the C-terminal intein, or any other suitable portion of an intein that can facilitate release of the actuator moiety. The intein sequences can be from any suitable source. The first and second portion can be from the same or different sources (e.g., organism, protein).

In an illustrative example shown in FIG. 13A, a chimeric receptor polypeptide comprises an actuator moiety 1301 covalently linked (e.g., at its N-terminus or C-terminus) via a peptide bond to a first portion of the intein sequence 1302, which comprises an N-terminal intein. The actuator moiety-N-terminal intein fusion can be contacted with a second portion of the intein sequence 1303 comprising a C-terminal intein as shown in FIG. 13B, for example a second portion of the intein sequence linked to an adaptor polypeptide. This contacting of the first and second portion of the intein sequences can result in a site specific cleavage (e.g., at a site between the actuator moiety and the N-terminal intein) as shown in FIG. 13C, thereby releasing the actuator moiety as shown in FIG. 13D. In an alternative configuration shown in FIGS. 13E-H, the actuator moiety is linked and/or complexed to the adaptor polypeptide rather than the receptor polypeptide. In another illustrative example, an actuator moiety can be covalently linked (e.g., at its N-terminus or C-terminus) via a peptide bond to a first portion of the intein comprising a C-terminal intein. The actuator moiety-C-terminal intein fusion can be contacted with a second portion of the intein sequence comprising an N-terminal intein. This contacting of the first and second portion of the inteins can result in a site-specific cleavage (e.g., at a suitable site between the actuator moiety and the C-terminal intein), thereby releasing the actuator moiety.

In some embodiments, the cleavage recognition site comprises a disulfide bond. The disulfide bond can link the actuator moiety to the chimeric receptor polypeptide. The disulfide bond can be formed between one or more cysteines of the actuator moiety and the receptor. The cysteines can be engineered into the actuator moiety or receptor. The cysteines can be a part of the native or wild-type sequence. The cysteines can be present in a linker peptide appended to the actuator moiety or the receptor. Cleavage of the disulfide bond can be facilitated by, for example, altering the redox conditions of the disulfide bond. Alteration of the redox conditions can lead to reduction of the disulfide bond to thiols and release of the actuator moiety. Cleavage of the disulfide bond can be facilitated by a cleavage moiety comprising a redox agent that can catalyze reduction of the disulfide bond. The redox agent can be an enzyme, or any derivative, variant or fragment thereof. The enzyme can be an oxidoreductase. Examples of oxidoreductases include protein-disulfide reductase, thioredoxins, glutaredoxins, thiol disulfide oxidoreductases (e.g., DsbA, BdbA-D, MdbA, and SdbA), and glutathione disulfide reductase. The redox agent can be from any suitable source including prokaryotes and eukaryotes. Cofactors (e.g., nicotinamide cofactors, flavins, and derivatives and analogs thereof) can be supplied for optimal activity of the enzyme.

In an illustrative example shown in FIG. 14A, a chimeric receptor polypeptide comprises an actuator moiety 1401 linked by disulfide bond. The disulfide bond can be cleaved by a cleavage moiety 1402 comprising an enzyme such as an oxidoreductase, for example an oxidoreductase complexed and/or linked to an adaptor polypeptide as shown in FIG. 14B. Cleaving of the disulfide bond can release the actuator moiety as shown in FIG. 14C. The actuator moiety, upon release, can translocate to a cell nucleus where it is operable to regulate expression of a target polynucleotide (e.g., gene expression) and/or activity or edit a nucleic acid sequence as shown in FIG. 14D. FIGS. 14E-H illustrate an alternative configuration wherein the actuator moiety is complexed and/or linked to the adaptor polypeptide and the cleavage moiety (e.g., oxidoreductase) is linked to the receptor.

In some embodiments, the chimeric receptor polypeptide comprises at least one targeting sequence which directs transport of the receptor to a specific region of a cell. A targeting sequence can be used to direct transport of a polypeptide to which the targeting sequence is linked to a specific region of a cell. For example, a targeting sequence can direct the receptor to a cell nucleus utilizing a nuclear localization signal (NLS), outside of the nucleus (e.g., the cytoplasm) utilizing a nuclear export signal (NES), the mitochondria, the endoplasmic reticulum (ER), the Golgi, chloroplasts, apoplasts, peroxisomes, plasma membrane, or membrane of various organelles of a cell. In some embodiments, a targeting sequence comprises a nuclear export signal (NES) and directs a polypeptide outside of a nucleus, for example to the cytoplasm of a cell. A targeting sequence can direct a polypeptide to the cytoplasm utilizing various nuclear export signals. Nuclear export signals are generally short amino acid sequences of hydrophobic residues (e.g., at least about 2, 3, 4, or 5 hydrophobic residues) that target a protein for export from the cell nucleus to the cytoplasm through the nuclear pore complex using nuclear transport.

Not all NES substrates can be constitutively exported from the nucleus. In some embodiments, a targeting sequence comprises a nuclear localization signal (NLS, e.g., a SV40 NLS) and directs a polypeptide to a cell nucleus. A targeting sequence can direct a polypeptide to a cell nucleus utilizing various nuclear localization signals (NLS). An NLS can be a monopartite sequence or a bipartite sequence.

Non-limiting examples of NLSs include and NLS sequence derived from: the NLS of the SV40 virus large T-antigen, having the amino acid sequence PKKKRKV (SEQ ID NO: 40); the NLS from nucleoplasmin (e.g. the nucleoplasmin bipartite NLS with the sequence KRPAATKKAGQAKKKK (SEQ ID NO: 41)); the c-myc NLS having the amino acid sequence PAAKRVKLD (SEQ ID NO: 42) or RQRRNELKRSP (SEQ ID NO: 43); the hRNPA1 M9 NLS having the sequence NQSSNFGPMKGGNFG-GRSSGPYGGGGQYFAKPRNQGGY (SEQ ID NO: 44); the sequence RMRIZFKNKGKDTAELRRRRVEVS-VELRKAKKDEQILKRRNV (SEQ ID NO: 45) of the IBB domain from importin-alpha; the sequences VSRKRPRP (SEQ ID NO: 46) and PPKKARED (SEQ ID NO: 47) of the myoma T protein; the sequence PQPKKKPL (SEQ ID NO: 48) of human p53; the sequence SALIKKKKKMAP (SEQ ID NO: 49) of mouse c-abl IV; the sequences DRLRR (SEQ ID NO: 50) and PKQKKRK (SEQ ID NO: 51) of the influenza virus NS1; the sequence RKLKKKIKKL (SEQ ID NO: 52) of the Hepatitis virus delta antigen; the sequence REKKKFLKRR (SEQ ID NO: 53) of the mouse Mxl protein; the sequence KRKGDEVDGVDEVAKKKSKK (SEQ ID NO: 54) of the human poly(ADP-ribose) polymerase; and the sequence RKCLQAGMNLEARKTKK (SEQ ID NO: 55) of the steroid hormone receptors (human) glucocorticoid.

In some embodiments, a targeting sequence comprises a membrane targeting peptide and directs a polypeptide to a plasma membrane or membrane of a cellular organelle. A membrane-targeting sequence can provide for transport of the chimeric transmembrane receptor polypeptide to a cell surface membrane or other cellular membrane. Molecules in association with cell membranes contain certain regions that facilitate membrane association, and such regions can be incorporated into a membrane targeting sequence. For example, some proteins contain sequences at the N-terminus or C-terminus that are acylated, and these acyl moieties facilitate membrane association. Such sequences can be recognized by acyltransferases and often conform to a particular sequence motif. Certain acylation motifs are capable of being modified with a single acyl moiety (often followed by several positively charged residues (e.g. human c-Src) to improve association with anionic lipid head groups) and others are capable of being modified with multiple acyl moieties. For example the N-terminal sequence of the protein tyrosine kinase Src can comprise a single myristoyl moiety. Dual acylation regions are located within the N-terminal regions of certain protein kinases, such as a subset of Src family members (e.g., Yes, Fyn, Lck) and G-protein alpha subunits. Such dual acylation regions often are located within the first eighteen amino acids of such proteins, and conform to the sequence motif Met-Gly-Cys-Xaa-Cys (SEQ ID NO: 56), where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (so called "CAAX boxes"), which can modified with C15 or C10 isoprenyl moieties, from the C-terminus of G-protein gamma subunits and other proteins also can be utilized. These and other acylation motifs include, for example, those discussed in Gauthier-Campbell et al., Molecular Biology of the Cell 15: 2205-2217 (2004); Glabati et al., Biochem. J. 303: 697-700 (1994) and Zlakine et al., J. Cell Science 110: 673-679

(1997), and can be incorporated in a targeting sequence to induce membrane localization.

In certain embodiments, a native sequence from a protein containing an acylation motif is incorporated into a targeting sequence. For example, in some embodiments, an N-terminal portion of Lck, Fyn or Yes or a G-protein alpha subunit, such as the first twenty-five N-terminal amino acids or fewer from such proteins (e.g., about 5 to about 20 amino acids, about 10 to about 19 amino acids, or about 15 to about 19 amino acids of the native sequence with optional mutations), may be incorporated within the N-terminus of a chimeric polypeptide. In certain embodiments, a C-terminal sequence of about 25 amino acids or less from a G-protein gamma subunit containing a CAAX box motif sequence (e.g., about 5 to about 20 amino acids, about 10 to about 18 amino acids, or about 15 to about 18 amino acids of the native sequence with optional mutations) can be linked to the C-terminus of a chimeric polypeptide.

Any membrane-targeting sequence can be employed. In some embodiments, such sequences include, but are not limited to myristoylation-targeting sequence, palmitoylation-targeting sequence, prenylation sequences (i.e., farnesylation, geranyl-geranylation, CAAX Box), protein-protein interaction motifs or transmembrane sequences (utilizing signal peptides) from receptors. Examples include those discussed in, for example, ten Klooster, J. P. et al, Biology of the Cell (2007) 99, 1-12; Vincent, S., et al., Nature Biotechnology 21:936-40, 1098 (2003).

Additional protein domains exist that can increase protein retention at various membranes. For example, an ~120 amino acid pleckstrin homology (PH) domain is found in over 200 human proteins that are typically involved in intracellular signaling. PH domains can bind various phosphatidylinositol (PI) lipids within membranes (e.g. PI (3,4,5)-P3, PI (3,4)-P2, PI (4,5)-P2) and thus can play a key role in recruiting proteins to different membrane or cellular compartments. Often the phosphorylation state of PI lipids is regulated, such as by PI-3 kinase or PTEN, and thus, interaction of membranes with PH domains may not be as stable as by acyl lipids.

In some embodiments, a targeting sequence directing a polypeptide to a cellular membrane can utilize a membrane anchoring signal sequence. Various membrane-anchoring sequences are available. For example, membrane anchoring signal sequences of various membrane bound proteins can be used. Sequences can include those from: 1) class I integral membrane proteins such as IL-2 receptor beta-chain and insulin receptor beta chain; 2) class II integral membrane proteins such as neutral endopeptidase; 3) type III proteins such as human cytochrome P450 NF25; and 4) type IV proteins such as human P-glycoprotein.

In some embodiments, the chimeric receptor polypeptide is linked to a polypeptide folding domain which can assist in protein folding. In some embodiments, an actuator moiety is linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. The cell-penetrating domain can be located at the N-terminus, the C-terminus, or anywhere within the actuator moiety.

Figure 5:
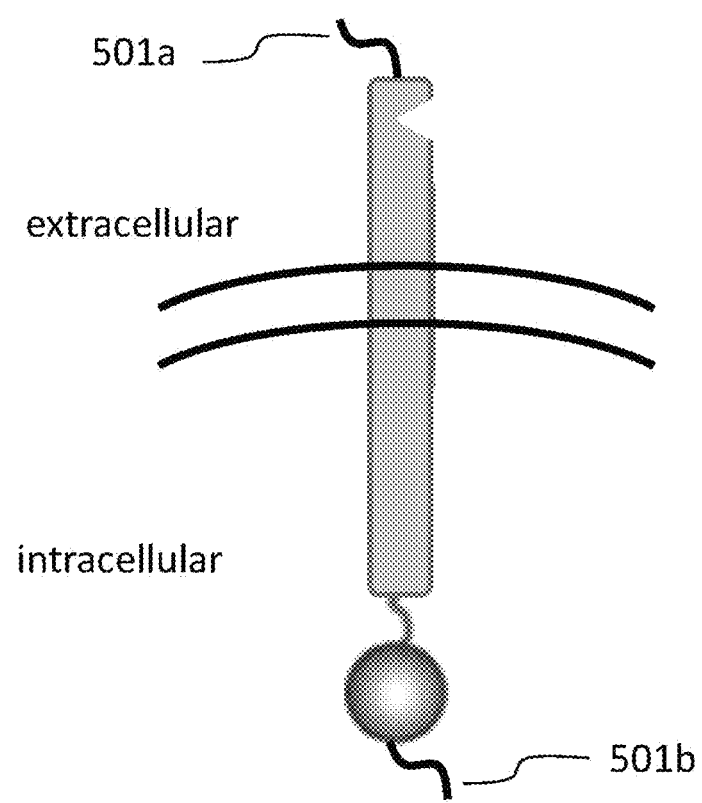
FIG. 5 shows an exemplary chimeric receptor polypeptide comprising at least one targeting sequence.

The targeting sequence can be linked to any appropriate region of the chimeric receptor polypeptide, for example at the N-terminus, the C-terminus, or in an internal region of the receptor. In some embodiments, at least two targeting sequences are linked to the receptor. In an exemplary chimeric receptor polypeptide shown in FIG. 5, a first targeting sequence 501a can be linked to the extracellular region of the receptor and a second targeting sequence 501b can be linked to the intracellular region of the receptor, such as to the GMP. When a receptor is linked to multiple targeting sequences, for example targeting sequences directed to different locations of a cell, the final localization of the receptor can be determined by the relative strengths of the targeting sequences. For example, a receptor having both a targeting sequence comprising an NES and a targeting sequence comprising an NLS can localize to the cytoplasm if the NES is stronger than NLS. Alternatively, if the NLS is stronger than the NES, the receptor can localize to the nucleus even though both a nuclear localization signal and nuclear export signal are present on the receptor. A targeting sequence can comprise multiple copies of, for example, each a NLS and NES, to fine-tune the degree of the cellular localization.

In some cases, a targeting sequence is linked to the actuator moiety. Following release of the actuator moiety from the GMP (and receptor) by cleavage of the cleavage recognition site, the targeting sequence can direct the actuator moiety to a cellular location that is different from the receptor. For example, a chimeric transmembrane receptor can comprise a first targeting sequence directing the receptor to a plasma membrane and the actuator moiety can separately comprise a second targeting sequence directing localization to a cell nucleus. Initially, the actuator moiety (forming a portion of the receptor) can be localized to a plasma membrane due to the first targeting sequence. Following release of the actuator moiety from the GMP by cleavage of the cleavage recognition site, the actuator moiety can localize to a cell nucleus via targeting by the second targeting sequence. In some embodiments, the actuator moiety translocates to a cell nucleus after cleavage of the cleavage recognition sequence.

Binding of the chimeric adaptor polypeptide to a chimeric receptor polypeptide when the receptor has undergone modification upon binding to an antigen can bring the cleavage moiety in proximity to the cleavage recognition site. Cleavage of the recognition site can release the actuator moiety from the GMP. Following release, the actuator moiety is operable to complex with a target polynucleotide, for example in the cell cytoplasm or a cell nucleus. Complexing of the actuator moiety with a target polynucleotide can regulate the expression and/or activity of at least one gene or edit a nucleic acid sequence.

Figure 6A:
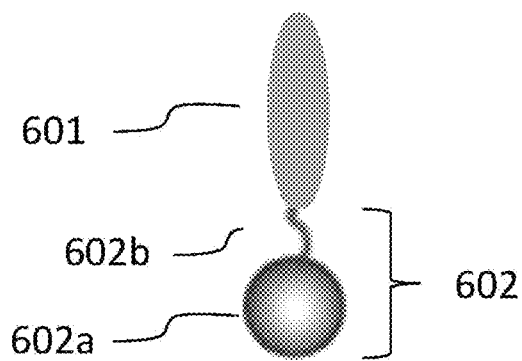
FIG. 6A shows an exemplary chimeric adaptor polypeptide comprising a receptor binding moiety and a gene modulating polypeptide (GMP).

In another exemplary configuration, the GMP forms a portion of the chimeric adaptor polypeptide and the cleavage moiety forms a portion of a chimeric receptor polypeptide. A chimeric adaptor polypeptide of an exemplary configuration can comprise (a) a receptor binding moiety that binds a receptor that has undergone modification upon binding to an antigen; and (b) a gene modulating polypeptide (GMP) linked to the receptor binding moiety, wherein the GMP comprises an actuator moiety linked to a cleavage recognition site; wherein (i) the cleavage recognition site is cleavable by a cleavage moiety in response to receptor binding, and (ii) the actuator moiety is operable to complex with a target polynucleotide in response to cleavage of the cleavage recognition site. FIG. 6A shows an exemplary chimeric adaptor polypeptide. A chimeric adaptor polypeptide can comprise a receptor binding moiety 601 linked to a GMP 602. A GMP can comprise an actuator moiety 602a linked to a cleavage recognition site 602b.

A receptor binding moiety of a chimeric adaptor polypeptide can be any binding partner (e.g., protein) which can bind a receptor, or any derivative, variant or fragment thereof. In some embodiments, an adaptor comprises a binding partner of a receptor that is membrane-bound, or any derivative, variant or fragment thereof. In some embodiments, an adaptor comprises a binding partner of a receptor, or any derivative, variant or fragment thereof, that is not membrane-bound (e.g., intracellular or cytosolic). An adaptor polynucleotide may comprise a receptor binding domain of a signaling protein or other protein recruited to a receptor. The chimeric adaptor polypeptide can be recruited to the chimeric receptor polypeptide in response to receptor modification, e.g., a conformational change, chemical modification, or combination thereof. A receptor may undergo receptor modification in response to ligand binding. Receptors, or any derivative, variant or fragment thereof, and binding partners (e.g., proteins), or any derivative, variant or fragment thereof, can be selected so as to optimize the desired level of recruitment of the adaptor polypeptide to the receptor.

In some embodiments, a chimeric adaptor polypeptide comprises a molecule (e.g., protein), or any derivative, variant or fragment thereof, recruited to a Notch receptor when the Notch receptor is bound to a ligand. A chimeric adaptor polypeptide can comprise a protein, any derivative, variant or fragment thereof, selected from the group consisting of presenilin-1 (PSEN1), nicastrin, anterior pharynx-defective 1 (APH-1), and presenilin enhancer 2 (PEN-2).

In some embodiments, a chimeric adaptor polypeptide comprises a molecule (e.g., protein), or any derivative, variant or fragment thereof, recruited to a GPCR when the GPCR is bound to a ligand (e.g., a ligand-bound GPCR that has undergone conformational and/or biochemical modification). A chimeric adaptor polypeptide can comprise a protein, or any derivative, variant or fragment thereof, selected from the group consisting of AKAP79 (AKAP5) and AKAP250 (AKAP12, gravin), arrestin (e.g., β-arrestin), ATBP50, calmodulin, DRIP78 (DNAJC14), Homer, GASP1, GEC1 (GABARAPL1), INAD, JAK2, LARG (ARHGEF12), MAGI2, MAGI3, M10 MHC, MPP3, MRAP and MRAP2, MUPP1 (MPDZ), neurochondrin, NHERF1 (EBP50, SLC9A3R1), NHERF2 (SLC9A3R2), NINAA, ODR4, p85, PDZ-RhoGEF (ARHGEF11), periplakin, PICK 1, PSD95, RACK1 (GNB2L1), RAMP1, RAMP2, RAMP3, RanBP2, REEPs, RTPs, RTP4, Shank, SNX1, syntrophin, spinophilin, TCTEXT1 (DYNLT1), and USP4.

In some embodiments, a chimeric adaptor polypeptide comprises a molecule (e.g., protein), or any derivative, variant or fragment thereof, that is recruited to an integrin receptor when the receptor is bound to a ligand. Examples of adaptor proteins that are recruited to an integrin receptor include, but are not limited to, structural adaptor proteins, scaffolding adaptor proteins, and adaptor proteins having catalytic activity. In some embodiments, a chimeric adaptor polypeptide comprises a protein, or any derivative, variant or fragment thereof, selected from talin, kindlin, filamin and tensin. In some embodiments, a chimeric adaptor polypeptide comprises a protein, or any derivative, variant or fragment thereof, selected from paxillin and kindlin. In some embodiments, a chimeric adaptor polypeptide comprises a protein, or any derivative, variant or fragment thereof, selected from focal adhesion kinase (FAK), Src, and protein phosphatase 2A (PP2A). In some embodiments, a chimeric adaptor polypeptide comprises a protein, or any derivative, variant or fragment thereof, selected from RAB21, PTPN2, AUP1, BIN1, COL8A1, and ITGB1.

In some embodiments, a chimeric adaptor polypeptide comprises a molecule (e.g., protein), or any derivative, variant or fragment thereof, recruited to a cadherin receptor. The molecule may be recruited to the receptor as a result of a receptor modification (e.g., chemical modification e.g., phosphorylation, and/or conformational change). In some embodiments, a chimeric adaptor polypeptide comprises a protein, or any derivative, variant or fragment thereof, selected from α-catenin, β-catenin, γ-catenin, catenin delta-1 (p120-catenin), AJAP1, CTNND1, DLGAP5, TBC1D2, LIMA1, CAV1, TRPV4, CTNNB1 complex, PIP5K1C, RAB8B, RAPGEF2, DDR1, PSEN1, CDH1, CDC27, CTNNA1, and EGFR.

In some embodiments, a chimeric adaptor polypeptide comprises a molecule (e.g., protein) that is recruited to chimeric receptor polypeptide comprising a RTSK, or any derivative, variant or fragment thereof. In some embodiments, a chimeric adaptor polypeptide comprises a protein, or any derivative, variant or fragment thereof, selected from a SMAD family member including SMAD1, SMAD2, SMAD3, SMAD5, SMAD6, and SMAD7, and SMAD9 (sometimes referred to as SMAD8); the SMAD anchor for receptor activation (SARA); a SMURF protein (e.g., SMURF1, SMURF2); and any derivative, variant or fragment thereof. In some embodiments, a chimeric adaptor polypeptide comprises a molecule (e.g., protein) that is recruited to chimeric receptor polypeptide comprising a cytokine receptor, or any derivative, variant or fragment thereof. In some embodiments, an adaptor polypeptide comprises a gp130, CD131, CD132, or any derivative, variant or fragment thereof.

In some embodiments, a chimeric adaptor polypeptide comprises a molecule recruited to a phosphorylated RTK or RTSK, or a receptor phosphorylated by a non-covalently associated intracellular kinase. The phosphorylation of specific amino acid residues (e.g., tyrosine residues) within an activated receptor (e.g., a chimeric receptor polypeptide) can create binding sites for molecules such as Src homology 2 (SH2) domain- and phosphotyrosine binding (PTB) domain-containing proteins. In some embodiments, an adaptor polypeptide comprises a protein containing an SH2 domain, such as ABL1, ABL2, BCAR3, BLK, BLNK, BMX, BTK, CHN2, CISH, CRK, CRKL, CSK, DAPP1, EAT-2, FER, FES, FGR, FRK, FYN, GADS, GRAP, GRAP2, GRB10, GRB14, GRB2, GRB7, HCK, HSH2D, INPP5D, INPPL1, ITK, JAK2, LCK, LCP2, LYN, MATK, NCK1, NCK2, PIK3R1, PIK3R2, PIK3R3, PLCG1, PLCG2, PTK6, PTPN11, PTPN6, RASA1, SAP, SH2B1, SH2B2, SH2B3, SH2D1A, SH2D1B, SH2D2A, SH2D3A, SH2D3C, SH2D4A, SH2D4B, SH2D5, SH2D6, SH3BP2, SHB, SHC1, SHC2, SHC3, SHC4, SHD, SHE, SHP1, SHP2, SLA, SLA2, SOCS1, SOCS2, SOCS3, SOCS4, SOCS5, SOCS6, SOCS7, SRC, SRMS, STAT1, STAT2, STAT3, STAT4, STAT5A, STAT5B, STAT6, SUPT6H, SYK, TEC, TENC1, TNS, TNS1, TNS3, TNS4, TXK, VAV1, VAV2, VAV3, YES1, ZAP70, or any derivative, variant or fragment thereof. In some embodiments, an adaptor polypeptide comprises a protein containing a PTB domain, such as APBA1, APBA2, APBA3, EPS8, EPS8L1, EPS8L2, EPS8L3, TENC1, TNS, TNS1, TNS3, TNS4, DOK1, DOK2, DOK3, DOK4, DOK5, DOK6, DOK7, FRS2, FRS3, IRS1, IRS2, IRS3, IRS4, SHC1, SHC2, SHC3, SHC4, TLN1, TLN2, X11a, or any derivative, variant or fragment thereof.

In some embodiments, a chimeric adaptor polypeptide comprises a protein that is recruited to a TNF receptor, or any derivative, variant or fragment thereof. Such proteins are sometimes referred to as TNR receptor associated factors or TRAFS and include TRAF1, TRAF2, TRAF3, TRAF4, TRAF5, TRAF6, and TRAF7. In some embodiments, a chimeric adaptor polypeptide comprises a receptor-interacting serine/threonine-protein kinase 1 (RIP1 or RIPK1) and receptor-interacting serine/threonine-protein kinase 3 (RIP3 or RIPK3), or any derivative, variant or fragment thereof. In some embodiments, a chimeric adaptor polypeptide comprises an adaptor protein that is recruited to a TNFR, such as Fas-associated protein with Dead Domain (FADD) and tumor necrosis factor receptor type-1 associated DEATH domain (TRADD) which binds TRAF2, or any derivative, variant or fragment thereof.

In some embodiments, a chimeric adaptor polypeptide comprises a molecule (e.g., protein), or any derivative, variant or fragment thereof, recruited to a phosphorylated ITAM, for example an ITAM of a chimeric polypeptide receptor comprising an immune receptor such as a TCR. The phosphorylation of specific tyrosine residues within the activated receptor can create binding sites for molecules such as Src homology 2 (SH2) domain- and phosphotyrosine binding (PTB) domain-containing proteins. In some embodiments, a chimeric adaptor polypeptide comprises ABL1, ABL2, BCAR3, BLK, BLNK, BMX, BTK, CHN2, CISH, CRK, CRKL, CSK, DAPP1, EAT-2, FER, FES, FGR, FRK, FYN, GADS, GRAP, GRAP2, GRB10, GRB14, GRB2, GRB7, HCK, HSH2D, INPP5D, INPPL1, ITK, JAK2, LCK, LCP2, LYN, MATK, NCK1, NCK2, PIK3R1, PIK3R2, PIK3R3, PLCG1, PLCG2, PTK6, PTPN11, PTPN6, RASA1, SAP, SH2B1, SH2B2, SH2B3, SH2D1A, SH2D1B, SH2D2A, SH2D3A, SH2D3C, SH2D4A, SH2D4B, SH2D5, SH2D6, SH3BP2, SHB, SHC1, SHC2, SHC3, SHC4, SHD, SHE, SHP1, SHP2, SLA, SLA2, SOCS1, SOCS2, SOCS3, SOCS4, SOCS5, SOCS6, SOCS7, SRC, SRMS, STAT1, STAT2, STAT3, STAT4, STAT5A, STAT5B, STAT6, SUPT6H, SYK, TEC, TENC1, TNS, TNS1, TNS3, TNS4, TXK, VAV1, VAV2, VAV3, YES1, ZAP70, or any derivative, variant or fragment thereof. In some embodiments, a chimeric adaptor polypeptide comprises APBA1, APBA2, APBA3, EPS8, EPS8L1, EPS8L2, EPS8L3, TENC1, TNS, TNS1, TNS3, TNS4, DOK1, DOK2, DOK3, DOK4, DOK5, DOK6, DOK7, FRS2, FRS3, IRS1, IRS2, IRS3, IRS4, SHC1, SHC2, SHC3, SHC4, TLN1, TLN2, X11a, or any derivative, variant or fragment thereof.

In some configurations, a chimeric adaptor polypeptide of a subject system can comprise a gene modulating polypeptide (GMP). A GMP, as described elsewhere herein, can comprise an actuator moiety linked to a cleavage recognition site. The actuator moiety can comprise a nuclease (e.g., DNA nuclease and/or RNA nuclease), modified nuclease (e.g., DNA nuclease and/or RNA nuclease) that is nuclease-deficient or has reduced nuclease activity compared to a wild-type nuclease, a variant thereof, a derivative thereof, or a fragment thereof as described elsewhere herein. The actuator moiety can regulate expression or activity of a gene and/or edit the sequence of a nucleic acid (e.g., a gene and/or gene product). In some embodiments, the actuator moiety comprises a DNA nuclease such as an engineered (e.g., programmable or targetable) DNA nuclease to induce genome editing of a target DNA sequence. In some embodiments, the actuator moiety comprises a RNA nuclease such as an engineered (e.g., programmable or targetable) RNA nuclease to induce editing of a target RNA sequence. In some embodiments, the actuator moiety has reduced or minimal nuclease activity. An actuator moiety having reduced or minimal nuclease activity can regulate expression and/or activity of a gene by physical obstruction of a target polynucleotide or recruitment of additional factors effective to suppress or enhance expression of the target polynucleotide. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. In some embodiments, the actuator moiety is a nucleic acid-guided actuator moiety. In some embodiments, the actuator moiety is a DNA-guided actuator moiety. In some embodiments, the actuator moiety is an RNA-guided actuator moiety. An actuator moiety can regulate expression or activity of a gene and/or edit a nucleic acid sequence, whether exogenous or endogenous. For example, an actuator moiety can comprise a Cas protein which lacks cleavage activity.

Any suitable nuclease can be used in an actuator moiety. Suitable nucleases include, but are not limited to, CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute (Ago) proteins (e.g., prokaryotic Argonaute (pAgo), archaeal Argonaute (aAgo), and eukaryotic Argonaute (eAgo)); any derivative thereof; any variant thereof; and any fragment thereof. In some embodiments, the actuator moiety comprises a Cas protein that forms a complex with a guide nucleic acid, such as a guide RNA. In some embodiments, the actuator moiety comprises a RNA-binding protein (RBP) optionally complexed with a guide nucleic acid, such as a guide RNA, which is able to form a complex with a Cas protein.

Figure 6B:
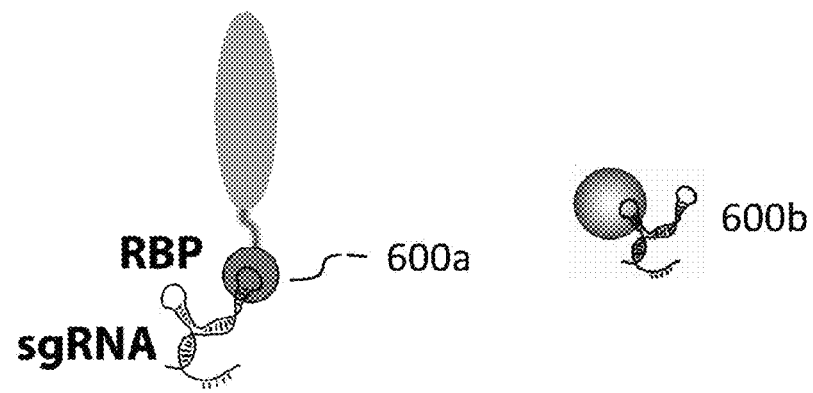
FIG. 6B shows an exemplary chimeric adaptor polypeptide including an actuator moiety comprising an RNA-binding protein optionally complexed to a guide nucleic acid (e.g., sgRNA).

In some embodiments, the actuator moiety comprises a RNA-binding protein (RBP) optionally complexed with a guide nucleic acid, such as a guide RNA, which is able to form a complex with a Cas protein. FIG. 6B shows an exemplary chimeric adaptor polypeptide in which the actuator moiety comprises an RNA-binding protein 600a optionally complexed with a guide nucleic acid. Upon release from the RNA-binding protein (RBP), for example by dissociation of the guide nucleic acid from the RBP or cleavage of the cleavage recognition site, the guide nucleic acid can form a complex with a Cas protein 600b which is operable to regulate expression of a target polynucleotide (e.g., gene expression) and/or activity or edit a nucleic acid sequence. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. For example, an actuator moiety can comprise a Cas protein which lacks cleavage activity.

Figure 7:
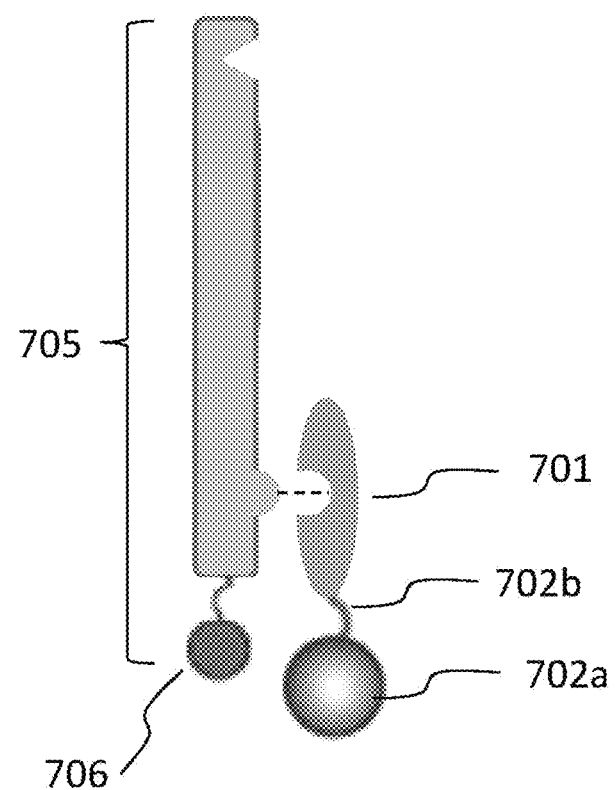
FIG. 7 shows an exemplary system comprising a chimeric receptor polypeptide comprising a cleavage moiety and a chimeric adaptor polypeptide comprising a GMP.

In some embodiments, the cleavage recognition site is flanked by the receptor binding moiety and the actuator moiety. The actuator moiety can be released from the GMP and from the chimeric adaptor polypeptide by cleavage of the recognition site by a cleavage moiety. The cleavage moiety can recognize and/or cleave a cleavage recognition site, for example, when in proximity to the cleavage recognition site. A cleavage moiety can comprise a polypeptide sequence. The cleavage moiety, in some configurations, forms a portion of the chimeric receptor polypeptide. The cleavage moiety can form the N-terminus, C-terminus or an internal portion of the chimeric receptor polypeptide. In some embodiments, the cleavage moiety is complexed to the chimeric receptor polypeptide. The cleavage moiety can be complexed to the N-terminus, C-terminus, or an internal portion of the chimeric receptor polypeptide. In an exemplary configuration shown in FIG. 7, the cleavage recognition site 702b is flanked by the receptor binding moiety 701 and the actuator moiety 702a, and the cleavage moiety 706 forms a portion a chimeric receptor polypeptide 705.

FIGS. 8A-D illustrate schematically the release of an actuator moiety from a GMP. FIG. 8A shows the binding of an antigen to a transmembrane chimeric receptor polypeptide. The transmembrane chimeric receptor polypeptide comprises an extracellular region having an antigen interacting domain 805 and an intracellular region comprising a cleavage moiety 806. The cleavage moiety can be complexed with the receptor or linked, for example by a peptide bond and/or peptide linker, to the receptor. The GMP forms a portion of the chimeric adaptor polypeptide. The GMP, linked to the receptor binding moiety 801, includes an actuator moiety 802a linked to a cleavage recognition site 802b. In response to antigen binding, the receptor is modified by phosphorylation 803 in the intracellular region of the receptor (FIG. 8B). Following receptor modification (e.g., phosphorylation), the chimeric adaptor polypeptide is recruited to the receptor as shown in FIG. 8C. The receptor comprises a cleavage moiety 806. When in proximity to the cleavage recognition site, the cleavage moiety can cleave the recognition site to release the actuator moiety from the GMP as shown in FIG. 8D. Upon release, the actuator moiety can enter the nucleus to regulate the expression and/or activity of a target gene or edit a nucleic acid sequence. FIGS. 8E-H show an analogous system wherein receptor modification comprises a conformational change. In some embodiments, the chimeric adaptor protein is tethered to the membrane (e.g., as a membrane bound protein).

Figure 9:
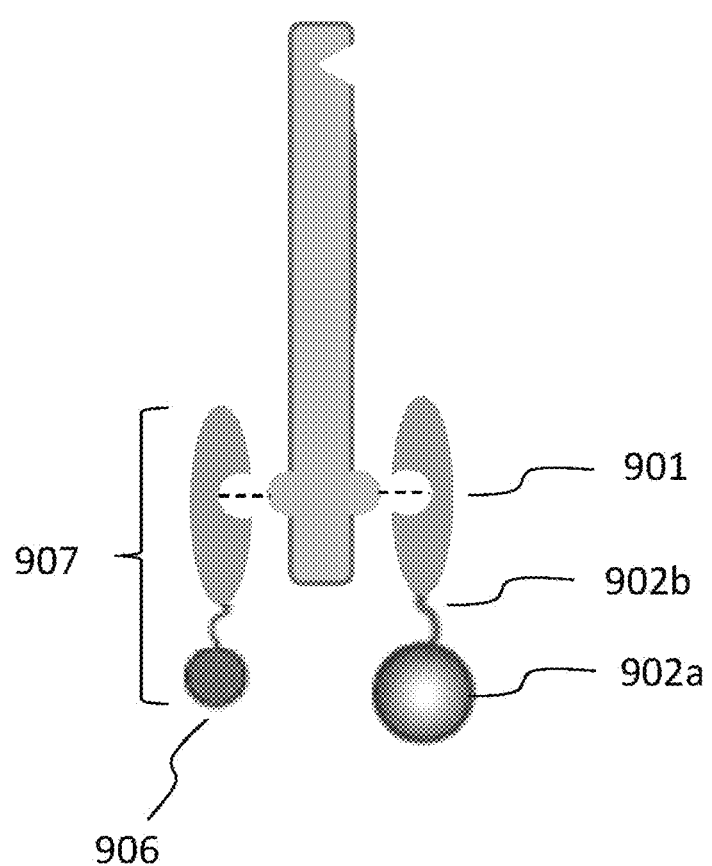
FIG. 9 shows an exemplary system comprising a chimeric receptor polypeptide, a chimeric adaptor polypeptide comprising a GMP, and a second adaptor polypeptide comprising a cleavage moiety.

In another configuration, the cleavage moiety is complexed to a second adaptor polypeptide which binds the chimeric receptor polypeptide when the receptor polypeptide has undergone modification. An illustrative example is shown in FIG. 9. The cleavage recognition site 902b is flanked by the receptor binding moiety 901 and the actuator moiety 902a, and the cleavage moiety 906 forms a portion a second adaptor polypeptide 907.

Figure 10:
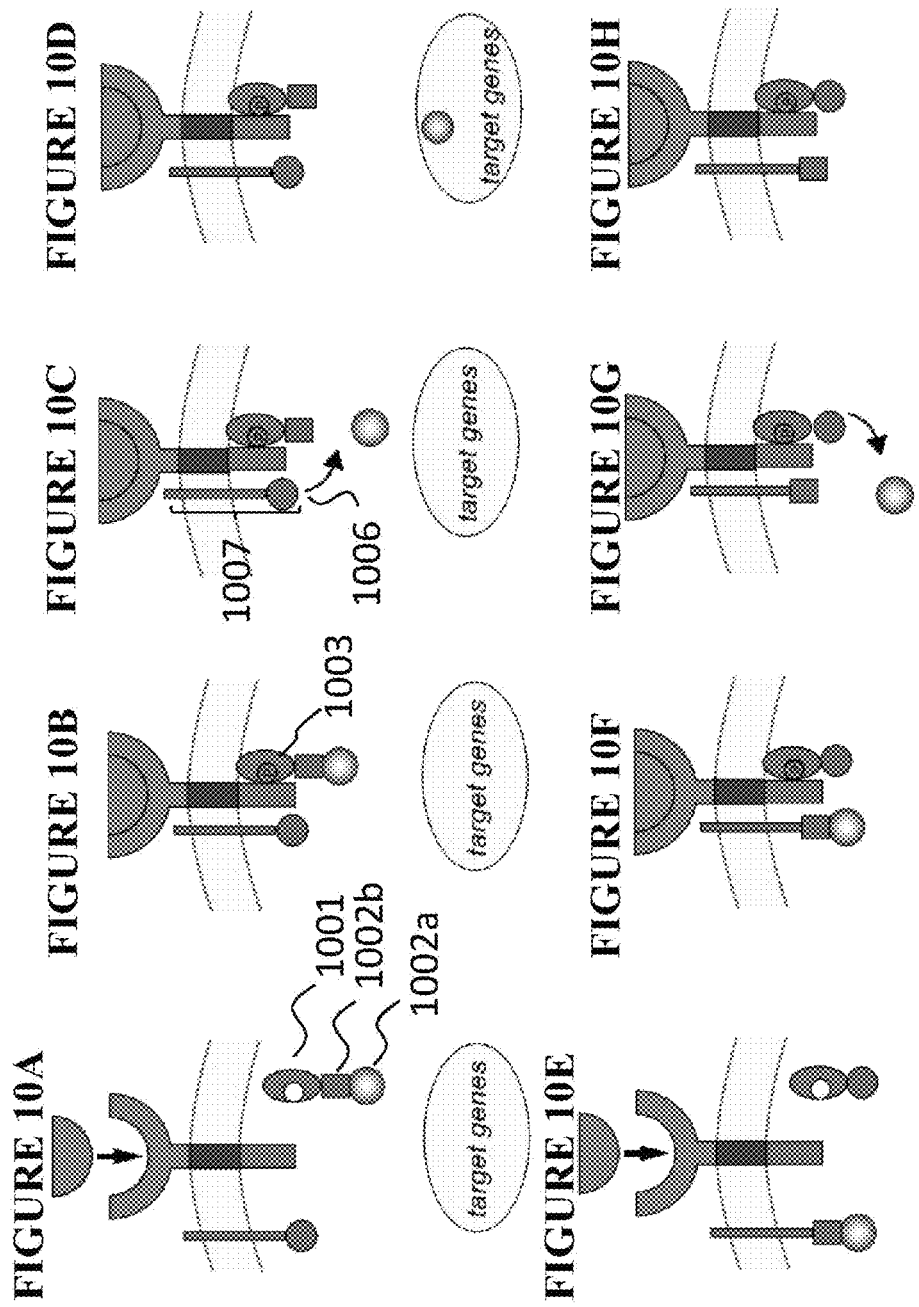
FIGS. 10A-10D illustrate schematically the release of an actuator moiety from a GMP in a system comprising at least two adaptor polypeptides and a receptor which undergoes phosphorylation.
FIGS. 10E-10H illustrate schematically the release of an actuator moiety from a GMP in a system comprising at least two adaptor polypeptides and a receptor which undergoes a conformational change.

FIGS. 10A-D illustrate schematically the release of an actuator moiety from a GMP. FIG. 10A shows the binding of an antigen to a transmembrane chimeric receptor polypeptide. The transmembrane chimeric receptor polypeptide comprises an extracellular region having an antigen interacting domain and an intracellular region. The GMP, comprising an actuator moiety linked to a cleavage recognition site, forms a portion of a chimeric adaptor polypeptide. The cleavage recognition site 1002b is flanked by the receptor binding moiety 1001 and the actuator moiety 1002a. In response to antigen binding, the receptor is modified by phosphorylation 1003 in the intracellular region (FIG. 10B). Following receptor modification (e.g., phosphorylation), the chimeric adaptor polypeptide is recruited to the receptor as shown in FIG. 10B. A second adaptor polypeptide 1007 comprising a cleavage moiety 1006 is also recruited to the modified receptor (FIG. 10C). The cleavage moiety may be complexed with the second adaptor polypeptide or linked, for example by a peptide bond and/or peptide linker, to the adaptor. When in proximity to the cleavage recognition site, the cleavage moiety can cleave the recognition site to release the actuator moiety from the GMP as shown in FIG. 10D. Upon release, the actuator moiety can enter the nucleus to regulate the expression and/or activity of a target gene or edit a nucleic acid sequence. FIGS. 10E-H show an analogous system wherein receptor modification comprises a conformational change. In some embodiments, the chimeric adaptor polypeptide is tethered to the membrane (e.g., as a membrane bound protein). In some embodiments, the second adaptor polypeptide is tethered to the membrane (e.g., as a membrane bound protein).

Figure 16:
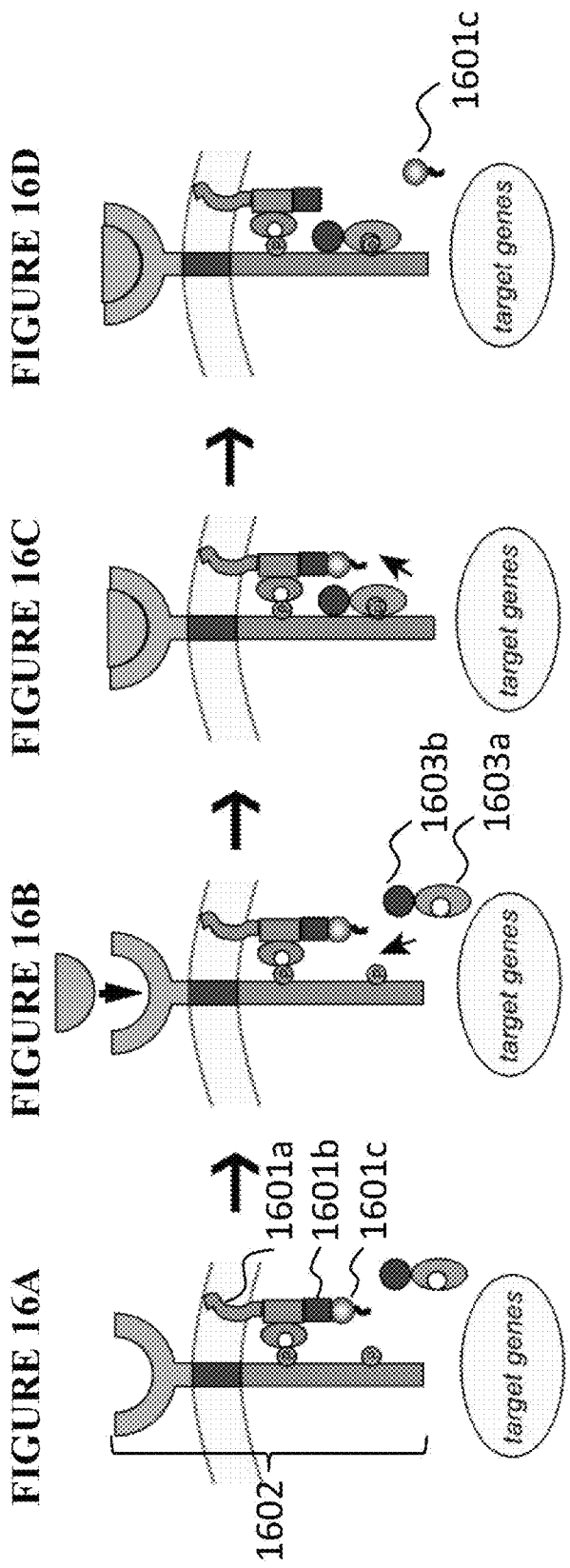
FIGS. 16A-16D illustrate schematically the release of an actuator moiety from a GMP in a system comprising at least two adaptor polypeptides.

FIGS. 16A-D illustrate schematically the release of an actuator moiety in a system comprising a first membrane-tethered adaptor and a second cytoplasmic adaptor. FIG. 16A shows the association of a first membrane-tethered adaptor comprising a membrane tethering domain 1601a (e.g., CAAX), a protease recognition site 1601b (e.g., TEV), and an actuator moiety 1601c with a chimeric transmembrane receptor 1602. The chimeric transmembrane receptor can function as a scaffold and includes at least two adaptor binding sites (e.g., EGFR or receptor tyrosine kinase (RTK)). One adaptor binding site can be associated with a membrane-tethered adaptor as shown in FIG. 16B. The association of the membrane-tethered adaptor, in some cases, is dependent on antigen binding to the receptor. In some systems, the membrane-tethered adaptor is located in proximity to the receptor and association may not depend on antigen binding to the receptor. As shown in FIGS. 16B and 16C, antigen interaction with the receptor can conditionally recruit a second adaptor protein comprising a cytoplasmic receptor binding moiety 1603a and protease 1603b, to the other adaptor binding site of the receptor. The second adaptor protein comprising the protease, when recruited to the transmembrane receptor, can cleave the protease recognition site 1601b of the membrane-tethered molecule, thereby releasing the actuator moiety 1601c as shown in FIG. 16D.

In some embodiments, the cleavage moiety only cleaves at the recognition site when in proximity to the cleavage recognition site. In some embodiments, the cleavage recognition site comprises a polypeptide sequence (e.g., a peptide cleavage domain) that is a recognition sequence of a protease. The cleavage moiety can comprise protease activity which recognizes the polypeptide sequence. A cleavage moiety comprising protease activity can be a protease including, but not limited to, any protease described elsewhere herein, or any derivative, variant or fragment thereof. In some embodiments, the cleavage recognition site comprises multiple cleavage recognition sequences, and each cleavage recognition sequence can be recognized by the same or different cleavage moiety comprising protease activity (e.g., protease).

In some embodiments, the cleavage recognition site comprises a first portion of an intein sequence that reacts with the second portion of the intein sequence to release the actuator moiety. A heterologous split intein system can be used to facilitate release of the actuator moiety from the chimeric adaptor polypeptide. The actuator moiety can be covalently linked to the first portion of the intein sequence. The actuator moiety can be linked via its N-terminus or C-terminus to the first portion of the intein sequence. The cleavage moiety can comprise the second portion of the intein sequence. The first portion or second portion of the intein sequence can be the N-terminal intein, the C-terminal intein, or any other suitable portion of an intein that can facilitate release of the actuator moiety. The intein sequences can be from any suitable source. The first and second portion can be from the same or different sources (e.g., organism, protein). In an illustrative example, an actuator moiety can be covalently linked (e.g., at its N-terminus or C-terminus) via a peptide bond to a first portion of the intein sequence, which comprises an N-terminal intein. The actuator moiety-N-terminal intein fusion can be contacted with a second portion of the intein sequence comprising a C-terminal intein. This contacting of the first and second portion of the intein sequences can result in a site specific cleavage (e.g., at a site between the actuator moiety and the N-terminal intein), thereby releasing the actuator moiety. In another illustrative example, an actuator moiety can be covalently linked (e.g., at its N-terminus or C-terminus) via a peptide bond to a first portion of the intein comprising a C-terminal intein. The actuator moiety-C-terminal intein fusion can be contacted with a second portion of the intein sequence comprising an N-terminal intein. This contacting of the first and second portion of the inteins can result in a site-specific cleavage (e.g., at a suitable site between the actuator moiety and the C-terminal intein), thereby releasing the actuator moiety.

In some embodiments, the cleavage recognition site comprises a disulfide bond. The disulfide bond can link the actuator moiety to the receptor binding moiety in a chimeric adaptor polypeptide. The disulfide bond can be formed between one or more cysteines of the actuator moiety and the receptor binding moiety. The cysteines can be engineered into the actuator moiety or receptor binding moiety. The cysteines can be a part of the native or wild-type sequence of the actuator moiety or receptor binding moiety. The cysteines can be present in a linker peptide appended to the actuator moiety or the receptor binding moiety. Cleavage of the disulfide bond can be facilitated by, for example, altering the redox conditions of the disulfide bond. Alteration of the redox conditions can lead to reduction of the disulfide bond to thiols and release of the actuator moiety. Cleavage of the disulfide bond can be facilitated by a cleavage moiety comprising a redox agent that can lead to reduction of the disulfide bond. The redox agent can be an enzyme, or any derivative, variant or fragment thereof. The enzyme can be an oxidoreductase. Examples of oxidoreductases include protein-disulfide reductase, thioredoxins, glutaredoxins, thiol disulfide oxidoreductases (e.g., DsbA, BdbA-D, MdbA, SdbA), and glutathione disulfide reductase. The redox agent can be from any suitable source including prokaryotes and eukaryotes. Cofactors (e.g., nicotinamide cofactors, flavins, and derivatives and analogs thereof) can be supplied for optimal activity of the enzyme.

In some embodiments, the chimeric adaptor polypeptide comprises at least one targeting sequence which directs transport of the adaptor to a specific region of a cell. For example, a targeting sequence can direct the adaptor to a cell nucleus utilizing a nuclear localization signal (NLS), outside of a cell nucleus (e.g., to the cytoplasm) utilizing a nuclear export signal (NES), the mitochondria, the endoplasmic reticulum (ER), the Golgi, chloroplasts, apoplasts, peroxisomes, plasma membrane, or membrane of various organelles of a cell. In some embodiments, a targeting sequence comprises a nuclear export signal (NES) and directs the chimeric adaptor polypeptide outside of a cell nucleus. In some embodiments, a targeting sequence comprises a nuclear localization signal (NLS) and directs the adaptor to a cell nucleus. A targeting sequence can direct the adaptor to a cell nucleus utilizing various nuclear localization signals (NLS). In some embodiments, a targeting sequence comprises a membrane targeting sequence and directs the adaptor to a plasma membrane or membrane of a cellular organelle. A targeting sequence can direct a polypeptide to a membrane utilizing a membrane anchoring signal sequence as previously described. Various membrane-anchoring sequences are available.

Figure 11:
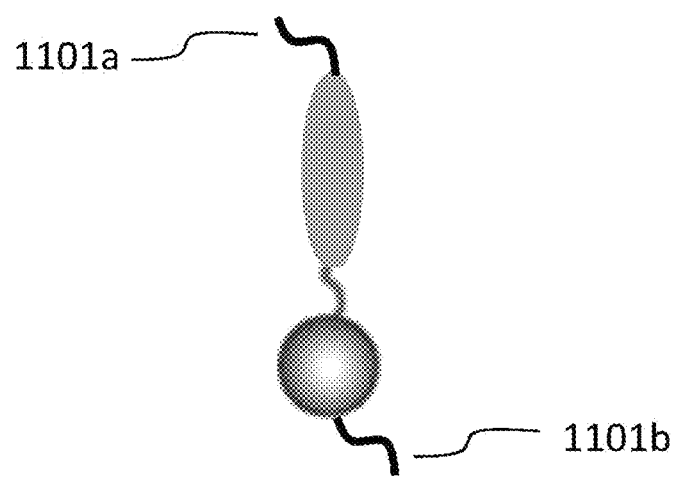
FIG. 11 shows an exemplary chimeric adaptor polypeptide comprising at least one targeting sequence.

The targeting sequence can be linked to any appropriate region of the chimeric adaptor polypeptide, for example at the N-terminus or the C-terminus of the polypeptide or in an internal region of the adaptor. In some embodiments, at least two targeting sequences are linked to the adaptor. For example, as shown in FIG. 11, a first targeting sequence 1101a can be linked to the receptor binding moiety of the adaptor and a second targeting sequence 1101b can be linked to the GMP of the adaptor, for example to the actuator moiety. When an adaptor is linked to multiple targeting sequences, for example targeting sequences directed to different locations of a cell, the final localization of the adaptor can be determined by the relative strengths of the targeting sequences. For example, an adaptor having both a targeting sequence comprising an NES and a targeting sequence comprising an NLS can localize to the cytosol if the NES is stronger than the NLS. Alternatively, if the NLS is stronger than the NES, the adaptor can localize to the nucleus even though both a nuclear localization signal and nuclear export signal are present on the adaptor. A targeting sequence can comprise multiple copies of, for example, each a NLS and NES, to fine-tune the degree of the cellular localization.

In some cases, a targeting sequence is linked to the actuator moiety. Following release of the actuator moiety from the GMP (and adaptor) by cleavage of the cleavage recognition site, the targeting sequence can direct the actuator moiety to a cellular location that is different from the adaptor. For example, a chimeric adaptor polypeptide can comprise a first targeting sequence directing the adaptor to the cell cytoplasm and the actuator moiety can separately comprise a second targeting sequence directing localization to a cell nucleus. Initially, the actuator moiety (forming a portion of the adaptor) can be localized to the cell cytoplasm due to the first targeting sequence. Following release of the actuator moiety from the GMP by cleavage of the cleavage recognition site, the actuator moiety can localize to a cell nucleus via targeting by the second targeting sequence. In some embodiments, the actuator moiety translocates to a cell nucleus after cleavage of the cleavage recognition sequence.

In some embodiments, a targeting sequence comprises a membrane targeting peptide and directs a polypeptide to a plasma membrane or membrane of a cellular organelle. A membrane-targeting sequence can provide for transport of the chimeric transmembrane receptor polypeptide to a cell surface membrane or other cellular membrane. Any suitable membrane target sequence previously described herein may be used.

In some embodiments, the chimeric adaptor polypeptide is linked to a polypeptide folding domain which can assist in protein folding. In some embodiments, an actuator moiety can be linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. The cell-penetrating domain can be located at the N-terminus, the C-terminus, or anywhere within the actuator moiety.

The actuator moiety of a subject system, upon release from a chimeric adaptor polypeptide or chimeric receptor polypeptide, can bind to a target polynucleotide to regulate expression and/or activity of the target polynucleotide by physical obstruction of the target polynucleotide or recruitment of additional factors effective to suppress or enhance expression of the target polynucleotide. In some embodiments, the actuator moiety comprises a transcriptional activator effective to increase expression of the target polynucleotide. The actuator moiety can comprise a transcriptional repressor effective to decrease expression of the target polynucleotide. In some embodiments, the target polynucleotide comprises genomic DNA. In some embodiments, the target polynucleotide comprises a region of a plasmid, for example a plasmid carrying an exogenous gene. In some embodiments, the target polynucleotide comprises RNA, for example mRNA. In some embodiments, the target polynucleotide comprises an endogenous gene or gene product. The actuator moiety can include one or more copies of a nuclear localization signal that allows the actuator to translocate into the nucleus upon cleavage from the GMP.

In some aspects, the chimeric receptor polypeptide is a chimeric intracellular receptor. An exemplary chimeric intracellular receptor comprises (a) an antigen interacting domain that specifically binds an antigen, and (b) an actuator moiety linked to the antigen interacting domain. In some embodiments, (i) the chimeric intracellular receptor is modified in response to antigen binding, (ii) the chimeric intracellular receptor polypeptide translocates to a nucleus of a cell in response to modification, and (iii) the actuator moiety complexes with a target polynucleotide in the nucleus.

In some embodiments, a chimeric intracellular receptor is a nuclear receptor. For example, a chimeric intracellular receptor polypeptide can comprise a nuclear receptor, or any derivative, variant or fragment thereof, selected from a thyroid hormone receptor α (TRα), thyroid hormone receptor β (TRβ), retinoic acid receptor-α (RAR-α), retinoic acid receptor-β (RAR-β), retinoic acid receptor-γ (RAR-γ), peroxisome proliferator-activated receptor-α (PPARα), peroxisome proliferator-activated receptor-β/δ (PPAR-β/δ), peroxisome proliferator-activated receptor-γ (PPARγ), Rev-ErbAα, Rev-ErbAβ, RAR-related orphan receptor-α (RORα), RAR-related orphan receptor-β (RORβ), RAR-related orphan receptor-γ (RORγ), Liver X receptor-α, Liver X receptor-β, Farnesoid X receptor, Farnesoid X receptor-β, Vitamin D receptor, Pregnane X receptor, constitutive adrostane receptor, hepatocyte nuclear factor-4-α (HNF4α), hepatocyte nuclear factor-4-γ (HNF4γ), retinoid X receptor-α (RXRα), retinoid X receptor-β (RXRβ), retinoid X receptor-γ (RXRγ), testicular receptor 2 (TR2), testicular receptor 4 (TR4), homologue of the *Drosophila* tailless gene (TLX), photoreceptor cell-specific nuclear receptor (PNR), chicken ovalbumin upstream promoter-transcription factor I (COUP-TFI), chicken ovalbumin upstream promoter-transcription factor II (COUP-TFII), V-erbA-related (EAR-2), estrogen receptor-α (ERα), estrogen receptor-β (ERβ), estrogen-related receptor-α (ERRα), estrogen-related receptor-β (ERRβ), estrogen-related receptor-γ (ERRγ), glucocorticoid receptor (GR), mineralocorticoid receptor (MR), progesterone receptor (PR), androgen receptor (AR), nerve growth factor IB (NGFIB), nuclear receptor related 1 (NURR1), neuron-derived orphan receptor 1 (NOR1), steroidogenic factor 1 (SF1), liver receptor homolog-1 (LRH-1), and germ cell nuclear factor (GCNF).

A chimeric intracellular receptor comprising a nuclear receptor, or any derivative, variant or fragment thereof, can bind an antigen comprising any suitable ligand of a nuclear receptor, or any derivative, variant or fragment thereof. Non-limiting examples of ligands of nuclear receptors include thyroid hormone, vitamin A and related compounds, fatty acids, prostaglandins, heme, cholesterol, ATRA, oxysterols, vitamin D, xenobiotics, androstane, retinoids, estrogens, cortisol, aldosterone, progesterone, testosterone, and phosphatidylinositols. In some embodiments, the antigen is a hormone.

Figure 12A:
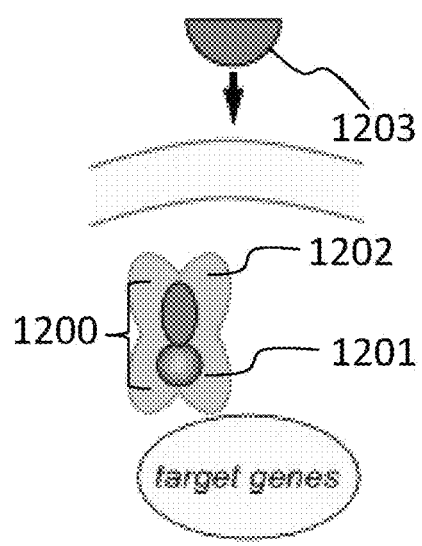
FIGS. 12A-12C illustrate schematically a system comprising an exemplary intracellular receptor.
Figure 12B:
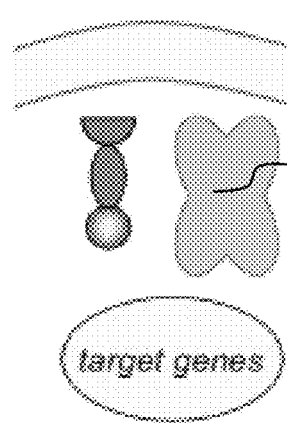
Figure 12C:
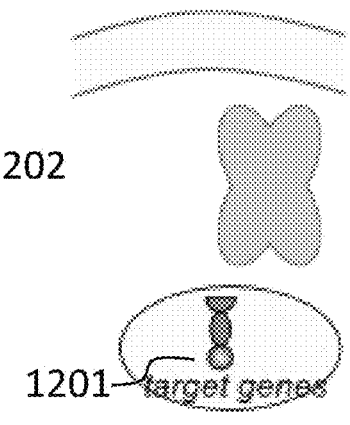

FIGS. 12A-C illustrates schematically a system comprising an exemplary intracellular receptor comprising a nuclear receptor. The system includes a receptor 1200 comprising an actuator moiety 1201. In the absence of a ligand binding to the nuclear receptor, the receptor can be sequestered in a certain compartment of a cell, for example the cytoplasm, by interaction with a binding protein 1202 as shown in FIG. 12A. Upon binding of a ligand 1203 to the intracellular receptor as shown in FIG. 12B, the receptor can dissociate from the binding protein 1202 and translocate to the nucleus. The actuator moiety 1201 which is complexed and/or linked to the receptor enters the nucleus with the receptor where it is operable to regulate expression of a target polynucleotide (e.g., gene expression) and/or activity or edit a nucleic acid sequence.

The actuator moiety can comprise a nuclease (e.g., DNA nuclease and/or RNA nuclease), modified nuclease (e.g., DNA nuclease and/or RNA nuclease) that is nuclease-deficient or has reduced nuclease activity compared to a wild-type nuclease, a variant thereof, a derivative thereof, or a fragment thereof as described elsewhere herein. The actuator moiety can regulate expression or activity of a gene and/or edit the sequence of a nucleic acid (e.g., a gene and/or gene product). In some embodiments, the actuator moiety comprises a DNA nuclease such as an engineered (e.g., programmable or targetable) DNA nuclease to induce genome editing of a target DNA sequence. In some embodiments, the actuator moiety comprises a RNA nuclease such as an engineered (e.g., programmable or targetable) RNA nuclease to induce editing of a target RNA sequence. In some embodiments, the actuator moiety has reduced or minimal nuclease activity. An actuator moiety having reduced or minimal nuclease activity can regulate expression and/or activity of a gene by physical obstruction of a target polynucleotide or recruitment of additional factors effective to suppress or enhance expression of the target polynucleotide. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. In some embodiments, the actuator moiety is a nucleic acid-guided actuator moiety. In some embodiments, the actuator moiety is a DNA-guided actuator moiety. In some embodiments, the actuator moiety is an RNA-guided actuator moiety. An actuator moiety can regulate expression or activity of a gene and/or edit a nucleic acid sequence, whether exogenous or endogenous.

Any suitable nuclease can be used in an actuator moiety. Suitable nucleases include, but are not limited to, CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute proteins (e.g., prokaryotic Argonaute (pAgo), archaeal Argonaute (aAgo), and eukaryotic Argonaute (eAgo)); any derivative thereof;

any variant thereof; and any fragment thereof. In some embodiments, the actuator moiety comprises a Cas protein that forms a complex with a guide nucleic acid, such as a guide RNA.

The actuator moiety of an intracellular receptor, upon translocation to a cell nucleus (e.g., with the intracellular receptor), can bind to a target polynucleotide to regulate expression and/or activity of the target polynucleotide by physical obstruction of the target polynucleotide or recruitment of additional factors effective to suppress or enhance expression of the target polynucleotide. In some embodiments, the actuator moiety comprises a transcriptional activator effective to increase expression of the target polynucleotide. The actuator moiety can comprise a transcriptional repressor effective to decrease expression of the target polynucleotide.

In some embodiments, the target polynucleotide comprises genomic DNA. In some embodiments, the target polynucleotide comprises a region of a plasmid, for example a plasmid carrying an exogenous gene. In some embodiments, the target polynucleotide comprises RNA, for example mRNA. In some embodiments, the target polynucleotide comprises an endogenous gene or gene product.

In some cases, a targeting sequence is linked to the intracellular receptor. For example, a targeting sequence can direct the receptor to a cell nucleus utilizing a nuclear localization signal (NLS), outside of a cell nucleus (e.g., to the cytoplasm) utilizing a nuclear export signal (NES), the mitochondria, the endoplasmic reticulum (ER), the Golgi, chloroplasts, apoplasts, or peroxisomes. In some embodiments, a targeting sequence comprises a nuclear export signal (NES) and directs the receptor outside of a cell nucleus. In some embodiments, a targeting sequence comprises a nuclear localization signal (NLS) and directs the receptor to a cell nucleus. A targeting sequence can direct the receptor to a cell nucleus utilizing various nuclear localization signals (NLS). In some embodiments, the chimeric intracellular receptor is linked to a polypeptide folding domain which can assist in protein folding.

A subject system can be introduced into a variety of cells. A cell can be in vitro. A cell can be in vivo. A cell can be ex vivo. A cell can be an isolated cell. A cell can be a cell inside of an organism. A cell can be an organism. A cell can be a cell in a cell culture. A cell can be one of a collection of cells. A cell can be a mammalian cell or derived from a mammalian cell. A cell can be a rodent cell or derived from a rodent cell. A cell can be a human cell or derived from a human cell. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a pluripotent stem cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a microbe cell or derived from a microbe cell. A cell can be a fungi cell or derived from a fungi cell. A cell can be from a specific organ or tissue.

A cell can be a stem cell or progenitor cell. Cells can include stem cells (e.g., adult stem cells, embryonic stem cells, iPS cells) and progenitor cells (e.g., cardiac progenitor cells, neural progenitor cells, etc.). Cells can include mammalian stem cells and progenitor cells, including rodent stem cells, rodent progenitor cells, human stem cells, human progenitor cells, etc. Clonal cells can comprise the progeny of a cell. A cell can comprise a target nucleic acid. A cell can be in a living organism. A cell can be a genetically modified cell. A cell can be a host cell.

A cell can be a totipotent stem cell, however, in some embodiments of this disclosure, the term "cell" may be used but may not refer to a totipotent stem cell. A cell can be a plant cell, but in some embodiments of this disclosure, the term "cell" may be used but may not refer to a plant cell. A cell can be a pluripotent cell. For example, a cell can be a pluripotent hematopoietic cell that can differentiate into other cells in the hematopoietic cell lineage but may not be able to differentiate into any other non-hematopoetic cell. A cell may be able to develop into a whole organism. A cell may or may not be able to develop into a whole organism. A cell may be a whole organism.

A cell can be a primary cell. For example, cultures of primary cells can be passaged 0 times, 1 time, 2 times, 4 times, 5 times, 10 times, 15 times or more. Cells can be unicellular organisms. Cells can be grown in culture.

A cell can be a diseased cell. A diseased cell can have altered metabolic, gene expression, and/or morphologic features. A diseased cell can be a cancer cell, a diabetic cell, and a apoptotic cell. A diseased cell can be a cell from a diseased subject. Exemplary diseases can include blood disorders, cancers, metabolic disorders, eye disorders, organ disorders, musculoskeletal disorders, cardiac disease, and the like.

If the cells are primary cells, they may be harvested from an individual by any method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy. An appropriate solution may be used for dispersion or suspension of the harvested cells. Such solution can generally be a balanced salt solution, (e.g. normal saline, phosphate-buffered saline (PBS), Hank's balanced salt solution, etc.), conveniently supplemented with fetal calf serum or other naturally occurring factors, in conjunction with an acceptable buffer at low concentration. Buffers can include HEPES, phosphate buffers, lactate buffers, etc. Cells may be used immediately, or they may be stored (e.g., by freezing). Frozen cells can be thawed and can be capable of being reused. Cells can be frozen in a DMSO, serum, medium buffer (e.g., 10% DMSO, 50% serum, 40% buffered medium), and/or some other such common solution used to preserve cells at freezing temperatures.

Non-limiting examples of cells in which a subject system can be utilized include, but are not limited to, lymphoid cells, such as B cell, T cell (Cytotoxic T cell, Natural Killer T cell, Regulatory T cell, T helper cell), Natural killer cell, cytokine induced killer (CIK) cells (see e.g. US20080241194); myeloid cells, such as granulocytes (Basophil granulocyte, Eosinophil granulocyte, Neutrophil granulocyte/Hypersegmented neutrophil), Monocyte/Macrophage, Red blood cell (Reticulocyte), Mast cell, Thrombocyte/Megakaryocyte, Dendritic cell; cells from the endocrine system, including thyroid (Thyroid epithelial cell, Parafollicular cell), parathyroid (Parathyroid chief cell, Oxyphil cell), adrenal (Chromaffin cell), pineal (Pinealocyte) cells; cells of the nervous system, including glial cells (Astrocyte, Microglia), Magnocellular neurosecretory cell, Stellate cell, Boettcher cell, and pituitary (Gonadotrope, Corticotrope, Thyrotrope, Somatotrope, Lactotroph); cells of the Respiratory system, including Pneumocyte (Type I pneumocyte, Type II pneumocyte), Clara cell, Goblet cell, Dust cell; cells of the circulatory system, including Myocardiocyte, Pericyte; cells of the digestive system, including stomach (Gastric chief cell, Parietal cell), Goblet cell, Paneth cell, G cells, D cells, ECL cells, I cells, K cells, S cells; enteroendocrine cells, including enterochromaffin cell, APUD cell, liver (Hepatocyte, Kupffer cell), Cartilage/bone/muscle; bone cells, including Osteoblast, Osteocyte, Osteoclast, teeth (Cementoblast, Ameloblast); cartilage cells, including Chondroblast, Chondrocyte; skin cells, including Trichocyte, Keratinocyte, Melanocyte (Nevus cell); muscle cells, including Myocyte; urinary system cells, including Podocyte, Juxtaglomerular cell, Intraglomerular mesangial cell/Extraglomerular mesangial cell, Kidney proximal tubule brush border cell, Macula densa cell; reproductive system cells, including Spermatozoon, Sertoli cell, Leydig cell, Ovum; and other cells, including Adipocyte, Fibroblast, Tendon cell, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Exocrine secretory epithelial cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion). Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion), Clara cell of lung, Hormone secreting cells, Anterior pituitary cells, Somatotropes, Lactotropes, Thyrotropes, Gonadotropes, Corticotropes, Intermediate pituitary cell, Magnocellular neurosecretory cells, Gut and respiratory tract cells, Thyroid gland cells, thyroid epithelial cell, parafollicular cell, Parathyroid gland cells, Parathyroid chief cell, Oxyphil cell, Adrenal gland cells, chromaffin cells, Leydig cell of testes, Theca interna cell of ovarian follicle, Corpus luteum cell of ruptured ovarian follicle, Granulosa lutein cells, Theca lutein cells, Juxtaglomerular cell (renin secretion), Macula densa cell of kidney, Metabolism and storage cells, Barrier function cells (Lung, Gut, Exocrine Glands and Urogenital Tract), Kidney, Type I pneumocyte (lining air space of lung), Pancreatic duct cell (centroacinar cell), Nonstriated duct cell (of sweat gland, salivary gland, mammary gland, etc.), Duct cell (of seminal vesicle, prostate gland, etc.), Epithelial cells lining closed internal body cavities, Ciliated cells with propulsive function, Extracellular matrix secretion cells, Contractile cells; Skeletal muscle cells, stem cell, Heart muscle cells, Blood and immune system cells, Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), Pluripotent stem cells, Totipotent stem cells, Induced pluripotent stem cells, adult stem cells, Sensory transducer cells, Autonomic neuron cells, Sense organ and peripheral neuron supporting cells, Central nervous system neurons and glial cells, Lens cells, Pigment cells, Melanocyte, Retinal pigmented epithelial cell, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, and Interstitial kidney cells.

A subject system introduced into a cell can be used for regulating expression of a target polynucleotide (e.g., gene expression). In an aspect, the disclosure provides methods of regulating expression of a target polynucleotide in a cell. In some embodiments, the method comprises (a) exposing a chimeric receptor polypeptide to an antigen, wherein (i) the chimeric receptor polypeptide is modified upon exposure to the antigen, and (ii) receptor modification comprises a conformational change or a chemical modification; (b) binding a chimeric adaptor polypeptide to the receptor in response to the modification to form a complex between a gene modulating polypeptide (GMP) and a cleavage moiety, wherein the GMP comprises an actuator moiety linked to a cleavage recognition site; and (c) cleaving the cleavage recognition site with the cleavage moiety, wherein upon cleavage of the cleavage recognition site, the actuator moiety is activated to complex with a target polynucleotide. In some embodiments, the GMP forms a portion of an intracellular region of the chimeric receptor polypeptide, and the cleavage moiety forms part of the chimeric adaptor polypeptide. In some embodiments, the GMP forms a portion of the chimeric adaptor polypeptide, and the cleavage moiety forms a portion of an intracellular portion of the chimeric receptor polypeptide. In some embodiments, the cleavage moiety is complexed with a second adaptor polypeptide that binds the receptor in response to the receptor modification, and the GMP forms a portion of the chimeric adaptor polypeptide.

A chimeric receptor polypeptide can be any chimeric receptor polypeptide described herein. In some embodiments, the chimeric receptor polypeptide is a transmembrane receptor. For example, a chimeric transmembrane receptor polypeptide comprises a G-protein coupled receptor (GPCR) such as Wnt receptor (e.g., Frizzled family receptors); integrin receptor; cadherin receptor; catalytic receptor including receptors possessing enzymatic activity and receptors which, rather than possessing intrinsic enzymatic activity, act by stimulating non-covalently associated enzymes (e.g., kinases); death receptor such as members of the tumor necrosis factor receptor superfamily; immune receptor such as T-cell receptors; or any derivative, variant, or fragment thereof. In some embodiments, the receptor does not comprise SEQ ID NO: 39.

Exposing a chimeric receptor polypeptide expressed in a cell to an antigen can be conducted in vitro and/or in vivo. Exposing a chimeric receptor polypeptide expressed in a cell to an antigen can comprise to bringing the receptor in contact with the antigen, which can be a membrane-bound antigen or non-membrane bound antigen. The antigen is, in some cases, bound the membrane of a cell. The antigen is, in some cases, not bound the membrane of a cell. Exposing a cell to an antigen can be conducted in vitro by culturing the cell expressing a subject system in the presence of the antigen. For example, a cell expressing subject system can be cultured as an adherent cell or in suspension, and the antigen can be added to the cell culture media. In some cases, the antigen is expressed by a target cell, and exposing can comprise co-culturing the cell expressing a subject system and the target cell expressing the antigen. Cells can be co-cultured in various suitable types of cell culture media, for example with supplements, growth factors, ions, etc. Exposing a cell expressing a subject system to a target cell (e.g., a target cell expressing an antigen) can be accomplished in vivo, in some cases, by administering the cells to a subject, for example a human subject, and allowing the cells to localize to the target cell via the circulatory system.

Exposing can be performed for any suitable length of time, for example at least 1 minute, at least 5 minutes, at least 10 minutes, at least 30 minutes, at least 1 hour, at least 2 hours, at least 3 hours, at least 4 hours, at least 5 hours, at least 6 hours, at least 7 hours, at least 8 hours, at least 12 hours, at least 16 hours, at least 20 hours, at least 24 hours, at least 2 days, at least 3 days, at least 4 days, at least 5 days, at least 6 days, at least 1 week, at least 2 weeks, at least 3 weeks, at least 1 month or longer.

A chimeric receptor polypeptide can bind any suitable antigen as described herein. In some embodiments, the chimeric receptor polypeptide is a transmembrane receptor. In some embodiments, the chimeric receptor polypeptide is an intracellular receptor. In some embodiments, the chimeric receptor polypeptide is a nuclear receptor. The antigen interacting domain of a chimeric receptor polypeptide can bind a membrane bound antigen, for example an antigen bound to the extracellular surface of a cell (e.g., a target cell). In some embodiments, the antigen interacting domain binds a non-membrane bound antigen, for example an extracellular antigen that is secreted by a cell (e.g., a target cell) or an antigen located in the cytoplasm of a cell (e.g., a target cell). Antigens (e.g., membrane bound and non-membrane bound) can be associated with a disease such as a viral, bacterial, and/or parasitic infection; inflammatory and/or autoimmune disease; or neoplasm such as a cancer and/or tumor.

Upon exposure to the antigen, the chimeric receptor can undergo receptor modification. Receptor modification can comprise a conformational change, chemical modification, or combination thereof. A chemical modification can comprise, for example, phosphorylation or dephosphorylation of at least one amino acid residue of the receptor. Phosphorylation and/or dephosphorylation can occur at, for example, a tyrosine, serine, threonine, or any other suitable amino acid residue of a chimeric receptor polypeptide. Binding of a chimeric adaptor polypeptide to the chimeric receptor polypeptide in response to receptor modification can form a complex between a GMP and a cleavage moiety. Formation of a complex between the GMP and cleavage moiety can result in cleavage of the cleavage recognition site by the cleavage moiety. In some embodiments, the cleavage recognition site comprises a polypeptide sequence (e.g., a peptide cleavage domain) recognized by a cleavage moiety comprising protease activity. The cleavage moiety can comprise protease activity which recognizes the polypeptide sequence. A cleavage moiety comprising protease activity can be a protease including, but not limited, to any protease described elsewhere herein, or any derivative, variant or fragment thereof. In some embodiments, the cleavage recognition site comprises multiple cleavage recognition sequences, and each cleavage recognition sequence can be recognized by the same or different cleavage moiety comprising protease activity (e.g., protease). In some embodiments, receptor modification comprises modification at multiple modification sites, and each modification is effective to bind a chimeric adaptor polypeptide. In some embodiments, (i) the GMP forms a portion of the chimeric adaptor polypeptide, (ii) the chimeric adaptor polypeptide is released from the chimeric receptor polypeptide following cleavage of the cleavage recognition site, and (iii) a further chimeric adaptor polypeptide comprising a GMP binds the modified receptor.

In some embodiments, the cleavage recognition site comprises a first portion of an intein sequence that reacts with the second portion of the intein sequence to release the actuator moiety. A heterologous split intein system, as described elsewhere herein, can be used to facilitate release of the actuator moiety. The actuator moiety can be covalently linked to the first portion of the intein sequence. The actuator moiety can be linked via its N-terminus or C-terminus to the first portion of the intein sequence. The cleavage moiety can comprise the second portion of the intein sequence. The first portion or second portion of the intein sequence can be the N-terminal intein, the C-terminal intein, or any other suitable portion of an intein that can facilitate release of the actuator moiety. The intein sequences can be from any suitable source. The first and second portion can be from the same or different sources (e.g., organism, protein). In an illustrative example, an actuator moiety can be covalently linked (e.g., at its N-terminus or C-terminus) via a peptide bond to a first portion of the intein sequence, which comprises an N-terminal intein. The actuator moiety-N-terminal intein fusion can be contacted with a second portion of the intein sequence comprising a C-terminal intein. This contacting of the first and second portion of the intein sequences can result in a site specific cleavage (e.g., at a site between the actuator moiety and the N-terminal intein), thereby releasing the actuator moiety. In another illustrative example, an actuator moiety can be covalently linked (e.g., at its N-terminus or C-terminus) via a peptide bond to a first portion of the intein comprising a C-terminal intein. The actuator moiety-C-terminal intein fusion can be contacted with a second portion of the intein sequence comprising an N-terminal intein. This contacting of the first and second portion of the inteins can result in a site-specific cleavage (e.g., at a suitable site between the actuator moiety and the C-terminal intein), thereby releasing the actuator moiety.

In some embodiments, the cleavage recognition site comprises a disulfide bond. In some embodiments, the cleavage moiety comprises oxidoreductase activity. The disulfide bond can link the actuator moiety to a portion of the chimeric adaptor polypeptide or chimeric receptor polypeptide. The disulfide bond can be formed by one or more cysteines of the actuator moiety. The cysteines can be engineered into the actuator moiety. The cysteines can be a part of the native or wild-type sequence of the actuator moiety. The cysteines can be present in a linker peptide appended to the actuator moiety. Cleavage of the disulfide bond can be facilitated by, for example, altering the redox conditions of the disulfide bond. Alteration of the redox conditions can lead to reduction of the disulfide bond to thiols and release of the actuator moiety. Cleavage of the disulfide bond can be facilitated by a cleavage moiety comprising a redox agent that can lead to reduction of the disulfide bond. The redox agent can be an enzyme, or any derivative, variant or fragment thereof. The enzyme can be an oxidoreductase. Examples of oxidoreductases include protein-disulfide reductase, thioredoxins, glutaredoxins, thiol disulfide oxidoreductases (e.g., DsbA, BdbA-D, MdbA, SdbA), and glutathione disulfide reductase. The redox agent can be from any suitable source including prokaryotes and eukaryotes. Cofactors (e.g., nicotinamide cofactors, flavins, and derivatives and analogs thereof) can be supplied for optimal activity of the enzyme.

A GMP, as described elsewhere herein, can comprise an actuator moiety linked to a cleavage recognition site. The actuator moiety can comprise a nuclease (e.g., DNA nuclease and/or RNA nuclease), modified nuclease (e.g., DNA nuclease and/or RNA nuclease) that is nuclease-deficient or has reduced nuclease activity compared to a wild-type nuclease, a variant thereof, a derivative thereof, or a fragment thereof as described elsewhere herein. The actuator moiety can regulate expression and/or activity of a gene or edit the sequence of a nucleic acid (e.g., a gene and/or gene product). In some embodiments, the actuator moiety comprises a DNA nuclease such as an engineered (e.g., programmable or targetable) DNA nuclease to induce genome editing of a target DNA sequence. In some embodiments, the actuator moiety comprises a RNA nuclease such as an engineered (e.g., programmable or targetable) RNA nuclease to induce editing of a target RNA sequence. In some embodiments, the actuator moiety has reduced or minimal nuclease activity. An actuator moiety having reduced or minimal nuclease activity can regulate expression and/or activity by physical obstruction of a target polynucleotide or recruitment of additional factors effective to suppress or enhance expression of the target polynucleotide. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. In some embodiments, the actuator moiety is a nucleic acid-guided actuator moiety. In some embodiments, the actuator moiety is a DNA-guided actuator moiety. In some embodiments, the actuator moiety is an RNA-guided actuator moiety. An actuator moiety can regulate expression or activity of a gene and/or edit a nucleic acid sequence, whether exogenous or endogenous. Upon cleavage of the cleavage recognition site, the actuator moiety is activated to complex with a target polynucleotide.

Any suitable nuclease can be used in an actuator moiety. Suitable nucleases include, but are not limited to, CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute proteins (e.g., prokaryotic Argonaute (pAgo), archaeal Argonaute (aAgo), and eukaryotic Argonaute (eAgo)); any derivative thereof; any variant thereof; and any fragment thereof.

In some embodiments, the actuator moiety comprises a Cas protein that forms a complex with a guide nucleic acid, such as a guide RNA. In some embodiments, the actuator moiety comprises a RNA-binding protein (RBP) optionally complexed with a guide nucleic acid, such as a guide RNA, which is able to form a complex with a Cas protein. In some embodiments, the actuator moiety comprises a Cas protein lacking cleavage activity.

The actuator moiety of a subject system can bind to a target polynucleotide to regulate expression and/or activity of the target polynucleotide by physical obstruction of the target polynucleotide or recruitment of additional factors effective to suppress or enhance expression of the target polynucleotide. In some embodiments, the actuator moiety comprises a transcriptional activator effective to increase expression of the target polynucleotide. The actuator moiety can comprise a transcriptional repressor effective to decrease expression of the target polynucleotide.

In some embodiments, the target polynucleotide comprises genomic DNA. In some embodiments, the target polynucleotide comprises a region of a plasmid, for example a plasmid carrying an exogenous gene. In some embodiments, the target polynucleotide comprises RNA, for example mRNA. In some embodiments, the target polynucleotide comprises an endogenous gene or gene product. The actuator moiety can include one or more copies of a nuclear localization signal that allows the actuator to translocate into the nucleus upon cleavage from the GMP.

A target polynucleotide of the various embodiments of the aspects herein can be DNA or RNA (e.g., mRNA). The target polynucleotide can be single-stranded or double-stranded. The target polynucleotide can be genomic DNA. The target polynucleotide can be any polynucleotide endogenous or exogenous to a cell. For example, the target polynucleotide can by a polynucleotide residing in the nucleus of a eukaryotic cell. The target polynucleotide can be a sequence coding a gene product (e.g., a protein) or a non-coding sequence (e.g., a regulatory polynucleotide). In some embodiments, the target polynucleotide comprises a region of a plasmid, for example a plasmid carrying an exogenous gene. In some embodiments, the target polynucleotide comprises RNA, for example mRNA. In some embodiments, the target polynucleotide comprises an endogenous gene or gene product.

The target polynucleotide may include a number of disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissue compared with tissue(s) or cells of a non-disease control. In some embodiments, it is a gene that becomes expressed at an abnormally high level. In some embodiments, it is a gene that becomes expressed at an abnormally low level. The altered expression can correlate with the occurrence and/or progression of the disease. A disease-associated gene also refers to a gene possessing mutation(s) or genetic variation that is directly responsible or is in linkage disequilibrium with a gene(s)

that is response for the etiology of a disease. The transcribed or translated products may be known or unknown, and may be at a normal or abnormal level.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web. Exemplary genes associated with certain diseases and disorders are provided in Tables 3 and 4. Examples of signaling biochemical pathway-associated genes and polynucleotides are listed in Table 5.

Mutations in these genes and pathways can result in production of improper proteins or proteins in improper amounts which affect function.

TABLE 3

| DISEASE/ DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf1 Receptor; Igf 2 Receptor; Bax; Bcl2; caspases family (9 members: 1, 2, 3, 4, 6, 7, 8, 9,12); Kras; Apc |
| Age-related Macular Degeneration | Aber; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FWX25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE 4

| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9546E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9546E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D175136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs) (JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/ Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral |

TABLE 4-continued

| | |
|---|---|
| | muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARKS, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1, Erb4 (receptor for Neuregulin), Complexin1 (Cplx1), Tph1 Tryptophan hydroxylase, Tph2, Tryptophan hydroxylase 2, Neurexin1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FWX25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Ocular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE 5

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; T5C22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL1; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; |

TABLE 5-continued

| CELLULAR FUNCTION | GENES |
|---|---|
| | PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MIMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RBI; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; |

TABLE 5-continued

| CELLULAR FUNCTION | GENES |
|---|---|
| Insulin Receptor | MYC; CSNK1A1; GSK3B; AKT3; SOX2 PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-Mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/ Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |

TABLE 5-continued

| CELLULAR FUNCTION | GENES |
|---|---|
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |

TABLE 5-continued

| CELLULAR FUNCTION | GENES |
| --- | --- |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b Wnt16); beta-catenin; Dkk-1; Frizzled related proteins; Otx-2; Gbx2; FGF-8; Reelin; Dab1; unc-86 (Pou4f1 or Brn3a); Numb; Reln |

The target polynucleotide sequence can comprise a target nucleic acid or a protospacer sequence (i.e. sequence recognized by the spacer region of a guide nucleic acid) of 20 nucleotides in length. The protospacer can be less than 20 nucleotides in length. The protospacer can be at least 5, 10, 15, 16, 17, 18, 19, 20, 21, 22, 23, 24, 25, 30 or more nucleotides in length. The protospacer sequence can be at most 5, 10, 15, 16, 17, 18, 19, 20, 21, 22, 23, 24, 25, 30 or more nucleotides in length. The protospacer sequence can be 16, 17, 18, 19, 20, 21, 22, or 23 bases immediately 5' of the first nucleotide of the PAM. The protospacer sequence can be 16, 17, 18, 19, 20, 21, 22, or 23 bases immediately 3' of the last nucleotide of the PAM sequence. The protospacer sequence can be 20 bases immediately 5' of the first nucleotide of the PAM sequence. The protospacer sequence can be 20 bases immediately 3' of the last nucleotide of the PAM. The target nucleic acid sequence can be 5' or 3' of the PAM.

A protospacer sequence can include a nucleic acid sequence present in a target polynucleotide to which a nucleic acid-targeting segment of a guide nucleic acid can bind. For example, a protospacer sequence can include a sequence to which a guide nucleic acid is designed to have complementarity. A protospacer sequence can comprise any polynucleotide, which can be located, for example, in the nucleus or cytoplasm of a cell or within an organelle of a cell, such as a mitochondrion or chloroplast. A protospacer sequence can include cleavage sites for Cas proteins. A protospacer sequence can be adjacent to cleavage sites for Cas proteins.

The Cas protein can bind the target polynucleotide at a site within or outside of the sequence to which the nucleic acid-targeting sequence of the guide nucleic acid can bind. The binding site can include the position of a nucleic acid at which a Cas protein can produce a single-strand break or a double-strand break.

Site-specific binding of a target nucleic acid by a Cas protein can occur at locations determined by base-pairing complementarity between the guide nucleic acid and the target nucleic acid. Site-specific binding of a target nucleic acid by a Cas protein can occur at locations determined by a short motif, called the protospacer adjacent motif (PAM), in the target nucleic acid. The PAM can flank the protospacer, for example at the 3' end of the protospacer sequence. For example, the binding site of Cas9 can be about 1 to about 25, or about 2 to about 5, or about 19 to about 23 base pairs (e.g., 3 base pairs) upstream or downstream of the PAM sequence. The binding site of Cas (e.g., Cas9) can be 3 base pairs upstream of the PAM sequence. The binding site of Cas (e.g., Cpf1) can be 19 bases on the (+) strand and 23 base on the (−) strand.

Different organisms can comprise different PAM sequences. Different Cas proteins can recognize different PAM sequences. For example, in S. pyogenes, the PAM can comprise the sequence 5'-XRR-3', where R can be either A or G, where X is any nucleotide and X is immediately 3' of the target nucleic acid sequence targeted by the spacer sequence. The PAM sequence of *S. pyogenes* Cas9 (SpyCas9) can be 5'-XGG-3', where X is any DNA nucleotide and is immediately 3' of the protospacer sequence of the non-complementary strand of the target DNA. The PAM of Cpf1 can be 5'-TTX-3', where X is any DNA nucleotide and is immediately 5' of the CRISPR recognition sequence.

The target sequence for the guide nucleic acid can be identified by bioinformatics approaches, for example, locating sequences within the target sequence adjacent to a PAM sequence. The optimal target sequence for the guide nucleic acid can be identified by experimental approaches, for example, testing a number of guide nucleic acid sequences to identify the sequence with the highest on-target activity and lowest off-target activity. The location of a target sequence can be determined by the desired experimental outcome. For example, a target protospacer can be located in a promoter in order to activate or repress a target gene. A target protospacer can be within a coding sequence, such as a 5' constitutively expressed exon or sequences encoding a known domain. A target protospacer can be a unique sequence within the genome in order to mitigate off-target effects. Many publicly available algorithms for determining and ranking potential target protospacers are known in the art and can be used.

In some aspects, systems disclosed herein can regulate the expression of at least one gene associated with a genetic disease or medical condition. A wide range of genetic diseases which are further described on the website of the National Institutes of Health under the topic subsection Genetic Disorders (website at health.nih.gov/topic/GeneticDisorders).

As will be apparent, it is envisaged that the present system can be used to target any polynucleotide sequence of interest. Some examples of conditions or diseases that might be usefully treated using the present system are included in the Tables 3-5 and examples of genes currently associated with those conditions are also provided there. However, the genes exemplified are not exhaustive.

A target nucleic acid can comprise one or more sequences that is at least partially complementary to one or more guide nucleic acids. A target nucleic acid can be part or all of a gene, a 5' end of a gene, a 3' end of a gene, a regulatory element (e.g. promoter, enhancer), a pseudogene, non-coding DNA, a microsatellite, an intron, an exon, chromosomal DNA, mitochondrial DNA, sense DNA, antisense DNA, nucleoid DNA, chloroplast DNA, or RNA among other nucleic acid entities. The target nucleic acid can be part or all of a plasmid DNA. A plasmid DNA or a portion thereof can be negatively supercoiled. A target nucleic acid can be in vitro or in vivo.

A target nucleic acid can comprise a sequence within a low GC content region. A target nucleic acid can be negatively supercoiled. By non-limiting example, the target nucleic acid can comprise a GC content of at least about 5, 10, 15, 20, 25, 30, 35, 40, 45, 50, 55, 60, or 65% or more. The target nucleic acid can comprise a GC content of at most about 5, 10, 15, 20, 25, 30, 35, 40, 45, 50, 55, 60, or 65% or more.

A region comprising a particular GC content can be the length of the target nucleic acid that hybridizes with the guide nucleic acid. A region comprising the GC content can be longer or shorter than the length of the region that hybridizes with the guide nucleic acid. A region comprising the GC content can be at least 30, 40, 50, 60, 70, 80, 90 or 100 or more nucleotides longer or shorter than the length of the region that hybridizes with the guide nucleic acid. A region comprising the GC content can be at most 30, 40, 50, 60, 70, 80, 90 or 100 or more nucleotides longer or shorter than the length of the region that hybridizes with the guide nucleic acid.

In an aspect, the present disclosure provides a method of regulating expression of a target polynucleotide in a cell comprising a nucleus. In some embodiments, the method comprises (a) exposing a chimeric intracellular receptor to an antigen, wherein (i) the receptor comprises an antigen interacting domain and actuator moiety, and (ii) the receptor is modified upon exposure to the antigen; (b) translocating the modified receptor to the nucleus; (c) forming a complex between the actuator moiety and a target polynucleotide. A chimeric intracellular receptor, as described elsewhere herein, can comprise a nuclear receptor, or any derivative, variant or fragment thereof. In some embodiments, the chimeric intracellular receptor binds a hormone.

Upon exposure to the antigen, the chimeric intracellular receptor can undergo receptor modification. Following receptor modification, the chimeric intracellular receptor can translocate to a cell nucleus. In the nucleus, the actuator moiety can form a complex with a target polynucleotide.

An actuator moiety, as previously described, can comprise a nuclease (e.g., DNA nuclease and/or RNA nuclease), modified nuclease (e.g., DNA nuclease and/or RNA nuclease) that is nuclease-deficient or has reduced nuclease activity compared to a wild-type nuclease, a variant thereof, a derivative thereof, or a fragment thereof as described elsewhere herein. The actuator moiety can regulate expression and/or activity of a gene or edit the sequence of a nucleic acid (e.g., a gene and/or gene product). In some embodiments, the actuator moiety comprises a DNA nuclease such as an engineered (e.g., programmable or targetable) DNA nuclease to induce genome editing of a target DNA sequence. In some embodiments, the actuator moiety comprises a RNA nuclease such as an engineered (e.g., programmable or targetable) RNA nuclease to induce editing of a target RNA sequence. In some embodiments, the actuator moiety has reduced or minimal nuclease activity. An actuator moiety having reduced or minimal nuclease activity can regulate expression and/or activity by physical obstruction of a target polynucleotide or recruitment of additional factors effective to suppress or enhance expression of the target polynucleotide. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. An actuator moiety can regulate expression or activity of a gene and/or edit a nucleic acid sequence, whether exogenous or endogenous.

Any suitable nuclease can be used in an actuator moiety. Suitable nucleases include, but are not limited to, CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute proteins In some embodiments, the target polynucleotide comprises genomic DNA. In some embodiments, the target polynucleotide comprises a region of a plasmid, for example a plasmid carrying an exogenous gene. In some embodiments, the target polynucleotide comprises RNA, for example mRNA. In some embodiments, the target polynucleotide comprises an endogenous gene or gene product; any derivative thereof, any variant thereof; and any fragment thereof.

In some embodiments, the actuator moiety comprises a Cas protein that forms a complex with a guide nucleic acid, such as a guide RNA. In some embodiments, the actuator moiety comprises a RNA-binding protein (RBP) optionally complexed with a guide nucleic acid, such as a guide RNA, which is able to form a complex with a Cas protein. In some embodiments, the actuator moiety comprises a Cas protein lacking cleavage activity.

In some aspects, the present disclosure provides a method of selectively modulating transcription of a target nucleic acid in a host cell. The method can involve: a) introducing into the host cell: i) an actuator moiety comprising a chimeric Cas protein (e.g., a Cas protein fused to a receptor or an adaptor protein), or a nucleic acid comprising a nucleotide sequence encoding the chimeric Cas protein, wherein the Cas protein is enzymatically inactive (e.g., dead Cas, dCas9) or exhibits reduced (e.g., endodeoxyribonuclease, endoribonuclease) activity; and ii) a guide nucleic acid, or a nucleic acid comprising a nucleotide sequence encoding the guide nucleic acid. The guide nucleic acid can comprise: i) a first segment (e.g., spacer region, nucleic acid targeting region) comprising a nucleotide sequence that is complementary to a target sequence in a target nucleic acid (e.g., genomic DNA, mRNA); and ii) a second segment (e.g., protein binding segment or Cas protein binding segment) that interacts with a Cas protein. The Cas protein can comprise: i) a guide nucleic acid binding portion that interacts with the guide nucleic acid; and ii) a portion that exhibits no or reduced nuclease activity. The guide nucleic acid and the dead Cas protein can form a complex in the host cell. The complex can selectively modulate transcription of a target DNA in the host cell. A target polynucleotide can be any target polynucleotide described herein, for example any target polynucleotide associated with a gene described elsewhere herein.

In various embodiments of the aspects herein, subject systems can be used for selectively modulating transcription (e.g., reduction or increase) of a target nucleic acid in a host cell. Selective modulation of transcription of a target nucleic acid can reduce or increase transcription of the target nucleic acid, but may not substantially modulate transcription of a non-target nucleic acid or off-target nucleic acid, e.g., transcription of a non-target nucleic acid may be modulated by less than 1%, less than 5%, less than 10%, less than 20%, less than 30%, less than 40%, or less than 50% compared to the level of transcription of the non-target nucleic acid in the absence of an actuator moiety, such as a guide nucleic acid/enzymatically inactive or enzymatically reduced Cas protein complex. For example, selective modulation (e.g., reduction or increase) of transcription of a target nucleic acid can reduce or increase transcription of the target nucleic acid by at least about 10%, at least about 20%, at least about 30%, at least about 40%, at least about 50%, at least about 60%, at least about 70%, at least about 80%, at least about 90%, or greater than 90%, compared to the level of transcription of the target nucleic acid in the absence of an actuator moiety, such as a guide nucleic acid/enzymatically inactive or enzymatically reduced Cas protein complex.

In some embodiments, the disclosure provides methods for increasing transcription of a target nucleic acid. The transcription of a target nucleic acid can increase by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 12 fold, at least about 15 fold, at least about 20-fold, at least about 50-fold, at least about 70-fold, or at least about 100-fold compared to the level of transcription of the target DNA in the absence of an actuator moiety, such as a guide nucleic acid/enzymatically inactive or enzymatically reduced Cas protein complex. Selective increase of transcription of a target nucleic acid increases transcription of the target nucleic acid, but may not substantially increase transcription of a non-target DNA, e.g., transcription of a non-target nucleic acid is increased, if at all, by less than about 5-fold, less than about 4-fold, less than about 3-fold, less than about 2-fold, less than about 1.8-fold, less than about 1.6-fold, less than about 1.4-fold, less than about 1.2-fold, or less than about 1.1-fold compared to the level of transcription of the non-targeted DNA in the absence of an actuator moiety, such as a guide nucleic acid/enzymatically inactive or enzymatically reduced Cas protein complex.

In some embodiments, the disclosure provides methods for decreasing transcription of a target nucleic acid. The transcription of a target nucleic acid can decrease by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 12 fold, at least about 15 fold, at least about 20-fold, at least about 50-fold, at least about 70-fold, or at least about 100-fold compared to the level of transcription of the target DNA in the absence of an actuator moiety, such as a guide nucleic acid/enzymatically inactive or enzymatically reduced Cas protein complex. Selective decrease of transcription of a target nucleic acid decreases transcription of the target nucleic acid, but may not substantially decrease transcription of a non-target DNA, e.g., transcription of a non-target nucleic acid is decreased, if at all, by less than about 5-fold, less than about 4-fold, less than about 3-fold, less than about 2-fold, less than about 1.8-fold, less than about 1.6-fold, less than about 1.4-fold, less than about 1.2-fold, or less than about 1.1-fold compared to the level of transcription of the non-targeted DNA in the absence of an actuator moiety, such as a guide nucleic acid/enzymatically inactive or enzymatically reduced Cas protein complex.

Transcription modulation can be achieved by fusing the actuator moiety, such as an enzymatically inactive Cas protein, to a heterologous sequence. The heterologous sequence can be a suitable fusion partner, e.g., a polypeptide that provides an activity that indirectly increases, decreases, or otherwise modulates transcription by acting directly on the target nucleic acid or on a polypeptide (e.g., a histone or other DNA-binding protein) associated with the target nucleic acid. Non-limiting examples of suitable fusion partners include a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

A suitable fusion partner can include a polypeptide that directly provides for increased transcription of the target nucleic acid. For example, a transcription activator or a fragment thereof, a protein or fragment thereof that recruits a transcription activator, or a small molecule/drug-responsive transcription regulator. A suitable fusion partner can include a polypeptide that directly provides for decreased transcription of the target nucleic acid. For example, a transcription repressor or a fragment thereof, a protein or fragment thereof that recruits a transcription repressor, or a small molecule/drug-responsive transcription regulator.

The heterologous sequence or fusion partner can be fused to the C-terminus, N-terminus, or an internal portion (i.e., a portion other than the N- or C-terminus) of the actuator moiety, for example a dead Cas protein. Non-limiting examples of fusion partners include transcription activators, transcription repressors, histone lysine methyltransferases (KMT), Histone Lysine Demethylates, Histone lysine acetyltransferases (KAT), Histone lysine deacetylase, DNA methylases (adenosine or cytosine modification), CTCF, periphery recruitment elements (e.g., Lamin A, Lamin B), and protein docking elements (e.g., FKBP/FRB).

Non-limiting examples of transcription activators include GAL4, VP16, VP64, and p65 subdomain (NFkappaB).

Non-limiting examples of transcription repressors include Kruippel associated box (KRAB or SKD), the Mad mSIN3 interaction domain (SID), and the ERF repressor domain (ERD).

Non-limiting examples of histone lysine methyltransferases (KMT) include members from KMT1 family (e.g., SUV39H1, SUV39H2, G9A, ESET/SETDB1, Clr4, Su(var) 3-9), KMT2 family members (e.g., hSET1A, hSET1 B, MLL 1 to 5, ASH1, and homologs (Trx, Trr, Ash1)), KMT3 family (SYMD2, NSD1), KMT4 (DOT1L and homologs), KMT5 family (Pr-SET7/8, SUV4-20H1, and homologs), KMT6 (EZH2), and KMT8 (e.g., RIZ1).

Non-limiting examples of Histone Lysine Demethylates (KDM) include members from KDM1 family (LSD1/BHC110, Splsd1/Swm1/Saf110, Su(var)3-3), KDM3 family (JHDM2a/b), KDM4 family (JMJD2A/JHDM3A, JMJD2B, JMJD2C/GASC1, JMJD2D, and homologs (Rph1)), KDM5 family (JARID1A/RBP2, JARID1B/PLU-1, JARIDIC/SMCX, JARID1D/SMCY, and homologs (Lid, Jhn2, Jmj2)), and KDM6 family (e.g., UTX, JMJD3).

Non-limiting examples of KAT include members of KAT2 family (hGCN5, PCAF, and homologs (dGCN5/PCAF, Gcn5), KAT3 family (CBP, p300, and homologs (dCBP/NEJ)), KAT4, KAT5, KAT6, KAT7, KAT8, and KAT13.

In some embodiments, an actuator moiety comprising a dead Cas protein or dead Cas fusion protein is targeted by a guide nucleic acid to a specific location (i.e., sequence) in the target nucleic acid and exerts locus-specific regulation such as blocking RNA polymerase binding to a promoter (e.g., which can selectively inhibit transcription activator function), and/or modifying the local chromatin status (e.g., when a fusion sequence is used that can modify the target nucleic acid or modifies a polypeptide associated with the target nucleic acid). In some cases, the changes are transient (e.g., transcription repression or activation). In some cases, the changes are inheritable (e.g., when epigenetic modifications are made to the target DNA or to proteins associated with the target DNA, e.g., nucleosomal histones).

In some embodiments, a guide nucleic acid can comprise a protein binding segment to recruit a heterologous polypeptide to a target nucleic acid to modulate transcription of a target nucleic acid. Non-limiting examples of the heterologous polypeptide include a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. The guide nucleic acid can comprise a protein binding segment to recruit a transcriptional activator, transcriptional repressor, or fragments thereof.

In some embodiments, gene expression modulation is achieved by using a guide nucleic acid designed to target a regulatory element of a target nucleic acid, for example, transcription response element (e.g., promoters, enhancers), upstream activating sequences (UAS), and/or sequences of unknown or known function that are suspected of being able to control expression of the target DNA.

In various embodiments of the aspects herein, the disclosure provides a guide nucleic acid for use in a CRISPR/Cas system. A guide nucleic acid (e.g., guide RNA) can bind to a Cas protein and target the Cas protein to a specific location within a target polynucleotide. A guide nucleic acid can comprise a nucleic acid-targeting segment and a Cas protein binding segment.

A guide nucleic acid can refer to a nucleic acid that can hybridize to another nucleic acid, for example, the target polynucleotide in the genome of a cell. A guide nucleic acid can be RNA, for example, a guide RNA. A guide nucleic acid can be DNA. A guide nucleic acid can comprise DNA and RNA. A guide nucleic acid can be single stranded. A guide nucleic acid can be double-stranded. A guide nucleic acid can comprise a nucleotide analog. A guide nucleic acid can comprise a modified nucleotide. The guide nucleic acid can be programmed or designed to bind to a sequence of nucleic acid site-specifically.

A guide nucleic acid can comprise one or more modifications to provide the nucleic acid with a new or enhanced feature. A guide nucleic acid can comprise a nucleic acid affinity tag. A guide nucleic acid can comprise synthetic nucleotide, synthetic nucleotide analog, nucleotide derivatives, and/or modified nucleotides.

The guide nucleic acid can comprise a nucleic acid-targeting region (e.g., a spacer region), for example, at or near the 5' end or 3' end, that is complementary to a protospacer sequence in a target polynucleotide. The spacer of a guide nucleic acid can interact with a protospacer in a sequence-specific manner via hybridization (i.e., base pairing). The protospacer sequence can be located 5' or 3' of protospacer adjacent motif (PAM) in the target polynucleotide. The nucleotide sequence of a spacer region can vary and determines the location within the target nucleic acid with which the guide nucleic acid can interact. The spacer region of a guide nucleic acid can be designed or modified to hybridize to any desired sequence within a target nucleic acid.

A guide nucleic acid can comprise two separate nucleic acid molecules, which can be referred to as a double guide nucleic acid. A guide nucleic acid can comprise a single nucleic acid molecule, which can be referred to as a single guide nucleic acid (e.g., sgRNA). In some embodiments, the guide nucleic acid is a single guide nucleic acid comprising a fused CRISPR RNA (crRNA) and a transactivating crRNA (tracrRNA). In some embodiments, the guide nucleic acid is a single guide nucleic acid comprising a crRNA. In some embodiments, the guide nucleic acid is a single guide nucleic acid comprising a crRNA but lacking a tracRNA. In some embodiments, the guide nucleic acid is a double guide nucleic acid comprising non-fused crRNA and tracrRNA. An exemplary double guide nucleic acid can comprise a crRNA-like molecule and a tracrRNA-like molecule. An exemplary single guide nucleic acid can comprise a crRNA-like molecule. An exemplary single guide nucleic acid can comprise a fused crRNA-like and tracrRNA-like molecules.

A crRNA can comprise the nucleic acid-targeting segment (e.g., spacer region) of the guide nucleic acid and a stretch of nucleotides that can form one half of a double-stranded duplex of the Cas protein-binding segment of the guide nucleic acid.

A tracrRNA can comprise a stretch of nucleotides that forms the other half of the double-stranded duplex of the Cas protein-binding segment of the gRNA. A stretch of nucleotides of a crRNA can be complementary to and hybridize with a stretch of nucleotides of a tracrRNA to form the double-stranded duplex of the Cas protein-binding domain of the guide nucleic acid.

The crRNA and tracrRNA can hybridize to form a guide nucleic acid. The crRNA can also provide a single-stranded nucleic acid targeting segment (e.g., a spacer region) that hybridizes to a target nucleic acid recognition sequence (e.g., protospacer). The sequence of a crRNA, including spacer region, or tracrRNA molecule can be designed to be specific to the species in which the guide nucleic acid is to be used.

In some embodiments, the nucleic acid-targeting region of a guide nucleic acid can be between 18 to 72 nucleotides in length. The nucleic acid-targeting region of a guide nucleic acid (e.g., spacer region) can have a length of from about 12 nucleotides to about 100 nucleotides. For example, the nucleic acid-targeting region of a guide nucleic acid (e.g., spacer region) can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, from about 12 nt to about 19 nt, from about 12 nt to about 18 nt, from about 12 nt to about 17 nt, from about 12 nt to about 16 nt, or from about 12 nt to about 15 nt. Alternatively, the DNA-targeting segment can have a length of from about 18 nt to about 20 nt, from about 18 nt to about 25 nt, from about 18 nt to about 30 nt, from about 18 nt to about 35 nt, from about 18 nt to about 40 nt, from about 18 nt to about 45 nt, from about 18 nt to about 50 nt, from about 18 nt to about 60 nt, from about 18 nt to about 70 nt, from about 18 nt to about 80 nt, from about 18 nt to about 90 nt, from about 18 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt. The length of the nucleic acid-targeting region can be at least 5, 10, 15, 16, 17, 18, 19, 20, 21, 22, 23, 24, 25, 30 or more nucleotides. The length of the nucleic acid-targeting region (e.g., spacer sequence) can be at most 5, 10, 15, 16, 17, 18, 19, 20, 21, 22, 23, 24, 25, 30 or more nucleotides.

In some embodiments, the nucleic acid-targeting region of a guide nucleic acid (e.g., spacer) is 20 nucleotides in length. In some embodiments, the nucleic acid-targeting region of a guide nucleic acid is 19 nucleotides in length. In some embodiments, the nucleic acid-targeting region of a guide nucleic acid is 18 nucleotides in length. In some embodiments, the nucleic acid-targeting region of a guide nucleic acid is 17 nucleotides in length. In some embodiments, the nucleic acid-targeting region of a guide nucleic acid is 16 nucleotides in length. In some embodiments, the nucleic acid-targeting region of a guide nucleic acid is 21 nucleotides in length. In some embodiments, the nucleic acid-targeting region of a guide nucleic acid is 22 nucleotides in length.

The nucleotide sequence of the guide nucleic acid that is complementary to a nucleotide sequence (target sequence) of the target nucleic acid can have a length of, for example, at least about 12 nt, at least about 15 nt, at least about 18 nt, at least about 19 nt, at least about 20 nt, at least about 25 nt, at least about 30 nt, at least about 35 nt or at least about 40 nt. The nucleotide sequence of the guide nucleic acid that is complementary to a nucleotide sequence (target sequence) of the target nucleic acid can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt.

A protospacer sequence can be identified by identifying a PAM within a region of interest and selecting a region of a desired size upstream or downstream of the PAM as the protospacer. A corresponding spacer sequence can be designed by determining the complementary sequence of the protospacer region.

A spacer sequence can be identified using a computer program (e.g., machine readable code). The computer program can use variables such as predicted melting temperature, secondary structure formation, and predicted annealing temperature, sequence identity, genomic context, chromatin accessibility, % GC, frequency of genomic occurrence, methylation status, presence of SNPs, and the like.

The percent complementarity between the nucleic acid-targeting sequence (e.g., spacer sequence) and the target nucleic acid (e.g., protospacer) can be at least 60%, at least 70%, at least 75%, at least 80%, at least 85%, at least 90%, at least 95%, at least 97%, at least 98%, at least 99%, or 100%. The percent complementarity between the nucleic acid-targeting sequence and the target nucleic acid can be at least 60%, at least 70%, at least 75%, at least 80%, at least 85%, at least 90%, at least 95%, at least 97%, at least 98%, at least 99%, or 100% over about 20 contiguous nucleotides.

The Cas protein-binding segment of a guide nucleic acid can comprise two stretches of nucleotides (e.g., crRNA and tracrRNA) that are complementary to one another. The two stretches of nucleotides (e.g., crRNA and tracrRNA) that are complementary to one another can be covalently linked by intervening nucleotides (e.g., a linker in the case of a single guide nucleic acid). The two stretches of nucleotides (e.g., crRNA and tracrRNA) that are complementary to one another can hybridize to form a double stranded RNA duplex or hairpin of the Cas protein-binding segment, thus resulting in a stem-loop structure. The crRNA and the tracrRNA can be covalently linked via the 3' end of the crRNA and the 5' end of the tracrRNA. Alternatively, tracrRNA and the crRNA can be covalently linked via the 5' end of the tracrRNA and the 3' end of the crRNA.

The Cas protein binding segment of a guide nucleic acid can have a length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the Cas protein-binding segment of a guide nucleic acid can have a length of from about 15 nucleotides (nt) to about 80 nt, from about 15 nt to about 50 nt, from about 15 nt to about 40 nt, from about 15 nt to about 30 nt or from about 15 nt to about 25 nt.

The dsRNA duplex of the Cas protein-binding segment of the guide nucleic acid can have a length from about 6 base pairs (bp) to about 50 bp. For example, the dsRNA duplex of the protein-binding segment can have a length from about 6 bp to about 40 bp, from about 6 bp to about 30 bp, from about 6 bp to about 25 bp, from about 6 bp to about 20 bp, from about 6 bp to about 15 bp, from about 8 bp to about 40 bp, from about 8 bp to about 30 bp, from about 8 bp to about 25 bp, from about 8 bp to about 20 bp or from about 8 bp to about 15 bp. For example, the dsRNA duplex of the Cas protein-binding segment can have a length from about from about 8 bp to about 10 bp, from about 10 bp to about 15 bp, from about 15 bp to about 18 bp, from about 18 bp to about 20 bp, from about 20 bp to about 25 bp, from about 25 bp to about 30 bp, from about 30 bp to about 35 bp, from about 35 bp to about 40 bp, or from about 40 bp to about 50 bp. In some embodiments, the dsRNA duplex of the Cas protein-binding segment can has a length of 36 base pairs. The percent complementarity between the nucleotide sequences that hybridize to form the dsRNA duplex of the protein-binding segment can be at least about 60%. For example, the percent complementarity between the nucleotide sequences that hybridize to form the dsRNA duplex of the protein-binding segment can be at least about 65%, at least about 70%, at least about 75%, at least about 80%, at least about 85%, at least about 90%, at least about 95%, at least about 98%, or at least about 99%. In some cases, the percent complementarity between the nucleotide sequences that hybridize to form the dsRNA duplex of the protein-binding segment is 100%.

The linker (e.g., that links a crRNA and a tracrRNA in a single guide nucleic acid) can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a DNA-targeting RNA is 4 nt.

Guide nucleic acids can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyl transferases, DNA demethylases, histone acetyltransferases, histone deacetylases, and combinations thereof.

A guide nucleic acid can comprise one or more modifications (e.g., a base modification, a backbone modification), to provide the nucleic acid with a new or enhanced feature (e.g., improved stability). A guide nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming guide nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within guide nucleic acids, the phosphate groups can commonly be referred to as forming the internucleoside backbone of the guide nucleic acid. The linkage or backbone of the guide nucleic acid can be a 3' to 5' phosphodiester linkage.

A guide nucleic acid can comprise a modified backbone and/or modified internucleoside linkages. Modified backbones can include those that retain a phosphorus atom in the backbone and those that do not have a phosphorus atom in the backbone.

Suitable modified guide nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage. Suitable guide nucleic acids having inverted polarity can comprise a single 3' to 3' linkage at the 3'-most internucleotide linkage (i.e. a single inverted nucleoside residue in which the nucleobase is missing or has a hydroxyl group in place thereof). Various salts (e.g., potassium chloride or sodium chloride), mixed salts, and free acid forms can also be included.

A guide nucleic acid can comprise one or more phosphorothioate and/or heteroatom internucleoside linkages, in particular —CH2-NH—O-CH2-, —CH2-N(CH3)-O-CH2- (i.e. a methylene (methylimino) or MMI backbone), —CH2-O-N(CH3)-CH2-, —CH2-N(CH3)-N(CH3)-CH2- and —O—N(CH3)-CH2-CH2- (wherein the native phosphodiester internucleotide linkage is represented as —O—P(=O)(OH)—O—CH2-).

A guide nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage replaces a phosphodiester linkage.

A guide nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A guide nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A guide nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be non-ionic mimics of guide nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A guide nucleic acid can comprise one or more substituted sugar moieties. Suitable polynucleotides can comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly suitable are O((CH2)nO)mCH3, O(CH2)nOCH3, O(CH2)nNH2, O(CH2)nCH3, O(CH2)nONH2, and O(CH2)nON((CH2)nCH3)2, where n and m are from 1 to about 10. A sugar substituent group can be selected from: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, S02CH3, ON02, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an guide nucleic acid, or a group for improving the pharmacodynamic properties of an guide nucleic acid, and other substituents having similar properties. A suitable modification can include 2'-methoxyethoxy (2'-O-CH2CH20CH3, also known as 2'-O-(2-methoxyethyl) or 2'-MOE i.e., an alkoxyalkoxy group). A further suitable modification can include 2'-dimethylaminooxyethoxy, (i.e., a O(CH2)20N(CH3)2 group, also known as 2'-DMAOE), and 2'-dimethylaminoethoxyethoxy (also known as 2'-O-dimethyl-amino-ethoxy-ethyl or 2'-DMAEOE), i.e., 2'-O-CH2-O-CH2-N(CH3)2.

Other suitable sugar substituent groups can include methoxy (—O—CH3), aminopropoxy (—OCH2 CH2 CH2NH2), allyl (—CH2-CH=CH2), —O-allyl (—O—CH2-CH=CH2) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked nucleotides and the 5' position of 5' terminal nucleotide. Oligomeric compounds may also have sugar mimetics such as cyclobutyl moieties in place of the pentofuranosyl sugar.

A guide nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C-CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino¬adenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (H¬pyrido(3',2':4,5)pyrrolo(2,3-d)pyrimidin-2-one).

Heterocyclic base moieties can include those in which the purine or pyrimidine base is replaced with other heterocycles, for example 7-deaza-adenine, 7-deazaguanosine, 2-aminopyridine and 2-pyridone. Nucleobases can be useful for increasing the binding affinity of a polynucleotide compound. These can include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions can increase nucleic acid duplex stability by 0.6-1.2° C. and can be suitable base substitutions (e.g., when combined with 2'-O-methoxyethyl sugar modifications).

A modification of a guide nucleic acid can comprise chemically linking to the guide nucleic acid one or more moieties or conjugates that can enhance the activity, cellular distribution or cellular uptake of the guide nucleic acid. These moieties or conjugates can include conjugate groups covalently bound to functional groups such as primary or secondary hydroxyl groups. Conjugate groups can include, but are not limited to, intercalators, reporter molecules, polyamines, polyamides, polyethylene glycols, polyethers, groups that enhance the pharmacodynamic properties of oligomers, and groups that can enhance the pharmacokinetic properties of oligomers. Conjugate groups can include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that can enhance the pharmacokinetic properties include groups that improve uptake, distribution, metabolism or excretion of a nucleic acid. Conjugate moieties can include but are not limited to lipid moieties such as a cholesterol moiety, cholic acid a thioether, (e.g., hexyl-S-tritylthiol), a thiocholesterol, an aliphatic chain (e.g., dodecandiol or undecyl residues), a phospholipid (e.g., di-hexadecyl-rac-glycerol or triethylammonium 1,2-di-O-hexadecyl-rac-glycero-3-H-phosphonate), a polyamine or a polyethylene glycol chain, or adamantane acetic acid, a palmityl moiety, or an octadecylamine or hexylamino-carbonyl-oxycholesterol moiety.

A modification may include a "Protein Transduction Domain" or PTD (i.e. a cell penetrating peptide (CPP)). The PTD can refer to a polypeptide, polynucleotide, carbohydrate, or organic or inorganic compound that facilitates traversing a lipid bilayer, micelle, cell membrane, organelle membrane, or vesicle membrane. A PTD can be attached to another molecule, which can range from a small polar molecule to a large macromolecule and/or a nanoparticle, and can facilitate the molecule traversing a membrane, for example going from extracellular space to intracellular space, or cytosol to within an organelle. A PTD can be covalently linked to the amino terminus of a polypeptide. A PTD can be covalently linked to the carboxyl terminus of a polypeptide. A PTD can be covalently linked to a nucleic acid. Exemplary PTDs can include, but are not limited to, a minimal peptide protein transduction domain; a polyarginine sequence comprising a number of arginines sufficient to direct entry into a cell (e.g., 3, 4, 5, 6, 7, 8, 9, 10, or 10-50 arginines), a VP22 domain, a Drosophila Antennapedia protein transduction domain, a truncated human calcitonin peptide, polylysine, and transportan, arginine homopolymer of from 3 arginine residues to 50 arginine residues. The PTD can be an activatable CPP (ACPP). ACPPs can comprise a polycationic CPP (e.g., Arg9 or "R9") connected via a cleavable linker to a matching polyanion (e.g., Glu9 or "E9"), which can reduce the net charge to nearly zero and thereby inhibits adhesion and uptake into cells. Upon cleavage of the linker, the polyanion can be released, locally unmasking the polyarginine and its inherent adhesiveness, thus "activating" the ACPP to traverse the membrane.

Guide nucleic acids can be provided in any form. For example, the guide nucleic acid can be provided in the form of RNA, either as two molecules (e.g., separate crRNA and tracrRNA) or as one molecule (e.g., sgRNA). The guide nucleic acid can be provided in the form of a complex with a Cas protein. The guide nucleic acid can also be provided in the form of DNA encoding the RNA. The DNA encoding the guide nucleic acid can encode a single guide nucleic acid (e.g., sgRNA) or separate RNA molecules (e.g., separate crRNA and tracrRNA). In the latter case, the DNA encoding the guide nucleic acid can be provided as separate DNA molecules encoding the crRNA and tracrRNA, respectively.

DNAs encoding guide nucleic acid can be stably integrated in the genome of the cell and, optionally, operably linked to a promoter active in the cell. DNAs encoding guide nucleic acids can be operably linked to a promoter in an expression construct.

Guide nucleic acids can be prepared by any suitable method. For example, guide nucleic acids can be prepared by in vitro transcription using, for example, T7 RNA polymerase. Guide nucleic acids can also be a synthetically produced molecule prepared by chemical synthesis.

A guide nucleic acid can comprise a sequence for increasing stability. For example, a guide nucleic acid can comprise a transcriptional terminator segment (i.e., a transcription termination sequence). A transcriptional terminator segment can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt. The transcription termination sequence can be functional in a eukaryotic cell or a prokaryotic cell.

In various embodiments of the aspects herein, a plurality of actuator moieties are used simultaneously in the same cell. In some embodiments, an actuator moiety comprising a Cas protein can be used simultaneously with a second actuator moiety comprising a zinc finger nuclease (ZFN), transcription activator-like effector nuclease (TALEN), meganuclease, RNA-binding protein (RBP), CRISPR-associated RNA binding protein, recombinase, flippase, transposase, or Argonaute protein. In some embodiments, an actuator moiety comprising a ZFN can be used simultaneously with a second actuator moiety comprising a Cas protein, transcription activator-like effector nuclease (TALEN), meganuclease, RNA-binding protein (RBP), CRISPR-associated RNA binding protein, recombinase, flippase, transposase, or Argonaute protein. In some embodiments, an actuator moiety comprising a TALEN can be used simultaneously with a second actuator moiety comprising a Cas protein, a zinc finger nuclease (ZFN), meganuclease, RNA-binding protein (RBP), CRISPR-associated RNA binding protein, recombinase, flippase, transposase, or Argonaute protein. In some embodiments, an actuator moiety comprising a meganuclease can be used simultaneously with a second actuator moiety comprising a Cas protein, a zinc finger nuclease (ZFN), transcription activator-like effector nuclease (TALEN), RNA-binding protein (RBP), CRISPR-associated RNA binding protein, recombinase, flippase, transposase, or Argonaute protein. In some embodiments, an actuator moiety comprising a RNA-binding protein (RBP) can be used simultaneously with a second actuator moiety comprising a Cas protein, a zinc finger nuclease (ZFN), transcription activator-like effector nuclease (TALEN), meganuclease, CRISPR-associated RNA binding protein, recombinase, flippase, transposase, or Argonaute protein. In some embodiments, an actuator moiety comprising a CRISPR-associated RNA binding protein can be used simultaneously with a second actuator moiety comprising a Cas protein, a zinc finger nuclease (ZFN), transcription activator-like effector nuclease (TALEN), meganuclease, RNA-binding protein (RBP), recombinase, flippase, transposase, or Argonaute protein. In some embodiments, an actuator moiety comprising a recombinase can be used simultaneously with a second actuator moiety comprising a Cas protein, a zinc finger nuclease (ZFN), transcription activator-like effector nuclease (TALEN), meganuclease, RNA-binding protein (RBP), CRISPR-associated RNA binding protein, flippase, transposase, or Argonaute protein. In some embodiments, an actuator moiety comprising a flippase can be used simultaneously with a second actuator moiety comprising a Cas protein, a zinc finger nuclease (ZFN), transcription activator-like effector nuclease (TALEN), meganuclease, RNA-binding protein (RBP), CRISPR-associated RNA binding protein, recombinase, transposase, or Argonaute protein. In some embodiments, an actuator moiety comprising a transposase can be used simultaneously with a second actuator moiety comprising a Cas protein, a zinc finger nuclease (ZFN), transcription activator-like effector nuclease (TALEN), meganuclease, RNA-binding protein (RBP), CRISPR-associated RNA binding protein, recombinase, flippase, or Argonaute protein. In some embodiments, an actuator moiety comprising a Argonaute protein can be used simultaneously with a second actuator moiety comprising a Cas protein, a zinc finger nuclease (ZFN), transcription activator-like effector nuclease (TALEN), meganuclease, RNA-binding protein (RBP), CRISPR-associated RNA binding protein, recombinase, flippase, or transposase.

In various embodiments of the aspects herein, a plurality of CRISPR/Cas complexes are used simultaneously in the same cell to simultaneously modulate transcription at different locations on the same target DNA or on different target DNAs. The plurality of CRISPR/Cas complexes can use a single source or type of Cas protein with a plurality of guide nucleic acids to target different nucleic acids. Alternatively, the plurality of CRISPR/Cas complexes can use orthologous Cas proteins (e.g., dead Cas9 proteins from different organisms such as *S. pyogenes, S. aureus, S. thermophilus, L. innocua,* and *N. meningitides*) to target multiple nucleic acids.

In some embodiments, a plurality of guide nucleic acids can be used simultaneously in the same cell to simultaneously modulate transcription at different locations on the same target DNA or on different target DNAs. In some embodiments, two or more guide nucleic acids target the same gene or transcript or locus. In some embodiments, two or more guide nucleic acids target different unrelated loci. In some embodiments, two or more guide nucleic acids target different, but related loci.

The two or more guide nucleic acids can be simultaneously present on the same expression vector. The two or more guide nucleic acids can be under the same transcriptional control. In some embodiments, two or more (e.g., 3 or more, 4 or more, 5 or more, 10 or more, 15 or more, 20 or more, 25 or more, 30 or more, 35 or more, 40 or more, 45 or more, or 50 or more) guide nucleic acids are simultaneously expressed in a target cell (from the same or different vectors). The expressed guide nucleic acids can be differently recognized by dead Cas proteins (e.g., dCas9 proteins from different bacteria, such as *S. pyogenes, S. aureus, S. thermophilus, L. innocua,* and *N. meningitides*).

To express multiple guide nucleic acids, an artificial guide nucleic acid processing system mediated by an endonuclease (e.g., Csy4 endoribonuclease can be used for processing guide RNAs) can be utilized. For example, multiple guide RNAs can be concatenated into a tandem array on a precursor transcript (e.g., expressed from a U6 promoter), and separated by Csy4-specific RNA sequence. Co-expressed Csy4 protein can cleave the precursor transcript into multiple guide RNAs. Since all guide RNAs are processed from a precursor transcript, their concentrations can be normalized for similar dCas9-binding.

Promoters that can be used with the methods and compositions of the disclosure include, for example, promoters active in a eukaryotic, mammalian, non-human mammalian or human cell. The promoter can be an inducible or constitutively active promoter. Alternatively or additionally, the promoter can be tissue or cell specific.

Non-limiting examples of suitable eukaryotic promoters (i.e. promoters functional in a eukaryotic cell) can include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-active promoter (CAG), murine stem cell virus promoter (MSCV), phosphoglycerate kinase-1 locus promoter (PGK) and mouse metallothionein-I. The promoter can be a fungi promoter. The promoter can be a plant promoter. A database of plant promoters can be found (e.g., PlantProm). The expression vector may also contain a ribosome binding site for translation initiation and a transcription terminator. The expression vector may also include appropriate sequences for amplifying expression.

Any suitable delivery method can be used for introducing the compositions and molecules (e.g., polypeptides and/or nucleic acid encoding polypeptides) of the disclosure into a host cell. The compositions (e.g., actuator moiety such as Cas protein, fusion, or chimera; chimeric receptor; adaptor; guide nucleic acid) can be delivered simultaneously or temporally separated. The choice of method of genetic modification can be dependent on the type of cell being transformed and/or the circumstances under which the transformation is taking place (e.g., in vitro, ex vivo, or in vivo).

A method of delivery can involve contacting a target polynucleotide or introducing into a cell (or a population of cells) one or more nucleic acids comprising nucleotide sequences encoding the compositions of the disclosure (e.g., actuator moiety such as Cas protein, Cas chimera, chimeric receptor, adaptor, guide nucleic acid). Suitable nucleic acids comprising nucleotide sequences encoding the compositions of the disclosure can include expression vectors, where an expression vector comprising a nucleotide sequence encoding one or more compositions of the disclosure (e.g., actuator moiety such as Cas protein, Cas chimera, chimeric receptor, adaptor, guide nucleic acid) is a recombinant expression vector.

Non-limiting examples of delivery methods or transformation include, for example, viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, use of cell permeable peptides, and nanoparticle-mediated nucleic acid delivery.

In some aspects, the present disclosure provides methods comprising delivering one or more polynucleotides, or one or more oligonucleotides as described herein, or vectors as described herein, or one or more transcripts thereof, and/or one or proteins transcribed therefrom, to a host cell. In some aspects, the disclosure further provides cells produced by such methods, and organisms (such as animals, plants, or fungi) comprising or produced from such cells. In some embodiments, a Cas protein and/or chimeric receptor and/or adaptor, in combination with, and optionally complexed with, a guide sequence is delivered to a cell.

A polynucleotide encoding any of the polypeptides disclosed herein (e.g., receptor polypeptide, adaptor polypeptide, actuator moiety such as a Cas protein, etc.) can be codon-optimized. Codon optimization can entail the mutation of foreign-derived (e.g., recombinant) DNA to mimic the codon preferences of an intended host organism or cell while encoding the same protein. Thus, the codons can be changed, but the encoded protein remains unchanged. For example, if the intended target cell was a human cell, a human codon-optimized polynucleotide could be used for producing a suitable Cas protein. As another non-limiting example, if the intended host cell were a mouse cell, then a mouse codon-optimized polynucleotide encoding a Cas protein could be a suitable Cas protein. A polynucleotide encoding a polypeptide such as an actuator moiety (e.g., a Cas protein) can be codon optimized for many host cells of interest. A host cell can be a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens C. Agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), etc. In some cases, codon optimization may not be required. In some instances, codon optimization can be preferable.

Conventional viral and non-viral based gene transfer methods can be used to introduce nucleic acids in mammalian cells or target tissues. Such methods can be used to administer nucleic acids encoding compositions of the disclosure to cells in culture, or in a host organism. Non-viral vector delivery systems can include DNA plasmids, RNA (e.g. a transcript of a vector described herein), naked nucleic acid, and nucleic acid complexed with a delivery vehicle, such as a liposome. Viral vector delivery systems can include DNA and RNA viruses, which can have either episomal or integrated genomes after delivery to the cell.

Methods of non-viral delivery of nucleic acids can include lipofection, nucleofection, microinjection, biolistics, virosomes, liposomes, immunoliposomes, polycation or lipid: nucleic acid conjugates, naked DNA, artificial virions, and agent-enhanced uptake of DNA. Cationic and neutral lipids that are suitable for efficient receptor-recognition lipofection of polynucleotides can be used. Delivery can be to cells (e.g. in vitro or ex vivo administration) or target tissues (e.g. in vivo administration). The preparation of lipid:nucleic acid complexes, including targeted liposomes such as immunolipid complexes, can be used.

RNA or DNA viral based systems can be used to target specific cells in the body and trafficking the viral payload to the nucleus of the cell. Viral vectors can be administered directly (in vivo) or they can be used to treat cells in vitro, and the modified cells can optionally be administered (ex vivo). Viral based systems can include retroviral, lentivirus, adenoviral, adeno-associated and herpes simplex virus vectors for gene transfer. Integration in the host genome can occur with the retrovirus, lentivirus, and adeno-associated virus gene transfer methods, which can result in long term expression of the inserted transgene. High transduction efficiencies can be observed in many different cell types and target tissues.

The tropism of a retrovirus can be altered by incorporating foreign envelope proteins, expanding the potential target population of target cells. Lentiviral vectors are retroviral vectors that can transduce or infect non-dividing cells and produce high viral titers. Selection of a retroviral gene transfer system can depend on the target tissue. Retroviral vectors can comprise cis-acting long terminal repeats with packaging capacity for up to 6-10 kb of foreign sequence. The minimum cis-acting LTRs can be sufficient for replication and packaging of the vectors, which can be used to integrate the therapeutic gene into the target cell to provide permanent transgene expression. Retroviral vectors can include those based upon murine leukemia virus (MuLV), gibbon ape leukemia virus (GaLV), Simian Immuno deficiency virus (SIV), human immuno deficiency virus (HIV), and combinations thereof.

An adenoviral-based systems can be used. Adenoviral-based systems can lead to transient expression of the transgene. Adenoviral based vectors can have high transduction efficiency in cells and may not require cell division. High titer and levels of expression can be obtained with adenoviral based vectors. Adeno-associated virus ("AAV") vectors can be used to transduce cells with target nucleic acids, e.g., in the in vitro production of nucleic acids and peptides, and for in vivo and ex vivo gene therapy procedures.

Packaging cells can be used to form virus particles capable of infecting a host cell. Such cells can include 293 cells, (e.g., for packaging adenovirus), and .psi.2 cells or PA317 cells (e.g., for packaging retrovirus). Viral vectors can be generated by producing a cell line that packages a nucleic acid vector into a viral particle. The vectors can contain the minimal viral sequences required for packaging and subsequent integration into a host. The vectors can contain other viral sequences being replaced by an expression cassette for the polynucleotide(s) to be expressed. The missing viral functions can be supplied in trans by the packaging cell line. For example, AAV vectors can comprise ITR sequences from the AAV genome which are required for packaging and integration into the host genome. Viral DNA can be packaged in a cell line, which can contain a helper plasmid encoding the other AAV genes, namely rep and cap, while lacking ITR sequences. The cell line can also be infected with adenovirus as a helper. The helper virus can promote replication of the AAV vector and expression of AAV genes from the helper plasmid. Contamination with adenovirus can be reduced by, e.g., heat treatment to which adenovirus is more sensitive than AAV. Additional methods for the delivery of nucleic acids to cells can be used, for example, as described in US20030087817, incorporated herein by reference.

A host cell can be transiently or non-transiently transfected with one or more vectors described herein. A cell can be transfected as it naturally occurs in a subject. A cell can be taken or derived from a subject and transfected. A cell can be derived from cells taken from a subject, such as a cell line. In some embodiments, a cell transfected with one or more vectors described herein is used to establish a new cell line comprising one or more vector-derived sequences. In some embodiments, a cell transiently transfected with the compositions of the disclosure (such as by transient transfection of one or more vectors, or transfection with RNA), and modified through the activity of a an actuator moiety such as a CRISPR complex, is used to establish a new cell line comprising cells containing the modification but lacking any other exogenous sequence.

Any suitable vector compatible with the host cell can be used with the methods of the disclosure. Non-limiting examples of vectors for eukaryotic host cells include pXT1, pSG5 (Stratagene™), pSVK3, pBPV, pMSG, and pSVLSV40 (Pharmacia™).

In some embodiments, a nucleotide sequence encoding a guide nucleic acid and/or Cas protein or chimera is operably linked to a control element, e.g., a transcriptional control element, such as a promoter. The transcriptional control element can be functional in either a eukaryotic cell, e.g., a mammalian cell, or a prokaryotic cell (e.g., bacterial or archaeal cell). In some embodiments, a nucleotide sequence encoding a guide nucleic acid and/or a Cas protein or chimera is operably linked to multiple control elements that allow expression of the nucleotide sequence encoding a guide nucleic acid and/or a Cas protein or chimera in prokaryotic and/or eukaryotic cells.

Depending on the host/vector system utilized, any of a number of suitable transcription and translation control elements, including constitutive and inducible promoters, transcription enhancer elements, transcription terminators, etc. may be used in the expression vector (e.g., U6 promoter, H1 promoter, etc.; see above) (see e.g., Bitter et al. (1987) Methods in Enzymology, 153:516-544).

In some embodiments, compositions of the disclosure (e.g., actuator moiety such as a Cas protein or Cas chimera, chimeric receptor, adaptor, guide nucleic acid, etc.) can be provided as RNA. In such cases, the compositions of the disclosure (e.g., actuator moiety such as a Cas protein or Cas chimera, chimeric receptor, adaptor, guide nucleic acid, etc.) can be produced by direct chemical synthesis or may be transcribed in vitro from a DNA. The compositions of the disclosure (e.g., actuator moiety such as a Cas protein or Cas chimera, chimeric receptor, adaptor, guide nucleic acid, etc.) can be synthesized in vitro using an RNA polymerase enzyme (e.g., T7 polymerase, T3 polymerase, SP6 polymerase, etc.). Once synthesized, the RNA can directly contact a target DNA or can be introduced into a cell using any suitable technique for introducing nucleic acids into cells (e.g., microinjection, electroporation, transfection, etc.).

Nucleotides encoding a guide nucleic acid (introduced either as DNA or RNA) and/or a Cas protein or chimera (introduced as DNA or RNA) can be provided to the cells using a suitable transfection technique; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) Efficient gene targeting in *Drosophila* by direct embryo injection with zinc-finger nucleases. PNAS 105(50):19821-19826. Nucleic acids encoding the compositions of the disclosure (e.g., actuator moiety such as a Cas protein or Cas chimera, chimeric receptor, adaptor, guide nucleic acid, etc.) may be provided on DNA vectors or oligonucleotides. Many vectors, e.g. plasmids, cosmids, minicircles, phage, viruses, etc., useful for transferring nucleic acids into target cells are available. The vectors comprising the nucleic acid(s) can be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, and ALV.

An actuator moiety such as a Cas protein or chimera, chimeric receptor, and/or adaptor can be provided to cells as a polypeptide. Such a protein may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

The compositions of the disclosure (e.g., actuator moiety such as a Cas protein or Cas chimera, chimeric receptor, adaptor, guide nucleic acid, etc.) may be fused to a polypeptide permeant domain to promote uptake by the cell. A number of permeant domains can be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK. As another example, the permeant peptide can comprise the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A. 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence can be used. (Wender et al. 2000; Uemura et al. 2002). The site at which the fusion is made may be selected in order to optimize the biological activity, secretion or binding characteristics of the polypeptide.

The compositions of the disclosure (e.g., an actuator moiety such as a Cas protein or Cas chimera, chimeric receptor, adaptor, guide nucleic acid, etc.) may be produced in vitro or by eukaryotic cells or by prokaryotic cells, and it may be further processed by unfolding, e.g. heat denaturation, DTT reduction, etc. and may be further refolded.

The compositions of the disclosure (e.g., an actuator moiety such as a Cas protein or Cas chimera, chimeric receptor, adaptor, guide nucleic acid, etc.) may be prepared by in vitro synthesis. Various commercial synthetic apparatuses can be used, for example, automated synthesizers by Applied Biosystems, Inc., Beckman, etc. By using synthesizers, naturally occurring amino acids can be substituted with unnatural amino acids. The particular sequence and the manner of preparation can be determined by convenience, economics, purity required, and the like.

The compositions of the disclosure (e.g., an actuator moiety such as a Cas protein or Cas chimera, chimeric receptor, adaptor, guide nucleic acid, etc.) may also be isolated and purified in accordance with conventional methods of recombinant synthesis. A lysate may be prepared of the expression host and the lysate purified using HPLC, exclusion chromatography, gel electrophoresis, affinity chromatography, or other purification technique. The compositions can comprise, for example, at least 20% by weight of the desired product, at least about 75% by weight, at least about 95% by weight, and for therapeutic purposes, for example, at least about 99.5% by weight, in relation to contaminants related to the method of preparation of the product and its purification. The percentages can be based upon total protein.

The compositions of the disclosure (e.g., an actuator moiety such as a Cas protein or Cas chimera, chimeric receptor, adaptor, guide nucleic acid, etc.), whether introduced as nucleic acids or polypeptides, can be provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which can be repeated with a frequency of about every day to about every 4 days, e.g., every 1.5 days, every 2 days, every 3 days, or any other frequency from about every day to about every four days. The compositions may be provided to the subject cells one or more times, e.g. one time, twice, three times, or more than three times, and the cells allowed to incubate with the agent(s) for some amount of time following each contacting event e.g. 16-24 hours, after which time the media can be replaced with fresh media and the cells can be cultured further.

In cases in which two or more different targeting complexes are provided to the cell (e.g., two different guide nucleic acids that are complementary to different sequences within the same or different target DNA), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

An effective amount of the compositions of the disclosure (e.g., actuator moiety such as Cas protein or Cas chimera, chimeric receptor, adaptor, guide nucleic acid, etc.) can be provided to the target DNA or cells. An effective amount can be the amount to induce, for example, at least about a 2-fold change (increase or decrease) or more in the amount of target regulation observed between two homologous sequences relative to a negative control, e.g. a cell contacted with an empty vector or irrelevant polypeptide. An effective amount or dose can induce, for example, about 2-fold change, about 3-fold change, about 4-fold change, about a 7-fold, about 8-fold increase, about 10-fold, about 50-fold, about 100-fold, about 200-fold, about 500-fold, about 700-fold, about 1000-fold, about 5000-fold, or about 10.000-fold change in target gene regulation. The amount of target gene regulation may be measured by any suitable method.

Contacting the cells with a composition of the can occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors can include polypeptides and non-polypeptide factors.

In numerous embodiments, the chosen delivery system is targeted to specific tissue or cell types. In some cases, tissue- or cell-targeting of the delivery system is achieved by binding the delivery system to tissue- or cell-specific markers, such as cell surface proteins. Viral and non-viral delivery systems can be customized to target tissue or cell-types of interest.

Pharmaceutical compositions containing molecules described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Amounts effective for this use can vary based on the severity and course of the disease or condition, previous therapy, the subject's health status, weight, and response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills. The molecules can be packed together or separately, in a single package or in a plurality of packages. One or all of the therapeutic agents can be given in multiple doses. If not simultaneous, the timing between the multiple doses may vary to as much as about a month.

Molecules described herein can be administered before, during, or after the occurrence of a disease or condition, and the timing of administering the composition containing a compound can vary. For example, the pharmaceutical compositions can be used as a prophylactic and can be administered continuously to subjects with a propensity to conditions or diseases in order to prevent the occurrence of the disease or condition. The molecules and pharmaceutical compositions can be administered to a subject during or as soon as possible after the onset of the symptoms. The administration of the molecules can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A molecule can be administered as soon as is practicable after the onset of a disease or condition is detected or suspected, and for a length of time necessary for the treatment of the disease, such as, for example, from about 1 month to about 3 months. The length of treatment can vary for each subject.

A molecule can be packaged into a biological compartment. A biological compartment comprising the molecule can be administered to a subject. Biological compartments can include, but are not limited to, viruses (lentivirus, adenovirus), nanospheres, liposomes, quantum dots, nanoparticles, microparticles, nanocapsules, vesicles, polyethylene glycol particles, hydrogels, and micelles.

For example, a biological compartment can comprise a liposome. A liposome can be a self-assembling structure comprising one or more lipid bilayers, each of which can comprise two monolayers containing oppositely oriented amphipathic lipid molecules. Amphipathic lipids can comprise a polar (hydrophilic) headgroup covalently linked to one or two or more non-polar (hydrophobic) acyl or alkyl chains. Energetically unfavorable contacts between the hydrophobic acyl chains and a surrounding aqueous medium induce amphipathic lipid molecules to arrange themselves such that polar headgroups can be oriented towards the bilayer's surface and acyl chains are oriented towards the interior of the bilayer, effectively shielding the acyl chains from contact with the aqueous environment.

Examples of preferred amphipathic compounds used in liposomes can include phosphoglycerides and sphingolipids, representative examples of which include phosphatidylcholine, phosphatidylethanolamine, phosphatidylserine, phosphatidylinositol, phosphatidic acid, phoasphatidylglycerol, palmitoyloleoyl phosphatidylcholine, lysophosphatidylcholine, lysophosphatidylethanolamine, dimyristoylphosphatidylcholine (DMPC), dipalmitoylphosphatidylcholine (DPPC), dioleoylphosphatidylcholine, distearoylphosphatidylcholine (DSPC), dilinoleoylphosphatidylcholine and egg sphingomyelin, or any combination thereof.

A biological compartment can comprise a nanoparticle. A nanoparticle can comprise a diameter of from about 40 nanometers to about 1.5 micrometers, from about 50 nanometers to about 1.2 micrometers, from about 60 nanometers to about 1 micrometer, from about 70 nanometers to about 800 nanometers, from about 80 nanometers to about 600 nanometers, from about 90 nanometers to about 400 nanometers, from about 100 nanometers to about 200 nanometers.

In some instances, as the size of the nanoparticle increases, the release rate can be slowed or prolonged and as the size of the nanoparticle decreases, the release rate can be increased.

The amount of albumin in the nanoparticles can range from about 5% to about 85% albumin (v/v), from about 10% to about 80%, from about 15% to about 80%, from about 20% to about 70% albumin (v/v), from about 25% to about 60%, from about 30% to about 50%, or from about 35% to about 40%. The pharmaceutical composition can comprise up to 30, 40, 50, 60, 70 or 80% or more of the nanoparticle.

In some instances, the nucleic acid molecules of the disclosure can be bound to the surface of the nanoparticle.

A biological compartment can comprise a virus. The virus can be a delivery system for the pharmaceutical compositions of the disclosure. Exemplary viruses can include lentivirus, retrovirus, adenovirus, herpes simplex virus I or II, parvovirus, reticuloendotheliosis virus, and adeno-associated virus (AAV). Pharmaceutical compositions of the disclosure can be delivered to a cell using a virus. The virus can infect and transduce the cell in vivo, ex vivo, or in vitro. In ex vivo and in vitro delivery, the transduced cells can be administered to a subject in need of therapy.

Pharmaceutical compositions can be packaged into viral delivery systems. For example, the compositions can be packaged into virions by a HSV-1 helper virus-free packaging system.

Viral delivery systems (e.g., viruses comprising the pharmaceutical compositions of the disclosure) can be administered by direct injection, stereotaxic injection, intracerebroventricularly, by minipump infusion systems, by convection, catheters, intravenous, parenteral, intraperitoneal, and/or subcutaneous injection, to a cell, tissue, or organ of a subject in need. In some instances, cells can be transduced in vitro or ex vivo with viral delivery systems. The transduced cells can be administered to a subject having a disease. For example, a stem cell can be transduced with a viral delivery system comprising a pharmaceutical composition and the stem cell can be implanted in the patient to treat a disease. In some instances, the dose of transduced cells given to a subject can be about $1 \times 10^5$ cells/kg, about $5 \times 10^5$ cells/kg, about $1 \times 10^6$ cells/kg, about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $5 \times 10^7$ cells/kg, about $1 \times 10^8$ cells/kg, or more in one single dose.

Introduction of the biological compartments into cells can occur by viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

A molecule described herein (e.g., polypeptide and/or nucleic acid) can be present in a composition in a range of from about 1 mg to about 2000 mg; from about 5 mg to about 1000 mg, from about 10 mg to about 25 mg to 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A molecule (e.g., polypeptide and/or nucleic acid) described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

A molecule (e.g., polypeptide and/or nucleic acid) described herein can be present in a composition that provides at least 0.1, 0.5, 1, 1.5, 2, 2.5 3, 3.5, 4, 4.5, 5, 5.5, 6, 6.5, 10 or more units of activity/mg molecule. The activity can be regulation of gene expression. In some embodiments, the total number of units of activity of the molecule delivered to a subject is at least 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, or 250,000 or more units. In some embodiments, the total number of units of activity of the molecule delivered to a subject is at most 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, or 250,000 or more units.

In some embodiments, at least about 10,000 units of activity is delivered to a subject, normalized per 50 kg body weight. In some embodiments, at least about 10,000, 15,000, 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, or 250,000 units or more of activity of the molecule is delivered to the subject, normalized per 50 kg body weight. In some embodiments, a therapeutically effective dose comprises at least 5×105, 1×106, 2×106, 3×106, 4, 106, 5×106, 6×106, 7×106, 8×106, 9×106, 1×107, 1.1×107, 1.2×107, 1.5×107, 1.6×107, 1.7×107, 1.8×107, 1.9×107, 2×107, 2.1×107, or 3×107 or more units of activity of the molecule. In some embodiments, a therapeutically effective dose comprises at most 5×105, 1×106, 2×106, 3×106, 4, 106, 5×106, 6×106, 7×106, 8×106, 9×106, 1×107, 1.1×107, 1.2×107, 1.5×107, 1.6×107, 1.7×107, 1.8×107, 1.9×107, 2×107, 2.1×107, or 3×107 or more units of activity of the molecule.

In some embodiments, a therapeutically effective dose is at least about 10,000, 15,000, 20,000, 22,000, 24,000, 25,000, 30,000, 40,000, 50,000, 60,000, 70,000, 80,000, 90,000, 100,000, 125,000, 150,000, 200,000, or 500,000 units/kg body weight. In some embodiments, a therapeutically effective dose is at most about 10,000, 15,000, 20,000, 22,000, 24,000, 25,000, 30,000, 40,000, 50,000, 60,000, 70,000, 80,000, 90,000, 100,000, 125,000, 150,000, 200,000, or 500,000 units/kg body weight.

In some embodiments, the activity of the molecule delivered to a subject is at least 10,000, 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, or 50,000 or more U/mg of molecule. In some embodiments, the activity of the molecule delivered to a subject is at most 10,000, 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, or 50,000 or more U/mg of molecule.

In various embodiments of the aspects herein, pharmacokinetic and pharmacodynamic data can be obtained. Various experimental techniques for obtaining such data are available. Appropriate pharmacokinetic and pharmacodynamic profile components describing a particular composition can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean can be determined by calculating the average of all subject's measurements for each parameter measured. A dose can be modulated to achieve a desired pharmacokinetic or pharmacodynamics profile, such as a desired or effective blood profile, as described herein.

The pharmacokinetic parameters can be any parameters suitable for describing a molecule. For example, the Cmax can be, for example, not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; or any other Cmax appropriate for describing a pharmacokinetic profile of a molecule described herein.

The Tmax of a molecule described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other Tmax appropriate for describing a pharmacokinetic profile of a molecule described herein.

The AUC(0-inf) of a molecule described herein can be, for example, not less than about 50 ng·hr/mL, not less than about 100 ng/hr/mL, not less than about 150 ng/hr/mL, not less than about 200 ng·hr/mL, not less than about 250 ng/hr/mL, not less than about 300 ng/hr/mL, not less than about 350 ng/hr/mL, not less than about 400 ng/hr/mL, not less than about 450 ng/hr/mL, not less than about 500 ng/hr/mL, not less than about 600 ng/hr/mL, not less than about 700 ng/hr/mL, not less than about 800 ng/hr/mL, not less than about 900 ng/hr/mL, not less than about 1000 ng·hr/mL, not less than about 1250 ng/hr/mL, not less than about 1500 ng/hr/mL, not less than about 1750 ng/hr/mL, not less than about 2000 ng/hr/mL, not less than about 2500 ng/hr/mL, not less than about 3000 ng/hr/mL, not less than about 3500 ng/hr/mL, not less than about 4000 ng/hr/mL, not less than about 5000 ng/hr/mL, not less than about 6000 ng/hr/mL, not less than about 7000 ng/hr/mL, not less than about 8000 ng/hr/mL, not less than about 9000 ng/hr/mL, not less than about 10,000 ng/hr/mL, or any other AUC(0-inf) appropriate for describing a pharmacokinetic profile of a molecule described herein.

The plasma concentration of a molecule described herein about one hour after administration can be, for example, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of a molecule described herein.

The pharmacodynamic parameters can be any parameters suitable for describing pharmaceutical compositions of the disclosure. For example, the pharmacodynamic profile can exhibit decreases in factors associated with inflammation after, for example, about 2 hours, about 4 hours, about 8 hours, about 12 hours, or about 24 hours.

In various embodiments of the aspects herein, methods of the disclosure are performed in a subject. A subject can be a human. A subject can be a mammal (e.g., rat, mouse, cow, dog, pig, sheep, horse). A subject can be a vertebrate or an invertebrate. A subject can be a laboratory animal. A subject can be a patient. A subject can be suffering from a disease. A subject can display symptoms of a disease. A subject may not display symptoms of a disease, but still have a disease. A subject can be under medical care of a caregiver (e.g., the subject is hospitalized and is treated by a physician). A subject can be a plant or a crop.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure.

Figure 17:
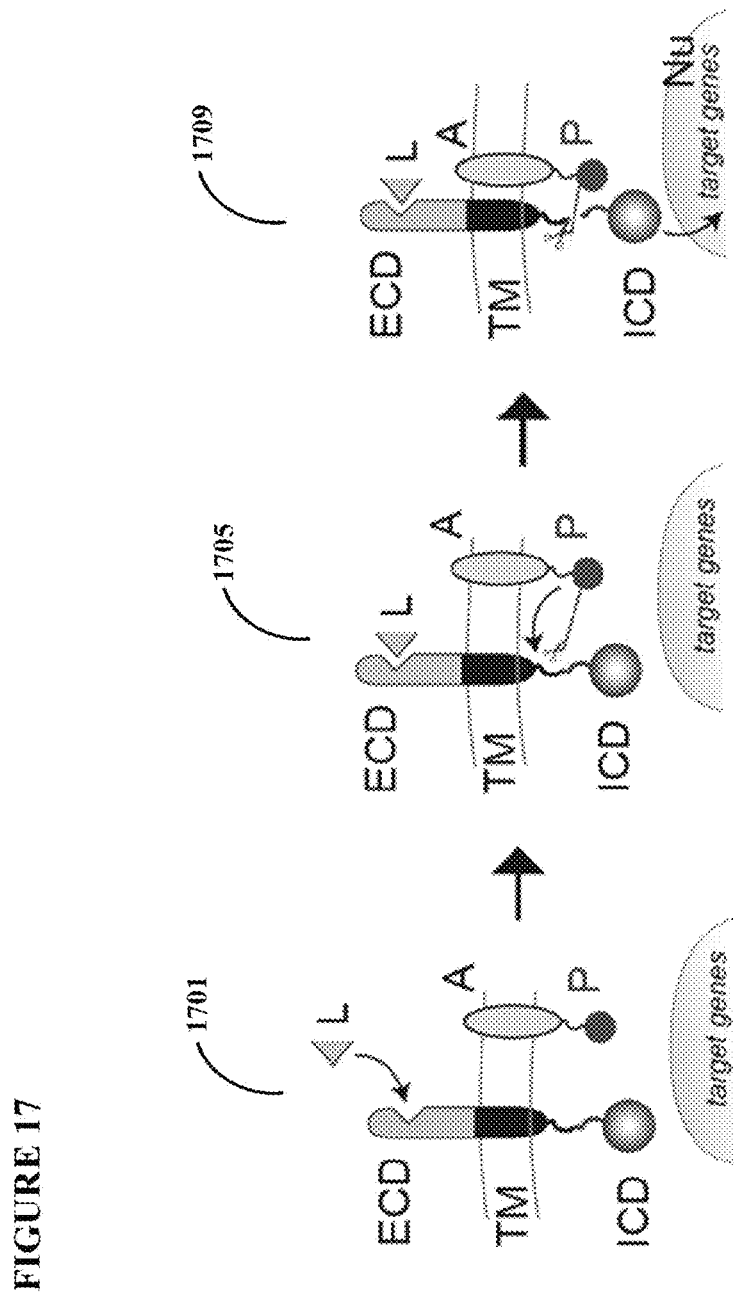
FIG. 17 shows a schematic diagram of engineered chimeric antigen receptors of the present invention for gene modulation such as genome editing and gene regulation.

Example 1: Engineered Recombinant Chimeric Receptors Tethered to Effector Proteins that can Modulate Gene Expression Via Genome Editing or Transcriptional Regulation An engineered chimeric antigen receptor containing a gene modulating domain is provided in FIG. 17. The engineered artificial recombinant receptor includes in a linear order an extracellular domain (ECD), transmembrane domain (TM), and an ICD (intracellular domain). The ECD has specific ligand binding activity. The TM spans the cell membrane and the ICD possess a genomic manipulation function. The TM and ICD are linked by a peptide linker sequence and the peptide sequence can be recognized by a protease. The receptor is expressed on a cell and can bind its ligand 1701. Upon ligand binding, an adaptor protein tethered (fused) to a protease is recruited to the receptor via a protein-protein interaction, clustering or scaffold-mediated interaction. After the adapter-protease associates with the engineered chimeric antigen receptor, the protease releases the gene modulating domain from the receptor 1705. The gene modulating domain is then free to translocate to the nucleus to regulate or edit target genes 1709. The ICD can include a transcription factor and can modulate gene expression or epigenetics (Nu, nucleus).

Figure 18:
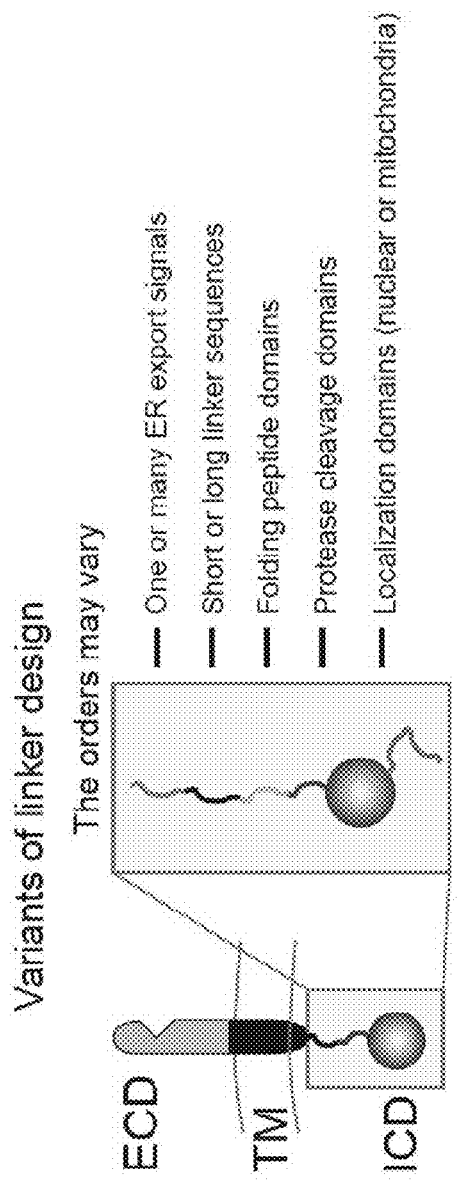
FIG. 18 shows variants of linkers located between the transmembrane domain and the gene modulation domain of the engineered chimeric antigen receptors of the present disclosure.

The receptor can be fused to the gene modulating domain via a linker (FIG. 18). The linker can be located between the transmembrane domain and the gene modulating domain (intracellular actuator domain) of the engineered receptor. The linker can contain one or more endoplasmic reticulum export signals, one or more peptide linker sequences, one or peptide folding domains, one or more protease cleavage domains, one or more cellular localization domains, e.g., a nuclear localization signal or a mitochondrial localization signal, or any combination thereof. In some instances, the components of the linker can be arranged in any order.

The engineered chimeric antigen receptor can be designed to bind cell surface antigens (FIG. 19A). In some cases, the engineered chimeric antigen receptor and the adaptor-protease are located on the cell surface of a receiving cell and the ligand is on the surface of the signaling cell. The receptor can be engineered to bind to soluble antigens located in the cell's local environment (FIG. 19B). Alternatively, the engineered chimeric antigen receptor can bind to signaling molecules or ligands of the extracellular matrix (ECM) (FIG. 19C). In other embodiments, the engineered chimeric antigen receptor can dimerize with an interacting receptor that is linked to a cytosolic protease (FIG. 19D). In other instances, the interacting receptor is not tethered to a protease, and the ligand-bound receptor may recruit an adaptor-protease polypeptide (FIG. 19E). In yet other embodiments, the chimeric receptors form a complex with other receptors (natural receptors, endogenous receptors, or synthetic receptors) that are on the same cell (FIG. 19F).

The engineered chimeric antigen receptor-gene modulating domain polypeptides can be based on receptors such as Notch, GPCRs, integrins, cadherins, death receptors, and chimeric antigen receptors (FIG. 20A). These polypeptides can be expressed along with an adaptor-protease fusion protein such as a presinillin-protease, a β2-arrestin-protease, a paxillin-protease, a βcatenin-protease, or a FADD-protease. If the gene modulating domain contains a CRISPR protein such as Cas9 or dCas9, the domain can bind to a guide RNA (gRNA, e.g., sgRNA). The protease can release the gene modulating domain-sgRNA which can translocate to the nucleus and bind to a DNA sequence complementary to the sgRNA (FIG. 20B). The DNA sequence can be in a regulatory region or promoter of a target gene.

Example 2: Engineered Recombinant Chimeric Receptors Based on GPCRS, Integrins and Notch This example describes three classes of engineered recombinant chimeric receptor systems. These receptors include G protein-coupled receptors (GPCRs), integrins, and Notch, which naturally detect diverse types of ligands and signals relevant to cancer microenvironments. For example, GPCRs, known as seven-transmembrane domain receptors, 7TM receptors, heptahelical receptors, serpentine receptor, and G protein-linked receptors (GPLR), constitute a large protein family of receptors that sense molecules outside the cell and activate signal transduction pathways and, ultimately, cellular responses inside the cell.

A1. Recombinant Chimeric GPCRs Containing dCas9.

G protein-coupled receptors are found only in eukaryotes. The ligands that bind and activate these receptors are highly diverse and include light-sensitive compounds, odors, pheromones, hormones, and neurotransmitters. GPCR ligands vary in size from small molecules to peptides to large proteins. Notably, G protein-coupled receptors are involved in many diseases, and are also the target of approximately 40% of all modern medicinal drugs. The natural principal signal transduction pathways involving the G protein-coupled receptors can be complex, involving either the cAMP signal pathway, or the phosphatidylinositol signal pathway.

When a ligand binds to the GPCR, it can cause a conformational change in the GPCR, which allows it to act as a guanine nucleotide exchange factor (GEF). The GPCR can then activate an associated G protein by exchanging its bound GDP for a GTP. The a subunit of the G protein, together with the bound GTP, can then dissociate from the β and γ subunits to further affect intracellular signaling proteins or target functional proteins directly depending on the a subunit type (Gαs, Gαi/o, Gαq/11, Gα12/13).

Importantly, GPCRs are involved in a wide variety of physiological processes. Some examples of their physiological roles include: the visual sense, the gustatory sense (taste), the sense of smell, behavioral and mood regulation, autonomic nervous system transmission, and homeostasis modulation. Among many GPCRs, three classes are particularly relevant to immune cell-mediated cancer therapy. The first class of GPCRs can regulate immune system activity and inflammation. For example, chemokine GPCR receptors bind to ligands that mediate intercellular communication between cells of the immune system. Histamine GPCR receptors bind inflammatory mediators and engage target cell types in the inflammatory response. Toll-like GPCR receptors (TLRs) are involved in immune-modulation and directly involved in suppression of immune responses of T cells, which has been closely related to recent discoveries that PDL-1 on cancer cells may suppress T cells via interaction with PD-1 receptor on T cells. The second class of GPCRs can modulate cell density sensing. Deficient contact inhibition is a hallmark of invasive cancer cells. There is evidence that cancer cells can manipulate their own sensing of cell densities such that high density cancers can grow, and subsequently block the function of immune cells. Being able to decrypt the density sensing behavior using engineered T cells will be a treatment scheme for cancer cells. The third class of GPCRs is involved in growth and metastasis of some types of tumors.

To create synthetic GPCRs that can enhance T cell recognition of cancer microenvironment, two GPCRs were initially tested: C-X-C chemokine receptor type 4 (CXCR4) and lysophosphatidic acid receptor (LPAR). CXCR4 is an alpha-chemokine receptor specific for stromal-derived-factor-1 (SDF1, also called CXCL12), a molecule endowed with potent chemotactic activity for lymphocytes. The CXCR4 expression is low or absent in many healthy tissues, but highly expressed in many types of cancer, including breast cancer, ovarian cancer, melanoma, and prostate cancer. High expression of this receptor in cancer cells has been linked to the high concentration of CXCL12 in cancer cells, wherein CXCL12 expression is positively correlated with CXCR4-positive cells. LPAR binds the lipid signaling molecule lysophosphatidic acid (LPA). Because of LPA's ability to stimulate cell proliferation, aberrant LPA-signaling has been linked to cancer in numerous ways. For example, dysregulation of autotaxin or the LPA receptors can lead to hyperproliferation, which may contribute to oncogenesis and metastasis.

Figure 21A:
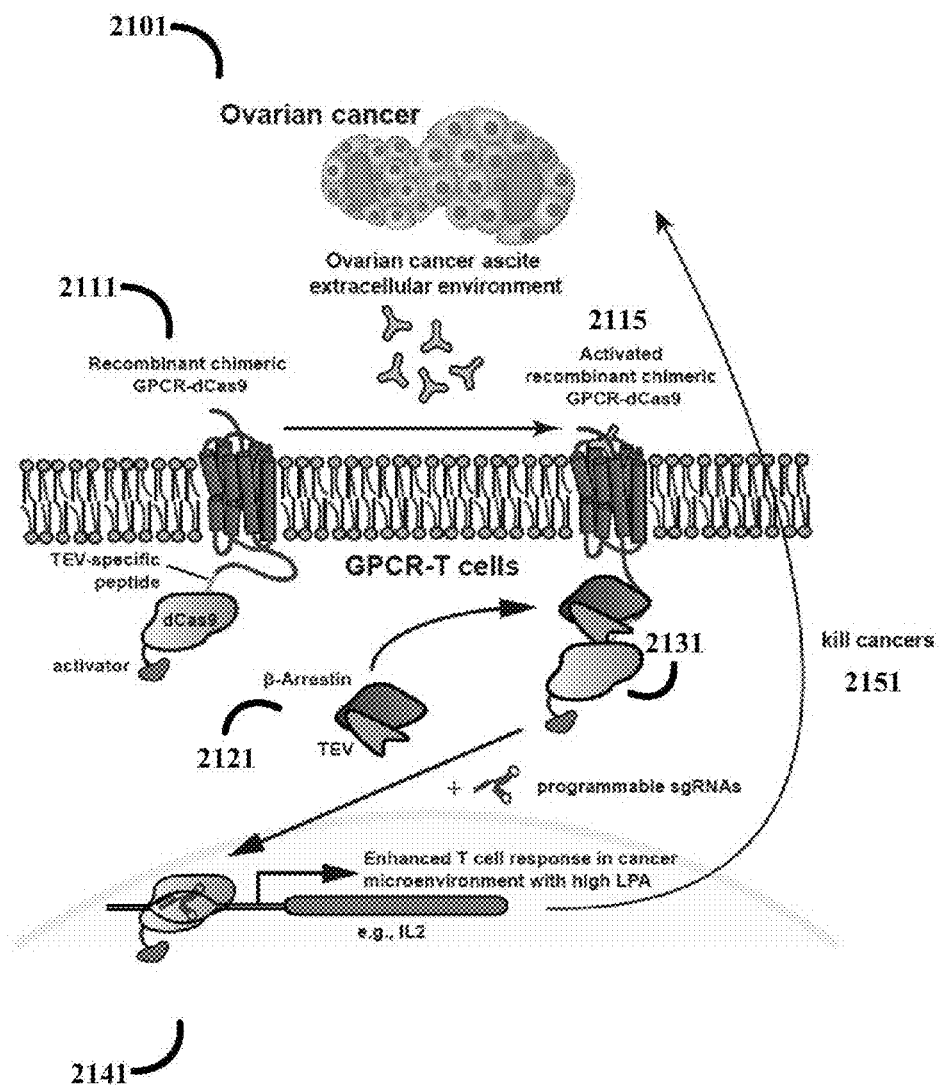
FIG. 21A show uses of chimeric antigen GPCRs coupled to dCas9-activators.

Synthetic GPCRs of the present disclosure can be created by replacing the G-protein domain of a GPCR with a dCas9-activator domain (FIG. 21A). For instance, a dCas9-VPR (a tripartite activator fusion containing VP64, p65AD, and Rta) can be fused to a GPCR via a TEV-cleavable sequence 2111. The dCas9-VPR can also be fused to two copies of a nuclear localization signal (NLS) to enhance the nuclear localization of the dCas9-VPR after TEV cleavage. The TEV protease can be fused to P-arrestin, a protein that is conditionally recruited to GPCRs upon ligand binding 2121. The embodiment of the present disclosure depicted in FIG. 21 shows that an engineered GPCR-dCas9 activator can be expressed on T cells 2111 and used to treat cancer such as ovarian cancer 2101. Increases in the extracellular concentration of LPA (a GPCR ligand) can activate the engineered LPAR1-dCas9 2131 which then recruits beta-arrestin fused to a TEV protease 2121. The protease can release the dCas9 to the nucleus by cleaving the TEV-specific peptide. The dCas9 can also complex with a guide RNA, e.g., a programmable sgRNA. In the nucleus, the dCas9-sgRNA can activate genes 2141 such as IL-2 that can enhance cell killing 2151.

Figure 23A:
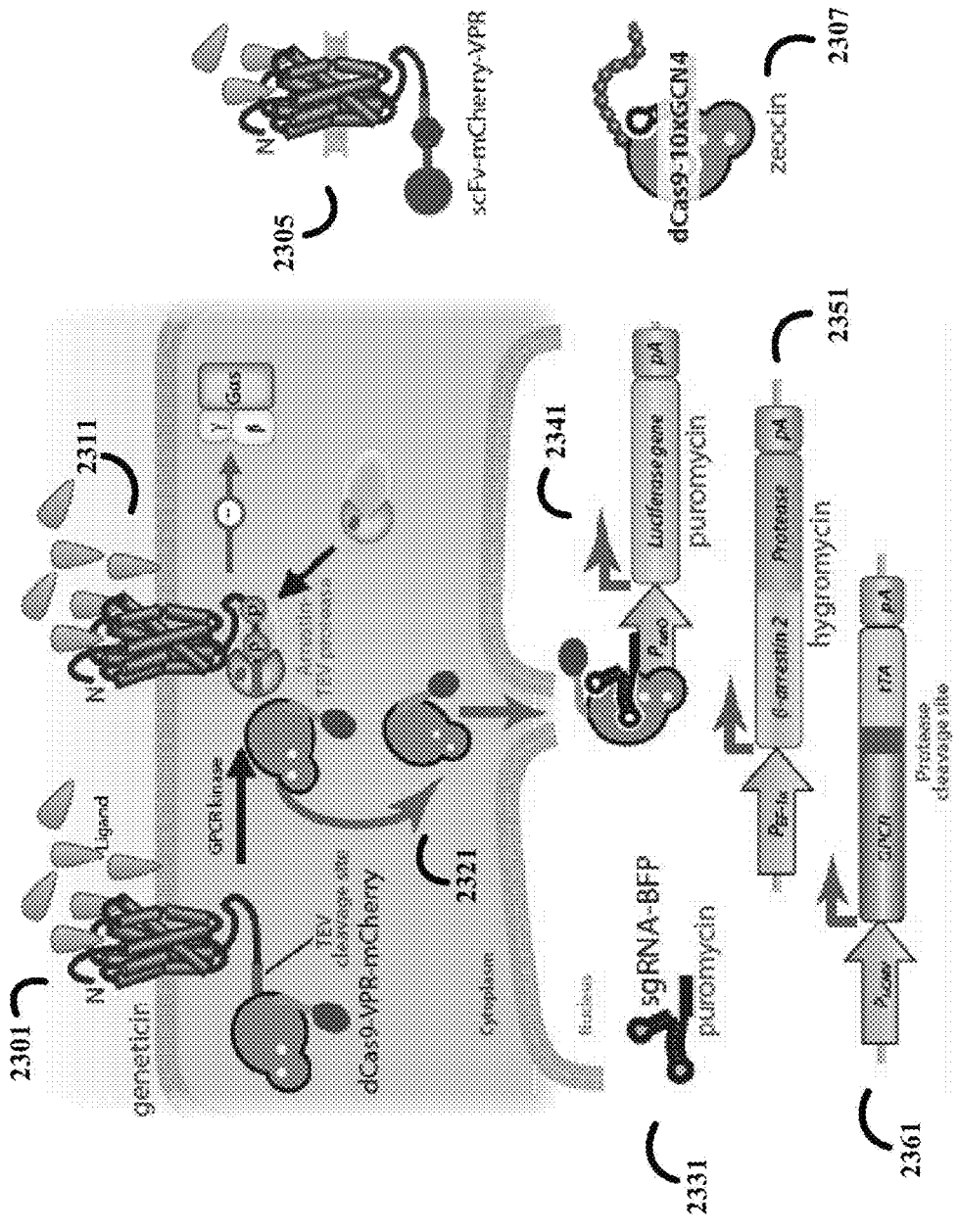
FIGS. 23A and 23B provide an exemplary embodiment of chimeric GPCR-gene modulating domain polypeptide.
Figure 23B:
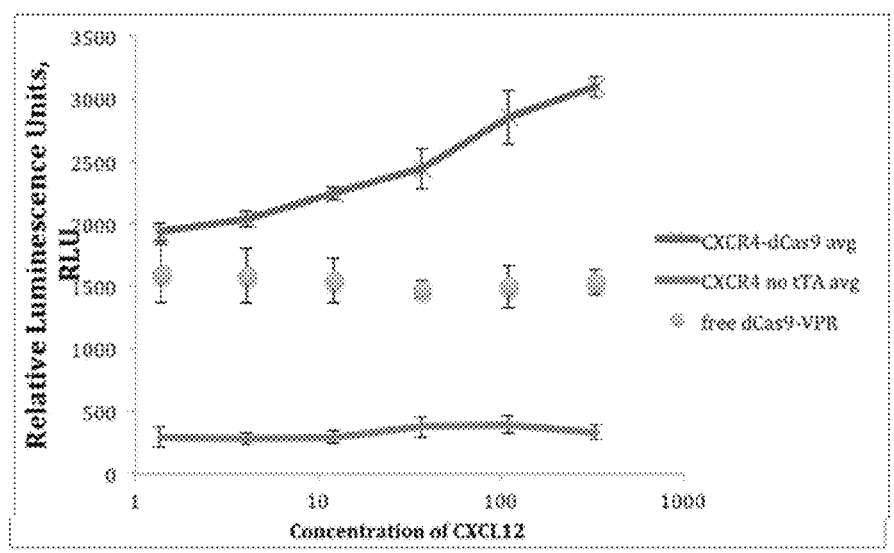

FIGS. 23A and 23B show the results from three independent experiments testing the activity of a chimeric CXCR4-dCas9-VPR-mCherry 2301 in host cells, e.g., HEK293 cells. After ligand binding 2311, the β2-arrestin-protease was recruited to the activated receptor and the protease released the dCas9-VPR-mCherry from the receptor 2321. The expression construct for the β2-arrestin-protease is shown as 2351. The reporter construct is shown in 2341. In each experiment, the dCas9-VPR was paired with a single guide RNA (sgRNA) that specifically activates luciferase expression, which in turn generates luminescence. In this experiment a sgRNA-BFP was used 2331. In some experiments, a scFv-mCherry-VPR 2305 and/or a dCas9-10×GCN4 2307 was used as a control.

The CXCR4-dCas9-VPR-mCherry 2361 was conditionally expressed from a doxycycline-inducible promoter (TRE3G), such that only addition of doxycycline (Dox) and the presence of a co-activator can trigger expression of the recombinant receptor. Without Dox, there is no luminescence (FIG. 23B). As a positive control, "free" dCas9-VPR (that is not fused to CXCR4) was added and as expected, luminescence was produced. Upon Dox addition, chimeric CXCR4-dCas9 was expressed, and luminescence was detected. FIG. 23B shows that the luminescence was sensitive to increasing concentrations of the CXCR4 ligand, CXCL12. Chimeric GPCR-dCas9 proteins described herein can be expressed in immune cells such as T cells and macrophages. Also, chemotactic experiments can be performed to determine if CXCL12 can serves as a chemoattractant to T cells expressing the chimeric GPCR-dCas9 proteins.

An example of an amino acid sequence for the CXCR4-dCas9-VPR-mCherry polypeptide is provided in SEQ ID NO:3.

Figure 23C:
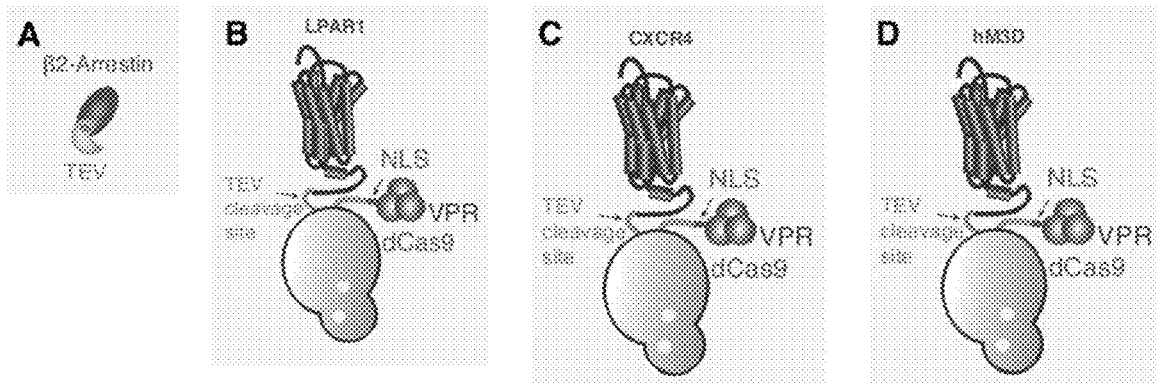
FIGS. 23C and 23D illustrate chimeric GPCR receptors comprising LPAR1, CXCR4, and hM3D and corresponding activation of a fluorescent reporter (GFP) in the presence of ligand, β-arrestin-protease, and sgRNA.
Figure 23D:
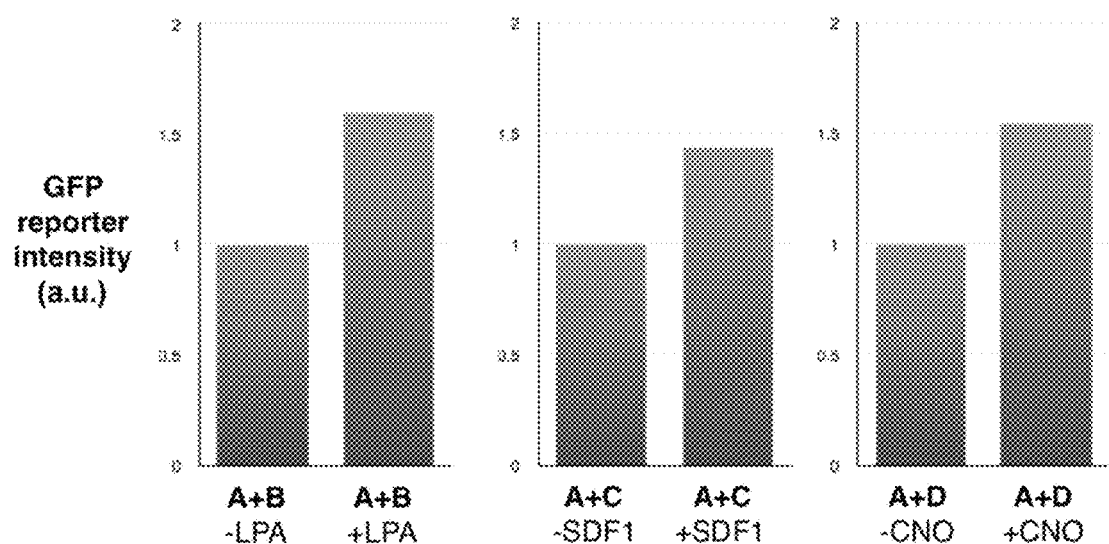

With reference to FIG. 23C, in HEK293T cells expressing sgRNA, β2-arrestin-protease ('A') and either LPAR1-dCas9-VPR ('B'), CXCR4-dCas9-VPR ('C'), or hM3D-dCas9-VPR ('D'), the presence of ligand (e.g., LPA, SDF1, or CNO) resulted in increased levels of GFP reporter protein compared to the absence of ligand (FIG. 23D). Ligand binding to each respective chimeric receptor resulted in receptor activation and adaptor-protease recruitment. The adaptor-protease recruited to the receptor resulted in cleavage of the dCas9-VPR from the receptor at the TEV cleavage site. The released dCas9-VPR was then targeted by sgRNA to a target polynucleotide to alter expression levels of a GFP reporter.

A2. Recombinant Chimeric GPCR Receptor Containing Cleavage Moiety.

Figure 21B:
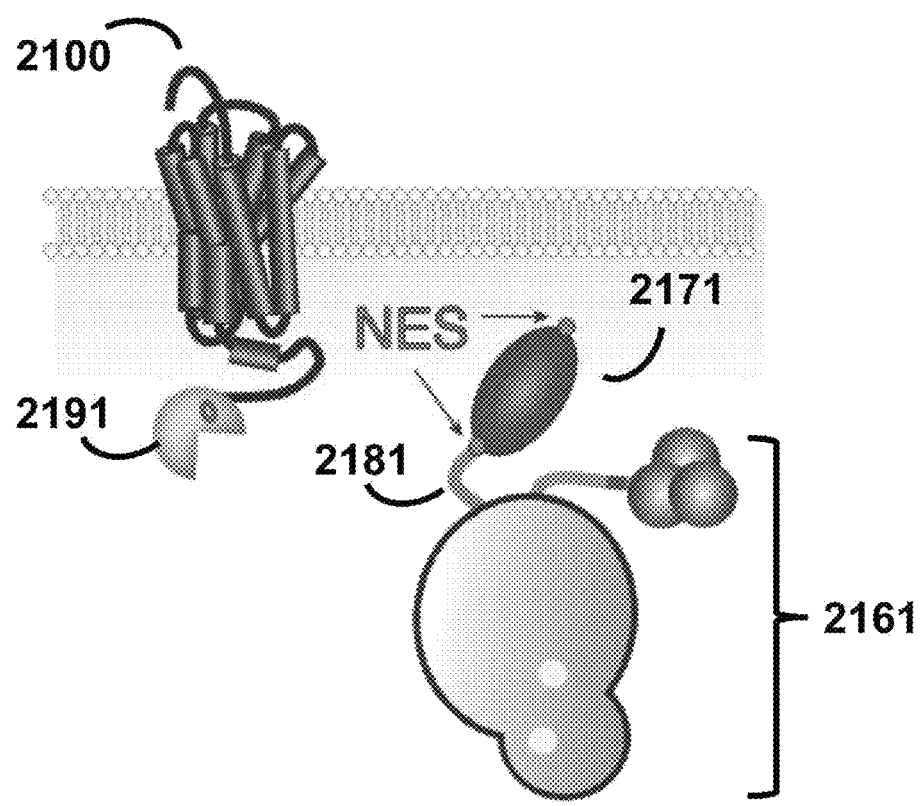
FIG. 21B illustrates an alternative configuration in which the protease moiety is coupled to the GPCR and the dCas9-activator domain is coupled to an adaptor protein recruited to an activated GPCR.

In an alternative configuration, synthetic GPCRs of the present disclosure comprise a cleavage moiety and an adaptor polypeptide comprises a dCas9-effector domain. For example, as shown in FIG. 21B, a dCas9-VPR (a tripartite activator fusion containing VP64, p65AD, and Rta) 2161 can be fused to an adaptor protein 2171, such as β2-arrestin, via a TEV-cleavable sequence 2181. The β2-arrestin-dCas9-

VPR can also comprise two copies of a nuclear export signal (NES) to enhance the nuclear export of the β2-arrestin-dCas9-VPR. The TEV protease 2191 can, in this configuration, be fused to a GPCR 2100 (GPCR-protease). When β2-arrestin-dCas9-VPR is recruited to an activated GPCR-protease, the protease can cleave TEV-cleavable sequence and release the dCas9-VPR from the β2-arrestin-dCas9-VPR polypeptide.

For example, an engineered β2-arrestin-dCas9-VPR can be expressed with synthetic GPCR-protease, such as a LPAR1 GPCR. Increases in the extracellular concentration of LPA (a GPCR ligand) can activate an engineered LPAR1-protease which then recruits β2-arrestin-dCas9-VPR. The protease can release the dCas9 to the nucleus by cleaving the TEV-cleavable peptide. The dCas9 can also complex with a guide RNA, e.g., a programmable sgRNA. In the nucleus, the dCas9-sgRNA can activate genes, such as a fluorescent reporter gene.

As another example, an engineered β2-arrestin-dCas9-VPR can be expressed with synthetic GPCR-protease, such as a CXCR4 GPCR. Increases in the extracellular concentration of SDF1 (a GPCR ligand) can activate an engineered CXCR4-protease which then recruits β2-arrestin-dCas9-VPR. The protease can release the dCas9 to the nucleus by cleaving the TEV-cleavable peptide. The dCas9 can also complex with a guide RNA, e.g., a programmable sgRNA. In the nucleus, the dCas9-sgRNA can activate genes, such as a fluorescent reporter gene.

As another example, an engineered β2-arrestin-dCas9-VPR can be expressed with synthetic GPCR-protease, such as hM3D (DREADD version of hM3 GPCR). Increases in the extracellular concentration of clozapine-N-oxide (CNO, a GPCR ligand) can activate an engineered hM3D-protease which then recruits β2-arrestin-dCas9-VPR. The protease can release the dCas9 to the nucleus by cleaving the TEV-cleavable peptide. The dCas9 can also complex with a guide RNA, e.g., a programmable sgRNA. In the nucleus, the dCas9-sgRNA can activate genes, such as a fluorescent reporter gene.

Figure 23E:
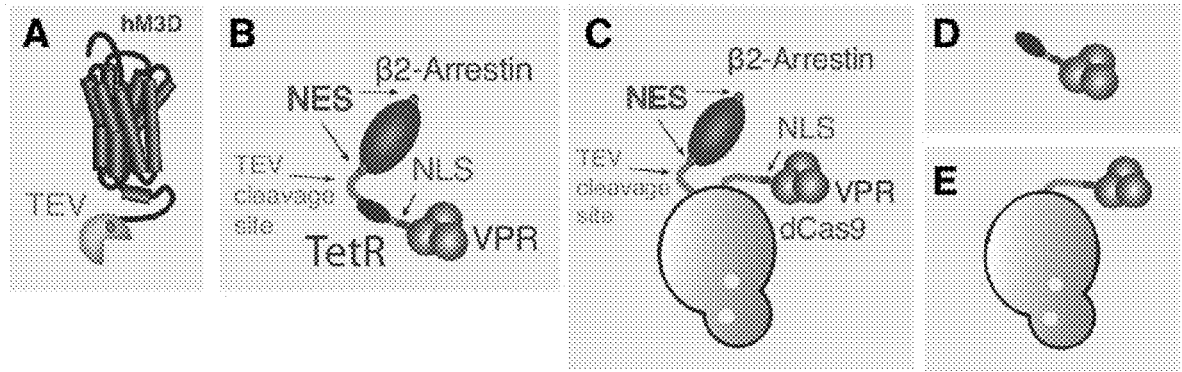
FIGS. 23E and 23F compare levels of transcriptional regulation of a reporter gene resulting from dCas9-VPR targeted by sgRNA after release from a chimeric receptor and a TetR-VPR which binds directly to the promoter of the reporter gene.
Figure 23F:
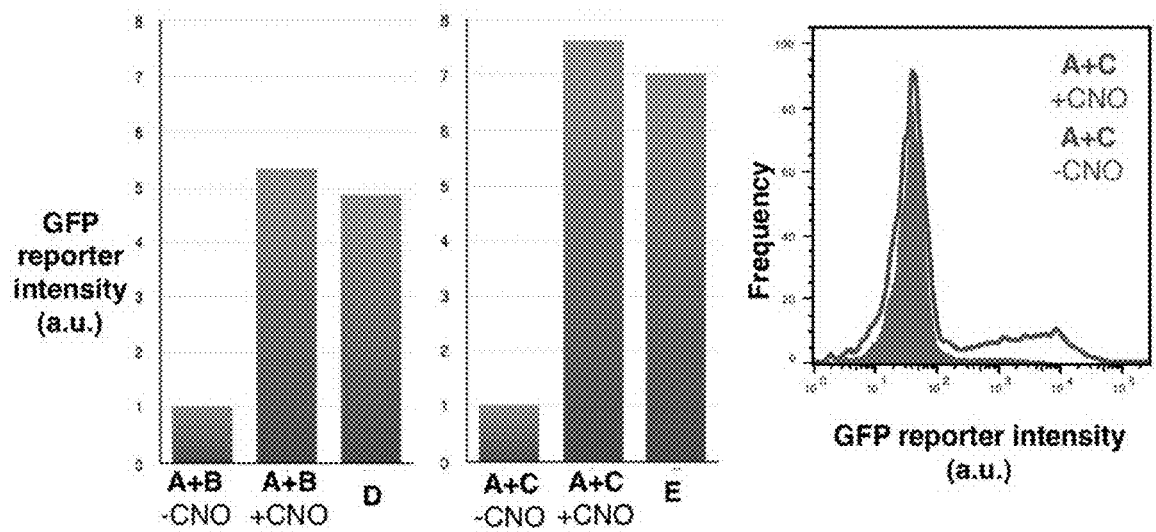
Figure 26A:
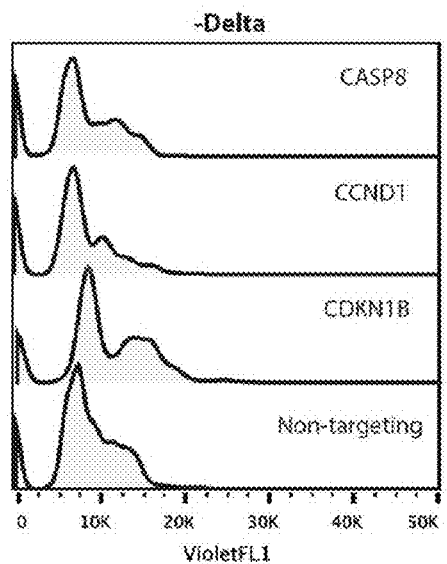
FIGS. 26A-26D show that the Notch-dCas9 activator, upon Delta binding, can activate target genes such as those that control cell apoptosis or the cell cycle. Cells expressing the Notch-dCas9 polypeptide activated the target genes when in the presence of Delta (FIGS. 26B and 26D). Notch chimeric antigen receptor did not activate transcription of the target genes in the absence of Delta (FIGS. 26A and 26C).
Figure 26B:
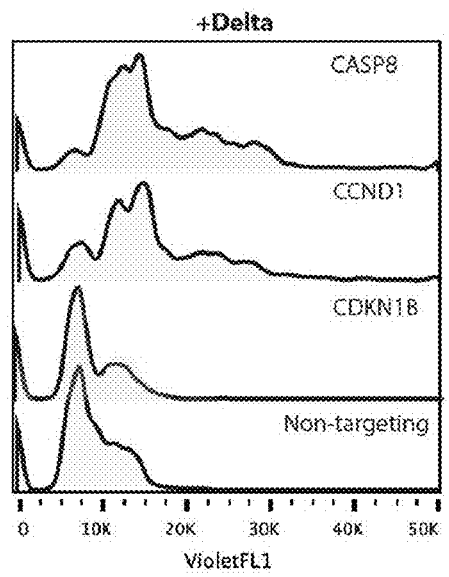
Figure 26C:
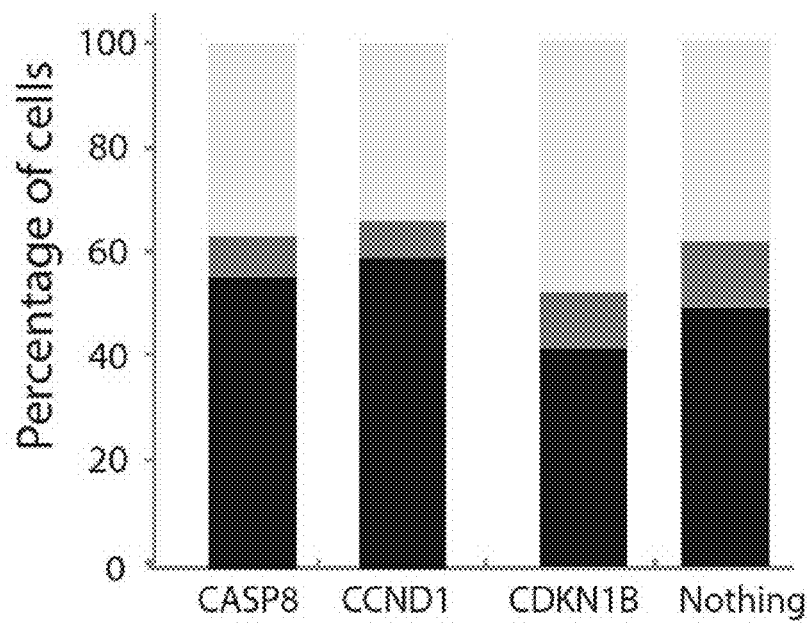
Figure 26D:
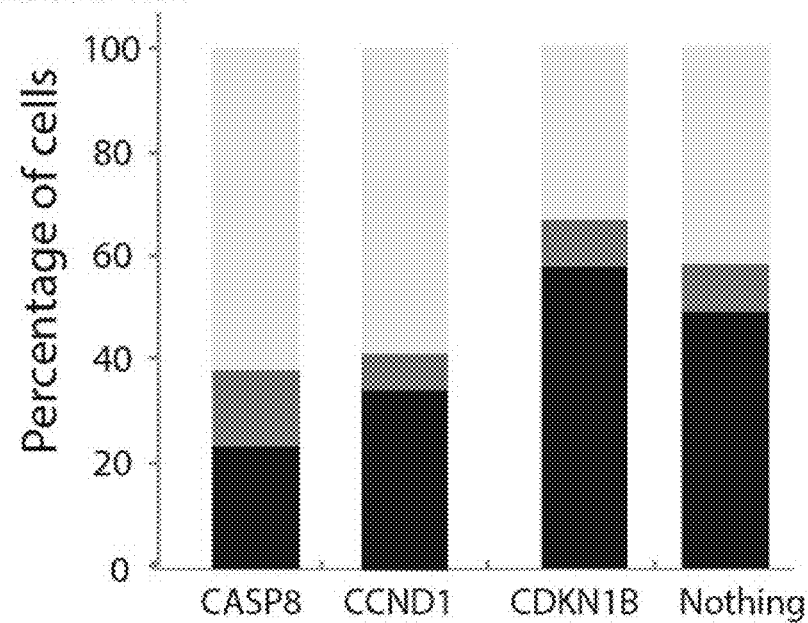

With reference to FIGS. 23E and 23F, GFP reporter levels of hM3D-protease (FIG. 23E, 'A')+β2-arrestin-dCas9-VPR (FIG. 23E, 'C')+sgRNA (sgTET which targets the TRE3G promoter of the GFP reporter gene) in the presence of ligand (CNO) are comparable to GFP reporter levels of hM3D-protease (FIG. 23E, 'A')+dCas9-VPR (FIG. 23E, 'E')+sgRNA (FIG. 23F, 'A+B+CNO' compared to 'D'). As a positive control, GFP reporter levels of hM3D-protease (FIG. 23E, 'A')+β2-arrestin-TetR-VPR (FIG. 23E, 'B')+sgRNA (in the presence of ligand, CNO) are comparable to GFP reporter levels of hM3D-protease (FIG. 23E, 'A')+TetR-VPR (FIG. 23E, 'D')+sgRNA (FIG. 23F, 'A+C+CNO' compared to 'E'). (TetR binds directly to the promoter of the reporter gene). Ligand (CNO) binding to hM3D-protease resulted in receptor activation and adaptor-dCas9-VPR recruitment. Recruitment of 02-arrestin-dCas9-VPR to the activated receptor resulted in cleavage of the dCas9-VPR from the adaptor at the TEV cleavage site. The released dCas9-VPR was then targeted by sgRNA to a target polynucleotide to alter expression levels of a GFP reporter.

B. Recombinant Chimeric Integrin Containing dCas9-Effector Domains.

Figure 22A:
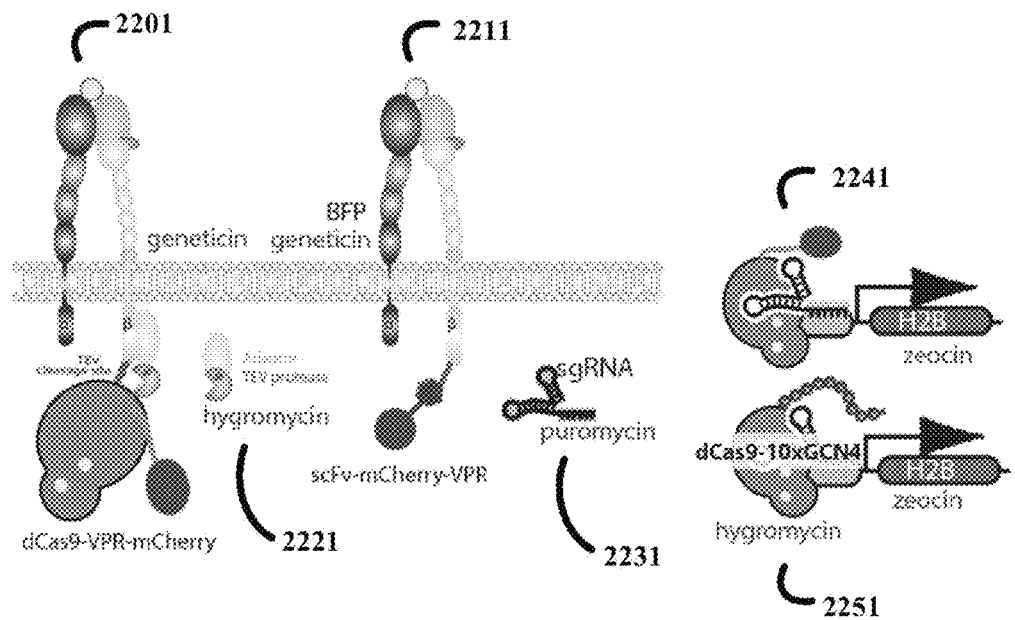
FIGS. 22A and 22B show integrin-dCas9 gene modulating polypeptides and their response to integrin ligands such as fibronectin.
Figure 22B:
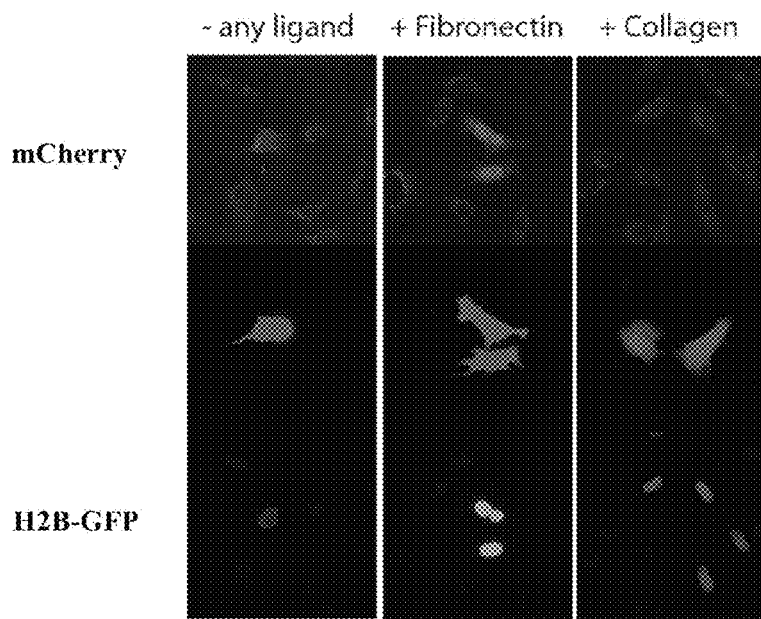
Figure 22C:
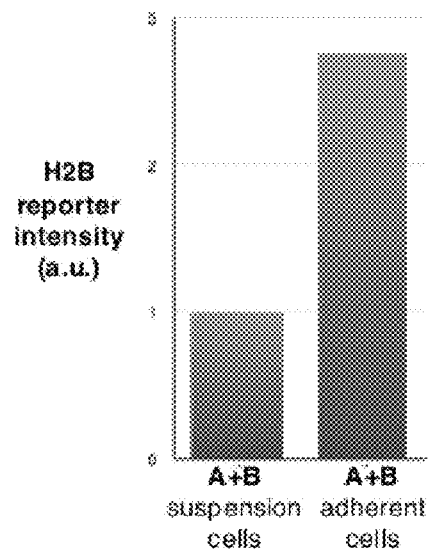
FIG. 22C illustrates the activity of integrin-dCas9 complex in adherent cells compared to suspension cells.
Figure 22D:
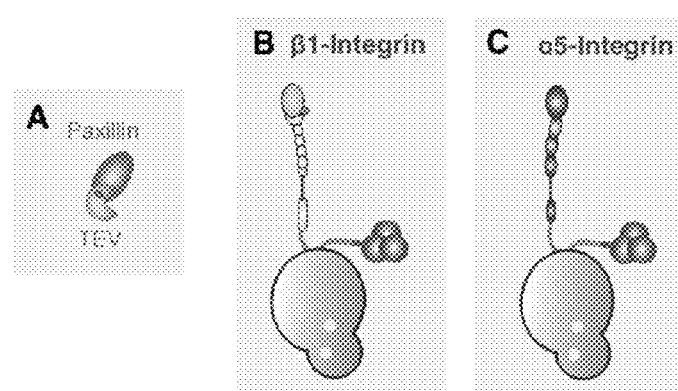
FIGS. 22D and 22E illustrates the binding specificity of paxillin-TEV for the beta subunit of integrin relative to the alpha subunit.
Figure 22E:
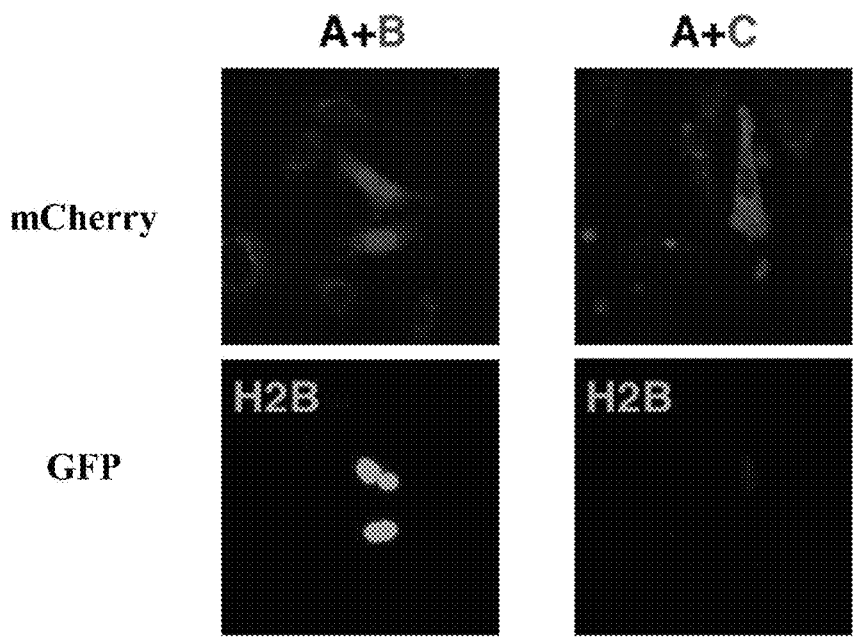

Provided herein are also engineered integrins fused to dCas9-effector domains, e.g., dCas9-activator domains (FIG. 22A). Integrins comprising different pairs of alpha and beta subunits can sense diverse matrix signals such as fibronectin, collagen, laminin, etc. dCas9-VPR-mCherry was fused via the TEV-cleavable peptide linker sequence to either the alpha or beta subunit of any integrin, e.g., $α_5β_1$ integrin 2201. The TEV protease was linked to paxillin, a protein conditionally recruited to paired integrins upon ligand binding 2221. An sgRNA that can bind the reporter gene was introduced into the host cell 2231. In addition, a transcriptional reporter gene (H2B-GFP gene) was introduced to visualize the sgRNA guided dCas9-VPR controlled activation 2241. As a receptor expression control, an integrin linked to scFv, mCherry, and VPR was used 2211. Other controls used in the experiment include a dCas9-10×GCN4 control 2251. dCas9-activator domain linked to a beta subunit (FIG. 22D, 'B'), without ligand, resulted in minimal GFP signal (the genomic copy of GFP is used as the reporter signal to detect the "released" amount of dCas9-VPR into the nucleus) as shown in FIG. 22B. In the presence of fibronectin, high GFP expression was detected, suggesting that the chimeric integrin-dCas9 protein activates transcription upon ligand binding. In the presence of collagen, the chimeric integrin-dCas9 protein did not activate transcription of the reporter gene. In addition to activation of integrins by ligand binding, integrin activation by surface engagement also results in the release of dCas-9VPR and GFP expression. An integrin-dCas9-VPR+paxillin-protease+sgRNA system, when expressed in adherent cells, results in higher levels of fluorescent reporter protein compared to suspension cultures (FIG. 22C). When dCas9-VPR is linked to an alpha subunit (FIG. 22D, 'C'), activation of integrin results in minimal expression of GFP (FIG. 22E, 'A+C' compared to dCas9-VPR linked to a beta subunit (FIG. 22E, 'A+B') as paxillin specifically binds to beta-integrin tails.

An example of an amino acid sequence for the integrin β1-dCas9-VPR-mCherry polypeptide is provided in SEQ ID NO:4.

C. Recombinant Chimeric Notch Containing dCas9-Effector Domains.

Also provided are chimeric Notch receptors containing dCas9-activator domain (FIGS. 24A-24D). In one embodiment, Notch was directly fused to a dCas9-activator without a TEV peptide cleavage sequence linker. In a second embodiment, Notch was directly fused to a dCas9-activator via a TEV peptide cleavage sequence. The TEV protease was linked to the Notch adapter protein, presenilin-1 (PS-1). Presenilin 1 is one of the four core proteins in the presenilin complex, which mediate the regulated proteolytic events of several proteins in the cell, including gamma secretase. Expression constructs of each of the chimeric receptors were generated and introduced into host cells, such as HEK293 cells. An example of an amino acid sequence for a Notch-dCas9-VPR-mCherry polypeptide is provided in SEQ ID NO: 5.

Example 3: Controlling Gene Regulation Using Engineered Chimeric Notch Receptors Fused to Nuclease-Deficient Cas9 Proteins This example describes a novel approach to cell therapy—the generation of modified immune cells that can recognize a diseased microenvironment and respond with precise therapeutic action. A patient's immune cells are promising reagents for these therapeutics as they employ innately complex systems that can sense and respond to specific cells and the cell's local environment.

Distinct from using nuclease Cas9 for gene editing, nuclease-deficient Cas9 (dCas9) protein can be used for transcriptional activation or repression without genetically altering the genome sequence. dCas9 protein paired with a small guide RNA (sgRNA) can recognize and regulate genes containing complementary sequences. Coupling to transcriptional activator or repressors, this system can offer a highly programmable approach for precise control of genes. While dCas9 offers a powerful approach for modulating cell activity, it lacks the ability to sense signals, such as external or environmental signals.

Cell signaling pathways have been shown to be critical molecules that can be rewired to respond to non-cognate signals by exchanging and recombining their underlying cognate signaling components. In particular, the Notch-Delta signaling pathway is particularly attractive for synthetic rewiring because of its simple mechanism of action, rapid dynamics, and important role in immune cell lineage regulation and cancer progression. Notch and Delta are single-pass transmembrane protein families in metazoans. Their interaction leads to the proteolytic release of the Notch intracellular domain (NICD), which translocates to the nucleus and activates target genes. Protein engineering approaches have been applied to alter the Notch molecule by either replacing the NICD with synthetic transcription factors (GAL4-AD) for activating alternative genes of the Notch pathway or by replacing the Notch extracellular domain (NECD) with recognition motifs against specific receptor-antigens.

A. Engineering a Modular Chimeric Artificial Notch Receptor for CD47-Triggered, CRISPR-Mediated Transcriptional Regulation.

This example describes chimeric receptors that combine Notch and CRISPR/Cas protein to produce a customizable, orthogonal signaling system for target-cell recognition (via Notch) and programmed cell response (via CRISPR/dCas9). Provided herein is a highly programmable cancer recognition platform that harnessing contact-mediated Notch-Delta signaling and RNA-guided CRISPR genome engineering. These chimeric Notch receptors (FIGS. 24A-24C) can be used to activate any target gene by substituting the NICD of Notch with Cas9 components. A wide range of complex cellular behaviors can be controlled upon Notch-Delta interaction. The chimeric antigen receptors described herein can be used to modulate transcription and cellular activity of T cells in response to local cell-cell microenvironment.

A modular chimeric artificial Notch receptor for CD47-triggered, CRISPR-mediated transcriptional regulation can be produced. Wild-type Notch receptors contain two modules: the extracellular domain (NECD) and the intracellular domain (NICD). To make the chimeric artificial Notch receptor (caN), the NICD domain can be replaced with dCas9 fused to a transcriptional activator or repressor (also fused with blue fluorescent protein, BFP, for visualization). For example, dCas9 can be fused with the activator domain of VP64 or VPR. The dCas9 fusion can translocate into the nucleus upon Notch-Delta interaction (FIG. 24B). The construct encoding the chimeric artificial Notch receptor can be transformed into a cell. To test nuclear translocation of dCas9 fusion as an NICD, an sgRNA that targets the GAL4 UAS-GFP reporter construct can be co-expressed. Upon co-culture with another cell line expressing Delta, Notch-Delta transactivation can be monitored over time by dCas9-VP64-BFP fluorescence and translocation from the plasma membrane to nucleus.

The NECD of Notch contains 29-36 tandem epidermal growth factor (EGF)-like repeats, of which EGF repeats 11-12 promote productive interactions with Delta. For non-canonical sensing, select regions of the NECD can be replaced with a cognate single-chain fragment variable (scFv). Various regions of the EGF repeats can be replaced with MABL, a scFv against human CD47 (hCD47). A minimal activator GAL4esn can be linked to the ECD to measure the transcriptional activity of the receptor fusion. Specifically, MABL(ECD)-GAL4esn variants using UAS-GFP reporter expression upon co-culture with cells expressing hCD47 can be used (FIG. 24C). The Notch chimeric antigen receptors can recruit a presinillin-TEV protease after the receptor binds Delta or its desired ligand.

To create a novel CD47-binding scFv-Notch receptor, the NICD and NECD modules can be combined. The expected combinatorial effect is that the hCD47 activates the CD47scFv-Notch-dCas9 receptor, leading to cleavage and nuclear translocation of dCas9-VP64, which can be guided by an sgRNA to activate reporter expression. Variants can be made by using dCas9 variants and different sgRNAs. The chimeric receptors can be transfected into cell lines such as CHO, HEK293, and Jurkat.

The Notch-dCas9-activators present in FIGS. 24A-24C were tested in HEK293 cells (FIG. 24E), T cells (Jurkat cells; FIG. 24F) and macrophages (THP-1; FIG. 24G) for activity and function. In the experiments, the Notch-dCas9-activator was expressed in each cell line. Upon Delta-Notch interaction, fluorescent reporter expression was activated from the genome. The cells showed high levels of reporter protein expression when the recombinant cells were exposed to Delta, and low expression when they were not. The results show that the artificial chimeric receptor is fully functional in the immune cells. To test the use of such receptors on activation of cell proliferation, short guide RNAs specific to cell apoptosis genes (caspase 8 (CASP8)) or cell cycle genes (cyclin D1 (CCND1) and cyclin-dependent kinase inhibitor 1B (CDKN1B)) were introduced into the host cells along with the chimeric receptors. The results are provided in FIGS. 26A-26D.

In another experiment, a Notch-dCas9-activator was expressed in cells along with a guide RNA (sgUAS; SEQ ID NO:1; gtactccgacctctagtgt) that can bind to an upstream activating sequence (UAS) in proximity to the promoter of a fluorescent reporter gene (FIG. 27A). The chimeric artificial Notch receptor contained the ECM and TM domains of wild-type Notch, a nuclease-dead Cas9 (dCas), and a tripartite effector domain consisting of VP64, p65 and Rta proteins (VPR). Delta, a ligand that binds to Notch, can be either immobilized on a surface or presented by another cell. Notch-Delta binding leads to cleavage and translocation of dCas9-VPR into the nucleus. dCas9 and a single-guide RNA (sgUAS) that targets the UAS regulator element (promoter) leads to expression of a fluorescent citrine-tagged histone-2B (H2B). FIG. 27B shows single-cell fluorescence via flow cytometry of the cells of FIG. 27A. Overexpression of H2B-citrine was detected in cells that were cultured on a Delta-coated surface, compared to cells cultured on a surface without Delta.

B. Characterization of Chimeric Antigen Notch Receptor (caN) Behavior Including Parameters that Shape Signal Response Function in Silico and In Vitro.

The simplicity of Notch-Delta activation allows tuning the signal response. Mathematical modeling and experiments can explore how mutual cis-inhibition between Notch and Delta affects the response function when both endogenous and synthetic Notch are present. This can be done by expressin both caN-dCas9-EGFP and Delta-mCherry in the same cells using promoters of varying strengths.

To study how caN reshapes cellular response (e.g., phagocytic activity, P) to an external signal (e.g., Delta or CD47), one situation to consider includes that in which endogenous Notch in a receiving cell (R in FIGS. 25A-25C) and Delta in the signaling cell (DT in FIGS. 25A-25C) leads to repression of a receiving cell's P response (FIGS. 25A-25C). Similar rate constants can be assumed for simplicity without loss of generality. The models can show that P decreases hyperbolically with increasing DT at the steady state. Upon addition of caN-dCas9 receptor (N, in receiving cell) that now represses endogenous Notch (R) expression at a stronger cooperativity coefficient (ηR, a critical parameter modulated by dCas9 with a repressive domain) than endogenous repression of P by R, one can rewire the output into a bimodal response with increasing DT levels (FIG. 25B). Finally, an additional layer of cis-Delta inhibition (DC) that competes with DT on binding to N (but not to R) is another critical parameter that dictates the threshold at which P-response shifts from repression to activation in response to DT (FIG. 25C).

The critical parameters identified in silico can be optimized using in vitro experiments. In particular, expression levels of various receptor components (DC, DT, R and N of FIGS. 25A-25C) can be modulated by applying constitutive promoter constructs with known strengths. Various dCas9-effectors can be chosen to tune repressive strength. The activating and repressive strength of the receptor-dCas9-effector variants can be tested using known and effective sgRNAs that regulate specific endogenous genes. This method also allows for modification of R with minimal off-target effects.

C. Engineering Macrophages with CD47-Binding caN-dCas9 Receptors that Activate Phagocytic Response Against CD47-High Cancer Cells.

The CD47-binding chimeric antigen Notch receptor-dCas9 fusion protein described herein can be used in the field of cancer, such as cancer progression and immune evasion. To test the efficacy of the CD47-binding caN-dCas9 receptor to mediate or regulate immune evasion in cancer, the CD47scFv-Notch-dCas9 receptor described previously can be expressed in THP-1-derived macrophages. Human CD47 can be expressed in CHO cells. Flow-cytometry analyses of surface expression of SIRPα (an endogenous response), caN-dCas9 on macrophages, and hCD47 on target CHO cells can be performed to formulate and validate theoretical models of these cells in an iterative fashion To test whether the natural or native macrophage phagocytic response is reshaped with the chimeric antigen Notch receptor, a comparison of phagocytic behaviors of caN-dCas9-encoding THP-1 macrophages transduced with or without sgRNA against SIRPα can be made. sgSIRPA and dCas9-repressor of appropriate strengths can be designed to inform the iterated model. Engineered macrophages can be challenged with adenocarcinomic human epithelial cell lines (A549) that express low, medium, or high levels of hCD47 (target-cell DT). The design of CD47-binding caN-dCas9 fusion protein can be optimized such that CD47-low and -high A549 cells are phagocytosed by the engineered macrophages, while CD47-low cells are phagocytosed by non-sgSIRPA containing macrophages.

This example provides new receptors for cancer immunotherapy, such as rationally engineered chimeric receptors that contain Notch and dCas9 domains. The receptors allow programmable transcriptional control of immune cells by sensing cancer-specific receptor levels.

Figure 28A:
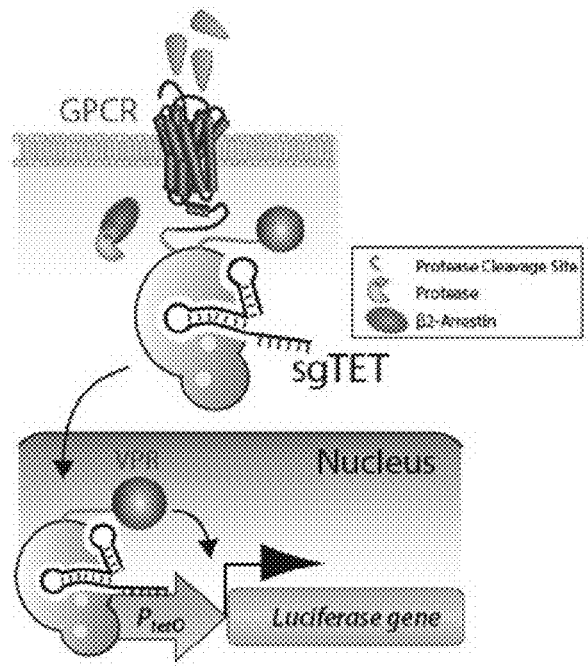
FIGS. 28A and 28B show that the CXCR4-dCas9-VPR polypeptide is responsive to CXCL12 ligand and activates transcription of a reporter gene (luciferase).
Figure 28B:
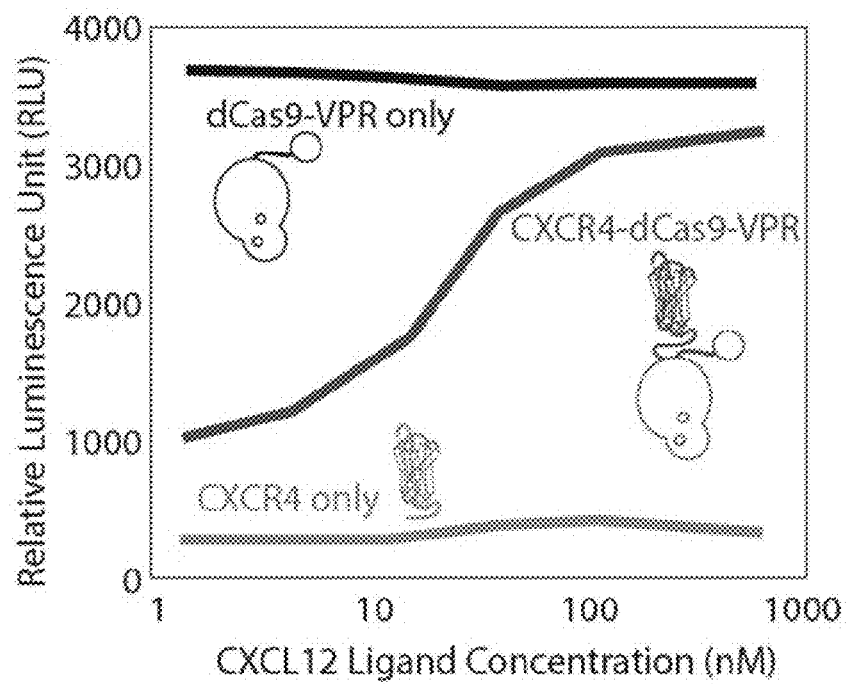

Example 4: Controlling Gene Regulation Using Engineered Chimeric GPCR Receptors Fused to Nuclease-Deficient Cas9 Proteins A chimeric artificial GPCR receptor was produced to include a full-length GPCR with a C-terminal β2-arrestin binding site derived from AVPR2 (27 amino acid residues), a protease cleavage site, and a nuclease-dead Cas9 (dCas) with a tripartite effector domain (VPR) (FIG. 28A). A chimeric β2-arrestin-protease recognizes and cleaves the protease cleavage site upon ligand-mediated GPCR activation. dCas9-VPR translocates into the nucleus and together with a single-guide RNA (sgTet, SEQ ID NO:2; gtacgttctc-tatcactgata) which specifically targets the tetO promoter, leading to gene expression of the reporter luciferase gene. HEK293 cells stably expressing a tetO-driven luciferase gene and a p2-arrestin-protease construct were transfected with one of the following expression constructs encoding: dCas9-VPR, CXCR4, or chimeric CXCR4-dCas9-VPR. The transfected cells were treated with CXCL12 (a ligand for CXCR4) for 18 hours at varying concentrations. To measure the extent of luciferase expression, luciferin was introduced, such that, when cleaved by luciferase, a luminescence signal is released and detectable (FIG. 28B).

Figure 29A:
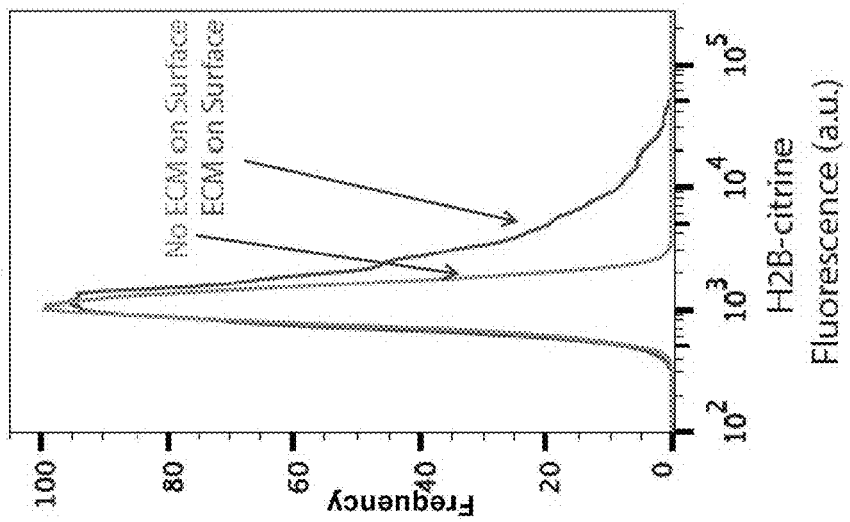
FIGS. 29A and 29B show that the integrin-dCas9-VPR polypeptide is responsive to an extracellular matrix ligand and activates transcription of a reporter gene (H2B-citrine).
Figure 29B:
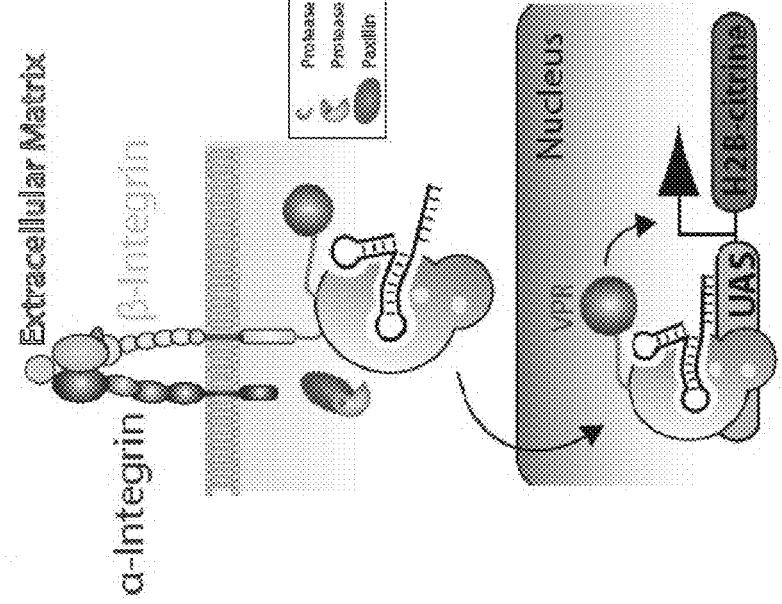

Example 5: Controlling Gene Regulation Using Engineered Chimeric Integrin Receptors Fused to Nuclease-Deficient Cas9 Proteins A chimeric artificial integrin receptor can be produced to include a full-length β1-integrin, a protease cleavage site, and a nuclease-dead Cas9 (dCas) with a tripartite effector domain (VPR) (FIG. 29A). The extracellular matrix that binds to αβ-integrin dimers can be immobilized on a surface or presented by another cell. Integrin activation leads to binding of a chimeric paxillin-protease to the C-terminus of β-integrin, cleavage of the protease cleavage site, and translocation of the dCas9-VPR into the nucleus. Paxillin recognizes the HDRK motif of β-integrin. dCas9 and a single-guide RNA, sgUAS (SEQ ID NO:1; gtactccgacctctagtgt) that targets the upstream activation sequence (UAS) promoter can activate expression of the reporter gene, e.g., a gene encoding fluorescent citrine-tagged histone 2B. HEK293 cells stably expressing both a UAS-driven H2B-citrine gene and a paxillin-protease construct were transfected with an expression construct encoding chimeric β1-integrin-dCas9-VPR and α-integrin. The transfected cells were cultured on an ECM-coated surface. Flow cytometry data shows that cells contacted by an ECM surface overexpressed H2B-citrine, compared to cell that were not contacted by the ECM (FIG. 29B).

Example 6: Multiple Engineered Chimeric Receptors Fused to Gene Modulating Domains for Logic, Cascade, and Networks for Programmable Functions By chaining two receptors together such that the first receptor upon ligand-binding activates expression of the second receptor to form an 'AND' gate. In this way, only the presence of both ligands can trigger a cellular response. Also possible is an 'A AND NOT B' gate. For example, to determine if a cancer cell has a first antigen but lacks a second different antigen, receptor A can be fused to an activator and receptor B can be fused to a repressor. This allows integration of multiple cancer-related signals for more specific signal engineering. This system can also be used to test the construction of "genetic memory" that can change the epigenetic states of the cells upon activation.

The AND gate as described herein is a device that supports co-stimulation. Natural processes such as activation of lymphocytes require co-stimulation for the development of an effective immune response. T-cell co-stimulation is important for T-cell proliferation, differentiation and survival. Activation of T-cells without co-stimulation may lead to T cell anergy, T cell deletion, or the development of immune tolerance. For example, T-cells may depend on two signals to become fully activated: the first signal is antigen-specific, which includes T-cell receptors (TCRs) interacting with peptide-MHC molecules on the membrane of antigen presenting cells (APC), and the second signal is antigen non-specific, which is provided by the interaction between co-stimulatory molecules expressed on the membrane of APC and the T-cell. The co-stimulatory molecules can be replaced with the engineered recombinant chimeric receptors described herein to provide arbitrary co-stimulatory signals to TCRs. For example, one co-stimulatory receptor expressed by T-cells is CD28, which interacts with CD80 (B7.1) and CD86 (B7.2) on the membrane of APC. Another co-stimulatory receptor expressed by T-cells is ICOS (Inducible Co-stimulator), which interacts with ICOS-L. CD28 and ICOS can be engineered to support the co-stimulatory process of TCRs.

Figure 30A:
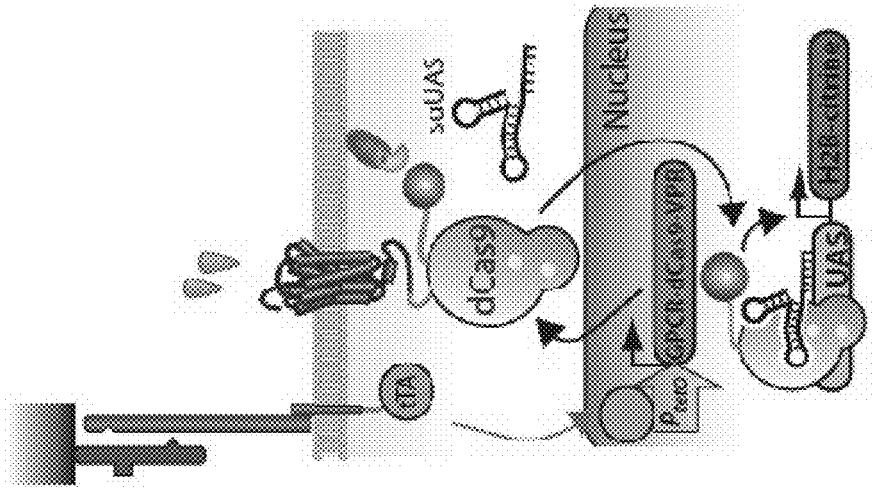
FIGS. 30A and 30B show exemplary embodiments of the chimeric antigen receptor-effector polypeptides described herein that are based on a "Split AND gate" or "Cascade AND gate" logic.

In a "Split AND" gate (FIG. 30A), a dCas9 polypeptide can be split into non-functional components or domains that can be individually tethered into desired receptors (e.g., Notch and GPCR) to recognize their respective ligands. The activation of the chimeric receptors by both ligands can allow cleavage and reconstitution of dCas9 function and subsequent gene activation. This method of gene modulation is not activated if none or only one of the ligands binds the chimeric receptors.

Figure 30B:
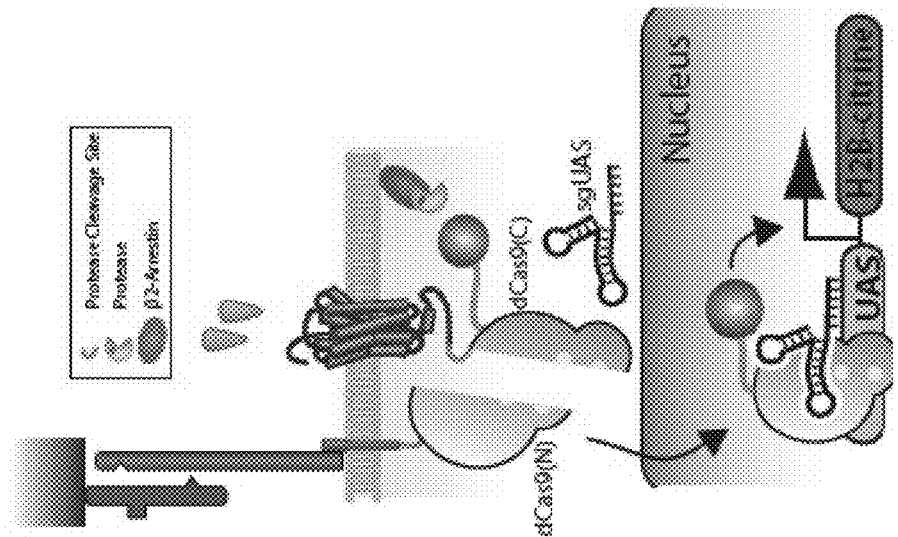

In a "Cascade AND" gate (FIG. 30B), a first chimeric receptor (e.g., Notch) when bound to its ligand (e.g., Delta) induces expression of a TetO-driven second chimeric receptor-dCas9 fusion via a tetracycline transactivator tTa. The second chimeric receptor (e.g., GPCR) can recognize its ligand, and in turn dCas9 can be cleaved and sgRNA-directed target gene expression (e.g., H2B-citrine) can be induced. In a "Cascade AND" gate, binding of the first ligand and second ligand to their respective receptors are important for the signal cascade to occur.

Example 7: Conversion of Extracellular Signals to Genome Regulation

Human NOTCH1-Cas9 chimeric receptors disclosed herein have been developed that, upon binding with an extracellular Delta ligand, release membrane-tethered Cas9 for manipulating mammalian gene expression. These chimeric receptors show robust Delta-dependent, Cas9-mediated reporter gene expression and modulation of endogenous gene function. This chimeric receptor-Cas9 technology opens up extracellular cue-dependent genome engineering, which can be useful for dissecting signaling pathways and enabling microenvironment-sensing cellular functions.

The microbial clustered, regularly interspaced, short palindromic repeats (CRISPR)-associated protein 9 (Cas9) has been harnessed to edit, activate, or repress virtually any gene in a targeted manner. A single guide RNA (sgRNA) binds at the complementary DNA sequences with Cas9, which then catalyzes a double-stranded break through its RuvC and HNH domains. Mutation of these domains and fusion with effector domains can repurpose a catalytically dead Cas9 (dCas9) to perform targeted genome regulation in mammalian cells.

Figure 31A:
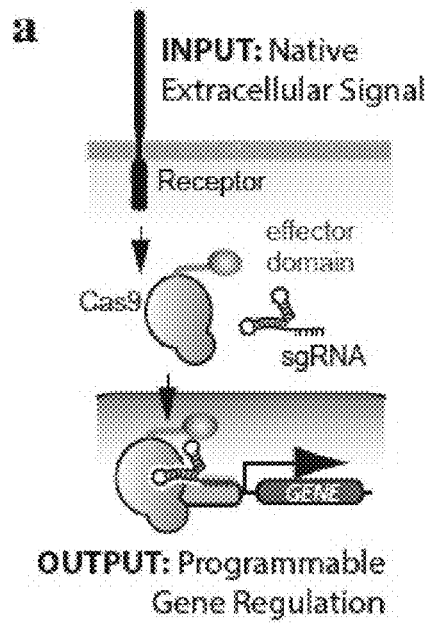
FIGS. 31A-31I illustrate embodiments of a receptor-based strategy to mobilize Cas9 in response to extracellular signals.

Genome regulation via CRISPR-Cas9 is an "inside-out" process where genotypic changes can impact cellular behavior. Conversely, the extracellular microenvironment can also impact cellular behavior via an "outside-in" signaling process. Thus, a previously unexplored strategy was taken for connecting both cellular processes (FIG. 31A). Direct fusion of Cas9 to the single-pass transmembrane Notch receptor forms the basis of the Notch chimeric receptor, a first-of-its-class tool that routes extracellular signals to CRISPR-based genome regulation. The Notch receptor is, in some cases, an attractive candidate due to its simple mechanism. Binding of its cognate ligand, Delta, to the Notch extracellular domain (NECD) allows the y-secretase complex to cleave the Notch intracellular domain (NICD), which then translocates to the nucleus and functions as a transcription factor. Analysis of species-specific Notch homologs and their domains previously demonstrated the modularity of both extracellular and intracellular domains of Notch.

Figure 31B:
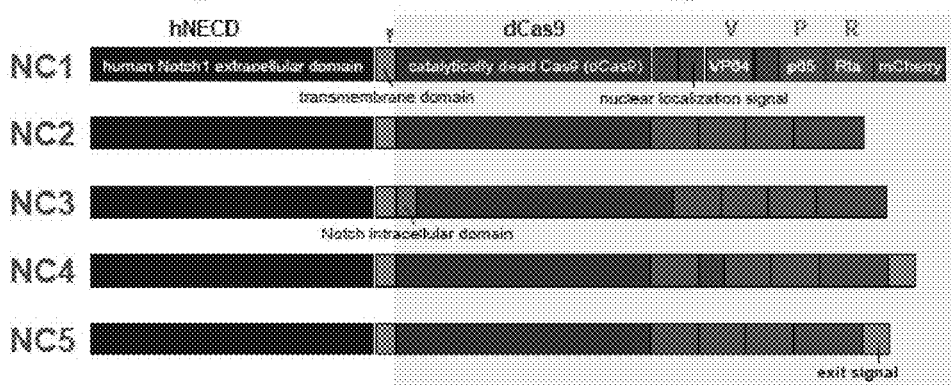
Figure 31C:
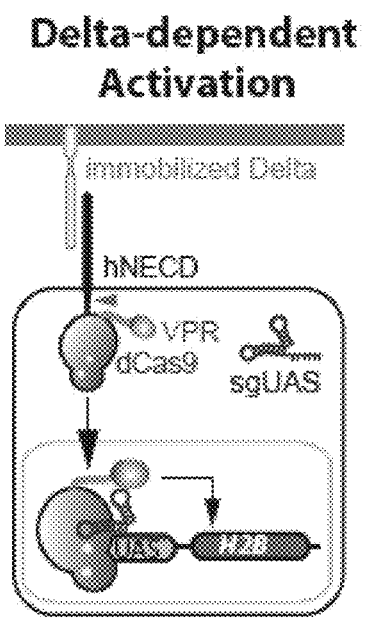

A fusion construct, NC1, was created by replacing the NICD from human NOTCH1 with the *Streptococcus pyogenes* dCas9 fused to a tripartite activation domain (VP64, p65, and Rta) (FIG. 31B) with three copies of a nuclear localization signal (NLS) sequence. The construct was fluorescently tagged with mCherry to determine its subcellular distribution. Next, it was determined how the NC fusion construct responded to extracellular Delta ligands when transfected in mammalian cells. A Chinese hamster ovary (CHO) reporter cell line was used that was previously developed to dissect Notch-Delta signaling (Sprinzak, D. et al. Cis-interactions between Notch and Delta generate mutually exclusive signalling states. *Nature* 465, 86-90, doi: 10.1038/nature08959 (2010)). The CHO cell line contained an inducible UAS (upstream activating sequence) promoter controlling the citrine (YFP)-tagged reporter gene, histone 2B (H2B). sgRNAs (sgUAS) were stably expressed via lentiviral transduction that allow cleaved dCas9 to bind to the UAS promoter (see Table 6). The chimeric hNECD-dCas9-VPR construct was transfected in CHO cells, which were then cultured for 4 days on bare plate surface or surface coated with saturating amounts of Delta (DLL4 with affinity-enhancing mutations (Luca, V. C. et al. Structural biology. Structural basis for Notch1 engagement of Delta-like 4. *Science* 347, 847-853, doi:10.1126/science.1261093 (2015))). By imaging the fluorescence of nucleus-bound H2B-citrine, it was determined whether NC1 induced H2B expression upon exposure to surface-adsorbed Delta (FIG. 31C). It was observed in some cells that nascent NC molecules remained stuck in the endoplasmic reticulum (ER) and prematurely activated H2B expression, possibly due in part to the presence of 3 NLS motifs (FIG. 33).

Figure 33:
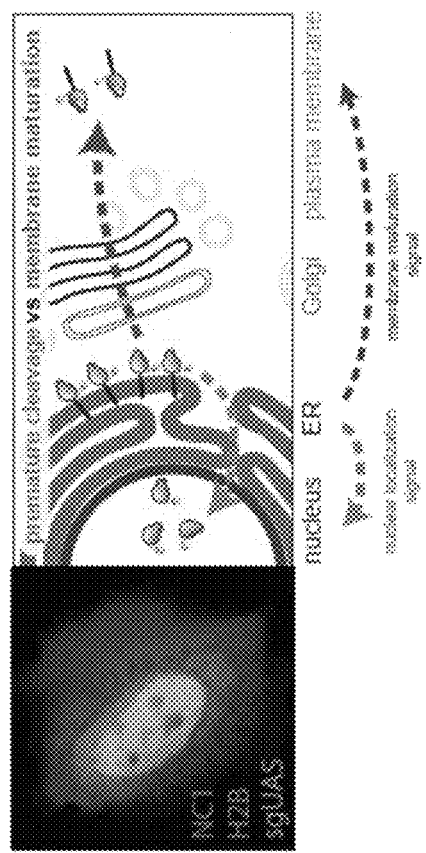
FIG. 33 left panel shows an example confocal fluorescence micrograph of a CHO cell transfected with construct NC1 (red) and sgUAS (blue). Premature activation of H2B (green, nucleus) is observed. Right panel shows a schematic representation of balance between the strengths of nuclear localization signals and membrane maturation signals in Delta-dependent cleavage of Notch-Cas9 chimeras.
Figure 34:
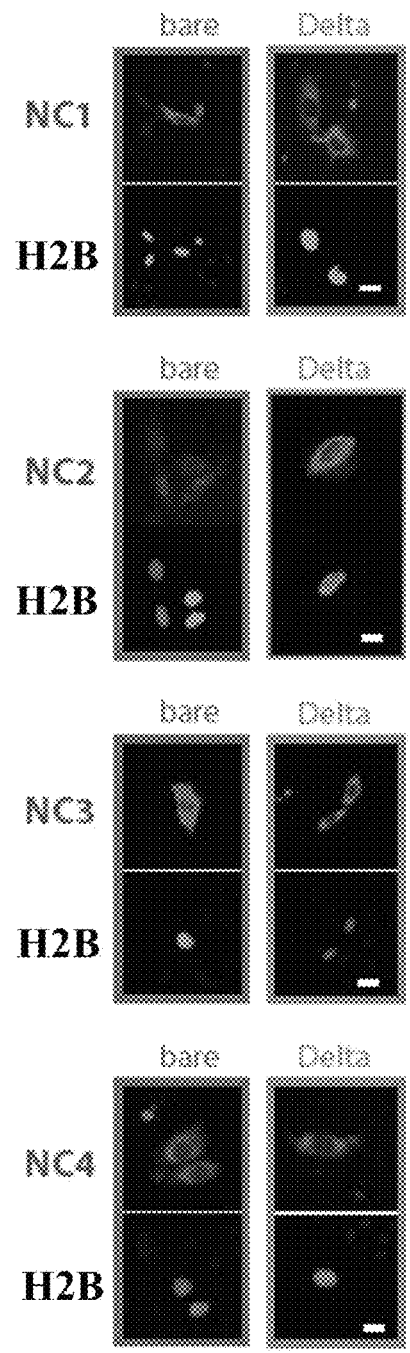
FIG. 34 shows fluorescence microscopy images of CHO cells transfected with constructs NC1-NC4 (top, see FIG. 31B) and having H2B expression (bottom) in the absence of Delta. Scale bar, 20 m.

Implementing extracellular signal-triggered dCas9-mediated genome regulation in this exampled involved balancing pre-cleavage membrane localization of receptor chimeras and post-cleavage nuclear translocation of dCas9 (FIG. 33). To optimize its function, the copy numbers of NLS and known membrane-maturation signals (MMS) were varied in several hNECD-dCas9 variants (FIG. 31B). The NC2 variant, which did not have any NLS, also induced H2B expression in the absence of the Delta ligand, suggesting that the sheer size of the intracellular domain comprising of dCas9-VPR-mCherry (243 kDa; hNECD is 188 kDa in size) may have caused its premature cleavage. So a 22-aa NICD sequence was reintroduced back in construct NC3; this construct did not fare better than NC1 nor NC2 (FIG. 34). An MMS sequence (sequence: RSQQEAAAKKFF (SEQ ID NO: 30)) from LMAN1 a transmembrane protein involved in protein sorting and recycling, was also introduced into the C-terminus of the fusion chimera resulting in variants NC4 and NC5. NC4 has one synthetic NLS, while NC5 does not. Only NC5 exhibited Delta-dependent activation of H2B (FIG. 31D), suggesting that proper membrane maturation was compromised by the synthetic NLSs, and MMSs such as in NC5 promote proper maturation. Finally, NC5 and sgUAS were stably integrated into the reporter cells, and a single clone was isolated based on minimal basal H2B expression in the absence of Delta. Three-fold H2B activation in response to Delta (FIGS. 31E and 31F) was observed, thus the NC5 design was used for downstream studies.

Figure 35A:
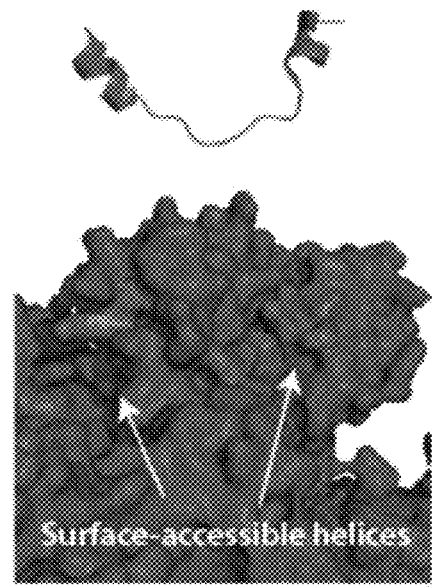
FIG. 35A shows a naturally occurring NLS sequence in S. py. Cas9 found at amino acid residues 647-670. The illustration shows this 'intrinsic' NLS (iNLS) can form a surface-accessible helix-linker-helix structure (PDB ID: 4UN3) (SEQ ID NO: 33, 34).
Figure 35B:
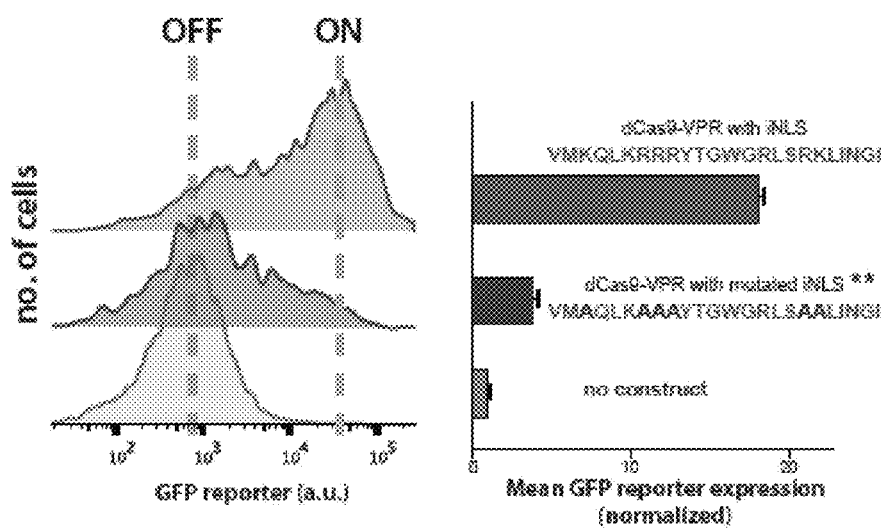
FIG. 35B shows example results for HEK293 cells stably integrated with pTET-EGFP reporter and targeting sgRNA (sgTET) that were transfected with dCas9-VPR (top) or mutated-iNLS dCas9-VPR (center). Representative histograms of EGFP activation in the presence or absence (bottom) of constructs and quantification of EGFP activation (normalized to untransfected cells) is shown (SEQ ID NO: 31, 32).

In the absence of a synthetic NLS in constructs NC2 and NC5, the cleaved dCas9-VPR-mCherry still exhibited nuclear translocation, which was possibly due in part to a predicted intrinsic NLS (iNLS) motif at residues 647-670 of S. py. Cas9. This iNLS sequence (VMKQLKRR-RYTGWGRLSRKLINGI (SEQ ID NO: 31)) of amino-acid residues was mapped to α helix-linker-helix motif in the crystal structure of S. py. Cas9. Surface exposure of both helices suggested their accessibility for importin-dependent nuclear transport (FIG. 35A). Mutating 6 arginine or lysine residues of the iNLS to alanines (VMAQLK AAAYTGWGRLSAALINGI (SEQ ID NO: 32)) in a dCas9-VPR-mCherry construct impaired EGFP activation (from 18-fold down to 4-fold) in HEK293 reporter cells. A small percentage (16%) of cells did activate EGFP, suggesting that this mutated-iNLS variant remained functional and/or that other non-canonical cryptic NLSs remain unidentified (FIG. 35B). Disrupting this iNLS motif by mutating arginine and lysine residues to alanines VMAQLKAAAYTGWGRLS AALINGI (SEQ ID NO: 32) in a dCas9-VPR-mCherry construct severely impaired nuclear localization and EGFP reporter activation in human embryonic kidney (HEK293T) cells as shown in the representative confocal microscopy images of FIG. 35C. Representative histograms of EGFP reporter are shown to the right; percentage of cells considered 'ON' had reporter intensities above untransfected 'OFF' cells. Adding back a synthetic NLS to the N-terminus of iNLS-mutated dCas9-VPR partially restored EGFP activation, suggesting that mutating the iNLS of dCas9 did not alter its DNA-binding function (FIG. 35D).

Chimera modularity was further explored by testing another Cas9 ortholog in a similar reporter assay (H2B-citrine driven by a 12×CSL promoter that also allows wild-type NICD to bind). A *Staphylococcus aureus* dCas9 was introduced in the NC5 design. This resulting S. au. NC5 dCas9 variant, together with a *S. aureus*-specific sgRNA (sasgCSL), also exhibited Delta-dependent activation levels similar to wild-type human NOTCH1.

Figure 31D:
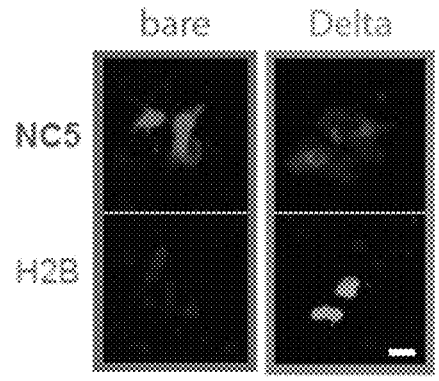
Figure 31E:
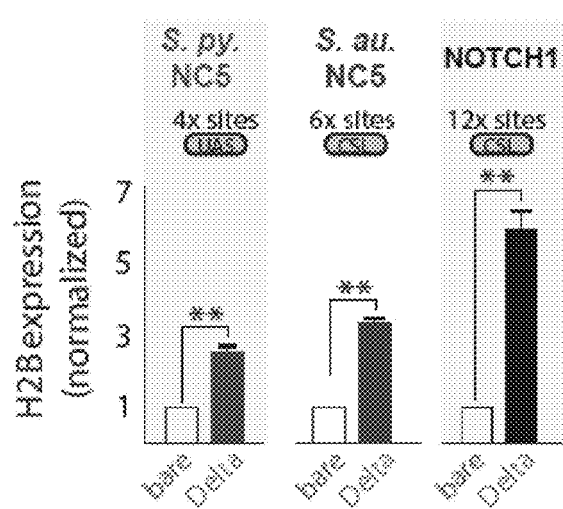
Figure 31F:
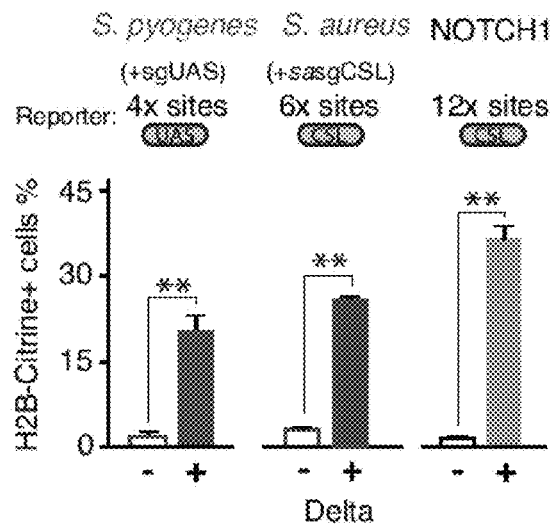
Figure 31G:
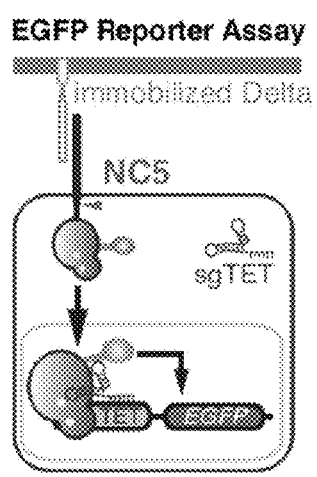
Figure 31H:
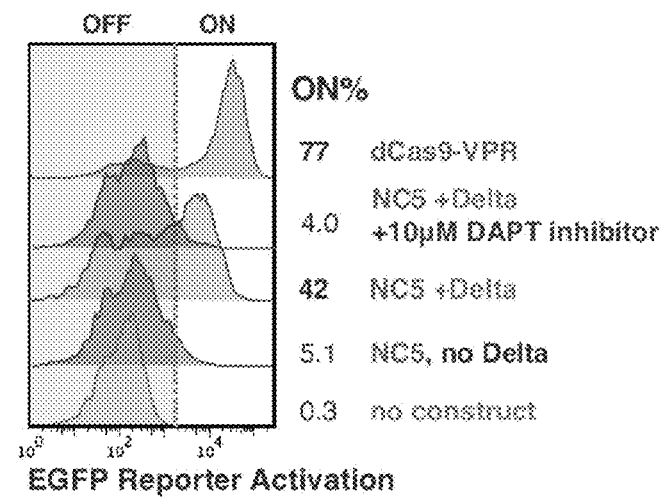
Figure 31I:
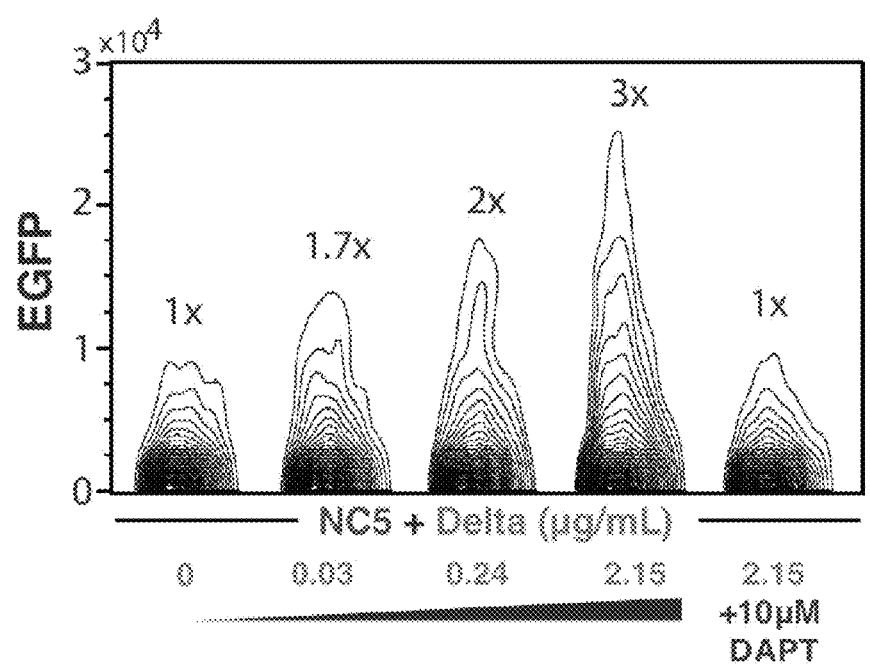

Activation of NC5 receptors by immobilized Delta ligand leads to cleavage and nuclear translocation of dCas9-VPR. dCas9-VPR complexed with a sequence-specific sgRNA (e.g., sgTET) allows for binding of the complex to the (e.g., TET) promoter and activation of EGFP gene (FIG. 31G). FIG. 31H shows EGFP reporter intensity histograms from HEK293T reporter cells stably expressing a tet-inducible EGFP gene and a targeting sgRNA (sgTET). Cells transfected with dCas9-VPR or NC5 receptor (with or without the y-secretase inhibitor, DAPT) were cultured with or without immbolized Delta for 3 days. Percentage of activated cells (ON %) is also indicated. Cells are considered ON above the basal intensity of all cells with no construct. FIG. 31I shows contour plots (where the same number of cells fall between each pair of contour lines) of EGFP activation of HEK293T reporter cells transfected with NC5 receptor and cultured on various concentrations of immobilized Delta for 3 days. Cells cultured without Delta and DAPT-treated cells cultured with the highest Delta concentration did not activate EGFP. Mean fold change compared to DAPT-treated condition is indicated.

Combining the ability to route native extracellular signals with the discriminatory power of sgRNA-mediated Cas9 binding to virtually any genomic target opens up an exponential amount of signaling pathways and functions (FIG. 32A). The Notch chimeric receptors disclosed herein were used to elicit a novel Delta-dependent arrest of the cell-division cycle. HEK293 cells were stably transduced with lentivirus-packaged sgRNAs that specifically target cyclin-dependent kinase inhibitor 1B (CDKN1B), an endogenous regulator of the cell cycle. Overexpression of CDKN1B has been shown to induce G0/G1 arrest (FIG. 32B). NC5 was transfected into HEK293 cells stably expressing sgRNAs for CDKN1B (sgCDKN1B) and the cells were subsequently introduced onto bare or Delta-containing surfaces. After 4 days on Delta, >2-fold upregulation of CDKN1B (compared to bare-surface, untransfected controls) was observed in cells expressing NC5 (FIG. 32C). 38% of Delta-exposed, NC5-transfected, and sgCDKN1B$^+$ cells were determined to be sequestered at the G0/G1 phase, and only 2-16% of cells in all other conditions tested. It was speculated that the leakiness of NC5 in sgCDKN1B$^+$ cells cultured without Delta was possibly due in part to endogenous DLL4 in HEK293 cells, which could induce CDKN1B expression upon cell-cell contact (FIG. 32C, 'NC5+sgRNA' condition), resulting in phenotypes similar to but in a slightly smaller proportion than cells in contact with surface-adsorbed affinity-enhanced DLL4.

The Notch chimeric receptor approach illustrated in this example allows one to modulate gene expression and cellular function in response to an extracellular signal. Combining the modular replacement of the NICD with Cas9 orthologs herein that possess genome-targeting features (e.g. different PAM recognition motifs) to the recent modular replacement of the NECD with single-chain variable fragments that recognize other extracellular ligands, the Notch chimeric receptor will be able to interface with a larger number of extracellular signals beyond the natural Notch ligands and with broader genomic coverage. It is envisioned that Notch chimeric receptors will be broadly useful for the study and manipulation of endogenous signaling pathways by routing to single or multiple downstream components, and for cell-based therapeutics that utilize sensing of the extracellular microenvironment.

Methods

Generation of genetic constructs. Standard molecular cloning techniques were performed to assemble all constructs described in this example (Tables 6 and 8). All Notch chimeric receptors were cloned into a pcDNA3 vector under a CMV promoter and a geneticin resistance marker. All sgRNA constructs were cloned in a pHR vector with a U6 promoter and with either puromycin resistance or fluorescence markers.

Generation of stable cell lines. All cell lines used in FIGS. 31A-31F were based on the cell line T-Rex-CHO-K1 (Invitrogen). Stable cell clones of UAS-H2B-citrine and 12×CSL-H2B-citrine were obtained. Additional cell lines were generated from lentiviral transduction (of all sgRNAs and SV40-EGFP) or plasmid transfection using TransIT-LT1 reagent (Mirus Bio) per manufacturer's instructions, followed by appropriate antibiotic selection and maintenance. Stably transfected clones expressing NC5 and sgUAS in the UAS-H2B-citrine line were isolated by FACS, after 2 weeks of puromycin and geneticin selection. All CHO cell lines were grown in Alpha MEM with Earle's Salts (Irvine Scientific) supplemented with 10% Tet System Approved FBS (Clontech), 100 U/mL of penicillin and streptomycin, 2 mM L-glutamine (Gibco) and 10 μg/mL blasticidin (VWR International) at 37° C. with 5% $CO_2$ in a humidified incubator.

Lentiviral production and transduction. HEK293T cells (ATCC) were used for lentiviral packaging. Cells were maintained in DMEM High Glucose with GlutaMAX™ media (Thermo Fisher) supplemented with 10% Tet System Approved FBS (Clontech) and 100 U/mL of penicillin and streptomycin (Gibco) at 37° C. with 5% $CO_2$. Cells were seeded at 2.0-3.0×105 cells/mL in a six-well plate format (Corning) at day 1. At day 2, cells were 50-70% confluent at the time of transfection. For each well, 1.51 μg/mL of pHR plasmid vector, 1.32 g of dR8.91 and 165 ng of pMD2.G (Addgene) were mixed in 250 μL of Opti-MEM reduced serum media (Gibco) with 7.5 μL of TransIT-LT1 reagent and incubated at room temperature for 15-30 minutes. The transfection complex solution was distributed evenly to HEK293T cultures drop-wise. Media was replaced at day 3 with fresh media appropriate for downstream transduction (e.g. Alpha MEM for CHO cell lines). At day 4, lentiviruses were harvested from the supernatant with a sterile syringe and filtered through a 0.45-μm polyvinylidene fluoride filter (Millipore) into cryovials for storage at −80° C. or immediate transduction of target cell cultures.

Filtered lentiviral supernatants were mixed 1:1 with appropriate fresh media to replace media of target cells for transduction. Adherent cell cultures were transduced at 50% confluence. Polybrene (Millipore) was added at 5 g/mL. For sgRNA integration, fresh media was replaced 2 days after transduction with appropriate antibiotic selection; it was routinely observed via flow cytometry that at least 90% of cells contained stably integrated sgRNAs 2 days post-transduction. Antibiotics were maintained in subsequent cell cultures. Transduced cell lines were used for experiments after antibiotic selection killed all non-transduced control cells and after one round of passaging. Cell lines were not tested for *mycoplasma* contamination.

Experimental techniques. Surface adsorption of Delta: Experiments described in this example were performed with cells plated on 24- or 48-well plates (Corning) at 1.5×10⁴ cells/mL. Plate surfaces were adsorbed with Delta at a saturating concentration of 2.15 μg/mL, using an affinity-enhanced variant (E12) of DLL4 with an 8-histidine tag, and incubated for 2 hours at 37° C. before cell seeding. For experiments with CHO cells, 5 μg/mL of hamster fibronectin (Innovative Research) was also adsorbed together with Delta.

Flow cytometry analysis. Cells were trypsinized and analyzed for reporter fluorescence or protein immunofluorescence using a Scanford FACScan analyzer (Becton Dickinson) and standard protocols. For intracellular proteins, cells were trypsinized and fixed in 4% paraformaldehyde solution for 15 minutes, were incubated for 2 h at room temperature with the appropriate primary antibody in a solution of 0.300Triton-X 100 (Sigma) with 2% normal donkey serum (ThermoFisher) in PBS. Primary antibody against CDKNB (D69C12, Cell Signaling) was used at concentrations per manufacturers' suggestions. Cell samples were then incubated for 30 minutes with appropriate species-specific Alexa 647 donkey secondary antibodies (Life Technologies) at 1:1000 dilution. Secondary antibody-only stained cells were used as negative controls.

TABLE 6

Plasmid constructs

| FIG. | Construct | Promoter | Product | Mammalian Selection |
|---|---|---|---|---|
| FIG. 31C, FIG. 31D | pHR-sgUAS-puro-t2a-BFP | U6 and EF1a | sgUAS and BFP | Puromycin (5 μg/mL) |
| | pHR-sasgCSL-mCherry | U6 and CMV | sasgCSL and mCherry | Fluorescence sort |
| | pHULK-EF1a-hNotch1-tagBFP | EF1a | hNotch1-tagBFP | Geneticin (600 μg/mL) |
| | pcDNA3-hNECD-SpdCas9-VPR-mCherry | CMV | S. pyogenes NC5 | Geneticin (600 μg/mL) |
| | pcDNA3-hNECD-SadCas9-VPR-mCherry | CMV | S. aureus NC5 | Geneticin (600 μg/mL) |
| FIG. 31E, FIG. 31F | pHR-EGFP | SV40 | EGFP | Fluorescence sort |
| | pHR-sgEGFP | U6 | sgEGFP | Puromycin (5 μg/mL) |
| | pcDNA3-hNECD-SpCas9-BFP | CMV | hNECD-SpCas9-BFP | Geneticin (600 μg/mL) |
| FIG. 32 | pHR-sgCDKN1B-puro | U6 and CMV | sgCDKN1B | Puromycin (5 μg/mL) |
| FIG. 34 | pcDNA3-SpdCas9-VPR-mCherry | CMV | S. pyogenes dCas9-VPR-mCherry | Geneticin (600 μg/mL) |
| | pcDNA3-SpdCas9-mut-iNLS-VPR-mCherry | CMV | S. pyogenes dCas9-VPR-mCherry with mutated iNLS | Geneticin (600 μg/mL) |
| FIG. 35 | pHR-Tet-EGFP | TetO | EGFP | Fluorescence sort |

TABLE 7

Stable cell lines

| FIG. | Stable Cell Line | Parental Line | Transfected/Transduced Construct | Antibiotic Selection |
|---|---|---|---|---|
| FIG. 31C | sgUAS + UAS-H2B | UAS-H2B-citrine | pHR-sgUAS-puro-t2a-BFP | Blasticidin (10 μg/mL), Zeocin (400 μg/mL), Puromycin (5 μg/mL) |
| | sasgCSL + CSL-H2B | 12xCSL-H2B-citrine | pHR-sasgCSL-mCherry | Blasticidin (10 μg/mL), Zeocin (400 μg/mL) |
| FIG. 31D | S. pyogenes NC5 | sgUAS-BFP + UAS-H2B | pcDNA3-hNECD-SpdCas9-VPR-mCherry | Blasticidin (10 μg/mL), Zeocin (400 μg/mL), Geneticin (600 μg/mL) |
| | S. aureus NC5 | sasgCSL + CSL-H2B | pcDNA3-hNECD-SadCas9-VPR-mCherry | Blasticidin (10 μg/mL), Zeocin (400 μg/mL), Geneticin (600 μg/mL) |
| | hNotch1 | 12xCSL-H2B-citrine | pHULK-EF1a-hNotch1-tagBFP | Blasticidin (10 μg/mL), Zeocin (400 μg/mL), Geneticin (600 μg/mL) |
| FIG. 31E, FIG. 31F | EGFP | T-Rex-CHO-K1 | pHR-EGFP | Blasticidin (10 μg/mL) |
| | sgEGFP + EGFP | EGFP | pHR-sgEGFP-puro | Blasticidin (10 μg/mL), Puromycin (5 μg/mL) |

TABLE 7-continued

Stable cell lines

| FIG. | Stable Cell Line | Parental Line | Transfected/ Transduced Construct | Antibiotic Selection |
|---|---|---|---|---|
| FIG. 32 | sgCDKN1B-HEK | HEK293T | pHR-sgCDKN1B-puro | Puromycin (5 µg/mL) |

TABLE 8

Select Sequences

| SEQ ID NO:Name | | Sequence |
|---|---|---|
| 33 | Standard *S. pyogenes* sgRNA scaffold | NNNNNNNNNNNNNNNNNNNNNGTTTAAGAGCTAT GCTGGAAACAGCATAGCAAGTTTAAATAAGGCTA GTCCGTTATCAACTTGAAAAAGTGGCACCGAGTC GGTGCTTTTTT |
| 34 | Standard *S. aureus* sasgRNA scaffold | NNNNNNNNNNNNNNNNNNNNNNGTTTTAGTAC TCTGGAAACAGAATCTACTAAAACAAGGCAAAAT GCCGTGTTTATCTCGTCAACTTGTTGGCGAGATTT TT |
| 35 | sgUAS (# of binding sites to the UAS promoter: 4) | GTACTCCGACCTCTAGTGT |
| 36 | sasgC SL (# of binding sites to the 12xCSL promoter: 6) | GGTGCCCTTCCGCCCATTTTCCC |
| 37 | sgEGFP | GACCAGGATGGGCACCACCC |
| 38 | sgCDKN1B | GGCTGGCGAGCGCGGCCTTA |

Figure 36A:
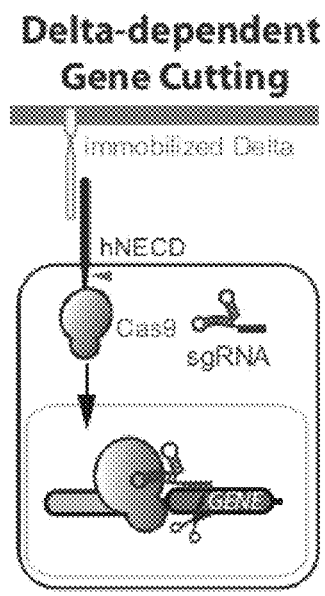
FIGS. 36A-36E show Delta-dependent gene editing.
Figure 36B:
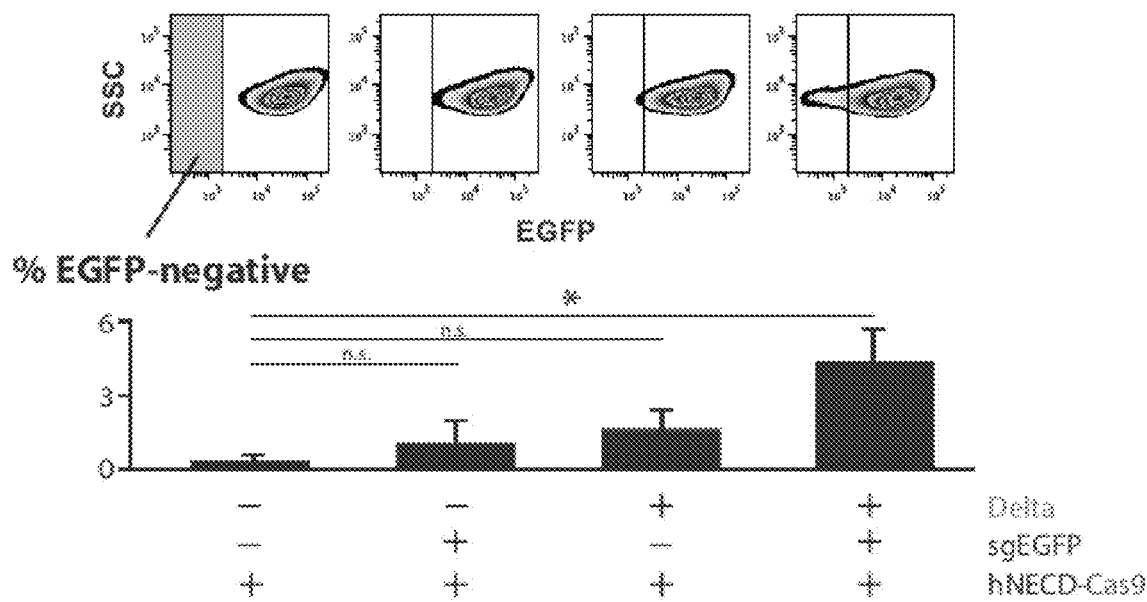

Use of a catalytically active Cas9 can be used, in some cases, for gene regulation by gene editing. FIG. 36A shows Delta-dependent DNA-cutting with an NC5 variant: hNECD fused to wild-type *S. pyogenes* nuclease-active Cas9 (hNECD-Cas9). A constitutively expressed EGFP transgene was targeted with sgEGFP as sgRNA. FIG. 36B shows the efficacy of hNECD-Cas9 in CHO cells with stably integrated SV40-driven EGFP and a targeting sgRNA (e.g., sgEGFP). A significant portion of EGFP-negative cells was observed in hNECD-Cas9- and sgEGFP-positive cells that were exposed to Delta over 4 days of culture. Representative density plots, top, show side scatter (SSC) versus EGFP under various conditions after 4 days of culture are shown. Cells were considered EGFP-negative if they fall below the intensity threshold set below 99% of EGFP-positive CHO cells lacking sgEGFP but transfected with hNECD-Cas9. Quantitative analysis of EGFP-negative cells, bottom, is provided (n=3). Mean SEM. ***p<0.001.

Figure 36C:
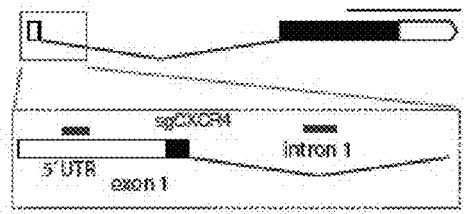
Figure 36D:
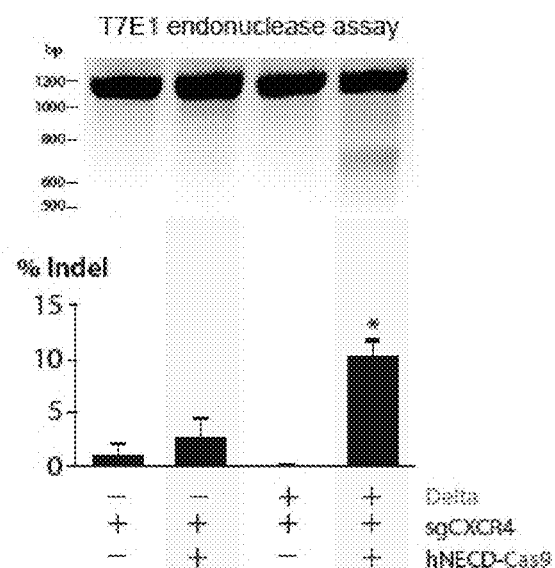
Figure 36E:
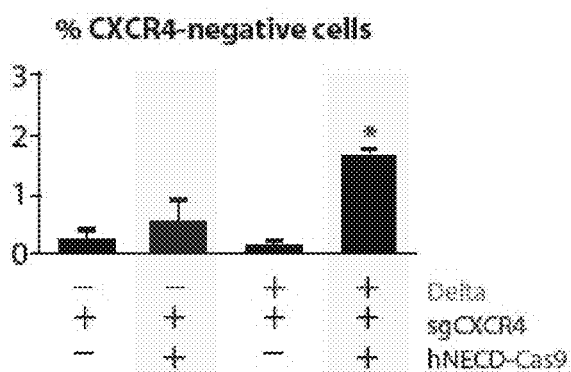

FIG. 36C shows an example schematic for two sgRNAs (short bars to left and right of "sgCXCR4") that were stably expressed in HEK293T cells and were designed to target the 5' untranslated region (UTR) and intron 1 of CXCR4. Scale bar, 1000 bp. FIG. 36D, top panel, shows example results for use of T7E1 endonuclease to assay the extent of Delta-induced hNECD-Cas9-mediated modification of CXCR4 gene in HEK293T cells, as detected by amount of products cleaved by T7E1 in SDS-PAGE gels. The bottom panel shows example results for frequency of CXCR4 indel mutations estimated by the ratio of cleaved to uncleaved products (n=3 independent experiments). Mean SEM. *p<0.05, compared to all other conditions. FIG. 36E shows example results for the quantification of flow cytometry-based immunofluorescence staining of CXCR4 protein expression in HEK293T cells cultured for 4 days under indicated conditions (n=3 independent experiments). Mean SEM. *p<0.05, compared to all other conditions.

Example 8: Developing a Minimal Notch (NC5) Receptor Variant

Developing a minimal NC5 receptor variant may be desired, in some cases, for applications in vivo. One area of interest is the NECD, which is ~1,700 amino acids (compared to dCas9, ~1,300 amino acids). The NECD domain consists of multiple epidermal growth factor (EGF) repeats; functional analysis pinpointed epidermal growth factor (EGF) repeats 11 and 12 to be an important Delta-binding unit. The EGF 11,12 repeats are highly conserved across phylogeny. Alignment of EGF 11,12 repeats of human, *Xenopus*, zebrafish, and *Drosophila* homologs show the presence of highly conserved consensus residues (FIG. 37A). FIG. 37B provides a schematic of full-length NECD and a series of deletion variants that were constructed to systematically determine a functionally minimal NC5 chimeric receptor variant. EGFP reporter intensity histograms of HEK293T cells transfected with the corresponding minimal NC5 receptor variants (histograms, right) and cultured with Delta (unless otherwise specified for 3 days) is provided. Deletion of all 36 EGF repeats results in complete loss of Delta activation (delta EGF, null). In *Drosophila* Notch, a function minimal variant has been reported by retaining only EGF 11,12 (e.g., EGF(10-12], interval notation followed as in Rebay, I. et al. Cell 67, 687-699 (1991)). However, the EGF(10-12] variant of the human NECD exhibited diminished activation relative to wild-type hNECD (13.5%, FIG. 37B). This suggested that other EGF repeats of human Notch might contribute to the stability of the Notch-Delta interaction. Reintroduction of 1-2 EGF repeats flanking EGF11,12 performed worse than EGF 11,12 alone, resulting in complete loss of activation. In contrast, adding an additional 3-5 EGF repeats gave better recovery of activation efficiencies, with the EGF(7-14] variant, exhibiting the highest percent activation (83.5%). Notably, the EGF(7-14] variant is only one-third the length of the wild-type NECD.

Example 9: Targeting the Genome and Constructing Novel Pathways

Figure 38:
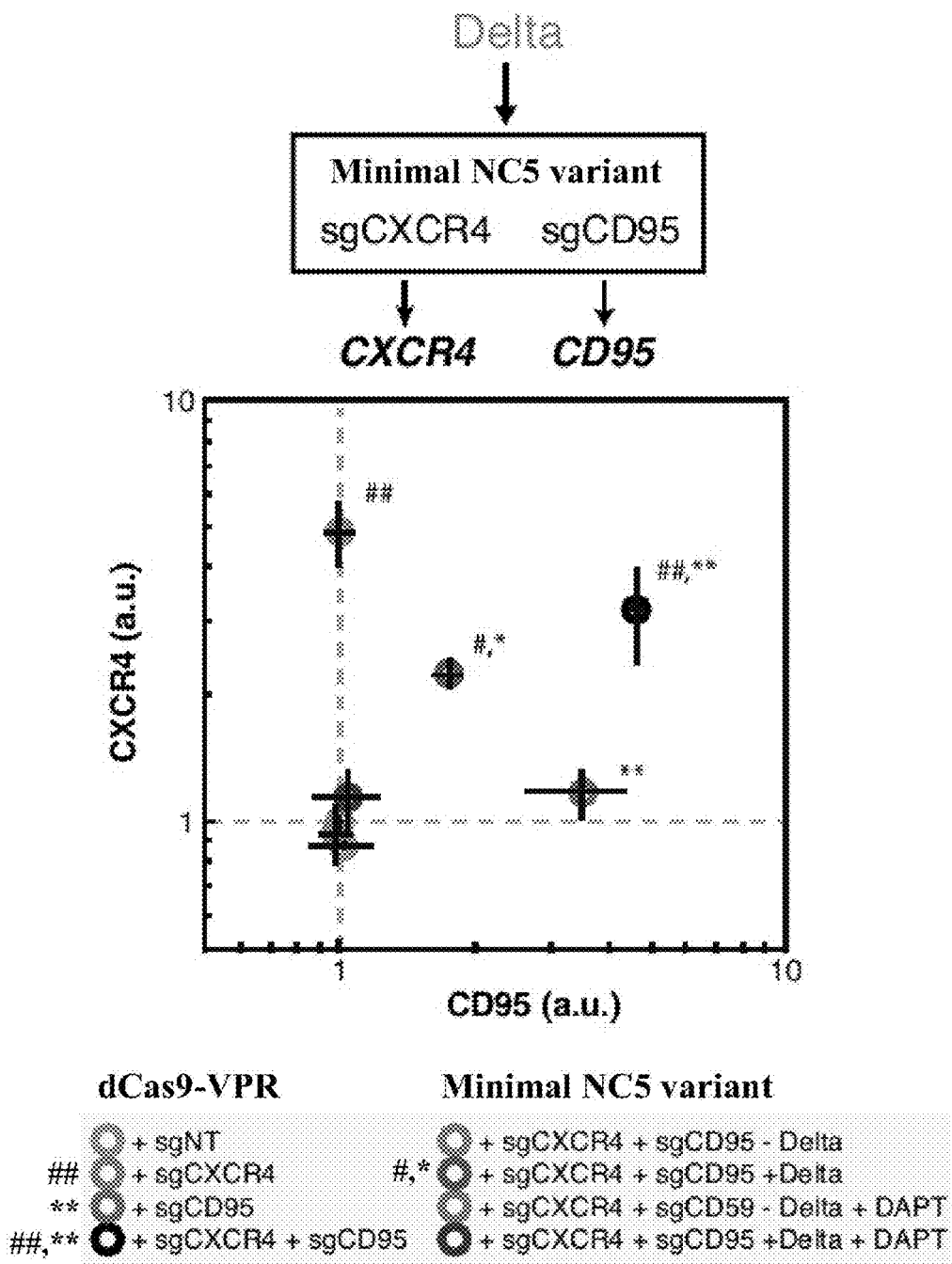
FIG. 38 shows the simultaneous activation of CXCR4 and CD95 genes targeted by gene-specific sgRNAs (2 per gene). Relative activation levels of CXCR4 and CD95 under indicated conditions in 4-day cultures are shown (a.u., arbitrary units). Data is displayed as mean fluorescence intensity SEM (n=3 independent experiments). #,##$p<0.01$, 0.001, *,**$p<0.01$, 0.001, compared to CXCR4 and CD95 levels, respectively in negative control, dCas9-VPR+sgNT (non-targeting).

The simultaneous activation of two genes with minimal NC5 receptor variants was accomplished with multiple sgRNAs (2 per gene)—targeting CXCR4 (sgCXCR4) and targeting CD95 (sgCD95) in HEK293T cells. With 'free' dCas9-VPR and sgCXCR4 or sgCD95, 5.6-fold or 3.5-fold upregulation was observed compared to non-targeting sgRNA (e.g., sgNT). Simultaneous activation of CXCR4 and CD95 led to 3.7- and 4.6-fold increase over sgNT, respectively (FIG. 38). Using the minimal EGF(7-14] NC5 receptor variant and both sgRNAs, no significant upregulation of both genes was observed in cells cultured without Delta, with DAPT only, or with Delta and DAPT, relative to dCas9-VPR+sgNT. When these cells were cultured on Delta, simultaneous activation of CXCR4 (2.2-fold upregulation) and CD95 (1.7-fold upregulation) was observed compared to cells with dCas9-VPR+sgNT (FIG. 38).

Figure 39A:
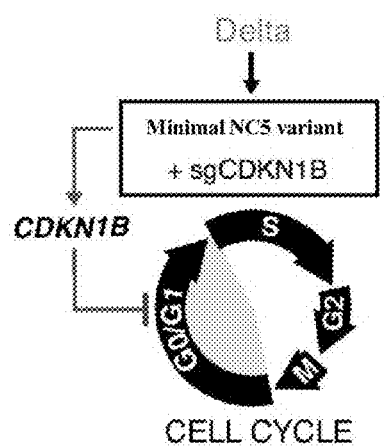
FIGS. 39A-39F show the conversion of Delta signals to cell cycle phase-specific arrest.
Figure 39B:
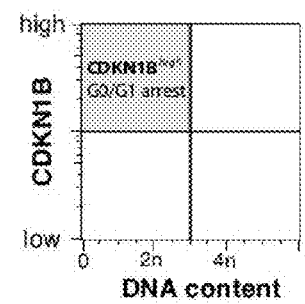
Figure 39C:
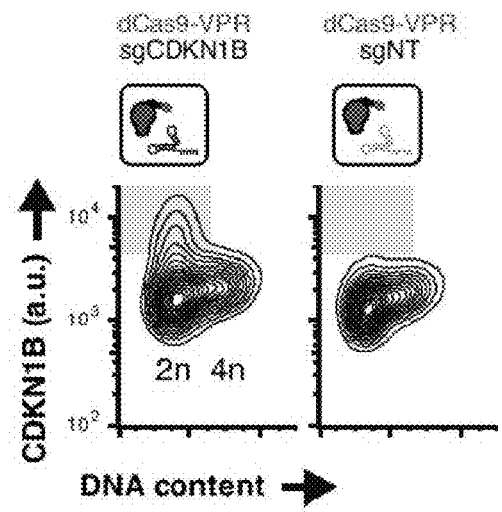
Figure 39D:
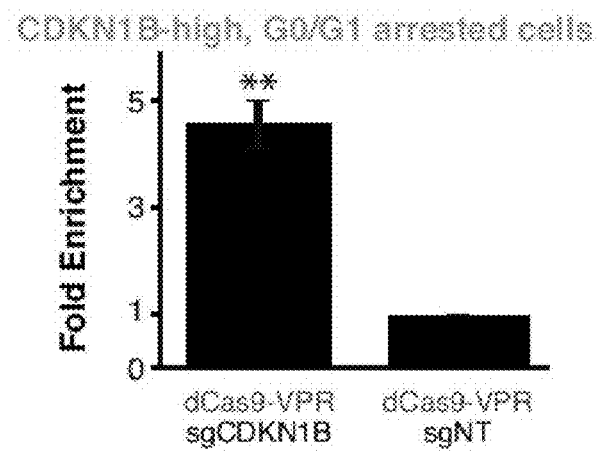
Figure 39E:
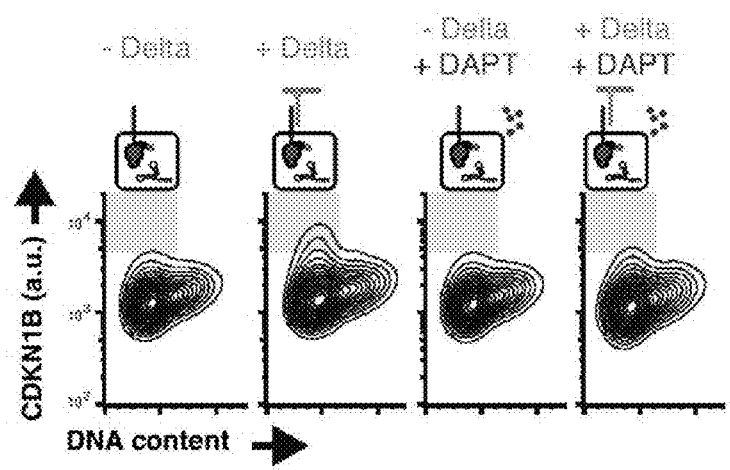
Figure 39F:
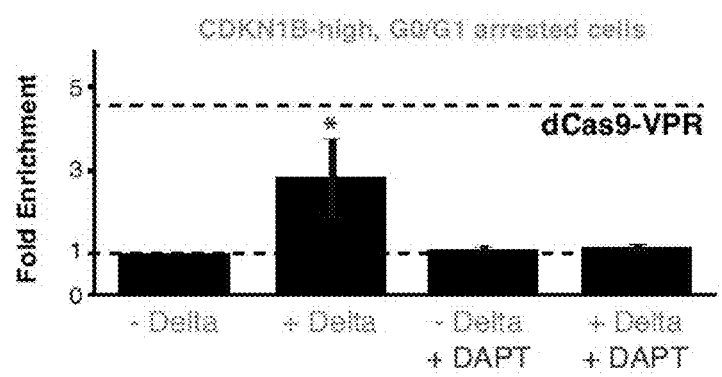

Minimal NC5 receptor variants were used to elicit Delta-dependent arrest of the cell cycle (FIG. 39A). CDKN1B (cyclin-dependent kinase inhibitor 1B) was targeted in HEK293T cells with sgRNAs (sgCDKN1B). CDKN1B overexpression leads to cellular arrest at the G0/G1 phase (FIG. 39B). In cells with 'free' dCas9-VPR and sgCDKN1B, CDKN1B upregulation was concomitant with G0/G1 enrichment; minimal CDKN1B increases were observed with dCas9-VPR and non-targeting gsRNA (sgNT, FIGS. 39C and 39D). The Delta-induced CDKN1B upregulation and G0/G1 arrest in cells was abrogated with DAPT (FIGS. 39E and 39F).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for regulating expression of a target polynucleotide in a cell, the method comprising:
   (a) contacting a ligand to a chimeric transmembrane receptor polypeptide (receptor) comprising a cleavage moiety, wherein the receptor is modified upon contacting to the ligand, and wherein the receptor modification comprises a conformational change or a chemical modification;
   (b) binding a chimeric adaptor polypeptide (adaptor) comprising a gene modulating polypeptide (GMP) to the receptor in response to the receptor modification, wherein the GMP comprises an actuator moiety linked to a cleavage recognition site, wherein the receptor is activatable upon binding of the receptor to the ligand to recruit the adaptor to the receptor, and wherein the adaptor does not bind any extracellular ligand; and
   (c) releasing the actuator moiety from the GMP of the recruited adaptor by action of the cleavage moiety at the cleavage recognition site, to effect regulating expression of the target polynucleotide in the cell, wherein the target polynucleotide encodes a protein selected from the group consisting of Jun, Fos, and IL-12.

2. The method of claim 1, wherein the protein is Jun.

3. The method of claim 1, wherein the protein is Fos.

4. The method of claim 1, wherein the protein is IL-12.

5. The method of claim 1, wherein the target polynucleotide is an endogenous gene of the cell.

6. The method of claim 1, wherein the receptor modification is phosphorylation.

7. The method of claim 1, wherein the actuator moiety comprises a transcriptional activation domain effective to increase expression of the target polynucleotide.

8. The method of claim 1, wherein the actuator moiety comprises a ribonucleic acid (RNA)-guided actuator moiety that complexes with the actuator moiety.

9. The method of claim 8, wherein the RNA-guided actuator moiety is Cas or fragment thereof that substantially lacks DNA cleavage activity.

10. The method of claim 1, wherein the transmembrane receptor (i) comprises a chimeric antigen receptor comprising an antibody or a fragment thereof against the ligand or (ii) a T cell receptor.

11. The method of claim 1, wherein the adaptor binds to an intracellular domain of the receptor upon the receptor modification.

12. The method of claim 1, wherein the cell is a lymphocyte.

13. The method of claim 12, wherein the lymphocyte is a T cell or a natural killer cell.

* * * * *